United States Patent
Pons et al.

(10) Patent No.: US 11,208,459 B2
(45) Date of Patent: *Dec. 28, 2021

(54) CONSTRUCTS HAVING A SIRP-ALPHA DOMAIN OR VARIANT THEREOF

(71) Applicant: ALX Oncology Inc., South San Francisco, CO (US)

(72) Inventors: Jaume Pons, San Francisco, CA (US); Bang Janet Sim, Brisbane, CA (US); Steven Elliot Kauder, San Mateo, CA (US); Hong Wan, Foster City, CA (US); Tracy Chia-Chien Kuo, San Carlos, CA (US)

(73) Assignee: ALX Oncology Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/825,850

(22) Filed: Mar. 20, 2020

(65) Prior Publication Data
US 2021/0070838 A1    Mar. 11, 2021

Related U.S. Application Data

(63) Continuation of application No. 16/153,404, filed on Oct. 5, 2018, now Pat. No. 10,696,730, which is a (Continued)

(51) Int. Cl.
*A61K 38/17* (2006.01)
*A61K 47/68* (2017.01)
(Continued)

(52) U.S. Cl.
CPC ...... *C07K 14/70596* (2013.01); *A61K 38/177* (2013.01); *A61K 39/395* (2013.01);
(Continued)

(58) Field of Classification Search
CPC .............. A61K 38/1709; A61K 39/395; A61K 39/39591; A61K 47/68; A61K 47/6811;
(Continued)

(56) References Cited

U.S. PATENT DOCUMENTS 3,773,919 A    11/1973    Boswell et al.
5,116,964 A    5/1992    Capon et al.
(Continued)

FOREIGN PATENT DOCUMENTS

CN    102257001 A    11/2011
CN    102596233 A    7/2012
(Continued)

OTHER PUBLICATIONS

Kim et al. (2019). "A Phase 1 Study of ALX148, a CD47 Blocker, in Combination with Rituximab in Patients with Non-Hodgkin Lymphoma," Blood, 134, Supplement_1, Abstract #1953.
(Continued)

*Primary Examiner* — Jeffrey E. Russel
(74) *Attorney, Agent, or Firm* — Morrison & Foerster LLP

(57) ABSTRACT

The present disclosure features signal-regulatory protein α (SIRP-α) polypeptides and constructs that are useful, e.g., to target a cell (e.g., a cancer cell or a cell of the immune system), to increase phagocytosis of the target cell, to eliminate immune cells such as regulatory T-cells, to kill cancer cells, to treat a disease (e.g., cancer) in a subject, or any combinations thereof. The SIRP-α constructs include a high affinity SIRP-α D1 domain or variant thereof that binds CD47 with higher affinity than a wild-type SIRP-α. The SIRP-α polypeptides or constructs include a SIRP-α D1 variant fused to an Fc domain monomer, a human serum albumin (HSA), an albumin-binding peptide, or a polyethylene glycol (PEG) polymer. Compositions provided herein
(Continued)

include (i) a polypeptide including a signal-regulatory protein α (SIRP-α) D1 variant and (ii) an antibody.

54 Claims, 22 Drawing Sheets

Specification includes a Sequence Listing.

Related U.S. Application Data continuation of application No. 15/230,186, filed on Aug. 5, 2016, now Pat. No. 10,259,859.

(60) Provisional application No. 62/346,414, filed on Jun. 6, 2016, provisional application No. 62/276,796, filed on Jan. 8, 2016, provisional application No. 62/276,801, filed on Jan. 8, 2016, provisional application No. 62/265,887, filed on Dec. 10, 2015, provisional application No. 62/202,772, filed on Aug. 7, 2015, provisional application No. 62/202,775, filed on Aug. 7, 2015, provisional application No. 62/202,779, filed on Aug. 7, 2015.

(51) Int. Cl.
| | |
|---|---|
| *C07K 14/47* | (2006.01) |
| *C07K 16/28* | (2006.01) |
| *C07K 19/00* | (2006.01) |
| *C07K 14/705* | (2006.01) |
| *A61K 39/395* | (2006.01) |
| *A61K 45/06* | (2006.01) |
| *C07K 16/00* | (2006.01) |
| *A61K 38/00* | (2006.01) |
| *A61K 39/00* | (2006.01) |

(52) U.S. Cl.
CPC .... *A61K 39/3955* (2013.01); *A61K 39/39558* (2013.01); *A61K 45/06* (2013.01); *A61K 47/6811* (2017.08); *C07K 14/70503* (2013.01); *C07K 16/00* (2013.01); *C07K 16/2803* (2013.01); *C07K 16/2818* (2013.01); *C07K 16/2863* (2013.01); *A61K 38/00* (2013.01); *A61K 38/1709* (2013.01); *A61K 2039/505* (2013.01); *C07K 14/4703* (2013.01); *C07K 2317/24* (2013.01); *C07K 2317/31* (2013.01); *C07K 2317/524* (2013.01); *C07K 2317/526* (2013.01); *C07K 2317/73* (2013.01); *C07K 2317/732* (2013.01); *C07K 2317/76* (2013.01); *C07K 2317/92* (2013.01); *C07K 2317/94* (2013.01); *C07K 2319/30* (2013.01)

(58) Field of Classification Search
CPC ............... C07K 14/47; C07K 14/4703; C07K 14/70596; C07K 16/00; C07K 16/2863; C07K 2319/30
See application file for complete search history.

(56) References Cited

U.S. PATENT DOCUMENTS

| | | | |
|---|---|---|---|
| 5,306,809 A | 4/1994 | Boon et al. |
| 5,478,925 A | 12/1995 | Wallach et al. |
| 5,505,931 A | 4/1996 | Pribish |
| 5,648,237 A | 7/1997 | Carter |
| 5,697,901 A | 12/1997 | Eriksson |
| 5,972,707 A | 10/1999 | Roy et al. |
| 6,174,529 B1 | 1/2001 | Michael et al. |
| 6,261,554 B1 | 7/2001 | Valerio et al. |
| 6,541,615 B1 | 4/2003 | Ullrich et al. |
| 6,591,129 B1 | 7/2003 | Ben-Haim et al. |
| 6,613,332 B1 | 9/2003 | Michael et al. |
| 7,402,155 B2 | 7/2008 | Palasis et al. |
| 7,514,229 B2 | 4/2009 | Jamieson et al. |
| 7,662,367 B2 | 2/2010 | Desjarlais et al. |
| 7,691,970 B2 | 4/2010 | Skerra et al. |
| 7,892,558 B2 | 2/2011 | Zagury |
| 8,216,805 B2 | 7/2012 | Carter et al. |
| 8,399,219 B2 | 3/2013 | Stagliano et al. |
| 8,518,404 B2 | 8/2013 | Daugherty et al. |
| 8,518,869 B2 | 8/2013 | Hallström et al. |
| 8,529,898 B2 | 9/2013 | Daugherty et al. |
| 8,541,203 B2 | 9/2013 | Daugherty et al. |
| 8,562,997 B2 | 10/2013 | Jaiswal et al. |
| 8,603,778 B2 | 12/2013 | Heavner et al. |
| 8,613,922 B2 | 12/2013 | Clemmons et al. |
| 8,728,476 B2 | 5/2014 | Van Den Berg |
| 8,748,399 B2 | 6/2014 | Bedzyk et al. |
| 8,993,266 B2 | 3/2015 | Stagliano et al. |
| 9,017,675 B2 | 4/2015 | Liu et al. |
| 9,169,321 B2 | 10/2015 | Daugherty et al. |
| 9,352,037 B2 | 5/2016 | Van Den Berg |
| 9,382,320 B2 | 7/2016 | Liu et al. |
| 9,394,365 B1 | 7/2016 | Eisenbach-Schwartz et al. |
| 9,475,882 B2 | 10/2016 | Clemmons et al. |
| 9,512,225 B2 | 12/2016 | Eisenbach-Schwartz et al. |
| 9,512,227 B2 | 12/2016 | Eisenbach-Schwartz et al. |
| 9,534,052 B2 | 1/2017 | Eisenbach-Schwartz et al. |
| 9,546,206 B2 | 1/2017 | Ring et al. |
| 9,562,087 B2 | 2/2017 | Ring et al. |
| 9,944,911 B2 | 4/2018 | Ring et al. |
| 10,259,859 B2 | 4/2019 | Pons et al. |
| 10,696,730 B2 | 6/2020 | Pons et al. |
| 2004/0213792 A1 | 10/2004 | Clemmons et al. |
| 2007/0148201 A1 | 6/2007 | Skerra et al. |
| 2008/0160013 A1 | 7/2008 | Clemmons et al. |
| 2009/0068195 A1 | 3/2009 | Vugmeyster et al. |
| 2010/0189651 A1 | 7/2010 | Stagliano et al. |
| 2010/0215640 A1 | 8/2010 | Clemmons et al. |
| 2010/0239578 A1 | 9/2010 | Danska et al. |
| 2010/0239579 A1 | 9/2010 | Smith et al. |
| 2011/0081345 A1 | 4/2011 | Moore et al. |
| 2011/0110938 A1 | 5/2011 | Chiu et al. |
| 2011/0184145 A1 | 7/2011 | Silence et al. |
| 2011/0237498 A1 | 9/2011 | Raymond et al. |
| 2012/0189625 A1 | 7/2012 | Wang et al. |
| 2012/0283408 A1 | 11/2012 | Lee et al. |
| 2013/0011401 A1 | 1/2013 | Huber et al. |
| 2014/0010810 A1 | 1/2014 | West et al. |
| 2014/0023664 A1 | 1/2014 | Lowman et al. |
| 2014/0024111 A1 | 1/2014 | Kannan et al. |
| 2014/0051634 A1 | 2/2014 | Hallström et al. |
| 2014/0113348 A1 | 4/2014 | Williams et al. |
| 2014/0140926 A1 | 5/2014 | Discher et al. |
| 2014/0161800 A1 | 6/2014 | Blankenship et al. |
| 2014/0193408 A1 | 7/2014 | Huber et al. |
| 2014/0242095 A1 | 8/2014 | Wang et al. |
| 2015/0071905 A1 | 3/2015 | Ring et al. |
| 2015/0203559 A1 | 7/2015 | Stagliano et al. |
| 2015/0329616 A1 | 11/2015 | Uger et al. |
| 2015/0353642 A1 | 12/2015 | Tykocinski |
| 2015/0376288 A1 | 12/2015 | Weiskopf et al. |
| 2016/0000909 A1 | 1/2016 | Eisenbach-Schwartz et al. |
| 2016/0008429 A1 | 1/2016 | Willingham et al. |
| 2016/0008463 A1 | 1/2016 | Eisenbach-Schwartz et al. |
| 2016/0045532 A1 | 2/2016 | Roberts et al. |
| 2016/0069898 A1 | 3/2016 | Weiskopf et al. |
| 2016/0144009 A1 | 5/2016 | Tseng et al. |
| 2016/0177276 A1 | 6/2016 | Lo et al. |
| 2016/0186150 A1 | 6/2016 | Deming et al. |
| 2016/0193295 A1 | 7/2016 | Kannan et al. |
| 2016/0194406 A1 | 7/2016 | Leeper et al. |
| 2016/0244522 A1 | 8/2016 | Van Den Berg |
| 2016/0297866 A1 | 10/2016 | Clemmons et al. |
| 2016/0304609 A1 | 10/2016 | Liu et al. |
| 2017/0029508 A1 | 2/2017 | Eisenbach-Schwartz et al. |
| 2017/0044258 A1 | 2/2017 | Van Den Berg et al. |
| 2017/0107270 A1 | 4/2017 | Pons et al. |
| 2018/0141986 A1 | 5/2018 | Tian et al. |
| 2018/0195054 A1 | 7/2018 | Ring et al. |

(56) References Cited

U.S. PATENT DOCUMENTS

| | | |
|---|---|---|
| 2018/0371435 A1 | 12/2018 | Deming et al. |
| 2019/0169266 A1 | 6/2019 | Pons et al. |
| 2020/0239543 A1 | 7/2020 | Pons et al. |
| 2020/0263154 A1 | 8/2020 | Deming et al. |
| 2020/0392199 A1 | 12/2020 | Pons et al. |
| 2020/0400662 A1 | 12/2020 | Wan et al. |
| 2021/0154269 A1 | 5/2021 | Wan et al. |

FOREIGN PATENT DOCUMENTS

| | | |
|---|---|---|
| CN | 102939303 A | 2/2013 |
| CN | 103635490 A | 3/2014 |
| CN | 104812413 A | 7/2015 |
| CN | 107252476 A | 10/2017 |
| CO | 20180002471 A2 | 5/2018 |
| JP | 2011-500005 A | 1/2011 |
| JP | 2012-533631 A | 12/2012 |
| JP | 2013-541542 A | 11/2013 |
| JP | 2015-504899 A | 2/2015 |
| WO | WO-1993/000077 A1 | 1/1993 |
| WO | WO-1999/040940 A1 | 8/1999 |
| WO | WO-2000/077026 A1 | 12/2000 |
| WO | WO-2001/048020 A1 | 7/2001 |
| WO | WO-2003/031650 A2 | 4/2003 |
| WO | WO-2003/095618 A2 | 11/2003 |
| WO | WO-2004/011618 A2 | 2/2004 |
| WO | WO-2004/096133 A2 | 11/2004 |
| WO | WO-2005/108415 A2 | 11/2005 |
| WO | WO-2009/046541 A1 | 4/2009 |
| WO | WO-2009/091601 A1 | 7/2009 |
| WO | WO-2009/131453 A1 | 10/2009 |
| WO | WO-2010/070047 A1 | 6/2010 |
| WO | WO-2010/096838 A2 | 8/2010 |
| WO | WO-2010/130053 A1 | 11/2010 |
| WO | WO-2011/011315 A1 | 1/2011 |
| WO | WO-2011/066501 A1 | 6/2011 |
| WO | WO-2011/076781 A1 | 6/2011 |
| WO | WO-2011/143624 A2 | 11/2011 |
| WO | WO-2012/048332 A2 | 4/2012 |
| WO | WO-2012/130831 A1 | 10/2012 |
| WO | WO-2012/142515 A2 | 10/2012 |
| WO | WO-2012/172521 A1 | 12/2012 |
| WO | WO-2013/032948 A1 | 3/2013 |
| WO | WO-2013/063076 A1 | 5/2013 |
| WO | WO-2013/109752 A1 | 7/2013 |
| WO | WO-2014/045022 A2 | 3/2014 |
| WO | WO-2014/094122 A1 | 6/2014 |
| WO | WO-2014/121093 A1 | 8/2014 |
| WO | WO-2014/124028 A1 | 8/2014 |
| WO | WO-2014/149477 A1 | 9/2014 |
| WO | WO-2014/160183 A1 | 10/2014 |
| WO | WO-2014/179132 A1 | 11/2014 |
| WO | WO-2014/186761 A2 | 11/2014 |
| WO | WO-2015/041987 A1 | 3/2015 |
| WO | WO-2015/042557 A1 | 3/2015 |
| WO | WO-2015/048329 A2 | 4/2015 |
| WO | WO-2015/057834 A1 | 4/2015 |
| WO | WO-2015/116933 A2 | 8/2015 |
| WO | WO-2015/136541 A2 | 9/2015 |
| WO | WO-2016/022971 A1 | 2/2016 |
| WO | WO-2016/022994 A2 | 2/2016 |
| WO | WO-2016/023001 A1 | 2/2016 |
| WO | WO-2016/023040 A1 | 2/2016 |
| WO | WO-2016/024021 A1 | 2/2016 |
| WO | WO-2016/033201 A1 | 3/2016 |
| WO | WO-2016/044021 A1 | 3/2016 |
| WO | WO-2016/057980 A1 | 4/2016 |
| WO | WO-2016/063233 A1 | 4/2016 |
| WO | WO-2016/065329 A1 | 4/2016 |
| WO | WO-2016/081423 A1 | 5/2016 |
| WO | WO-2016/138306 A1 | 9/2016 |
| WO | WO-2016/169261 A1 | 10/2016 |
| WO | WO-2017/009829 A1 | 1/2017 |
| WO | WO-2017/027422 A1 | 2/2017 |
| WO | WO-2017/178653 A2 | 10/2017 |
| WO | WO-2018/057669 A1 | 3/2018 |
| WO | WO-2020/243338 A1 | 12/2020 |
| WO | WO-2020/247820 A1 | 12/2020 |
| WO | WO-2021/108693 A1 | 6/2021 |

OTHER PUBLICATIONS

Wan et al. (2019). "Pharmacodynamic Biomarker Characterization of ALX148, a CD47 Blocker, in Combination with Established Anticancer Antibodies in Patients with Advanced Malignancy," Society for Immunotherapy of Cancer (SITC), Abstract #P449.

Ho et al. (2015). "'Velcro' Engineering of High Affinity CD47 Ectodomain as Signal Regulatory Protein α (SIRPα) Antagonists That Enhance Antibody-Dependent Cellular Phagocytosis," J Biol Chem, 290(20):12650-63.

U.S. Appl. No. 17/105,353, filed Nov. 25, 2020 for Wan et al. (pursuant to the waiver of 37 C.F.R. § 1.98(a)(2)(ii) issued by the Office Sep. 21, 2004).

Atwell, S. et al. (Jul. 4, 1997). "Stable heterodimers from remodeling the domain interface of a homodimer using a phage display library," *J Mol. Biol.* 270(1):26-35.

Barclay, A.N. et al. (Jun. 2006). "The SIRP family of receptors and immune regulation," *Nat. Rev. Immunol.* 6(6):457-464.

Borrok, M.J. et al. (epub Jul. 10, 2012). "Revisiting the role of glycosylation in the structure of human IgG Fc." *ACS Chemical Biology* 7(9):1596-1602.

Castañeda, L. et al. (Sep. 25, 2013). "Acid-cleavable thiomaleamic acid linker for homogeneous antibody-drug conjugation," *Chem Common (Camb).* 49(74):8187-8189.

Constantinou, A. et al. (epub Feb. 29, 2008). "Modulation of antibody pharmacokinetics by chemical polysialylation," *Bioconjug Chem.* 19(3):643-650.

DeLuca, P.P. et al. (1982). "Parenteral drug-delivery systems," Chapter 8 in Pharmaceutics and Pharmacy Practice, Banker, G.S. and Chalmers, R.K. ed., J. B. Lippincott & Co.: Philadelphia, PA, pp. 238-250.

Dennis, M.S. et al. (epub Jul. 15, 2002). "Albumin binding as a general strategy for improving the pharmacokinetics of proteins," *J. Biol. Chem.* 277(38):35035-35043.

Donaldson, J.M. et al. (epub Oct. 7, 2013). "Identification and grafting of a unique peptide-binding site in the Fab framework of monoclonal antibodies," *Proc Natl Acad Sci USA.* 110(43):17456-17461.

Duan, J.X. et al. (epub Feb. 8, 2008). "Potent and highly selective hypoxia-activated achiral phosphoramidate mustards as anticancer drugs," *J. Med. Chem.* 51(8):2412-2420.

Ducry, L. et al. (Jan. 2010). "Antibody-drug conjugates: linking cytotoxic payloads to monoclonal antibodies," *Bioconjug Chem.* 21(1):5-13.

European Search Report dated Nov. 7, 2016 for European Application No. 16183261.3, filed on Aug. 8, 2016, 14 pages.

European Search Report dated Oct. 23, 2015 for European Application No. 13738232.1, filed on Jan. 17, 2013, seven pages.

GenBank Accession No. NP_037148.2, (ROD Sep. 1, 2016, last updated Apr. 16, 2017), "tyrosine-protein phosphatase non-receptor type substrate 1 precursor [Rattus norvegicus]," located at <http://www.ncbi.nlm.nih.gov/protein/NP_037148.2>, last visited on Jun. 9, 2017, four pages.

Gentz, R. et al. (Feb. 1989). "Bioassay for trans-activation using purified human immunodeficiency virus tat-encoded protein: transactivation requires mRNA synthesis." *Proc. Natl. Acad. Sci. USA.* 86(3):821-824.

Gregoriadis, G. et al. (Dec. 2000). "Polysialic acids: potential in improving the stability and pharmacokinetics of proteins and other therapeutics," *Cell. Mol. Life Sci.* 57(13-14):1964-1969.

Gunasekaran, K. et al. (epub Apr. 16, 2010). "Enhancing antibody Fc heterodimer formation through electrostatic steering effects: applications to bispecific molecules and monovalent IgG," *J Biol Chem.* 285(25):19637-19646.

Hanes, J. et al. (Oct. 1997). "New advances in microsphere-based single-dose vaccines," *Advanced Drug Delivery Reviews* 28(1):97-119.

(56) References Cited

OTHER PUBLICATIONS

Hatherley, D. et al. (epub Jul. 23, 2009). "Structure of signal-regulatory protein alpha: a link to antigen receptor evolution," *J Biol Chem.* 284(39):26613-26619.

Hatherley, D. et al. (epub Mar. 16, 2007). "The structure of the macrophage signal regulatory protein alpha (SIRPalpha) inhibitory receptor reveals a binding face reminiscent of that used by T cell receptors." *J Biol Chem.* 282(19):14567-14575.

Hatherley, D. et al. (Jul. 25, 2008). "Paired receptor specificity explained by structures of signal regulatory proteins alone and complexed with CD47," *Mol. Cell.* 31(2):266-277.

Hezareh et al. (2001) "Effector function activities of a panel of mutants of a broadly neutralizing antibody against human immunodeficiency virus type 1," J Virol., 75(24):12161-8.

Icard, P. et al. (epub Jul. 25, 2012). "A global view of the biochemical pathways involved in the regulation of the metabolism of cancer cells," *Biochim Biophys Acta.* 1826(2):423-433.

International Preliminary Report on Patentability dated Feb. 23, 2017 for PCT Application No. PCT/US2015/044528, filed on Aug. 10, 2015, 11 pages.

International Preliminary Report on Patentability dated Jan. 24, 2017, for PCT Application No. PCT/US2016/045914, filed on Aug. 5, 2016, 20 pages.

International Preliminary Report on Patentability dated Jul. 31, 2014 for PCT Application No. PCT/US2013/021937, filed on Jan. 17, 2013, 7 pages.

International Search Report dated Dec. 22, 2015 for PCT Application No. PCT/US2015/044528, filed on Aug. 10, 2015, four pages.

International Search Report dated Jan. 24, 2017, for PCT Application No. PCT/US2016/045914, filed on Aug. 5, 2016, six pages.

International Search Report dated May 21, 2013, for PCT Application No. PCT/US2013/021937, filed on Jan. 17, 2013, five pages.

Jawa, V. et al. (epub Sep. 25, 2013). "T-cell dependent immunogenicity of protein therapeutics: Preclinical assessment and mitigation," *Clin Immunol.* 149(3):534-555.

Judd, R.C. (Aug. 1982). "Surface peptide mapping of protein I and protein III of four strains of Neisseria gonorrhoeae," *Infect Immun.* 37(2):632-641.

Kabat, E.A. et al. (1991). *Sequences of proteins of immunological interest*, 5th ed. U.S. Dept. of Health and Human Services, Public Health Service, National Institutes of Health: Bethesda, MD.

Kharitonenkov, A. et al., "A family of proteins that inhibit signalling through tyrosine kinase receptors," Nature (Mar. 13, 1997), 386(6621):181-186.

Kling, J. (May 7, 2012). "Hypoxia-activated prodrugs forge ahead in cancer," *Nature Biotechnology* 30(5):381.

Koblinski, J.E. et al. (Feb. 2000). "Unraveling the role of proteases in cancer," *Clin Chim Acta.* 291(2):113-135.

Kwon, E.D. et al. (Dec. 21, 1999). "Elimination of residual metastatic prostate cancer after surgery and adjunctive cytotoxic T lymphocyte-associated antigen 4 (CTLA-4) blockade immunotherapy," *Proc. Natl. Acad. Sci. USA.* 96(26):15074-15079.

La Rocca, G. et al. (Apr. 5, 2004). "Zymographic detection and clinical correlations of MMP-2 and MMP-9 in breast cancer sera," *Br J Cancer.* 90(7):1414-1421.

Langer, R. (Sep. 28, 1990). "New methods of drug delivery," *Science* 249(4976):1527-1533.

LeBeau, A.M. et al. (2013, epub Dec. 17, 2012). "Imaging a functional tumorigenic biomarker in the transformed epithelium," *Proc. Natl. Acad. Sci. USA* 110(1):93-98.

Lee, W.Y. et al. (Dec. 1, 2007). "Novel structural determinants on SIRP alpha that mediate binding to CD47," *The Journal of Immunology* 179(11):7741-7750.

Lee, W.Y. et al. (epub Sep. 7, 2010). "The role of cis dimerization of signal regulatory protein alpha (SIRPalpha) in binding to CD47," *J Biol Chem.* 285(49):37953-37963.

Lin, Y. et al. (epub Jul. 17, 2012). "Soluble extracellular domains of human SIRPα and CD47 expressed in *Escherichia coli* enhances the phagocytosis of leukemia cells by macrophages in vitro," *Protein Expr Purif.* 85(1):109-116.

Liu, C. et al. (Jun. 1, 2003). "Overexpression of legumain in tumors is significant for invasion/metastasis and a candidate enzymatic target for prodrug therapy," *Cancer Res.* 63(11):2957-2964.

Liu, Y. et al. (2007, epub Oct. 3, 2006). "Functional elements on SIRPalpha IgV domain mediate cell surface binding to CD47," *Journal of Molecular Biology* 365(3):680-693.

Liu, Y. et al. (Feb. 15, 2004). "Peptide-mediated inhibition of neutrophil transmigration by blocking CD47 interactions with signal regulatory protein alpha," *J Immunol.* 172 (4) 2578-2585.

Martens, T. et al. (Oct. 15, 2006). "A novel one-armed anti-c-Met antibody inhibits glioblastoma growth in vivo," *Clin Cancer Res.* 12(20 Pt 1):6144-6152.

Merchant, A.M. et al. (Jul. 1998). "An efficient route to human bispecific IgG," *Nat Biotechnol.* 16(7):677-681.

Merchant, M. et al. (epub Jul. 23, 2013). "Monovalent antibody design and mechanism of action of onartuzumab, a MET antagonist with anti-tumor activity as a therapeutic agent," *Proc. Natl. Acad. Sci. USA.* 110(32):E2987-E2996.

Milla, P. et al. (Jan. 2012). "PEGylation of proteins and liposomes: a powerful and flexible strategy to improve the drug delivery," *Curr Drug Metab.* 13(1):105-119.

Miyakawa, N. et al. (epub Mar. 5, 2013). "Gene delivery of albumin binding peptide-interferon-gamma fusion protein with improved pharmacokinetic properties and sustained biological activity," *J. Pharm. Sci.* 102(9):3110-3118.

Nakaishi, A. et al. (2008, epub Nov. 7, 2007). "Structural insight into the specific interaction between murine SHPS-1/SIRP alpha and its ligand CD47," *J Mol Biol.* 375(3):650-660.

Oldenborg, P.A. et al. (Jun. 16, 2000). "Role of CD47 as a marker of self on red blood cells," *Science* 288(5473):2051-2054.

Ridgway, J.B. et al. (Jul. 1996). "'Knobs-into-holes' engineering of antibody CH3 domains for heavy chain heterodimerization," *Protein Eng.* 9(7):617-621.

Schellenberger, V. et al. (Dec. 2009). "A recombinant polypeptide extends the in vivo half-life of peptides and proteins in a tunable manner," *Nat. Biotechnol.* 27(12):1186-1190.

Schlapschy, M. et al. (epub Jun. 10, 2013). "PASylation: a biological alternative to PEGylation for extending the plasma half-life of pharmaceutically active proteins," *Protein Eng Des Sel.* 26(8):489-501.

Shigenaga, A. et al. (epub Apr. 13, 2012). "Development of a reduction-responsive amino acid that induces peptide bond cleavage in hypoxic cells," *Chembiochem.* 13(7):968-971.

Sim et al., (2019). "Discovery of high affinity, pan-allelic, and pan-mammalian reactive antibodies against the myeloid checkpoint receptor SIRPα," mAbs, 11(6): 1-17.

Strauch, E.M. et al. (2014, epub Dec. 31, 2013). "Computational design of a pH-sensitive IgG binding protein," *Proc Natl Acad Sci U S A.* 111(2):675-680.

Subramanian, S. et al. (2007, epub Nov. 10, 2006). "Phylogenetic divergence of CD47 interactions with human signal regulatory protein alpha reveals locus of species specificity. Implications for the binding site," *J Biol Chem.* 282(3):1805-1818.

Takenaka, K. et al. (epub Nov. 4, 2007). "Polymorphism in SIRPα modulates engraftment of human hematopoietic stem cells," *Nat Immunol.* 8(12):1313-1323.

Trissel, L.A. (1986). *Handbook on Injectable Drugs*, 4th ed., ASHP: Bethesda, MD, pp. 622-630.

Trüssel, S. et al. (Dec. 2009). "New strategy for the extension of the serum half-life of antibody fragments," *Bioconjug Chem.* 20(12):2286-2292.

Tsai, R.K. et al. (epub Mar. 17, 2010). "Self inhibition of phagocytosis: the affinity of 'marker of self' CD47 for SIRPalpha dictates potency of inhibition but only at low expression levels," *Blood Cells Mol Dis.* 45(1):67-74.

U.S. Appl. No. 15/955,640, filed Apr. 17, 2018, for Deming et al. (pursuant to the waiver of 37 C.F.R. § 1.98(a)(2)(iii) issued by the Office Sep. 21, 2004).

U.S. Appl. No. 16/153,404, filed Oct. 5, 2018, for Pons et al. (pursuant to the waiver of 37 C.F.R. § 1.98(a)(2)(iii) issued by the Office Sep. 21, 2004).

(56) References Cited

OTHER PUBLICATIONS

U.S. Appl. No. 16/736,651, filed Jan. 7, 2020, for Pons et al. (pursuant to the waiver of 37 C.F.R. § 1.98(a)(2)(iii) issued by the Office Sep. 21, 2004).
U.S. Appl. No. 16/825,850, filed Oct. 21, 2019, for Deming et al. (pursuant to the waiver of 37 C.F.R. § 1.98(a)(2)(iii) issued by the Office Sep. 21, 2004).
Uhland, K. (Dec. 2006). "Matriptase and its putative role in cancer," *Cell Mol Life Sci*. 63(24):2968-2978.
Ulisse, S. et al. (Feb. 2009). "The urokinase plasminogen activator system: a target for anti-cancer therapy," *Curr Cancer Drug Targets*. 9(1):32-71.
Weiskopf, K. et al. (epub May 30, 2013). "Engineered SIRPα variants as immunotherapeutic adjuvants to anticancer antibodies," *Science* 341(6141):88-91.
Wilson, I. et al. (Jul. 1984). "The structure of an antigenic determinant in a protein," *Cell* 37(3):767-778.
Written Opinion dated Dec. 22, 2015 for PCT Application No. PCT/US2015/044528, filed on Aug. 10, 2015, nine pages.
Written Opinion dated Jan. 24, 2017 for PCT Application No. PCT/US2016/045914, filed on Aug. 5, 2016, 19 pages.
Written Opinion of the International Searching Authority dated May 21, 2013 for PCT Application No. PCT/US2013/021937, filed on Jan. 17, 2013, five pages.
Yamao, T. et al. (Feb. 3, 1997). "Mouse and human SHPS-1: molecular cloning of cDNAs and chromosomal localization of genes," *Biochem Biophys Res Commun*. 231(1):61-67.
Zhao, X.W. et al. (epub Oct. 31, 2011). "CD47-signal regulatory protein-α (SIRPα) interactions form a barrier for antibody-mediated tumor cell destruction," *Proc Natl Acad Sci USA*. 108(45):18342-18347.
U.S. Appl. No. 17/164,716, filed Feb. 1, 2021 for Deming et al. (pursuant to the waiver of 37 C.F.R. § 1.98(a)(2)(iii) issued by the Office Sep. 21, 2004).
Rudikoff et al. (1982). "Single amino acid substitution altering antigen-binding specificity," Immunology, vol. 79, pp. 1979-1983.

SIRPα D1 domain or variant thereof

IgG hinge domain

IgG $C_H2$ antibody constant domain

IgG $C_H3$ antibody constant domain

SEQUENCE LISTING

<160> NUMBER OF SEQ ID NOS: 225

<210> SEQ ID NO 1
<211> LENGTH: 119
<212> TYPE: PRT
<213> ORGANISM: Homo sapiens

<400> SEQUENCE: 1

Glu Glu Glu Leu Gln Val Ile Gln Pro Asp Lys Ser Val Leu Val Ala
1               5                   10                  15

```
Ala Gly Glu Thr Ala Thr Leu Arg Cys Thr Ala Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
                115

<210> SEQ ID NO 2
<211> LENGTH: 118
<212> TYPE: PRT
<213> ORGANISM: Homo sapiens

<400> SEQUENCE: 2

Glu Glu Glu Leu Gln Val Ile Gln Pro Asp Lys Ser Val Ser Val Ala
 1               5                  10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
 50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
                115

<210> SEQ ID NO 3
<211> LENGTH: 118
<212> TYPE: PRT
<213> ORGANISM: Homo sapiens

<400> SEQUENCE: 3

Glu Glu Glu Leu Gln Val Ile Gln Pro Asp Lys Ser Val Ser Val Ala
 1               5                  10                  15

Ala Gly Glu Ser Ala Ile Leu Leu Cys Thr Val Thr Ser Leu Ile Pro
            20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
 50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95
```

```
Gly Ser Pro Asp Thr Glu Phe Lys Ser Gly Ala Gly Thr Glu Leu Ser
            100                 105                 110
Val Arg Ala Lys Pro Ser
        115

<210> SEQ ID NO 4
<211> LENGTH: 119
<212> TYPE: PRT
<213> ORGANISM: Homo sapiens

<400> SEQUENCE: 4

Glu Glu Gly Leu Gln Val Ile Gln Pro Asp Lys Ser Val Ser Val Ala
1               5                   10                  15
Ala Gly Glu Ser Ala Ile Leu His Cys Thr Ala Thr Ser Leu Ile Pro
            20                  25                  30
Val Gly Pro Ile Gln Trp Phe Arg Gly Ala Gly Pro Gly Arg Glu Leu
        35                  40                  45
Ile Tyr Asn Gln Lys Glu Gly His Phe Pro Arg Val Thr Thr Val Ser
    50                  55                  60
Asp Leu Thr Lys Arg Asn Asn Met Asp Phe Ser Ile Arg Ile Gly Asn
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser
        115

<210> SEQ ID NO 5
<211> LENGTH: 119
<212> TYPE: PRT
<213> ORGANISM: Homo sapiens

<400> SEQUENCE: 5

Glu Glu Glu Leu Gln Val Ile Gln Pro Asp Lys Phe Val Leu Val Ala
1               5                   10                  15
Ala Gly Glu Thr Ala Thr Leu Arg Cys Thr Ala Thr Ser Leu Ile Pro
            20                  25                  30
Val Gly Pro Ile Gln Trp Phe Arg Gly Ala Gly Pro Gly Arg Glu Leu
        35                  40                  45
Ile Tyr Asn Gln Lys Glu Gly His Phe Pro Arg Val Thr Thr Val Ser
    50                  55                  60
Asp Leu Thr Lys Arg Asn Asn Met Asp Phe Ser Ile Arg Ile Gly Asn
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser
        115

<210> SEQ ID NO 6
<211> LENGTH: 119
<212> TYPE: PRT
<213> ORGANISM: Homo sapiens

<400> SEQUENCE: 6

Glu Glu Glu Leu Gln Val Ile Gln Pro Asp Lys Ser Val Leu Val Ala
```

| 1 | | | | 5 | | | | | 10 | | | | | 15 | |
|---|---|---|---|---|---|---|---|---|---|---|---|---|---|---|---|

Ala Gly Glu Thr Ala Thr Leu Arg Cys Thr Ala Thr Ser Leu Ile Pro
            20                   25                   30

Val Gly Pro Ile Gln Trp Phe Arg Gly Ala Gly Pro Gly Arg Glu Leu
            35                   40                   45

Ile Tyr Asn Gln Lys Glu Gly His Phe Pro Arg Val Thr Thr Val Ser
            50                   55                   60

Asp Leu Thr Lys Arg Asn Asn Met Asp Phe Pro Ile Arg Ile Gly Asn
65                   70                   75                   80

Ile Thr Pro Ala Asp Ala Gly Thr Tyr Tyr Cys Val Lys Phe Arg Lys
            85                   90                   95

Gly Ser Pro Asp Asp Val Glu Phe Lys Ser Gly Ala Gly Thr Glu Leu
           100                  105                 110

Ser Val Arg Ala Lys Pro Ser
           115

<210> SEQ ID NO 7
<211> LENGTH: 118
<212> TYPE: PRT
<213> ORGANISM: Homo sapiens

<400> SEQUENCE: 7

Glu Glu Glu Leu Gln Val Ile Gln Pro Asp Lys Ser Val Ser Val Ala
1                   5                   10                   15

Ala Gly Glu Ser Ala Ile Leu His Cys Thr Val Thr Ser Leu Ile Pro
            20                   25                   30

Val Gly Pro Ile Gln Trp Phe Arg Gly Ala Gly Pro Ala Arg Glu Leu
            35                   40                   45

Ile Tyr Asn Gln Lys Glu Gly His Phe Pro Arg Val Thr Thr Val Ser
            50                   55                   60

Glu Ser Thr Lys Arg Glu Asn Met Asp Phe Ser Ile Ser Ile Ser Asn
65                   70                   75                   80

Ile Thr Pro Ala Asp Ala Gly Thr Tyr Tyr Cys Val Lys Phe Arg Lys
            85                   90                   95

Gly Ser Pro Asp Thr Glu Phe Lys Ser Gly Ala Gly Thr Glu Leu Ser
           100                  105                 110

Val Arg Gly Lys Pro Ser
           115

<210> SEQ ID NO 8
<211> LENGTH: 118
<212> TYPE: PRT
<213> ORGANISM: Homo sapiens

<400> SEQUENCE: 8

Glu Glu Glu Leu Gln Val Ile Gln Pro Asp Lys Ser Val Leu Val Ala
1                   5                   10                   15

Ala Gly Glu Thr Ala Thr Leu Arg Cys Thr Ala Thr Ser Leu Ile Pro
            20                   25                   30

Val Gly Pro Ile Gln Trp Phe Arg Gly Ala Gly Pro Ala Arg Glu Leu
            35                   40                   45

Ile Tyr Asn Gln Lys Glu Gly His Phe Pro Arg Val Thr Thr Val Ser
            50                   55                   60

Glu Ser Thr Lys Arg Glu Asn Met Asp Phe Ser Ile Ser Ile Ser Asn
65                   70                   75                   80

Ile Thr Pro Ala Asp Ala Gly Thr Tyr Tyr Cys Val Lys Phe Arg Lys

```
                    85                   90                   95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 9
<211> LENGTH: 119
<212> TYPE: PRT
<213> ORGANISM: Homo sapiens

<400> SEQUENCE: 9

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 10
<211> LENGTH: 118
<212> TYPE: PRT
<213> ORGANISM: Homo sapiens

<400> SEQUENCE: 10

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 11
<211> LENGTH: 119
<212> TYPE: PRT
<213> ORGANISM: Homo sapiens
<220> FEATURE:
<221> NAME/KEY: VARIANT
```

```
<222> LOCATION: (3)..(3)
<223> OTHER INFORMATION: Xaa = E or G
<220> FEATURE:
<221> NAME/KEY: VARIANT
<222> LOCATION: (12)..(12)
<223> OTHER INFORMATION: Xaa = S or F
<220> FEATURE:
<221> NAME/KEY: VARIANT
<222> LOCATION: (14)..(14)
<223> OTHER INFORMATION: Xaa = L or S
<220> FEATURE:
<221> NAME/KEY: VARIANT
<222> LOCATION: (20)..(20)
<223> OTHER INFORMATION: Xaa = T or S
<220> FEATURE:
<221> NAME/KEY: VARIANT
<222> LOCATION: (22)..(22)
<223> OTHER INFORMATION: Xaa = T or I
<220> FEATURE:
<221> NAME/KEY: VARIANT
<222> LOCATION: (24)..(24)
<223> OTHER INFORMATION: Xaa = R or H or L
<220> FEATURE:
<221> NAME/KEY: VARIANT
<222> LOCATION: (27)..(27)
<223> OTHER INFORMATION: Xaa = A or V
<220> FEATURE:
<221> NAME/KEY: VARIANT
<222> LOCATION: (45)..(45)
<223> OTHER INFORMATION: Xaa = G or A
<220> FEATURE:
<221> NAME/KEY: VARIANT
<222> LOCATION: (65)..(65)
<223> OTHER INFORMATION: Xaa = D or E
<220> FEATURE:
<221> NAME/KEY: VARIANT
<222> LOCATION: (66)..(66)
<223> OTHER INFORMATION: Xaa = L or S
<220> FEATURE:
<221> NAME/KEY: VARIANT
<222> LOCATION: (70)..(70)
<223> OTHER INFORMATION: Xaa = N or E or D
<220> FEATURE:
<221> NAME/KEY: VARIANT
<222> LOCATION: (75)..(75)
<223> OTHER INFORMATION: Xaa = S or P
<220> FEATURE:
<221> NAME/KEY: VARIANT
<222> LOCATION: (77)..(77)
<223> OTHER INFORMATION: Xaa = R or S
<220> FEATURE:
<221> NAME/KEY: VARIANT
<222> LOCATION: (79)..(79)
<223> OTHER INFORMATION: Xaa = G or S
<220> FEATURE:
<221> NAME/KEY: MISC_FEATURE
<222> LOCATION: (99)..(99)
<223> OTHER INFORMATION: May or may not be present
<220> FEATURE:
<221> NAME/KEY: VARIANT
<222> LOCATION: (100)..(100)
<223> OTHER INFORMATION: Xaa = D or P
<220> FEATURE:
<221> NAME/KEY: VARIANT
<222> LOCATION: (102)..(102)
<223> OTHER INFORMATION: Xaa = V or T
<220> FEATURE:
<221> NAME/KEY: VARIANT
<222> LOCATION: (116)..(116)
<223> OTHER INFORMATION: Xaa = A or G

<400> SEQUENCE: 11

Glu Glu Xaa Leu Gln Val Ile Gln Pro Asp Lys Xaa Val Xaa Val Ala
1               5                   10                  15

Ala Gly Glu Xaa Ala Xaa Leu Xaa Cys Thr Xaa Thr Ser Leu Ile Pro
            20                  25                  30
```

```
Val Gly Pro Ile Gln Trp Phe Arg Gly Ala Gly Pro Xaa Arg Glu Leu
        35                  40                  45

Ile Tyr Asn Gln Lys Glu Gly His Phe Pro Arg Val Thr Thr Val Ser
 50                  55                  60

Xaa Xaa Thr Lys Arg Xaa Asn Met Asp Phe Xaa Ile Xaa Ile Xaa Asn
 65                  70                  75                  80

Ile Thr Pro Ala Asp Ala Gly Thr Tyr Tyr Cys Val Lys Phe Arg Lys
                 85                  90                  95

Gly Ser Pro Xaa Asp Xaa Glu Phe Lys Ser Gly Ala Gly Thr Glu Leu
                100                 105                 110

Ser Val Arg Xaa Lys Pro Ser
            115

<210> SEQ ID NO 12
<211> LENGTH: 585
<212> TYPE: PRT
<213> ORGANISM: Homo sapiens

<400> SEQUENCE: 12

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
                 20                  25                  30

Gln Cys Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
         50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

```
Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
```

```
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 13

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 14

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110
```

-continued

```
Val Arg Ala Lys Pro Ser
            115

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 15

Glu Glu Glu Xaa Gln Xaa Ile Gln Pro Asp Lys Ser Val Ser Val Ala
1               5                   10                  15

Ala Gly Glu Ser Xaa Ile Leu Leu Cys Thr Xaa Thr Ser Leu Xaa Pro
                20                  25                  30

Val Gly Pro Ile Gln Trp Phe Arg Gly Ala Gly Pro Ala Arg Xaa Leu
            35                  40                  45
```

```
Ile Tyr Asn Gln Xaa Xaa Gly Xaa Phe Pro Arg Val Thr Thr Val Ser
    50              55                  60

Glu Xaa Thr Xaa Arg Glu Asn Met Asp Phe Ser Ile Ser Ile Ser Asn
65              70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
            115

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V
```

<400> SEQUENCE: 16

Glu Glu Gly Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Gly Arg Xaa Leu
            35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Gly Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R

```
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 17

Glu Glu Glu Xaa Gln Xaa Ile Gln Pro Asp Lys Phe Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Asn
65              70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
```

```
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 18

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Pro Ile Arg Ile Gly Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 19
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
```

```
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 19

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Gly Lys Pro Ser
        115

<210> SEQ ID NO 20
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
```

```
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 20

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
                20                  25                  30

Val Gly Pro Ile Gln Trp Phe Arg Gly Ala Gly Pro Ala Arg Xaa Leu
            35                  40                  45

Ile Tyr Asn Gln Xaa Xaa Gly Xaa Phe Pro Arg Val Thr Thr Val Ser
        50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
                100                 105                 110

Val Arg Ala Lys Pro Ser
            115

<210> SEQ ID NO 21
<211> LENGTH: 119
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 21

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Ser Asn
65                  70                  75                  80

Ile Thr Pro Ala Asp Ala Gly Thr Tyr Tyr Cys Xaa Lys Xaa Arg Lys
```

```
                  85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 22

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
```

```
                20                  25                  30
Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
                100                 105                 110

Val Arg Ala Lys Pro Ser
        115

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (3)..(3)
<223> OTHER INFORMATION: Xaa = E or G
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (12)..(12)
<223> OTHER INFORMATION: Xaa = S or F
<220> FEATURE:
<221> NAME/KEY: VARIANT
<222> LOCATION: (14)..(14)
<223> OTHER INFORMATION: Xaa = L or S
<220> FEATURE:
<221> NAME/KEY: VARIANT
<222> LOCATION: (20)..(20)
<223> OTHER INFORMATION: Xaa = S or T
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (22)..(22)
<223> OTHER INFORMATION: Xaa = I or T
<220> FEATURE:
<221> NAME/KEY: VARIANT
<222> LOCATION: (24)..(24)
<223> OTHER INFORMATION: Xaa = H or R
<220> FEATURE:
<221> NAME/KEY: VARIANT
<222> LOCATION: (27)..(27)
<223> OTHER INFORMATION: Xaa = A or V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (45)..(45)
<223> OTHER INFORMATION: Xaa = A or G
<220> FEATURE:
<221> NAME/KEY: VARIANT
<222> LOCATION: (47)..(47)
```

```
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (65)..(65)
<223> OTHER INFORMATION: Xaa = D or E
<220> FEATURE:
<221> NAME/KEY: VARIANT
<222> LOCATION: (66)..(66)
<223> OTHER INFORMATION: Xaa = S or L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (70)..(70)
<223> OTHER INFORMATION: Xaa = E or D
<220> FEATURE:
<221> NAME/KEY: VARIANT
<222> LOCATION: (75)..(75)
<223> OTHER INFORMATION: Xaa = S or P
<220> FEATURE:
<221> NAME/KEY: VARIANT
<222> LOCATION: (77)..(77)
<223> OTHER INFORMATION: Xaa = S or R
<220> FEATURE:
<221> NAME/KEY: VARIANT
<222> LOCATION: (79)..(79)
<223> OTHER INFORMATION: Xaa = S or G
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: MISC_FEATURE
<222> LOCATION: (101)..(101)
<223> OTHER INFORMATION: May or may not be present
<220> FEATURE:
<221> NAME/KEY: VARIANT
<222> LOCATION: (102)..(102)
<223> OTHER INFORMATION: Xaa = T or V
<220> FEATURE:
<221> NAME/KEY: VARIANT
<222> LOCATION: (104)..(104)
<223> OTHER INFORMATION: Xaa = F or V
<220> FEATURE:
<221> NAME/KEY: VARIANT
<222> LOCATION: (116)..(116)
<223> OTHER INFORMATION: Xaa = A or G

<400> SEQUENCE: 23

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60
```

```
Xaa Xaa Thr Xaa Arg Xaa Asn Met Asp Phe Xaa Ile Xaa Ile Xaa Asn
 65                  70                  75                  80

Ile Thr Pro Ala Asp Ala Gly Thr Tyr Tyr Cys Xaa Lys Xaa Arg Lys
                 85                  90                  95

Gly Ser Pro Asp Asp Xaa Glu Xaa Lys Ser Gly Ala Gly Thr Glu Leu
            100                 105                 110

Ser Val Arg Xaa Lys Pro Ser
            115
```

<210> SEQ ID NO 24
<211> LENGTH: 102
<212> TYPE: PRT
<213> ORGANISM: Homo sapiens

<400> SEQUENCE: 24

```
Ala Pro Val Val Ser Gly Pro Ala Ala Arg Ala Thr Pro Gln His Thr
  1               5                  10                  15

Val Ser Phe Thr Cys Glu Ser His Gly Phe Ser Pro Arg Asp Ile Thr
                 20                  25                  30

Leu Lys Trp Phe Lys Asn Gly Asn Glu Leu Ser Asp Phe Gln Thr Asn
             35                  40                  45

Val Asp Pro Val Gly Glu Ser Val Ser Tyr Ser Ile His Ser Thr Ala
 50                  55                  60

Lys Val Val Leu Thr Arg Glu Asp Val His Ser Gln Val Ile Cys Glu
 65                  70                  75                  80

Val Ala His Val Thr Leu Gln Gly Asp Pro Leu Arg Gly Thr Ala Asn
                 85                  90                  95

Leu Ser Glu Thr Ile Arg
            100
```

<210> SEQ ID NO 25
<211> LENGTH: 99
<212> TYPE: PRT
<213> ORGANISM: Homo sapiens

<400> SEQUENCE: 25

```
Val Pro Pro Thr Leu Glu Val Thr Gln Gln Pro Val Arg Ala Glu Asn
  1               5                  10                  15

Gln Val Asn Val Thr Cys Gln Val Arg Lys Phe Tyr Pro Gln Arg Leu
                 20                  25                  30

Gln Leu Thr Trp Leu Glu Asn Gly Asn Val Ser Arg Thr Glu Thr Ala
             35                  40                  45

Ser Thr Val Thr Glu Asn Lys Asp Gly Thr Tyr Asn Trp Met Ser Trp
 50                  55                  60

Leu Leu Val Asn Val Ser Ala His Arg Asp Asp Val Lys Leu Thr Cys
 65                  70                  75                  80

Gln Val Glu His Asp Gly Gln Pro Ala Val Ser Lys Ser His Asp Leu
                 85                  90                  95

Lys Val Ser
```

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly His Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Glu Glu Val Gln Ile Ile Gln Pro Asp Lys Ser Val Ser Val Ala
1               5                   10                  15

Ala Gly Glu Ser Val Ile Leu His Cys Thr Ile Thr Ser Leu Thr Pro
            20                  25                  30

Val Gly Pro Ile Gln Trp Phe Arg Gly Ala Gly Pro Ala Arg Leu Leu

```
                35                  40                  45
Ile Tyr Asn Gln Arg Glu Gly Pro Phe Pro Arg Val Thr Thr Val Ser
 50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Glu Glu Leu Gln Ile Ile Gln Pro Asp Lys Ser Val Ser Val Ala
1               5                  10                  15

Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
 50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 30
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Glu Glu Ile Gln Val Ile Gln Pro Asp Lys Ser Val Ser Val Ala
1               5                  10                  15

Ala Gly Glu Ser Val Ile Ile His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Arg Phe Pro Arg Val Thr Thr Val Ser
 50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Val Arg Lys
```

```
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 32
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115
```

```
<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 34
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Leu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Lys Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
        115

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
                100                 105                 110

Val Arg Ala Lys Pro Ser
        115

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)

```
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or
      R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 37

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
```

```
                100             105             110
Ser Val Arg Ala Lys Pro Ser
        115

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or
      R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
```

<222> LOCATION: (103)..(103)
<223> OTHER INFORMATION: Xaa = F or V

<400> SEQUENCE: 38

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 39
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT

```
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or
      R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 39

Glu Glu Glu Xaa Gln Xaa Ile Gln Pro Asp Lys Ser Val Ser Val Ala
1               5                   10                  15

Ala Gly Glu Ser Xaa Ile Leu Leu Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
```

```
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or
      R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 40

Glu Glu Gly Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
        100                 105                 110

Ser Val Arg Ala Lys Pro Ser
        115

<210> SEQ ID NO 41
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or
      R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 41

Glu Glu Glu Xaa Gln Xaa Ile Gln Pro Asp Lys Phe Val Leu Val Ala
1               5                   10                  15
```

```
Ala Gly Glu Thr Xaa Thr Leu Arg Cys Thr Xaa Thr Ser Leu Xaa Pro
             20                  25                  30

Val Gly Pro Ile Gln Trp Phe Arg Gly Ala Gly Pro Gly Arg Xaa Leu
         35                  40                  45

Ile Tyr Asn Gln Xaa Xaa Gly Xaa Phe Pro Val Thr Thr Val Ser
 50                  55                  60

Asp Xaa Thr Xaa Arg Asn Asn Met Asp Phe Ser Ile Arg Ile Gly Xaa
 65              70                  75                      80

Ile Thr Xaa Ala Asp Ala Gly Thr Tyr Tyr Cys Xaa Lys Xaa Arg Lys
                 85                  90                  95

Gly Ser Pro Asp Asp Val Glu Xaa Lys Ser Gly Ala Gly Thr Glu Leu
             100                 105                 110

Ser Val Arg Ala Lys Pro Ser
        115
```

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or

```
            R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 42

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Pro Ile Arg Ile Gly Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
```

<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or
      R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 43

```
Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Gly Lys Pro Ser
        115
```

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
    H or I or K or L or M or P or Q or
    R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
    H or I or K or L or M or N or Q or
    R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 44

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45
```

```
Ile Tyr Asn Gln Xaa Xaa Gly Xaa Phe Pro Arg Val Thr Thr Val Ser
    50              55                  60

Glu Xaa Thr Xaa Arg Glu Asn Met Asp Phe Ser Ile Ser Ile Ser Xaa
65          70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100             105                 110

Val Arg Ala Lys Pro Ser
            115
```

```
<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
      H or I or K or L or M or P or Q or
      R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
      H or I or K or L or M or N or Q or
      R or S or T or V or W or Y
```

```
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (104)..(104)
<223> OTHER INFORMATION: Xaa = F or V

<400> SEQUENCE: 45

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Ser Xaa
65              70                  75                  80

Ile Thr Xaa Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 46
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Xaa = L or I or V
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
```

```
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (80)..(80)
<223> OTHER INFORMATION: Xaa = N or A or C or D or E or F or G or
     H or I or K or L or M or P or Q or
     R or S or T or V or W or Y
<220> FEATURE:
<221> NAME/KEY: VARIANT
<222> LOCATION: (83)..(83)
<223> OTHER INFORMATION: Xaa = P or A or C or D or E or F or G or
     H or I or K or L or M or N or Q or
     R or S or T or V or W or Y
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: VARIANT
<222> LOCATION: (103)..(103)
<223> OTHER INFORMATION: Xaa = F or V

<400> SEQUENCE: 46

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: VARIANT
<222> LOCATION: (3)..(3)
<223> OTHER INFORMATION: Xaa = E or G
<220> FEATURE:
<221> NAME/KEY: VARIANT
<222> LOCATION: (4)..(4)
<223> OTHER INFORMATION: Xaa = L or I or V
```

```
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (12)..(12)
<223> OTHER INFORMATION: Xaa = S or F
<220> FEATURE:
<221> NAME/KEY: VARIANT
<222> LOCATION: (14)..(14)
<223> OTHER INFORMATION: Xaa = L or S
<220> FEATURE:
<221> NAME/KEY: VARIANT
<222> LOCATION: (20)..(20)
<223> OTHER INFORMATION: Xaa = S or T
<220> FEATURE:
<221> NAME/KEY: VARIANT
<222> LOCATION: (21)..(21)
<223> OTHER INFORMATION: Xaa = A or V
<220> FEATURE:
<221> NAME/KEY: VARIANT
<222> LOCATION: (22)..(22)
<223> OTHER INFORMATION: Xaa = I or T
<220> FEATURE:
<221> NAME/KEY: VARIANT
<222> LOCATION: (24)..(24)
<223> OTHER INFORMATION: Xaa = H or R or L
<220> FEATURE:
<221> NAME/KEY: VARIANT
<222> LOCATION: (27)..(27)
<223> OTHER INFORMATION: Xaa = A or V or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (45)..(45)
<223> OTHER INFORMATION: Xaa = A or G
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (65)..(65)
<223> OTHER INFORMATION: Xaa = D or E
<220> FEATURE:
<221> NAME/KEY: VARIANT
<222> LOCATION: (66)..(66)
<223> OTHER INFORMATION: Xaa = S or L or T or G
<220> FEATURE:
<221> NAME/KEY: VARIANT
<222> LOCATION: (68)..(68)
<223> OTHER INFORMATION: Xaa = K or R
<220> FEATURE:
<221> NAME/KEY: VARIANT
<222> LOCATION: (70)..(70)
<223> OTHER INFORMATION: Xaa = E or N
<220> FEATURE:
<221> NAME/KEY: VARIANT
<222> LOCATION: (75)..(75)
<223> OTHER INFORMATION: Xaa = S or P
<220> FEATURE:
<221> NAME/KEY: VARIANT
<222> LOCATION: (77)..(77)
```

-continued

```
<223> OTHER INFORMATION: Xaa = S or R
<220> FEATURE:
<221> NAME/KEY: VARIANT
<222> LOCATION: (79)..(79)
<223> OTHER INFORMATION: Xaa = S or G
<220> FEATURE:
<221> NAME/KEY: VARIANT
<222> LOCATION: (80)..(80)
<223> OTHER INFORMATION: Xaa = Any amino acid
<220> FEATURE:
<221> NAME/KEY: VARIANT
<222> LOCATION: (83)..(83)
<223> OTHER INFORMATION: Xaa = Any amino acid
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (94)..(94)
<223> OTHER INFORMATION: Xaa = F or L or V
<220> FEATURE:
<221> NAME/KEY: MISC_FEATURE
<222> LOCATION: (101)..(101)
<223> OTHER INFORMATION: May or may not be present
<220> FEATURE:
<221> NAME/KEY: VARIANT
<222> LOCATION: (102)..(102)
<223> OTHER INFORMATION: Xaa = T or V
<220> FEATURE:
<221> NAME/KEY: VARIANT
<222> LOCATION: (104)..(104)
<223> OTHER INFORMATION: Xaa = F or V
<220> FEATURE:
<221> NAME/KEY: VARIANT
<222> LOCATION: (116)..(116)
<223> OTHER INFORMATION: Xaa = A or G

<400> SEQUENCE: 47

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
50                  55                  60

Xaa Xaa Thr Xaa Arg Xaa Asn Met Asp Phe Xaa Ile Xaa Ile Xaa Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Xaa Glu Xaa Lys Ser Gly Ala Gly Thr Glu Leu
            100                 105                 110

Ser Val Arg Xaa Lys Pro Ser
        115

<210> SEQ ID NO 48
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or I
<220> FEATURE:
<221> NAME/KEY: VARIANT
<222> LOCATION: (14)..(14)
```

```
<223> OTHER INFORMATION: Xaa = L or S
<220> FEATURE:
<221> NAME/KEY: VARIANT
<222> LOCATION: (20)..(20)
<223> OTHER INFORMATION: Xaa = T or S
<220> FEATURE:
<221> NAME/KEY: VARIANT
<222> LOCATION: (22)..(22)
<223> OTHER INFORMATION: Xaa = T or I
<220> FEATURE:
<221> NAME/KEY: VARIANT
<222> LOCATION: (24)..(24)
<223> OTHER INFORMATION: Xaa = R or H
<220> FEATURE:
<221> NAME/KEY: VARIANT
<222> LOCATION: (27)..(27)
<223> OTHER INFORMATION: Xaa = A or V or I
<220> FEATURE:
<221> NAME/KEY: VARIANT
<222> LOCATION: (31)..(31)
<223> OTHER INFORMATION: Xaa = I or R or Y or K or F
<220> FEATURE:
<221> NAME/KEY: VARIANT
<222> LOCATION: (45)..(45)
<223> OTHER INFORMATION: Xaa = G or A
<220> FEATURE:
<221> NAME/KEY: VARIANT
<222> LOCATION: (47)..(47)
<223> OTHER INFORMATION: Xaa = E or V
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or D or Q
<220> FEATURE:
<221> NAME/KEY: VARIANT
<222> LOCATION: (56)..(56)
<223> OTHER INFORMATION: Xaa = H or P
<220> FEATURE:
<221> NAME/KEY: VARIANT
<222> LOCATION: (65)..(65)
<223> OTHER INFORMATION: Xaa = D or E
<220> FEATURE:
<221> NAME/KEY: VARIANT
<222> LOCATION: (66)..(66)
<223> OTHER INFORMATION: Xaa = S or L or T
<220> FEATURE:
<221> NAME/KEY: VARIANT
<222> LOCATION: (70)..(70)
<223> OTHER INFORMATION: Xaa = N or E
<220> FEATURE:
<221> NAME/KEY: VARIANT
<222> LOCATION: (77)..(77)
<223> OTHER INFORMATION: Xaa = R or S
<220> FEATURE:
<221> NAME/KEY: VARIANT
<222> LOCATION: (79)..(79)
<223> OTHER INFORMATION: Xaa = G or S
<220> FEATURE:
<221> NAME/KEY: VARIANT
<222> LOCATION: (80)..(80)
<223> OTHER INFORMATION: Xaa = N or A
<220> FEATURE:
<221> NAME/KEY: VARIANT
<222> LOCATION: (92)..(92)
<223> OTHER INFORMATION: Xaa = V or I
<220> FEATURE:
<221> NAME/KEY: VARIANT
<222> LOCATION: (98)..(98)
<223> OTHER INFORMATION: Xaa = S or I or M
<220> FEATURE:
<221> NAME/KEY: MISC_FEATURE
<222> LOCATION: (99)..(99)
<223> OTHER INFORMATION: May or may not be present
<220> FEATURE:
<221> NAME/KEY: VARIANT
```

<222> LOCATION: (100)..(100)
<223> OTHER INFORMATION: Xaa = D or P
<220> FEATURE:
<221> NAME/KEY: VARIANT
<222> LOCATION: (102)..(102)
<223> OTHER INFORMATION: Xaa = V or T

<400> SEQUENCE: 48

Glu Glu Glu Leu Gln Xaa Ile Gln Pro Asp Lys Ser Val Xaa Val Ala
1               5                   10                  15

Ala Gly Glu Xaa Ala Xaa Leu Xaa Cys Thr Xaa Thr Ser Leu Xaa Pro
            20              25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60

Xaa Xaa Thr Lys Arg Xaa Asn Met Asp Phe Ser Ile Xaa Ile Xaa Xaa
65              70                  75                  80

Ile Thr Pro Ala Asp Ala Gly Thr Tyr Tyr Cys Xaa Lys Phe Arg Lys
            85                  90                  95

Gly Xaa Pro Xaa Asp Xaa Glu Phe Lys Ser Gly Ala Gly Thr Glu Leu
            100                 105                 110

Ser Val Arg Ala Lys Pro Ser
        115

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or I or L
<220> FEATURE:
<221> NAME/KEY: VARIANT
<222> LOCATION: (27)..(27)
<223> OTHER INFORMATION: Xaa = A or I or V or L
<220> FEATURE:
<221> NAME/KEY: VARIANT
<222> LOCATION: (31)..(31)
<223> OTHER INFORMATION: Xaa = I or F or S or T
<220> FEATURE:
<221> NAME/KEY: VARIANT
<222> LOCATION: (47)..(47)
<223> OTHER INFORMATION: Xaa = E or V or L
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or S or G
<220> FEATURE:
<221> NAME/KEY: VARIANT
<222> LOCATION: (80)..(80)
<223> OTHER INFORMATION: Xaa = A
<220> FEATURE:
<221> NAME/KEY: VARIANT

```
<222> LOCATION: (92)..(92)
<223> OTHER INFORMATION: Xaa = V or I

<400> SEQUENCE: 49

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 50
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or I
<220> FEATURE:
<221> NAME/KEY: VARIANT
<222> LOCATION: (27)..(27)
<223> OTHER INFORMATION: Xaa = V or I
<220> FEATURE:
<221> NAME/KEY: VARIANT
<222> LOCATION: (31)..(31)
<223> OTHER INFORMATION: Xaa = I or F
<220> FEATURE:
<221> NAME/KEY: VARIANT
<222> LOCATION: (47)..(47)
<223> OTHER INFORMATION: Xaa = E or V
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or P
<220> FEATURE:
<221> NAME/KEY: VARIANT
<222> LOCATION: (66)..(66)
<223> OTHER INFORMATION: Xaa = S or T
<220> FEATURE:
<221> NAME/KEY: VARIANT
<222> LOCATION: (80)..(80)
<223> OTHER INFORMATION: Xaa = N or A
<220> FEATURE:
<221> NAME/KEY: VARIANT
<222> LOCATION: (92)..(92)
<223> OTHER INFORMATION: Xaa = V or I

<400> SEQUENCE: 50
```

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Lys Arg Glu Asn Met Asp Phe Ser Ile Ser Ile Ser Xaa
65              70                  75                  80

Ile Thr Pro Ala Asp Ala Gly Thr Tyr Tyr Cys Xaa Lys Phe Arg Lys
            85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or I
<220> FEATURE:
<221> NAME/KEY: VARIANT
<222> LOCATION: (27)..(27)
<223> OTHER INFORMATION: Xaa = A or I
<220> FEATURE:
<221> NAME/KEY: VARIANT
<222> LOCATION: (31)..(31)
<223> OTHER INFORMATION: Xaa = I or F
<220> FEATURE:
<221> NAME/KEY: VARIANT
<222> LOCATION: (47)..(47)
<223> OTHER INFORMATION: Xaa = E or V
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (56)..(56)
<223> OTHER INFORMATION: Xaa = H or P
<220> FEATURE:
<221> NAME/KEY: VARIANT
<222> LOCATION: (66)..(66)
<223> OTHER INFORMATION: Xaa = L or T
<220> FEATURE:
<221> NAME/KEY: VARIANT
<222> LOCATION: (80)..(80)
<223> OTHER INFORMATION: Xaa = N or A
<220> FEATURE:
<221> NAME/KEY: VARIANT
<222> LOCATION: (92)..(92)
<223> OTHER INFORMATION: Xaa = V or I

<400> SEQUENCE: 51

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu

```
                35                  40                  45
Ile Tyr Asn Gln Xaa Glu Gly Xaa Phe Pro Arg Val Thr Thr Val Ser
         50                  55                  60

Asp Xaa Thr Lys Arg Asn Asn Met Asp Phe Ser Ile Arg Ile Gly Xaa
 65                  70                  75                  80

Ile Thr Pro Ala Asp Ala Gly Thr Tyr Tyr Cys Xaa Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (80)..(80)
<223> OTHER INFORMATION: Xaa = N or A

<400> SEQUENCE: 52

Glu Glu Glu Leu Gln Xaa Ile Gln Pro Asp Lys Ser Val Leu Val Ala
 1               5                  10                  15

Ala Gly Glu Thr Ala Thr Leu Arg Cys Thr Xaa Thr Ser Leu Xaa Pro
                20                  25                  30

Val Gly Pro Ile Gln Trp Phe Arg Gly Ala Gly Pro Gly Arg Glu Leu
             35                  40                  45

Ile Tyr Asn Gln Xaa Glu Gly Xaa Phe Pro Arg Val Thr Thr Val Ser
         50                  55                  60

Asp Xaa Thr Lys Arg Asn Asn Met Asp Phe Ser Ile Arg Ile Gly Xaa
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
        115
```

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Glu Glu Leu Gln Ile Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
 50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
            35                  40                  45

Ile Tyr Asn Gln Arg Gln Gly Pro Phe Pro Arg Val Thr Thr Val Ser
 50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
            35                  40                  45

Ile Tyr Asn Gln Lys Gln Gly Pro Phe Pro Arg Val Thr Thr Val Ser
 50                  55                  60

Glu Thr Thr Lys Arg Glu Asn Met Asp Phe Ser Ile Ser Ile Ser Asn
 65                  70                  75                  80

```
Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 64
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 64

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 66
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
```

```
                35                  40                  45
Ile Tyr Asn Gln Arg Glu Gly Pro Phe Pro Arg Val Thr Thr Val Ser
         50                  55                  60
Glu Ser Thr Lys Arg Glu Asn Met Asp Phe Ser Ile Ser Ile Ser Asn
 65                  70                  75                  80
Ile Thr Pro Ala Asp Ala Gly Thr Tyr Tyr Cys Val Lys Phe Arg Lys
                 85                  90                  95
Gly Ser Pro Asp Thr Glu Phe Lys Ser Gly Ala Gly Thr Glu Leu Ser
            100                 105                 110
Val Arg Ala Lys Pro Ser
            115

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Glu Glu Leu Gln Val Ile Gln Pro Asp Lys Ser Val Ser Val Ala
 1               5                  10                  15
Ala Gly Glu Ser Ala Ile Leu His Cys Thr Ile Thr Ser Leu Phe Pro
                 20                  25                  30
Val Gly Pro Ile Gln Trp Phe Arg Gly Ala Gly Pro Ala Arg Glu Leu
             35                  40                  45
Ile Tyr Asn Gln Arg Glu Gly Pro Phe Pro Arg Val Thr Thr Val Ser
         50                  55                  60
Glu Thr Thr Lys Arg Glu Asn Met Asp Phe Ser Ile Ser Ile Ser Asn
 65                  70                  75                  80
Ile Thr Pro Ala Asp Ala Gly Thr Tyr Tyr Cys Val Lys Phe Arg Lys
                 85                  90                  95
Gly Ser Pro Asp Thr Glu Phe Lys Ser Gly Ala Gly Thr Glu Leu Ser
            100                 105                 110
Val Arg Ala Lys Pro Ser
            115

<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Glu Glu Leu Gln Ile Ile Gln Pro Asp Lys Ser Val Ser Val Ala
 1               5                  10                  15
Ala Gly Glu Ser Ala Ile Leu His Cys Thr Ile Thr Ser Leu Phe Pro
                 20                  25                  30
Val Gly Pro Ile Gln Trp Phe Arg Gly Ala Gly Pro Ala Arg Glu Leu
             35                  40                  45
Ile Tyr Asn Gln Arg Glu Gly Pro Phe Pro Arg Val Thr Thr Val Ser
         50                  55                  60
Glu Ser Thr Lys Arg Glu Asn Met Asp Phe Ser Ile Ser Ile Ser Asn
 65                  70                  75                  80
Ile Thr Pro Ala Asp Ala Gly Thr Tyr Tyr Cys Val Lys Phe Arg Lys
```

```
                    85                  90                  95

Gly Ser Pro Asp Thr Glu Phe Lys Ser Gly Ala Gly Thr Glu Leu Ser
                100                 105                 110

Val Arg Ala Lys Pro Ser
        115

<210> SEQ ID NO 69
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
        115

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
        115
```

```
<210> SEQ ID NO 71
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 73
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73
```

-continued

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 74
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 75
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45
```

```
Ile Tyr Asn Gln Arg Glu Gly Pro Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
             100                 105                 110

Ser Val Arg Ala Lys Pro Ser
        115

<210> SEQ ID NO 76
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Phe Pro
             20                  25                  30

Val Gly Pro Ile Gln Trp Phe Arg Gly Ala Gly Pro Gly Arg Glu Leu
         35                  40                  45

Ile Tyr Asn Gln Arg Glu Gly Pro Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
             100                 105                 110

Ser Val Arg Ala Lys Pro Ser
        115

<210> SEQ ID NO 77
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
             20                  25                  30

Val Gly Pro Ile Gln Trp Phe Arg Gly Ala Gly Pro Gly Arg Val Leu
         35                  40                  45

Ile Tyr Asn Gln Arg Gln Gly Pro Phe Pro Arg Val Thr Thr Val Ser
 50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Ile Lys Phe Arg Lys
                 85                  90                  95
```

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 78
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 79
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 80

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 81
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 82
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82
```

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 83
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 84
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

```
Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 85
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 86
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95
```

Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 88
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 89
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
        50                  55                  60

Ser Ser Val Val Thr Val Pro Ser Ser Ser Leu Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
                100                 105                 110

Val Ala Gly Pro Ser Val Phe Leu Phe Pro Pro Lys Pro Lys Asp Thr
            115                 120                 125

Leu Met Ile Ser Arg Thr Pro Glu Val Thr Cys Val Val Val Asp Val
        130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270
```

```
Pro Pro Met Leu Asp Ser Asp Gly Ser Phe Phe Leu Tyr Ser Lys Leu
            275                 280                 285

Thr Val Asp Lys Ser Arg Trp Gln Gln Gly Asn Val Phe Ser Cys Ser
        290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 90
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 91
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91
```

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly
225

<210> SEQ ID NO 92
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
50                  55                  60

Thr Lys Pro Arg Glu Glu Gln Phe Ala Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Thr Lys Gly Gln Pro Arg Glu Pro Gln Val Tyr Thr Leu Pro
```

```
            115                 120                 125
Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
            165                 170                 175

Asp Gly Ser Phe Phe Leu Tyr Ser Lys Leu Thr Val Asp Lys Ser Arg
        180                 185                 190

Trp Gln Gln Gly Asn Val Phe Ser Cys Ser Val Met His Glu Ala Leu
    195                 200                 205

His Asn His Tyr Thr Gln Lys Ser Leu Ser Leu Ser Pro Gly Lys
210                 215                 220
```

<210> SEQ ID NO 93
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Ala Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220
```

<210> SEQ ID NO 94
<211> LENGTH: 228
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 94

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Ala Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 95
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Ala Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly
225

<210> SEQ ID NO 96
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

```
Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 97
<211> LENGTH: 346
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
```

```
            225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
                275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
                340                 345

<210> SEQ ID NO 98
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240
```

```
Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 99
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255
```

```
Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 100
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
```

```
                       260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
                340                 345

<210> SEQ ID NO 101
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270
```

```
Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly Lys
            340                 345

<210> SEQ ID NO 102
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285
```

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 103
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe

```
                290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 104
<211> LENGTH: 346
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300
```

```
Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
                340                 345

<210> SEQ ID NO 105
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320
```

Ser Val Met His Glu Ala Leu His Asn His Tyr Thr Gln Lys Ser Leu
            325                 330                 335

Ser Leu Ser Pro Gly Lys
            340

<210> SEQ ID NO 106
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu

Ser Leu Ser Pro Gly Lys
            340

<210> SEQ ID NO 107
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

```
Ser Leu Ser Pro Gly Lys
            340

<210> SEQ ID NO 108
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340
```

```
<210> SEQ ID NO 109
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340
```

```
<210> SEQ ID NO 110
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 111
<211> LENGTH: 342
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 112
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 113
<211> LENGTH: 342
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 114
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 114

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 115
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
        50                  55                  60

Asp Leu Thr Lys Arg Asn Asn Met Asp Phe Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Ser Ser Val Glu Cys Pro
            115                 120                 125

Pro Cys Pro Ala Pro Pro Val Ala Gly Pro Ser Val Phe Leu Phe Pro
            130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Ala Ser Thr Phe Arg Val Val Ser Val Leu Thr Val
            195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
        290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
                340                 345
```

<210> SEQ ID NO 116
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Glu Glu Glu Leu Gln Ile Ile Gln Pro Asp Lys Ser Val Leu Val Ala
1               5                   10                  15
```

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 117
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro 20                  25                  30
Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
        50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
                130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 118
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
          35                  40                  45

Ile Tyr Asn Gln Arg Glu Gly Pro Phe Pro Arg Val Thr Thr Val Ser
 50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Ser Ser Val Glu Cys Pro
                115                 120                 125

Pro Cys Pro Ala Pro Pro Val Ala Gly Pro Ser Val Phe Leu Phe Pro
        130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Ala Ser Thr Phe Arg Val Val Ser Val Leu Thr Val
            195                 200                 205

Val His Gln Asp Trp Leu Asn Gly Lys Glu Tyr Lys Cys Lys Val Ser
        210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
                340                 345

<210> SEQ ID NO 119
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
 50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Ser Ser Val Glu Cys Pro
            115                 120                 125

Pro Cys Pro Ala Pro Pro Val Ala Gly Pro Ser Val Phe Leu Phe Pro
        130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 120
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser

-continued

```
                    50                  55                  60
Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                    85                  90                  95

Gly Ser Pro Asp Asp Val Glu Phe Lys Ser Gly Ala Gly Thr Glu Leu
                   100                 105                 110

Ser Val Arg Ala Lys Pro Ser Glu Arg Lys Ser Ser Val Glu Cys Pro
                   115                 120                 125

Pro Cys Pro Ala Pro Pro Val Ala Gly Pro Ser Val Phe Leu Phe Pro
                   130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                   165                 170                 175

Trp Tyr Val Asp Gly Val Glu Val His Asn Ala Lys Thr Lys Pro Arg
                   180                 185                 190

Glu Glu Gln Phe Ala Ser Thr Phe Arg Val Val Ser Val Leu Thr Val
                   195                 200                 205

Val His Gln Asp Trp Leu Asn Gly Lys Glu Tyr Lys Cys Lys Val Ser
     210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                   245                 250                 255

Glu Met Thr Lys Asn Gln Val Ser Leu Thr Cys Leu Val Lys Gly Phe
                   260                 265                 270

Tyr Pro Ser Asp Ile Ala Val Glu Trp Glu Ser Asn Gly Gln Pro Glu
                   275                 280                 285

Asn Asn Tyr Lys Thr Thr Pro Pro Met Leu Asp Ser Asp Gly Ser Phe
     290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                   325                 330                 335

Thr Gln Lys Ser Leu Ser Leu Ser Pro Gly Lys
                   340                 345

<210> SEQ ID NO 121
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Glu Glu Leu Gln Val Ile Gln Pro Asp Lys Ser Val Leu Val Ala
 1                   5                  10                  15

Ala Gly Glu Thr Ala Thr Leu Arg Cys Thr Ile Thr Ser Leu Phe Pro
                    20                  25                  30

Val Gly Pro Ile Gln Trp Phe Arg Gly Ala Gly Pro Gly Arg Glu Leu
                    35                  40                  45

Ile Tyr Asn Gln Arg Glu Gly Pro Phe Pro Arg Val Thr Thr Val Ser
     50                  55                  60
```

```
Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 122
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Thr Thr Lys Arg Asn Asn Met Asp Phe Ser Ile Arg Ile Gly Ala
 65                  70                  75                  80
```

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 123
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys

```
                    85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
            115                 120                 125

Pro Ala Pro Glu Leu Leu Gly Gly Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
            210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 124
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
            50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
            85                  90                  95
```

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 125
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

```
Ser Val Arg Ala Lys Pro Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 126
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Cys Cys Val Glu Cys Pro
```

```
            115                 120                 125
Pro Cys Pro Ala Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Phe Arg Val Val Ser Val Leu Thr Val
                195                 200                 205

Val His Gln Asp Trp Leu Asn Gly Lys Glu Tyr Lys Cys Lys Val Ser
    210                 215                 220

Asn Lys Gly Leu Pro Ala Pro Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 127
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Cys Cys Val Glu Cys Pro
        115                 120                 125
```

```
Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 128
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Cys Cys Val Glu Cys Pro
        115                 120                 125

Pro Cys Pro Ala Pro Pro Val Ala Gly Pro Ser Val Phe Leu Phe Pro
    130                 135                 140
```

```
Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ala Pro Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
        290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 129
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Cys Cys Val Glu Cys Pro
            115                 120                 125

Pro Cys Pro Ala Pro Pro Val Ala Gly Pro Ser Val Phe Leu Phe Pro
        130                 135                 140

Pro Lys Pro Lys Asp Thr Leu Met Ile Ser Arg Thr Pro Glu Val Thr
```

145                 150                 155                 160
Cys Val Val Asp Val Ser His Glu Asp Pro Glu Val Gln Phe Asn
                    165                 170                 175
Trp Tyr Val Asp Gly Val Glu Val His Asn Ala Lys Thr Lys Pro Arg
                    180                 185                 190
Glu Glu Gln Phe Ala Ser Thr Phe Arg Val Val Ser Val Leu Thr Val
                    195                 200                 205
Val His Gln Asp Trp Leu Asn Gly Lys Glu Tyr Lys Cys Lys Val Ser
                210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                    245                 250                 255
Glu Met Thr Lys Asn Gln Val Ser Leu Thr Cys Leu Val Lys Gly Phe
                    260                 265                 270
Tyr Pro Ser Asp Ile Ala Val Glu Trp Glu Ser Asn Gly Gln Pro Glu
                    275                 280                 285
Asn Asn Tyr Lys Thr Thr Pro Pro Met Leu Asp Ser Asp Gly Ser Phe
                290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                    325                 330                 335
Thr Gln Lys Ser Leu Ser Leu Ser Pro Gly Lys
                    340                 345

<210> SEQ ID NO 130
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Glu Glu Leu Gln Val Ile Gln Pro Asp Lys Ser Val Ser Val Ala
1               5                   10                  15
Ala Gly Glu Ser Ala Ile Leu His Cys Thr Val Thr Ser Leu Ile Pro
                20                  25                  30
Val Gly Pro Ile Gln Trp Phe Arg Gly Ala Gly Pro Ala Arg Glu Leu
            35                  40                  45
Ile Tyr Asn Gln Lys Glu Gly His Phe Pro Arg Val Thr Thr Val Ser
    50                  55                  60
Glu Ser Thr Lys Arg Glu Asn Met Asp Phe Ser Ile Ser Ile Ser Asn
65                  70                  75                  80
Ile Thr Pro Ala Asp Ala Gly Thr Tyr Tyr Cys Val Lys Phe Arg Lys
                85                  90                  95
Gly Ser Pro Asp Thr Glu Phe Lys Ser Gly Ala Gly Thr Glu Leu Ser
                100                 105                 110
Val Arg Ala Lys Pro Ser Glu Ser Lys Tyr Gly Pro Pro Cys Pro Ser
            115                 120                 125
Cys Pro Ala Pro Glu Phe Leu Gly Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
            165                 170                 175

Trp Tyr Val Asp Gly Val Glu Val His Asn Ala Lys Thr Lys Pro Arg
        180                 185                 190

Glu Glu Gln Phe Asn Ser Thr Tyr Arg Val Val Ser Val Leu Thr Val
            195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 131
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 132
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Glu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro

```
                180             185             190
Arg Glu Glu Gln Phe Asn Ser Thr Tyr Arg Val Val Ser Val Leu Thr
            195                 200                 205

Val Leu His Gln Asp Trp Leu Asn Gly Lys Glu Tyr Lys Cys Lys Val
        210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 133
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190
```

```
Glu Glu Gln Phe Asn Ser Thr Tyr Arg Val Val Ser Val Leu Thr Val
                195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 134
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Ala Ala Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205
```

His Gln Asp Trp Leu Asn Gly Lys Glu Tyr Lys Cys Lys Val Ser Asn
        210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 135
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
            245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 136
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

```
Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
                340                 345

<210> SEQ ID NO 137
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240
```

```
Gln Pro Arg Glu Pro Gln Val Tyr Thr Leu Pro Pro Ser Arg Glu Glu
            245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly
            340                 345

<210> SEQ ID NO 138
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
            165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
            210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
```

```
                        245                 250                 255
Met Thr Lys Asn Gln Val Ser Leu Trp Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 139
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 140
<211> LENGTH: 346
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 141
<211> LENGTH: 227
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 141

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 142
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95
```

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 143
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu

```
                100                 105                 110
Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 144
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Arg Lys
210                 215                 220

Thr His Thr Cys Pro Arg Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 145
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Glu Glu Leu Gln Ile Ile Gln Pro Asp Lys Ser Val Leu Val Ala
1               5                   10                  15
```

```
Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Lys Thr His Thr Cys Pro Glu Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Glu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 146
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30
```

Val Gly Pro Ile Gln Trp Phe Arg Gly Ala Gly Pro Gly Arg Glu Leu
         35                  40                  45

Ile Tyr Asn Gln Arg Gln Gly Pro Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
        210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 147
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

-continued

```
                35                  40                  45
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225
```

<210> SEQ ID NO 148
<211> LENGTH: 346
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160
```

```
Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 149
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 150
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Ala His Lys Ser Glu Val Ala His
        115                 120                 125

Arg Phe Lys Asp Leu Gly Glu Glu Asn Phe Lys Ala Leu Val Leu Ile
    130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
                165                 170                 175

Ser Ala Glu Asn Cys Asp Lys Ser Leu His Thr Leu Phe Gly Asp Lys
            180                 185                 190

Leu Cys Thr Val Ala Thr Leu Arg Glu Thr Tyr Gly Glu Met Ala Asp
        195                 200                 205

Cys Cys Ala Lys Gln Glu Pro Glu Arg Asn Glu Cys Phe Leu Gln His
    210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
                245                 250                 255

Tyr Leu Tyr Glu Ile Ala Arg Arg His Pro Tyr Phe Tyr Ala Pro Glu
            260                 265                 270

Leu Leu Phe Phe Ala Lys Arg Tyr Lys Ala Ala Phe Thr Glu Cys Cys
        275                 280                 285

Gln Ala Ala Asp Lys Ala Ala Cys Leu Leu Pro Lys Leu Asp Glu Leu

```
            290                 295                 300
Arg Asp Glu Gly Lys Ala Ser Ser Ala Lys Gln Arg Leu Lys Cys Ala
305                 310                 315                 320

Ser Leu Gln Lys Phe Gly Arg Ala Phe Lys Ala Trp Ala Val Ala
                325                 330                 335

Arg Leu Ser Gln Arg Phe Pro Lys Ala Glu Phe Ala Glu Val Ser Lys
                340                 345                 350

Leu Val Thr Asp Leu Thr Lys Val His Thr Glu Cys Cys His Gly Asp
                355                 360                 365

Leu Leu Glu Cys Ala Asp Asp Arg Ala Asp Leu Ala Lys Tyr Ile Cys
            370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
                420                 425                 430

Asp Val Cys Lys Asn Tyr Ala Glu Ala Lys Asp Val Phe Leu Gly Met
            435                 440                 445

Phe Leu Tyr Glu Tyr Ala Arg Arg His Pro Asp Tyr Ser Val Val Leu
450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
                500                 505                 510

Leu Phe Glu Gln Leu Gly Glu Tyr Lys Phe Gln Asn Ala Leu Leu Val
                515                 520                 525

Arg Tyr Thr Lys Lys Val Pro Gln Val Ser Thr Pro Thr Leu Val Glu
            530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
                580                 585                 590

Thr Lys Cys Cys Thr Glu Ser Leu Val Asn Arg Arg Pro Cys Phe Ser
            595                 600                 605

Ala Leu Glu Val Asp Glu Thr Tyr Val Pro Lys Glu Phe Asn Ala Glu
610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
                660                 665                 670

Phe Val Glu Lys Cys Cys Lys Ala Asp Asp Lys Glu Thr Cys Phe Ala
            675                 680                 685

Glu Glu Gly Lys Lys Leu Val Ala Ala Ser Gln Ala Ala Leu Gly Leu
690                 695                 700

<210> SEQ ID NO 151
```

```
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151
```

| | | | | | | | | | | | | | | |
|---|---|---|---|---|---|---|---|---|---|---|---|---|---|---|
| Glu | Glu | Glu | Leu | Gln | Val | Ile | Gln | Pro | Asp | Lys | Ser | Val | Leu | Val | Ala |
| 1 | | | | 5 | | | | | 10 | | | | | 15 | |
| Ala | Gly | Glu | Thr | Ala | Thr | Leu | Arg | Cys | Thr | Ala | Thr | Ser | Leu | Phe | Pro |
| | | | 20 | | | | | 25 | | | | | 30 | | |
| Val | Gly | Pro | Ile | Gln | Trp | Phe | Arg | Gly | Ala | Gly | Pro | Gly | Arg | Glu | Leu |
| | | | 35 | | | | | 40 | | | | | 45 | | |
| Ile | Tyr | Asn | Gln | Arg | Gln | Gly | Pro | Phe | Pro | Arg | Val | Thr | Thr | Val | Ser |
| | | 50 | | | | | 55 | | | | | 60 | | | |
| Asp | Leu | Thr | Lys | Arg | Asn | Asn | Met | Asp | Phe | Ser | Ile | Arg | Ile | Gly | Asn |
| 65 | | | | | 70 | | | | | 75 | | | | | 80 |
| Ile | Thr | Pro | Ala | Asp | Ala | Gly | Thr | Tyr | Tyr | Cys | Val | Lys | Phe | Arg | Lys |
| | | | | 85 | | | | | 90 | | | | | 95 | |
| Gly | Ser | Pro | Asp | Asp | Val | Glu | Phe | Lys | Ser | Gly | Ala | Gly | Thr | Glu | Leu |
| | | | 100 | | | | | 105 | | | | | 110 | | |
| Ser | Val | Arg | Ala | Lys | Pro | Ser | Asp | Ala | His | Lys | Ser | Glu | Val | Ala | His |
| | | | 115 | | | | | 120 | | | | | 125 | | |
| Arg | Phe | Lys | Asp | Leu | Gly | Glu | Glu | Asn | Phe | Lys | Ala | Leu | Val | Leu | Ile |
| | | 130 | | | | | 135 | | | | | 140 | | | |
| Ala | Phe | Ala | Gln | Tyr | Leu | Gln | Gln | Ser | Pro | Phe | Glu | Asp | His | Val | Lys |
| 145 | | | | | 150 | | | | | 155 | | | | | 160 |
| Leu | Val | Asn | Glu | Val | Thr | Glu | Phe | Ala | Lys | Thr | Cys | Val | Ala | Asp | Glu |
| | | | | 165 | | | | | 170 | | | | | 175 | |
| Ser | Ala | Glu | Asn | Cys | Asp | Lys | Ser | Leu | His | Thr | Leu | Phe | Gly | Asp | Lys |
| | | | 180 | | | | | 185 | | | | | 190 | | |
| Leu | Cys | Thr | Val | Ala | Thr | Leu | Arg | Glu | Thr | Tyr | Gly | Glu | Met | Ala | Asp |
| | | | 195 | | | | | 200 | | | | | 205 | | |
| Cys | Cys | Ala | Lys | Gln | Glu | Pro | Glu | Arg | Asn | Glu | Cys | Phe | Leu | Gln | His |
| | | 210 | | | | | 215 | | | | | 220 | | | |
| Lys | Asp | Asp | Asn | Pro | Asn | Leu | Pro | Arg | Leu | Val | Arg | Pro | Glu | Val | Asp |
| 225 | | | | | 230 | | | | | 235 | | | | | 240 |
| Val | Met | Cys | Thr | Ala | Phe | His | Asp | Asn | Glu | Glu | Thr | Phe | Leu | Lys | Lys |
| | | | | 245 | | | | | 250 | | | | | 255 | |
| Tyr | Leu | Tyr | Glu | Ile | Ala | Arg | Arg | His | Pro | Tyr | Phe | Tyr | Ala | Pro | Glu |
| | | | 260 | | | | | 265 | | | | | 270 | | |
| Leu | Leu | Phe | Phe | Ala | Lys | Arg | Tyr | Lys | Ala | Ala | Phe | Thr | Glu | Cys | Cys |
| | | | 275 | | | | | 280 | | | | | 285 | | |
| Gln | Ala | Ala | Asp | Lys | Ala | Ala | Cys | Leu | Leu | Pro | Lys | Leu | Asp | Glu | Leu |
| | | 290 | | | | | 295 | | | | | 300 | | | |
| Arg | Asp | Glu | Gly | Lys | Ala | Ser | Ser | Ala | Lys | Gln | Arg | Leu | Lys | Cys | Ala |
| 305 | | | | | 310 | | | | | 315 | | | | | 320 |
| Ser | Leu | Gln | Lys | Phe | Gly | Glu | Arg | Ala | Phe | Lys | Ala | Trp | Ala | Val | Ala |
| | | | | 325 | | | | | 330 | | | | | 335 | |
| Arg | Leu | Ser | Gln | Arg | Phe | Pro | Lys | Ala | Glu | Phe | Ala | Glu | Val | Ser | Lys |
| | | | 340 | | | | | 345 | | | | | 350 | | |
| Leu | Val | Thr | Asp | Leu | Thr | Lys | Val | His | Thr | Glu | Cys | Cys | His | Gly | Asp |
| | | | 355 | | | | | 360 | | | | | 365 | | |
| Leu | Leu | Glu | Cys | Ala | Asp | Asp | Arg | Ala | Asp | Leu | Ala | Lys | Tyr | Ile | Cys |

```
                370                 375                 380
Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
            405                 410                 415

Met Pro Ala Asp Leu Pro Ser Leu Ala Ala Asp Phe Val Glu Ser Lys
        420                 425                 430

Asp Val Cys Lys Asn Tyr Ala Glu Ala Lys Asp Val Phe Leu Gly Met
            435                 440                 445

Phe Leu Tyr Glu Tyr Ala Arg Arg His Pro Asp Tyr Ser Val Val Leu
    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
            500                 505                 510

Leu Phe Glu Gln Leu Gly Glu Tyr Lys Phe Gln Asn Ala Leu Leu Val
    515                 520                 525

Arg Tyr Thr Lys Lys Val Pro Gln Val Ser Thr Pro Thr Leu Val Glu
530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
            580                 585                 590

Thr Lys Cys Cys Thr Glu Ser Leu Val Asn Arg Arg Pro Cys Phe Ser
    595                 600                 605

Ala Leu Glu Val Asp Glu Thr Tyr Val Pro Lys Glu Phe Asn Ala Glu
610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
            660                 665                 670

Phe Val Glu Lys Cys Cys Lys Ala Asp Asp Lys Glu Thr Cys Phe Ala
        675                 680                 685

Glu Glu Gly Lys Lys Leu Val Ala Ala Ser Gln Ala Ala Leu Gly Leu
    690                 695                 700

<210> SEQ ID NO 152
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30
```

```
Val Gly Pro Ile Gln Trp Phe Arg Gly Ala Gly Pro Gly Arg Val Leu
             35                  40                  45

Ile Tyr Asn Gln Arg Gln Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Ile Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Asp Ala His Lys Ser Glu Val Ala His
                115                 120                 125

Arg Phe Lys Asp Leu Gly Glu Glu Asn Phe Lys Ala Leu Val Leu Ile
            130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
                165                 170                 175

Ser Ala Glu Asn Cys Asp Lys Ser Leu His Thr Leu Phe Gly Asp Lys
                180                 185                 190

Leu Cys Thr Val Ala Thr Leu Arg Glu Thr Tyr Gly Glu Met Ala Asp
            195                 200                 205

Cys Cys Ala Lys Gln Glu Pro Glu Arg Asn Glu Cys Phe Leu Gln His
            210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
                245                 250                 255

Tyr Leu Tyr Glu Ile Ala Arg Arg His Pro Tyr Phe Tyr Ala Pro Glu
                260                 265                 270

Leu Leu Phe Phe Ala Lys Arg Tyr Lys Ala Ala Phe Thr Glu Cys Cys
            275                 280                 285

Gln Ala Ala Asp Lys Ala Ala Cys Leu Leu Pro Lys Leu Asp Glu Leu
290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
                325                 330                 335

Arg Leu Ser Gln Arg Phe Pro Lys Ala Glu Phe Ala Glu Val Ser Lys
            340                 345                 350

Leu Val Thr Asp Leu Thr Lys Val His Thr Glu Cys Cys His Gly Asp
            355                 360                 365

Leu Leu Glu Cys Ala Asp Asp Arg Ala Asp Leu Ala Lys Tyr Ile Cys
            370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
            420                 425                 430

Asp Val Cys Lys Asn Tyr Ala Glu Ala Lys Asp Val Phe Leu Gly Met
            435                 440                 445

Phe Leu Tyr Glu Tyr Ala Arg Arg His Pro Asp Tyr Ser Val Val Leu
```

```
                    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                    485                 490                 495

Lys Pro Leu Val Glu Glu Pro Gln Asn Leu Ile Lys Gln Asn Cys Glu
                500                 505                 510

Leu Phe Glu Gln Leu Gly Glu Tyr Lys Phe Gln Asn Ala Leu Leu Val
            515                 520                 525

Arg Tyr Thr Lys Lys Val Pro Gln Val Ser Thr Pro Thr Leu Val Glu
        530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
                580                 585                 590

Thr Lys Cys Cys Thr Glu Ser Leu Val Asn Arg Arg Pro Cys Phe Ser
            595                 600                 605

Ala Leu Glu Val Asp Glu Thr Tyr Val Pro Lys Glu Phe Asn Ala Glu
        610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
                660                 665                 670

Phe Val Glu Lys Cys Cys Lys Ala Asp Asp Lys Glu Thr Cys Phe Ala
            675                 680                 685

Glu Glu Gly Lys Lys Leu Val Ala Ala Ser Gln Ala Ala Leu Gly Leu
        690                 695                 700

<210> SEQ ID NO 153
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110
```

-continued

```
Ser Val Arg Ala Lys Pro Ser Asp Ala His Lys Ser Glu Val Ala His
        115                 120                 125
Arg Phe Lys Asp Leu Gly Glu Glu Asn Phe Lys Ala Leu Val Leu Ile
    130                 135                 140
Ala Phe Ala Gln Tyr Leu Gln Gln Ser Pro Phe Glu Asp His Val Lys
145                 150                 155                 160
Leu Val Asn Glu Val Thr Glu Phe Ala Lys Thr Cys Val Ala Asp Glu
                165                 170                 175
Ser Ala Glu Asn Cys Asp Lys Ser Leu His Thr Leu Phe Gly Asp Lys
            180                 185                 190
Leu Cys Thr Val Ala Thr Leu Arg Glu Thr Tyr Gly Glu Met Ala Asp
        195                 200                 205
Cys Cys Ala Lys Gln Glu Pro Glu Arg Asn Glu Cys Phe Leu Gln His
    210                 215                 220
Lys Asp Asp Asn Pro Asn Leu Pro Arg Leu Val Arg Pro Glu Val Asp
225                 230                 235                 240
Val Met Cys Thr Ala Phe His Asp Asn Glu Glu Thr Phe Leu Lys Lys
                245                 250                 255
Tyr Leu Tyr Glu Ile Ala Arg Arg His Pro Tyr Phe Tyr Ala Pro Glu
            260                 265                 270
Leu Leu Phe Phe Ala Lys Arg Tyr Lys Ala Ala Phe Thr Glu Cys Cys
        275                 280                 285
Gln Ala Ala Asp Lys Ala Ala Cys Leu Leu Pro Lys Leu Asp Glu Leu
    290                 295                 300
Arg Asp Glu Gly Lys Ala Ser Ser Ala Lys Gln Arg Leu Lys Cys Ala
305                 310                 315                 320
Ser Leu Gln Lys Phe Gly Glu Arg Ala Phe Lys Ala Trp Ala Val Ala
                325                 330                 335
Arg Leu Ser Gln Arg Phe Pro Lys Ala Glu Phe Ala Glu Val Ser Lys
            340                 345                 350
Leu Val Thr Asp Leu Thr Lys Val His Thr Glu Cys Cys His Gly Asp
        355                 360                 365
Leu Leu Glu Cys Ala Asp Asp Arg Ala Asp Leu Ala Lys Tyr Ile Cys
    370                 375                 380
Glu Asn Gln Asp Ser Ile Ser Ser Lys Leu Lys Glu Cys Cys Glu Lys
385                 390                 395                 400
Pro Leu Leu Glu Lys Ser His Cys Ile Ala Glu Val Glu Asn Asp Glu
                405                 410                 415
Met Pro Ala Asp Leu Pro Ser Leu Ala Ala Asp Phe Val Glu Ser Lys
            420                 425                 430
Asp Val Cys Lys Asn Tyr Ala Glu Ala Lys Asp Val Phe Leu Gly Met
        435                 440                 445
Phe Leu Tyr Glu Tyr Ala Arg Arg His Pro Asp Tyr Ser Val Val Leu
    450                 455                 460
Leu Leu Arg Leu Ala Lys Thr Tyr Glu Thr Thr Leu Glu Lys Cys Cys
465                 470                 475                 480
Ala Ala Ala Asp Pro His Glu Cys Tyr Ala Lys Val Phe Asp Glu Phe
                485                 490                 495
Lys Pro Leu Val Glu Glu Pro Gln Asn Leu Ile Lys Gln Asn Cys Glu
            500                 505                 510
Leu Phe Glu Gln Leu Gly Glu Tyr Lys Phe Gln Asn Ala Leu Leu Val
        515                 520                 525
Arg Tyr Thr Lys Lys Val Pro Gln Val Ser Thr Pro Thr Leu Val Glu
```

```
                530               535               540
Val Ser Arg Asn Leu Gly Lys Val Gly Ser Lys Cys Cys Lys His Pro
545               550               555               560

Glu Ala Lys Arg Met Pro Cys Ala Glu Asp Tyr Leu Ser Val Val Leu
                565               570               575

Asn Gln Leu Cys Val Leu His Glu Lys Thr Pro Val Ser Asp Arg Val
                580               585               590

Thr Lys Cys Cys Thr Glu Ser Leu Val Asn Arg Arg Pro Cys Phe Ser
                595               600               605

Ala Leu Glu Val Asp Glu Thr Tyr Val Pro Lys Glu Phe Asn Ala Glu
            610               615               620

Thr Phe Thr Phe His Ala Asp Ile Cys Thr Leu Ser Glu Lys Glu Arg
625               630               635               640

Gln Ile Lys Lys Gln Thr Ala Leu Val Glu Leu Val Lys His Lys Pro
                645               650               655

Lys Ala Thr Lys Glu Gln Leu Lys Ala Val Met Asp Asp Phe Ala Ala
                660               665               670

Phe Val Glu Lys Cys Cys Lys Ala Asp Asp Lys Glu Thr Cys Phe Ala
                675               680               685

Glu Glu Gly Lys Lys Leu Val Ala Ala Ser Gln Ala Ala Leu Gly Leu
                690               695               700

<210> SEQ ID NO 154
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Ala His Lys Ser Glu Val Ala His
        115                 120                 125

Arg Phe Lys Asp Leu Gly Glu Glu Asn Phe Lys Ala Leu Val Leu Ile
    130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
                165                 170                 175

Ser Ala Glu Asn Cys Asp Lys Ser Leu His Thr Leu Phe Gly Asp Lys
            180                 185                 190
```

```
Leu Cys Thr Val Ala Thr Leu Arg Glu Thr Tyr Gly Glu Met Ala Asp
            195                 200                 205

Cys Cys Ala Lys Gln Glu Pro Glu Arg Asn Glu Cys Phe Leu Gln His
    210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
                245                 250                 255

Tyr Leu Tyr Glu Ile Ala Arg Arg His Pro Tyr Phe Tyr Ala Pro Glu
            260                 265                 270

Leu Leu Phe Phe Ala Lys Arg Tyr Lys Ala Ala Phe Thr Glu Cys Cys
        275                 280                 285

Gln Ala Ala Asp Lys Ala Ala Cys Leu Leu Pro Lys Leu Asp Glu Leu
    290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
                325                 330                 335

Arg Leu Ser Gln Arg Phe Pro Lys Ala Glu Phe Ala Glu Val Ser Lys
            340                 345                 350

Leu Val Thr Asp Leu Thr Lys Val His Thr Glu Cys Cys His Gly Asp
        355                 360                 365

Leu Leu Glu Cys Ala Asp Asp Arg Ala Asp Leu Ala Lys Tyr Ile Cys
    370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
            420                 425                 430

Asp Val Cys Lys Asn Tyr Ala Glu Ala Lys Asp Val Phe Leu Gly Met
        435                 440                 445

Phe Leu Tyr Glu Tyr Ala Arg Arg His Pro Asp Tyr Ser Val Val Leu
    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
            500                 505                 510

Leu Phe Glu Gln Leu Gly Glu Tyr Lys Phe Gln Asn Ala Leu Leu Val
        515                 520                 525

Arg Tyr Thr Lys Lys Val Pro Gln Val Ser Thr Pro Thr Leu Val Glu
    530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
            580                 585                 590

Thr Lys Cys Cys Thr Glu Ser Leu Val Asn Arg Arg Pro Cys Phe Ser
        595                 600                 605

Ala Leu Glu Val Asp Glu Thr Tyr Val Pro Lys Glu Phe Asn Ala Glu
```

```
                610                 615                 620
Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Lys Ala Ala
                660                 665                 670

Phe Val Glu Lys Cys Cys Lys Ala Asp Asp Lys Glu Thr Cys Phe Ala
            675                 680                 685

Glu Glu Gly Lys Lys Leu Val Ala Ala Ser Gln Ala Ala Leu Gly Leu
            690                 695                 700

<210> SEQ ID NO 155
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Ala His Lys Ser Glu Val Ala His
        115                 120                 125

Arg Phe Lys Asp Leu Gly Glu Glu Asn Phe Lys Ala Leu Val Leu Ile
    130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
                165                 170                 175

Ser Ala Glu Asn Cys Asp Lys Ser Leu His Thr Leu Phe Gly Asp Lys
            180                 185                 190

Leu Cys Thr Val Ala Thr Leu Arg Glu Thr Tyr Gly Glu Met Ala Asp
        195                 200                 205

Cys Cys Ala Lys Gln Glu Pro Glu Arg Asn Glu Cys Phe Leu Gln His
    210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
                245                 250                 255

Tyr Leu Tyr Glu Ile Ala Arg Arg His Pro Tyr Phe Tyr Ala Pro Glu
            260                 265                 270
```

```
Leu Leu Phe Phe Ala Lys Arg Tyr Lys Ala Ala Phe Thr Glu Cys Cys
            275                 280                 285

Gln Ala Ala Asp Lys Ala Ala Cys Leu Leu Pro Lys Leu Asp Glu Leu
    290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
                325                 330                 335

Arg Leu Ser Gln Arg Phe Pro Lys Ala Glu Phe Ala Glu Val Ser Lys
            340                 345                 350

Leu Val Thr Asp Leu Thr Lys Val His Thr Glu Cys Cys His Gly Asp
        355                 360                 365

Leu Leu Glu Cys Ala Asp Asp Arg Ala Asp Leu Ala Lys Tyr Ile Cys
    370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
            420                 425                 430

Asp Val Cys Lys Asn Tyr Ala Glu Ala Lys Asp Val Phe Leu Gly Met
        435                 440                 445

Phe Leu Tyr Glu Tyr Ala Arg Arg His Pro Asp Tyr Ser Val Val Leu
    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
            500                 505                 510

Leu Phe Glu Gln Leu Gly Glu Tyr Lys Phe Gln Asn Ala Leu Leu Val
        515                 520                 525

Arg Tyr Thr Lys Lys Val Pro Gln Val Ser Thr Pro Thr Leu Val Glu
    530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
            580                 585                 590

Thr Lys Cys Cys Thr Glu Ser Leu Val Asn Arg Arg Pro Cys Phe Ser
        595                 600                 605

Ala Leu Glu Val Asp Glu Thr Tyr Val Pro Lys Glu Phe Asn Ala Glu
    610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
            660                 665                 670

Phe Val Glu Lys Cys Cys Lys Ala Asp Asp Lys Glu Thr Cys Phe Ala
        675                 680                 685

Glu Glu Gly Lys Lys Leu Val Ala Ala Ser Gln Ala Ala Leu Gly Leu
```

<210> SEQ ID NO 156
<211> LENGTH: 704
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Ala His Lys Ser Glu Val Ala His
        115                 120                 125

Arg Phe Lys Asp Leu Gly Glu Glu Asn Phe Lys Ala Leu Val Leu Ile
    130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
                165                 170                 175

Ser Ala Glu Asn Cys Asp Lys Ser Leu His Thr Leu Phe Gly Asp Lys
            180                 185                 190

Leu Cys Thr Val Ala Thr Leu Arg Glu Thr Tyr Gly Glu Met Ala Asp
        195                 200                 205

Cys Cys Ala Lys Gln Glu Pro Glu Arg Asn Glu Cys Phe Leu Gln His
    210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
                245                 250                 255

Tyr Leu Tyr Glu Ile Ala Arg Arg His Pro Tyr Phe Tyr Ala Pro Glu
            260                 265                 270

Leu Leu Phe Phe Ala Lys Arg Tyr Lys Ala Ala Phe Thr Glu Cys Cys
        275                 280                 285

Gln Ala Ala Asp Lys Ala Ala Cys Leu Leu Pro Lys Leu Asp Glu Leu
    290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
                325                 330                 335

Arg Leu Ser Gln Arg Phe Pro Lys Ala Glu Phe Ala Glu Val Ser Lys
            340                 345                 350
```

Leu Val Thr Asp Leu Thr Lys Val His Thr Glu Cys Cys His Gly Asp
            355                 360                 365

Leu Leu Glu Cys Ala Asp Asp Arg Ala Asp Leu Ala Lys Tyr Ile Cys
    370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
                420                 425                 430

Asp Val Cys Lys Asn Tyr Ala Glu Ala Lys Asp Val Phe Leu Gly Met
                435                 440                 445

Phe Leu Tyr Glu Tyr Ala Arg Arg His Pro Asp Tyr Ser Val Val Leu
    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
                500                 505                 510

Leu Phe Glu Gln Leu Gly Glu Tyr Lys Phe Gln Asn Ala Leu Leu Val
    515                 520                 525

Arg Tyr Thr Lys Lys Val Pro Gln Val Ser Thr Pro Thr Leu Val Glu
    530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
                580                 585                 590

Thr Lys Cys Cys Thr Glu Ser Leu Val Asn Arg Arg Pro Cys Phe Ser
    595                 600                 605

Ala Leu Glu Val Asp Glu Thr Tyr Val Pro Lys Glu Phe Asn Ala Glu
610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
                660                 665                 670

Phe Val Glu Lys Cys Cys Lys Ala Asp Asp Lys Glu Thr Cys Phe Ala
    675                 680                 685

Glu Glu Gly Lys Lys Leu Val Ala Ala Ser Gln Ala Ala Leu Gly Leu
    690                 695                 700

<210> SEQ ID NO 157
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Glu Glu Leu Gln Ile Ile Gln Pro Asp Lys Ser Val Leu Val Ala
1               5                   10                  15

```
Ala Gly Glu Thr Ala Thr Leu Arg Cys Thr Ile Thr Ser Leu Phe Pro
             20                  25                  30
Val Gly Pro Ile Gln Trp Phe Arg Gly Ala Gly Pro Gly Arg Glu Leu
         35                  40                  45
Ile Tyr Asn Gln Arg Glu Gly Pro Phe Pro Arg Val Thr Thr Val Ser
     50                  55                  60
Asp Leu Thr Lys Arg Asn Asn Met Asp Phe Ser Ile Arg Ile Gly Ala
 65                  70                  75                  80
Ile Thr Pro Ala Asp Ala Gly Thr Tyr Tyr Cys Val Lys Phe Arg Lys
                 85                  90                  95
Gly Ser Pro Asp Asp Val Glu Phe Lys Ser Gly Ala Gly Thr Glu Leu
             100                 105                 110
Ser Val Arg Ala Lys Pro Ser Asp Ala His Lys Ser Glu Val Ala His
         115                 120                 125
Arg Phe Lys Asp Leu Gly Glu Glu Asn Phe Lys Ala Leu Val Leu Ile
 130                 135                 140
Ala Phe Ala Gln Tyr Leu Gln Gln Ser Pro Phe Glu Asp His Val Lys
145                 150                 155                 160
Leu Val Asn Glu Val Thr Glu Phe Ala Lys Thr Cys Val Ala Asp Glu
                165                 170                 175
Ser Ala Glu Asn Cys Asp Lys Ser Leu His Thr Leu Phe Gly Asp Lys
            180                 185                 190
Leu Cys Thr Val Ala Thr Leu Arg Glu Thr Tyr Gly Glu Met Ala Asp
        195                 200                 205
Cys Cys Ala Lys Gln Glu Pro Glu Arg Asn Glu Cys Phe Leu Gln His
    210                 215                 220
Lys Asp Asp Asn Pro Asn Leu Pro Arg Leu Val Arg Pro Glu Val Asp
225                 230                 235                 240
Val Met Cys Thr Ala Phe His Asp Asn Glu Glu Thr Phe Leu Lys Lys
                245                 250                 255
Tyr Leu Tyr Glu Ile Ala Arg Arg His Pro Tyr Phe Tyr Ala Pro Glu
            260                 265                 270
Leu Leu Phe Phe Ala Lys Arg Tyr Lys Ala Ala Phe Thr Glu Cys Cys
        275                 280                 285
Gln Ala Ala Asp Lys Ala Ala Cys Leu Leu Pro Lys Leu Asp Glu Leu
    290                 295                 300
Arg Asp Glu Gly Lys Ala Ser Ser Ala Lys Gln Arg Leu Lys Cys Ala
305                 310                 315                 320
Ser Leu Gln Lys Phe Gly Glu Arg Ala Phe Lys Ala Trp Ala Val Ala
                325                 330                 335
Arg Leu Ser Gln Arg Phe Pro Lys Ala Glu Phe Ala Glu Val Ser Lys
            340                 345                 350
Leu Val Thr Asp Leu Thr Lys Val His Thr Glu Cys Cys His Gly Asp
        355                 360                 365
Leu Leu Glu Cys Ala Asp Asp Arg Ala Asp Leu Ala Lys Tyr Ile Cys
    370                 375                 380
Glu Asn Gln Asp Ser Ile Ser Ser Lys Leu Lys Glu Cys Cys Glu Lys
385                 390                 395                 400
Pro Leu Leu Glu Lys Ser His Cys Ile Ala Glu Val Glu Asn Asp Glu
                405                 410                 415
Met Pro Ala Asp Leu Pro Ser Leu Ala Ala Asp Phe Val Glu Ser Lys
            420                 425                 430
```

```
Asp Val Cys Lys Asn Tyr Ala Glu Ala Lys Asp Val Phe Leu Gly Met
            435                 440                 445

Phe Leu Tyr Glu Tyr Ala Arg Arg His Pro Asp Tyr Ser Val Val Leu
450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
                500                 505                 510

Leu Phe Glu Gln Leu Gly Glu Tyr Lys Phe Gln Asn Ala Leu Leu Val
                515                 520                 525

Arg Tyr Thr Lys Lys Val Pro Gln Val Ser Thr Pro Thr Leu Val Glu
            530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
                580                 585                 590

Thr Lys Cys Cys Thr Glu Ser Leu Val Asn Arg Arg Pro Cys Phe Ser
            595                 600                 605

Ala Leu Glu Val Asp Glu Thr Tyr Val Pro Lys Glu Phe Asn Ala Glu
                610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
                660                 665                 670

Phe Val Glu Lys Cys Cys Lys Ala Asp Asp Lys Glu Thr Cys Phe Ala
            675                 680                 685

Glu Glu Gly Lys Lys Leu Val Ala Ala Ser Gln Ala Ala Leu Gly Leu
                690                 695                 700

<210> SEQ ID NO 158
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95
```

```
Gly Ser Pro Asp Asp Val Glu Phe Lys Ser Ala Gly Thr Glu Leu
            100                 105                 110

Ser Val Arg Ala Lys Pro Ser Asp Ala His Lys Ser Glu Val Ala His
        115                 120                 125

Arg Phe Lys Asp Leu Gly Glu Glu Asn Phe Lys Ala Leu Val Leu Ile
    130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
                165                 170                 175

Ser Ala Glu Asn Cys Asp Lys Ser Leu His Thr Leu Phe Gly Asp Lys
            180                 185                 190

Leu Cys Thr Val Ala Thr Leu Arg Glu Thr Tyr Gly Glu Met Ala Asp
        195                 200                 205

Cys Cys Ala Lys Gln Glu Pro Glu Arg Asn Glu Cys Phe Leu Gln His
    210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
                245                 250                 255

Tyr Leu Tyr Glu Ile Ala Arg Arg His Pro Tyr Phe Tyr Ala Pro Glu
            260                 265                 270

Leu Leu Phe Phe Ala Lys Arg Tyr Lys Ala Ala Phe Thr Glu Cys Cys
        275                 280                 285

Gln Ala Ala Asp Lys Ala Ala Cys Leu Leu Pro Lys Leu Asp Glu Leu
    290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
                325                 330                 335

Arg Leu Ser Gln Arg Phe Pro Lys Ala Glu Phe Ala Glu Val Ser Lys
            340                 345                 350

Leu Val Thr Asp Leu Thr Lys Val His Thr Glu Cys Cys His Gly Asp
        355                 360                 365

Leu Leu Glu Cys Ala Asp Asp Arg Ala Asp Leu Ala Lys Tyr Ile Cys
    370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
            420                 425                 430

Asp Val Cys Lys Asn Tyr Ala Glu Ala Lys Asp Val Phe Leu Gly Met
        435                 440                 445

Phe Leu Tyr Glu Tyr Ala Arg Arg His Pro Asp Tyr Ser Val Val Leu
    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
            500                 505                 510
```

```
Leu Phe Glu Gln Leu Gly Glu Tyr Lys Phe Gln Asn Ala Leu Leu Val
            515                 520                 525

Arg Tyr Thr Lys Lys Val Pro Gln Val Ser Thr Pro Thr Leu Val Glu
530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
            580                 585                 590

Thr Lys Cys Cys Thr Glu Ser Leu Val Asn Arg Arg Pro Cys Phe Ser
        595                 600                 605

Ala Leu Glu Val Asp Glu Thr Tyr Val Pro Lys Glu Phe Asn Ala Glu
610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
                645                 650                 655

Lys Ala Thr Lys Glu Gln Leu Lys Ala Val Met Asp Asp Phe Ala Ala
            660                 665                 670

Phe Val Glu Lys Cys Cys Lys Ala Asp Asp Lys Glu Thr Cys Phe Ala
        675                 680                 685

Glu Glu Gly Lys Lys Leu Val Ala Ala Ser Gln Ala Ala Leu Gly Leu
690                 695                 700

<210> SEQ ID NO 159
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Ala His Lys Ser Glu Val Ala His
        115                 120                 125

Arg Phe Lys Asp Leu Gly Glu Glu Asn Phe Lys Ala Leu Val Leu Ile
130                 135                 140

Ala Phe Ala Gln Tyr Leu Gln Gln Ser Pro Phe Glu Asp His Val Lys
145                 150                 155                 160

Leu Val Asn Glu Val Thr Glu Phe Ala Lys Thr Cys Val Ala Asp Glu
                165                 170                 175
```

-continued

```
Ser Ala Glu Asn Cys Asp Lys Ser Leu His Thr Leu Phe Gly Asp Lys
                180                 185                 190

Leu Cys Thr Val Ala Thr Leu Arg Glu Thr Tyr Gly Glu Met Ala Asp
            195                 200                 205

Cys Cys Ala Lys Gln Pro Glu Arg Asn Glu Cys Phe Leu Gln His
    210                 215                 220

Lys Asp Asp Asn Pro Asn Leu Pro Arg Leu Val Arg Pro Glu Val Asp
225                 230                 235                 240

Val Met Cys Thr Ala Phe His Asp Asn Glu Glu Thr Phe Leu Lys Lys
            245                 250                 255

Tyr Leu Tyr Glu Ile Ala Arg Arg His Pro Tyr Phe Tyr Ala Pro Glu
            260                 265                 270

Leu Leu Phe Phe Ala Lys Arg Tyr Lys Ala Ala Phe Thr Glu Cys Cys
            275                 280                 285

Gln Ala Ala Asp Lys Ala Ala Cys Leu Leu Pro Lys Leu Asp Glu Leu
    290                 295                 300

Arg Asp Glu Gly Lys Ala Ser Ser Ala Lys Gln Arg Leu Lys Cys Ala
305                 310                 315                 320

Ser Leu Gln Lys Phe Gly Glu Arg Ala Phe Lys Ala Trp Ala Val Ala
                325                 330                 335

Arg Leu Ser Gln Arg Phe Pro Lys Ala Glu Phe Ala Glu Val Ser Lys
            340                 345                 350

Leu Val Thr Asp Leu Thr Lys Val His Thr Glu Cys Cys His Gly Asp
            355                 360                 365

Leu Leu Glu Cys Ala Asp Asp Arg Ala Asp Leu Ala Lys Tyr Ile Cys
            370                 375                 380

Glu Asn Gln Asp Ser Ile Ser Ser Lys Leu Lys Glu Cys Cys Glu Lys
385                 390                 395                 400

Pro Leu Leu Glu Lys Ser His Cys Ile Ala Glu Val Glu Asn Asp Glu
                405                 410                 415

Met Pro Ala Asp Leu Pro Ser Leu Ala Ala Asp Phe Val Glu Ser Lys
            420                 425                 430

Asp Val Cys Lys Asn Tyr Ala Glu Ala Lys Asp Val Phe Leu Gly Met
            435                 440                 445

Phe Leu Tyr Glu Tyr Ala Arg Arg His Pro Asp Tyr Ser Val Val Leu
    450                 455                 460

Leu Leu Arg Leu Ala Lys Thr Tyr Glu Thr Thr Leu Glu Lys Cys Cys
465                 470                 475                 480

Ala Ala Ala Asp Pro His Glu Cys Tyr Ala Lys Val Phe Asp Glu Phe
                485                 490                 495

Lys Pro Leu Val Glu Glu Pro Gln Asn Leu Ile Lys Gln Asn Cys Glu
            500                 505                 510

Leu Phe Glu Gln Leu Gly Glu Tyr Lys Phe Gln Asn Ala Leu Leu Val
            515                 520                 525

Arg Tyr Thr Lys Lys Val Pro Gln Val Ser Thr Pro Thr Leu Val Glu
    530                 535                 540

Val Ser Arg Asn Leu Gly Lys Val Gly Ser Lys Cys Cys Lys His Pro
545                 550                 555                 560

Glu Ala Lys Arg Met Pro Cys Ala Glu Asp Tyr Leu Ser Val Val Leu
                565                 570                 575

Asn Gln Leu Cys Val Leu His Glu Lys Thr Pro Val Ser Asp Arg Val
            580                 585                 590
```

```
Thr Lys Cys Cys Thr Glu Ser Leu Val Asn Arg Arg Pro Cys Phe Ser
            595                 600                 605

Ala Leu Glu Val Asp Glu Thr Tyr Val Pro Lys Glu Phe Asn Ala Glu
610                 615                 620

Thr Phe Thr Phe His Ala Asp Ile Cys Thr Leu Ser Glu Lys Glu Arg
625                 630                 635                 640

Gln Ile Lys Lys Gln Thr Ala Leu Val Glu Leu Val Lys His Lys Pro
            645                 650                 655

Lys Ala Thr Lys Glu Gln Leu Lys Ala Val Met Asp Asp Phe Ala Ala
                660                 665                 670

Phe Val Glu Lys Cys Cys Lys Ala Asp Asp Lys Glu Thr Cys Phe Ala
            675                 680                 685

Glu Glu Gly Lys Lys Leu Val Ala Ala Ser Gln Ala Ala Leu Gly Leu
690                 695                 700

<210> SEQ ID NO 160
<211> LENGTH: 11
<212> TYPE: PRT
<213> ORGANISM: Artificial Sequence
<220> FEATURE:
<223> OTHER INFORMATION: Albumin-binding peptide

<400> SEQUENCE: 160

Asp Ile Cys Leu Pro Arg Trp Gly Cys Leu Trp
1               5                   10

<210> SEQ ID NO 161
<211> LENGTH: 226
<212> TYPE: PRT
<213> ORGANISM: Homo sapiens

<400> SEQUENCE: 161

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
```

```
                195                 200                 205
His Glu Ala Leu His Asn His Tyr Thr Gln Lys Ser Leu Ser Leu Ser
    210                 215                 220

Pro Gly
225

<210> SEQ ID NO 162
<211> LENGTH: 228
<212> TYPE: PRT
<213> ORGANISM: Homo sapiens

<400> SEQUENCE: 162

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Gly Gly Ser
1               5

<210> SEQ ID NO 164
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 164

Gly Gly Ser Gly
1

<210> SEQ ID NO 165
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Gly Gly Gly
1

<210> SEQ ID NO 166
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Ser Gly Ser
1

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Ser Gly Ser Gly Ser
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Ser Gly Ser Gly Ser Gly Ser
1               5

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Ser Gly Ser Gly Ser Gly Ser Gly Ser
1               5                   10
```

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Ser Gly Ser Gly Ser Gly Ser Gly Ser Gly Ser
1               5                   10

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Gly Ser Gly Gly Ser
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Gly Ser Gly Gly Ser Gly Gly Ser
1               5

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Gly Ser Gly Gly Ser Gly Gly Ser Gly Gly Ser
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Gly Ser Gly Gly Gly Ser Gly
1               5

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Gly Ser Gly Gly Ser Gly Gly Ser Gly
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Gly Gly Gly Ser Gly Gly Gly Gly Ser Gly Gly Gly Gly Ser
1               5                   10                  15

<210> SEQ ID NO 177
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ala Ser
1

<210> SEQ ID NO 178
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Ala Ala Leu
1

<210> SEQ ID NO 179
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Ala Ala Lys
1

<210> SEQ ID NO 180
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Ala Ala Arg
1

<210> SEQ ID NO 181
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Glu Gly Lys Ser Ser Gly Ser Gly Ser Glu Ser Lys Ser Thr
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Ser Ala Gly Ser Ala Ala Gly Ser Gly Glu Phe
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Glu Ala Ala Ala Lys Glu Ala Ala Ala Lys Ala
1               5                   10

<210> SEQ ID NO 184
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Lys Glu Ser Gly Ser Val Ser Ser Glu Gln Leu Ala Gln Phe Arg Ser
1               5                   10                  15

Leu Asp

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Gly Gly Gly Ala Gly Gly Gly Gly
1               5

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186
```

Gly Glu Asn Leu Tyr Phe Gln Ser Gly Gly
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Ala Cys Tyr Cys Glu Leu Ser
1               5

<210> SEQ ID NO 188
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ser Ile Ala Thr
1               5

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Pro Ala Cys Lys Ile Pro Asn Asp Leu Lys Gln Lys Val Met Asn
1               5                   10                  15

His

<210> SEQ ID NO 190
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gly Gly Ser Ala Gly Gly Ser Gly Ser Gly Ser Ser Gly Ser Ser
1               5                   10                  15

Gly Ala Ser Gly Thr Gly Thr Ala Gly Gly Thr Gly Ser Gly Ser Gly
                20                  25                  30

Thr Gly Ser Gly
            35

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

```
Ala Ala Ala Asn Ser Ser Ile Asp Leu Ile Ser Val Pro Val Asp Ser
1               5                   10                  15

Arg
```

<210> SEQ ID NO 192
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

```
Gly Gly Ser Gly Gly Ser Glu Gly Gly Ser Glu Gly Gly
1               5                   10                  15

Ser Glu Gly Gly Gly Ser Glu Gly Gly Gly Ser Glu Gly Gly Gly Ser
            20                  25                  30

Gly Gly Gly Ser
        35
```

<210> SEQ ID NO 193
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

```
Glu Ala Ala Ala Lys
1               5
```

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

```
Pro Ala Pro Ala Pro
1               5
```

<210> SEQ ID NO 195
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Met Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80
```

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 196
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Lys Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 197
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 198
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 199
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 200
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 201
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Met Pro Asp Asp Val Glu Phe Lys Ser Gly Ala Gly Thr Glu Leu
            100                 105                 110

Ser Val Arg Ala Lys Pro Ser
        115

<210> SEQ ID NO 202
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu

-continued

```
                35                  40                  45

Ile Tyr Asn Gln Arg Glu Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Val Glu Phe Lys Ser Gly Ala Gly Thr Glu Leu Ser
            100                 105                 110

Val Arg Ala Lys Pro Ser
        115

<210> SEQ ID NO 203
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Ser Glu Pro Asp Val Glu Phe Lys Ser Gly Ala Gly Thr Glu
            100                 105                 110

Leu Ser Val Arg Ala Lys Pro Ser
        115                 120

<210> SEQ ID NO 204
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Arg Pro
                20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
```

85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 205
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 206
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

```
<210> SEQ ID NO 207
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 208
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 209
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209
```

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
        50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 210
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
        50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 211
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
            35                  40                  45

```
Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ile Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 212
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (27)..(27)
<223> OTHER INFORMATION: Xaa = V or I or L
<220> FEATURE:
<221> NAME/KEY: VARIANT
<222> LOCATION: (31)..(31)
<223> OTHER INFORMATION: Xaa = I or T or S or F
<220> FEATURE:
```

```
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (56)..(56)
<223> OTHER INFORMATION: Xaa = H or P or R
<220> FEATURE:
<221> NAME/KEY: VARIANT
<222> LOCATION: (66)..(66)
<223> OTHER INFORMATION: Xaa = S or T or G
<220> FEATURE:
<221> NAME/KEY: VARIANT
<222> LOCATION: (80)..(80)
<223> OTHER INFORMATION: Xaa = N or A

<400> SEQUENCE: 212

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Glu Leu
        35                  40                  45

Ile Tyr Asn Gln Xaa Glu Gly Xaa Phe Pro Arg Val Thr Thr Val Ser
50                  55                  60

Glu Xaa Thr Lys Arg Glu Asn Met Asp Phe Ser Ile Ser Ile Ser Xaa
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 213
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Val Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 214
```

<211> LENGTH: 346
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 214

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly
            340                 345

<210> SEQ ID NO 215
<211> LENGTH: 346
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 215

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Arg Gly Pro Ile Gln Trp Phe Arg Gly Ala Gly Pro Gly Arg Glu Leu
        35                  40                  45

Ile Tyr Asn Arg Lys Glu Gly His Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 216
<211> LENGTH: 346
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 216

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Asp Lys Thr His Thr Cys Pro Pro Cys
        115                 120                 125
Pro Ala Pro Glu Leu Leu Gly Gly Pro Ser Val Phe Leu Phe Pro Pro
    130                 135                 140
Lys Pro Lys Asp Thr Leu Met Ile Ser Arg Thr Pro Glu Val Thr Cys
145                 150                 155                 160
Val Val Val Asp Val Ser His Glu Asp Pro Glu Val Lys Phe Asn Trp
                165                 170                 175
Tyr Val Asp Gly Val Glu Val His Asn Ala Lys Thr Lys Pro Arg Glu
            180                 185                 190
Glu Gln Tyr Asn Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345
```

<210> SEQ ID NO 217
<211> LENGTH: 346
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 217

| | | | | | | | | | | | | | | | |
|---|---|---|---|---|---|---|---|---|---|---|---|---|---|---|---|
|Glu|Glu|Glu|Leu|Gln|Ile|Ile|Gln|Pro|Asp|Lys|Ser|Val|Leu|Val|Ala|
|1| | | |5| | | | |10| | | | |15| |
|Ala|Gly|Glu|Thr|Ala|Thr|Leu|Arg|Cys|Thr|Ile|Thr|Ser|Leu|Phe|Pro|
| | | |20| | | | |25| | | | |30| | |
|Val|Gly|Pro|Ile|Gln|Trp|Phe|Arg|Gly|Ala|Gly|Pro|Gly|Arg|Glu|Leu|
| | |35| | | | |40| | | | |45| | | |
|Ile|Tyr|Asn|Gln|Arg|Glu|Gly|Pro|Phe|Pro|Arg|Val|Thr|Thr|Val|Ser|
| |50| | | | |55| | | | |60| | | | |
|Asp|Thr|Thr|Lys|Arg|Asn|Asn|Met|Asp|Phe|Ser|Ile|Arg|Ile|Gly|Ala|
|65| | | | |70| | | | |75| | | | |80|
|Ile|Thr|Pro|Ala|Asp|Ala|Gly|Thr|Tyr|Tyr|Cys|Val|Lys|Phe|Arg|Lys|
| | | | |85| | | | |90| | | | |95| |
|Gly|Ser|Pro|Asp|Asp|Val|Glu|Phe|Lys|Ser|Gly|Ala|Gly|Thr|Glu|Leu|
| | | |100| | | | |105| | | | |110| | |
|Ser|Val|Arg|Ala|Lys|Pro|Ser|Glu|Lys|Thr|His|Thr|Cys|Pro|Glu|Cys|
| | |115| | | | |120| | | | |125| | | |
|Pro|Ala|Pro|Glu|Ala|Ala|Gly|Ala|Pro|Ser|Val|Phe|Leu|Phe|Pro|Pro|
| |130| | | | |135| | | | |140| | | | |
|Lys|Pro|Lys|Asp|Thr|Leu|Met|Ile|Ser|Arg|Thr|Pro|Glu|Val|Thr|Cys|
|145| | | | |150| | | | |155| | | | |160|
|Val|Val|Val|Asp|Val|Ser|His|Glu|Asp|Pro|Glu|Val|Lys|Phe|Asn|Trp|
| | | | |165| | | | |170| | | | |175| |
|Tyr|Val|Asp|Gly|Val|Glu|Val|His|Asn|Ala|Lys|Thr|Lys|Pro|Arg|Glu|
| | | |180| | | | |185| | | | |190| | |
|Glu|Gln|Tyr|Ala|Ser|Thr|Tyr|Arg|Val|Val|Ser|Val|Leu|Thr|Val|Leu|
| | |195| | | | |200| | | | |205| | | |
|His|Gln|Asp|Trp|Leu|Asn|Gly|Lys|Glu|Tyr|Lys|Cys|Lys|Val|Ser|Asn|
| |210| | | | |215| | | | |220| | | | |
|Lys|Ala|Leu|Pro|Ala|Pro|Ile|Glu|Lys|Thr|Ile|Ser|Lys|Ala|Lys|Gly|
|225| | | | |230| | | | |235| | | | |240|
|Gln|Pro|Arg|Glu|Pro|Gln|Val|Tyr|Thr|Leu|Pro|Pro|Ser|Arg|Glu|Glu|
| | | | |245| | | | |250| | | | |255| |
|Met|Thr|Lys|Asn|Gln|Val|Ser|Leu|Thr|Cys|Glu|Val|Lys|Gly|Phe|Tyr|
| | | |260| | | | |265| | | | |270| | |
|Pro|Ser|Asp|Ile|Ala|Val|Glu|Trp|Glu|Ser|Asn|Gly|Gln|Pro|Glu|Asn|
| | |275| | | | |280| | | | |285| | | |
|Asn|Tyr|Lys|Thr|Thr|Pro|Pro|Val|Leu|Asp|Ser|Asp|Gly|Ser|Phe|Phe|
| |290| | | | |295| | | | |300| | | | |
|Leu|Tyr|Ser|Lys|Leu|Thr|Val|Asp|Lys|Ser|Arg|Trp|Gln|Gln|Gly|Asn|
|305| | | | |310| | | | |315| | | | |320|
|Val|Phe|Ser|Cys|Ser|Val|Met|His|Glu|Ala|Leu|His|Asn|His|Tyr|Thr|
| | | | |325| | | | |330| | | | |335| |
|Gln|Lys|Ser|Leu|Ser|Leu|Ser|Pro|Gly|Lys| | | | | | |
| | | |340| | | | |345| | | | | | | |

<210> SEQ ID NO 218
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT

```
<222> LOCATION: (6)..(6)
<223> OTHER INFORMATION: Xaa = V or L or I
<220> FEATURE:
<221> NAME/KEY: VARIANT
<222> LOCATION: (27)..(27)
<223> OTHER INFORMATION: Xaa = A or V or L or I
<220> FEATURE:
<221> NAME/KEY: VARIANT
<222> LOCATION: (31)..(31)
<223> OTHER INFORMATION: Xaa = I or S or T or F
<220> FEATURE:
<221> NAME/KEY: VARIANT
<222> LOCATION: (47)..(47)
<223> OTHER INFORMATION: Xaa = E or L or V
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or R or P
<220> FEATURE:
<221> NAME/KEY: VARIANT
<222> LOCATION: (66)..(66)
<223> OTHER INFORMATION: Xaa = S or G or L or T
<220> FEATURE:
<221> NAME/KEY: VARIANT
<222> LOCATION: (80)..(80)
<223> OTHER INFORMATION: Xaa = Any amino acid
<220> FEATURE:
<221> NAME/KEY: VARIANT
<222> LOCATION: (81)..(81)
<223> OTHER INFORMATION: Xaa = Any amino acid
<220> FEATURE:
<221> NAME/KEY: VARIANT
<222> LOCATION: (82)..(82)
<223> OTHER INFORMATION: Xaa = Any amino acid
<220> FEATURE:
<221> NAME/KEY: VARIANT
<222> LOCATION: (83)..(83)
<223> OTHER INFORMATION: Xaa = Any amino acid
<220> FEATURE:
<221> NAME/KEY: VARIANT
<222> LOCATION: (92)..(92)
<223> OTHER INFORMATION: Xaa = V or I

<400> SEQUENCE: 218

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Xaa Xaa Xaa Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 219
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (27)..(27)
<223> OTHER INFORMATION: Xaa = A or V or L or I
<220> FEATURE:
<221> NAME/KEY: VARIANT
<222> LOCATION: (31)..(31)
<223> OTHER INFORMATION: Xaa = I or S or T or F
<220> FEATURE:
<221> NAME/KEY: VARIANT
<222> LOCATION: (47)..(47)
<223> OTHER INFORMATION: Xaa = E or L or V
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (54)..(54)
<223> OTHER INFORMATION: Xaa = E or Q
<220> FEATURE:
<221> NAME/KEY: VARIANT
<222> LOCATION: (56)..(56)
<223> OTHER INFORMATION: Xaa = H or R or P
<220> FEATURE:
<221> NAME/KEY: VARIANT
<222> LOCATION: (66)..(66)
<223> OTHER INFORMATION: Xaa = S or G or L or T
<220> FEATURE:
<221> NAME/KEY: VARIANT
<222> LOCATION: (80)..(80)
<223> OTHER INFORMATION: Xaa = N
<220> FEATURE:
<221> NAME/KEY: VARIANT
<222> LOCATION: (83)..(83)
<223> OTHER INFORMATION: Xaa = Any amino acid other than P
<220> FEATURE:
<221> NAME/KEY: VARIANT
<222> LOCATION: (92)..(92)
<223> OTHER INFORMATION: Xaa = V or I

<400> SEQUENCE: 219

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 220
```

<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 221
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or I
<220> FEATURE:
<221> NAME/KEY: VARIANT
<222> LOCATION: (27)..(27)
<223> OTHER INFORMATION: Xaa = A or I
<220> FEATURE:
<221> NAME/KEY: VARIANT
<222> LOCATION: (31)..(31)
<223> OTHER INFORMATION: Xaa = I or F
<220> FEATURE:
<221> NAME/KEY: VARIANT
<222> LOCATION: (47)..(47)
<223> OTHER INFORMATION: Xaa = E or V
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (56)..(56)
<223> OTHER INFORMATION: Xaa = H or P
<220> FEATURE:
<221> NAME/KEY: VARIANT
<222> LOCATION: (66)..(66)
<223> OTHER INFORMATION: Xaa = L or T
<220> FEATURE:
<221> NAME/KEY: VARIANT
<222> LOCATION: (80)..(80)
<223> OTHER INFORMATION: Xaa = Any amino acid other than N
<220> FEATURE:
<221> NAME/KEY: VARIANT
<222> LOCATION: (92)..(92)
<223> OTHER INFORMATION: Xaa = V or I

<400> SEQUENCE: 221

```
Glu Glu Glu Leu Gln Xaa Ile Gln Pro Asp Lys Ser Val Leu Val Ala
 1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Glu Gly Xaa Phe Pro Arg Val Thr Thr Val Ser
50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 222
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (6)..(6)
<223> OTHER INFORMATION: Xaa = V or L or I
<220> FEATURE:
<221> NAME/KEY: VARIANT
<222> LOCATION: (27)..(27)
<223> OTHER INFORMATION: Xaa = A or I or L
<220> FEATURE:
<221> NAME/KEY: VARIANT
<222> LOCATION: (31)..(31)
<223> OTHER INFORMATION: Xaa = I or T or S or F
<220> FEATURE:
<221> NAME/KEY: VARIANT
<222> LOCATION: (53)..(53)
<223> OTHER INFORMATION: Xaa = K or R
<220> FEATURE:
<221> NAME/KEY: VARIANT
<222> LOCATION: (56)..(56)
<223> OTHER INFORMATION: Xaa = H or P
<220> FEATURE:
<221> NAME/KEY: VARIANT
<222> LOCATION: (66)..(66)
<223> OTHER INFORMATION: Xaa = L or T or G
<220> FEATURE:
<221> NAME/KEY: VARIANT
<222> LOCATION: (80)..(80)
<223> OTHER INFORMATION: Xaa = N or A

<400> SEQUENCE: 222

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Glu Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 223

His His His His His His
1               5

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 224

His His His His His His His His His His
1               5                   10

<210> SEQ ID NO 225
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (2)..(2)
<223> OTHER INFORMATION: Xaa = Any amino acid other than P
<220> FEATURE:
<221> NAME/KEY: VARIANT
<222> LOCATION: (3)..(3)
<223> OTHER INFORMATION: Xaa = T , S or C
<220> FEATURE:
<221> NAME/KEY: VARIANT
<222> LOCATION: (4)..(4)
<223> OTHER INFORMATION: Xaa = Any amino acid other than P

```
<400> SEQUENCE: 225

Asn Xaa Xaa Xaa
1
```

CONSTRUCTS HAVING A SIRP-ALPHA DOMAIN OR VARIANT THEREOF

CROSS-REFERENCE

This application is a continuation of U.S. patent application Ser. No. 16/153,404, filed Oct. 5, 2018, which is a continuation of U.S. patent application Ser. No. 15/230,186, filed Aug. 5, 2016 (U.S. Pat. No. 10,259,859), which claims the benefit of U.S. Provisional Application No. 62/202,772, filed Aug. 7, 2015; U.S. Provisional Application No. 62/202,775, filed Aug. 7, 2015; U.S. Provisional Application No. 62/202,779, filed Aug. 7, 2015; U.S. Provisional Application No. 62/276,801, filed Jan. 8, 2016; U.S. Provisional Application No. 62/265,887 filed Dec. 10, 2015; U.S. Provisional Application No. 62/276,796 filed Jan. 8, 2016; and U.S. Provisional Application No. 62/346,414 filed Jun. 6, 2016 which applications are each incorporated herein in their entireties by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 757972000403SEQLIST.TXT, date recorded: Mar. 17, 2020, size: 427 KB)

SUMMARY OF THE INVENTION

Disclosed herein, in certain embodiments, are polypeptides comprising: a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92. In some embodiments, the wild type SIRP-α D1 domain has a sequence according to any one of SEQ ID NOs: 1-10. In some embodiments, the SIRP-α D1 domain comprises between one and nine additional amino acid mutations relative to a wild-type SIRP-α D1 domain at a residue selected from the group consisting of: residue 6, residue 27, residue 31, residue 47, residue 53, residue 54 residue 56, residue 66, and residue 92. In some embodiments, the SIRP-α D1 variant comprises the amino acid sequence, EEELQX$_1$IQPDKSVLVAAGETATLRCTX$_2$TSLX$_3$PVGPI QWFRGAGPGRX$_4$LIYNQX$_5$X$_6$GX$_7$FPRVTTVSDX$_8$TK RNNMDFSIRIGX$_9$ITPADAGTYYCX$_{10}$KFRKGSPDDV EFKSGAGTELSVRAKPS (SEQ ID NO: 49), wherein X$_1$ is V, L, or I; X$_2$ is A, I, V, or L; X$_3$ is I, F, S, or T; X$_4$ is E, V, or L; X$_5$ is K or R; X$_6$ is E or Q; X$_7$ is H, P, or R; X$_8$ is L, T, S, or G; X$_9$ is A; and X$_{10}$ is V or I; and wherein the SIRP-α D1 variant has at least two amino acid substitutions relative to a wild-type SIRP-α D1 domain having a sequence according to SEQ ID NO: 1. In some embodiments, the SIRP-α D1 variant has an amino acid sequence according to any one of SEQ ID NOs: 78-85. In some embodiments, the SIRP-α D1 variant comprises the amino acid sequence, EEEL QX$_1$IQPDKSVLVAAGETATLRCTX$_2$TSLX$_3$PVGPIQWF RGAGPGRX$_4$LIYNQX$_5$X$_6$GX$_7$FPRVTTVSDX$_8$TKRNN MDFSIRIGX$_9$X$_{10}$X$_{11}$X$_{12}$ADAGTYYCX$_{13}$KFRKGSPDD VEFKSGAGTELSVRAKPS (SEQ ID NO: 218), wherein X$_1$ is V, L, or I; X$_2$ is A, V, L, or I; X$_3$ is I, S, T, or F; X$_4$ is E, L, or V; X$_5$ is K or R; X$_6$ is E or Q; X$_7$ is H, R, or P; X$_8$ is S,G, L, or T; X$_9$ is any amino acid; X$_{10}$ is any amino acid; X$_{11}$ is any amino acid; X$_{12}$ is any amino acid; and X$_{13}$ is V or I; and wherein the SIRP-α D1 variant has at least two amino acid substitutions relative to a wild-type SIRP-α D1 domain having a sequence according to SEQ ID NO: 1. In some embodiments, X$_9$ is A. In some embodiments, X$_9$ is N. In some embodiments, X$_{10}$ is I. In some embodiments, X$_9$ is N and X10 is P. In some embodiments, X$_9$ is N and X11 is any amino acid other than S, T, or C. In some embodiments, X$_{11}$ is T. In some embodiments, X$_{11}$ is an amino acid other than T. In some embodiments, X$_{12}$ is P. In some embodiments, X$_9$ is N and X$_{12}$ is any amino acid other than P. In some embodiments, the SIRP-α D1 variant comprises the amino acid sequence, EEELQX$_1$ IQPDKSVLVAAGETATLRCTX$_2$TSLX$_3$PVGPIQWFRGA GPGRX$_4$LIYNQX$_5$X$_6$GX$_7$FPRVTTVSDX$_8$TKRNNMDFS IRIGX$_9$ITX$_{10}$ADAGTYYCX$_{11}$KFRKGSPDDVEFKSGA GTELSVRAKPS (SEQ ID NO: 219), wherein X$_1$ is V, L, or I; X$_2$ is A, V, L, or I; X$_3$ is I, S, T, or F; X$_4$ is E, L, or V; X$_5$ is K or R; X$_6$ is E or Q; X$_7$ is H, R, or P; X$_8$ is S, G, L, or T; X$_9$ is N; X$_{10}$ is any amino acid other than P; and X$_{11}$ is V or I; and wherein the SIRP-α D1 variant has at least two amino acid substitutions relative to a wild-type SIRP-α D1 domain having a sequence according to SEQ ID NO: 1. In some embodiments, the SIRP-α D1 variant comprises the amino acid sequence, EEELQX$_1$ IQPDKSVLVAAGETATLRCTX$_2$TSLX$_3$PVGPIQWFRGA GPGRELIYNQX$_4$EGX$_5$FPRVTTVSDX$_6$TKRNNMDFS IRIGX$_7$ITPADAGTYYCVKFRKGSPDDVEFKSGAGTE LSVRAKPS (SEQ ID NO: 52), wherein X$_1$ is V, L, or I; X$_2$ is A, I, or L; X$_3$ is I, T, S, or F; X$_4$ is K or R; X$_5$ is H, P, or R; X$_6$ is L, T, or G; and X$_7$ is A; and wherein the SIRP-α D1 variant has at least two amino acid substitutions relative to a wild-type SIRP-α D1 domain having a sequence according to SEQ ID NO: 1. In some embodiments, X$_1$ is V or I, X$_2$ is A or I, X$_3$ is I or F, X$_4$ is K or R, X$_5$ is H or P, X$_6$ is L or T, and X$_7$ is A. In some embodiments, the SIRP-α D1 variant has at least three amino acid substitutions relative to a wild-type SIRP-α D1 domain having a sequence according to SEQ ID NO: 1. In some embodiments, the SIRP-α D1 variant has at least four amino acid substitutions relative to a wild-type SIRP-α D1 domain having a sequence according to SEQ ID NO: 1. In some embodiments, the SIRP-α D1 variant has at least five amino acid substitutions relative to a wild-type SIRP-α D1 domain having a sequence according to SEQ ID NO: 1. In some embodiments, the SIRP-α D1 variant has at least six amino acid substitutions relative to a wild-type SIRP-α D1 domain having a sequence according to SEQ ID NO: 1. In some embodiments, the SIRP-α D1 variant has at least seven amino acid substitutions relative to a wild-type SIRP-α D1 domain having a sequence according to SEQ ID NO: 1. In some embodiments, X$_1$ is I. In some embodiments, X$_2$ is I. In some embodiments, X$_3$ is F. In some embodiments, X$_4$ is R. In some embodiments, X$_5$ is P. In some embodiments, X$_6$ is T. In some embodiments, each of X$_1$, X$_2$, X$_3$, X$_4$, X$_5$, and X$_6$ is not a wild-type amino acid. In some embodiments, the SIRP-α D1 variant has an amino acid sequence according to any one of SEQ ID NOs: 81-85. In some embodiments, the SIRP-α D1 variant comprises the amino acid sequence, EEELQX$_1$ IQPDKSVSVAAGESAILHCTX$_2$TSLX$_3$PVGPIQWFRGA GPARELIYNQX$_4$EGX$_5$FPRVTTVSEX$_6$TKRENMDFSIS ISX$_7$ITPADAGTYYCVKFRKGSPDTEFKSGAGTELSV RAKPS (SEQ ID NO: 212), wherein X$_1$ is V, L, or I; X$_2$ is V, I, or L; X$_3$ is I, T, S, or F; X$_4$ is K or R; X$_5$ is H, P, or R; X$_6$ is S, T, or G; and X$_7$ is A; and wherein the SIRP-α D1 variant has at least two amino acid substitutions relative to a wild-type SIRP-α D1 domain having the sequence of SEQ ID NO: 2. In some embodiments, the polypeptide binds to human CD47 with a $K_D$ less than about $5 \times 10^{-9}$ M. In some embodiments, the polypeptide further comprises an Fc domain monomer linked to the N-terminus or the C-terminus of the polypeptide, wherein the Fc domain monomer is a human IgG1, IgG2, or IgG4 Fc region. In some embodiments, the Fc domain monomer comprises at least one mutation relative to a wild-type human IgG1, IgG2, or IgG4 Fc region. In some embodiments, the polypeptide has the amino acid sequence of any one of SEQ ID NO: 135, SEQ ID NO: 136, or SEQ ID NO: 137. In some embodiments, the Fc domain monomer comprises (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; or (b) (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region. In some embodiments, the Fc domain monomer comprises (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; and (b) the Fc domain monomer further comprises (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG2 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region. In some embodiments, the polypeptide exhibits a reduction of phagocytosis in a phagocytosis assay compared to a polypeptide with a wild-type human IgG Fc region. In some embodiments, the Fc domain monomer is linked to a second polypeptide comprising a second Fc domain monomer to form an Fc domain dimer. In some embodiments, the second Fc domain monomer is linked to an additional polypeptide. In some embodiments, the additional polypeptide comprises an antibody variable domain. In some embodiments, the antibody variable domain targets an antigen expressed on a cell. In some embodiments, the cell is a cancer cell. In some embodiments, the antibody variable domain targets a cell surface protein involved in immune cell regulation. In some embodiments, the additional polypeptide comprises a therapeutic protein. In some embodiments, the therapeutic protein is a cytokine, an interleukin, an antigen, a steroid, an anti-inflammatory agent, or an immunomodulatory agent. In some embodiments, the additional polypeptide comprises a SIRP-α D1 variant. In some embodiments, the polypeptide further comprises a human serum albumin (HSA) (SEQ ID NO: 12). In some embodiments, the HSA comprises a C34S or K573P amino acid substitution relative to SEQ ID NO: 12. In some embodiments, the polypeptide has an amino acid sequence according to any one of SEQ ID NOs: 152-159. In some embodiments, the polypeptide further comprises an albumin-binding peptide. In some embodiments, the albumin-binding peptide comprises the amino acid sequence DICLPRWGCLW (SEQ ID NO: 160). In some embodiments, the polypeptide further comprises a polyethylene glycol (PEG) polymer. In some embodiments, the PEG polymer is joined to a cysteine substitution in the polypeptide.

Disclosed herein, in certain embodiments, are polypeptides comprising: a signal-regulatory protein α (SIRP-α) D1 variant, wherein the SIRP-α D1 variant comprises the amino acid sequence, EEX$_1$X$_2$QX$_3$IQPDKX$_4$VX$_5$ VAAGEX$_6$X$_7$X$_8$LX$_9$CTX$_{10}$TSLX$_{11}$PVGPIQWFRGAGP X$_{12}$RX$_{13}$LIYNQX$_{14}$X$_{15}$GX$_{16}$FPRVTTVSX$_{17}$X$_{18}$TX$_{19}$R X$_{20}$NMDFX$_{21}$IX$_{22}$IX$_{23}$X$_{24}$ITX$_{25}$ADAGTYYCX$_{26}$KX$_{27}$ RKGSPDX$_{28}$X$_{29}$EX$_{30}$KSGAGTELSVRX$_{31}$KPS (SEQ ID NO: 47), wherein X$_1$ is E, or G; X$_2$ is L, I, or V; X$_3$ is V, L, or I; X$_4$ is S, or F; X$_5$ is L, or S; X$_6$ is S, or T; X$_7$ is A, or V; X$_8$ is I, or T; X$_9$ is H, R, or L; X$_{10}$ is A, V, I, or L; X$_{11}$ is I, T, S, or F; X$_{12}$ is A, or G; X$_{13}$ is E, V, or L; X$_{14}$ is K, or R; X$_{15}$ is E, or Q; X$_{16}$ is H, P, or R; X$_{17}$ is D, or E; X$_{18}$ is S, L, T, or G; X$_{19}$ is K, or R; X$_{20}$ is E, or N; X$_{21}$ is S, or P; X$_{22}$ is S, or R; X$_{23}$ is S, or G; X$_{24}$ is any amino acid; X$_{25}$ is any amino acid; X$_{26}$ is V, or I; X$_{27}$ is F, L, or V; X$_{28}$ is D or absent; X$_{29}$ is T, or V; X$_{30}$ is F, or V; and X$_{31}$ is A, or G; and wherein the SIRP-α D1 variant has at least two amino acid substitutions relative to a wild-type SIRP-α D1 domain having a sequence according to any one of SEQ ID NOs: 1 to 10; and an Fc variant comprising an Fc domain dimer having two Fc domain monomers, wherein each Fc domain monomer independently is (i) a human IgG1 Fc region comprising a N297A mutation; (ii) a human IgG1 Fc region comprising L234A, L235A, and G237A mutations; (iii) a human IgG1 Fc region comprising L234A, L235A, G237A, and N297A mutations; (iv) a human IgG2 Fc region comprising a N297A mutation; (v) a human IgG2 Fc region comprising A330S and P331S mutations; (vi) a human IgG2 Fc region comprising A330S, P331S, and N297A mutations; (vii) a human IgG4 Fc region comprising S228P, E233P, F234V, L235A, and delG236 mutations; or (viii) a human IgG4 Fc region comprising S228P, E233P, F234V, L235A, delG236, and N297A mutations. In some embodiments, one of the Fc domain monomers in the Fc domain dimer comprises a human IgG1 Fc region comprising L234A, L235A, G237A, and N297A mutations. In some embodiments, the polypeptide comprises an amino acid sequence according to any one of SEQ ID NOs: 98-104, 107-113, 116-122, or 135-137. In some embodiments, the Fc variant exhibits ablated or reduced binding to an Fcγ receptor compared to a wild-type version of a human IgG Fc region. In some embodiments, the IgG1 or IgG2 Fc variant exhibits ablated or reduced binding to CD16a, CD32a, CD32b, CD32c, and CD64 Fcγ receptors compared to a wild-type version of a human IgG1 or IgG2 Fc region. In some embodiments, the IgG4 Fc variant exhibits ablated or reduced binding to CD16a and CD32b Fcγ receptors compared to a wild-type version of the human IgG4 Fc region. In some embodiments, the IgG1 or IgG2 Fc variant exhibits ablated or reduced binding to C1q compared to a wild-type version of a human IgG1 or IgG2 Fc fusion. In some embodiments, the Fc variant binds to an Fcγ receptor with a $K_D$ greater than about $5 \times 10^{-6}$ M.

Disclosed herein, in certain embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, at least one of the Fc domain monomers is a human IgG1 Fc region consisting of mutations L234A, L235A, G237A, and N297A. In some embodiments, at least one of the Fc domain monomers is a human IgG2 Fc region consisting of mutations A330S, P331S and N297A. In some embodiments, the Fc variant exhibits ablated or reduced binding to an Fcγ receptor compared to the wild-type version of the human IgG Fc region. In some embodiments, the Fc variant exhibits ablated or reduced binding to CD16a, CD32a, CD32b, CD32c, and CD64 Fcγ receptors compared to the wild-type version of the human IgG Fc region. In some embodiments, the Fc variant exhibits ablated or reduced binding to C1q compared to the wild-type version of the human IgG Fc fusion. In some embodiments, at least one of the Fc domain monomers is a human IgG4 Fc region comprising mutations S228P, E233P, F234V, L235A, delG236, and N297A. In some embodiments, the Fc variant exhibits ablated or reduced binding to a Fcγ receptor compared to the wild-type human IgG4 Fc region. In some embodiments, the Fc variant exhibits ablated or reduced binding to CD16a and CD32b Fcγ receptors compared to the wild-type version of its human IgG4 Fc region. In some embodiments, the Fc variant binds to an Fcγ receptor with a $K_D$ greater than about $5 \times 10^{-6}$ M. In some embodiments, the polypeptide further comprises a CD47 binding polypeptide. In some embodiments, the Fc variant exhibits ablated or reduced binding to an Fcγ receptor compared to a wild-type version of a human IgG Fc region. In some embodiments, the CD47 binding polypeptide does not cause acute anemia in rodents and non-human primates. In some embodiments, the CD47 binding polypeptide does not cause acute anemia in humans. In some embodiments, the CD47 binding polypeptide is a signal-regulatory protein α (SIRP-α) polypeptide or a fragment thereof. In some embodiments, the SIRP-α polypeptide comprises a SIRP-α D1 variant comprising the amino acid sequence, EEELQX$_1$IQPDKSVLVAAGETA TLRCTX$_2$TSLX$_3$PVGPIQWFRGAGPGRX$_4$LIYNQX$_5$EG X$_6$FPRVTTVSDX$_7$TKRNNMDFSIRIGX$_8$ITPADAGTYY CX$_9$KFRKGSPDDVEFKSGAGTELSVRAKPS (SEQ ID NO: 221), wherein X$_1$ is V or I; X$_2$ is A or I; X$_3$ is I or F; X$_4$ is E or V; X$_5$ is K or R; X$_6$ is H or P; X$_7$ is L or T; X$_8$ is any amino acid other than N; and X$_9$ is V or I. In some embodiments, the SIRP-α polypeptide comprises a SIRP-α D1 variant wherein X$_1$ is V or I; X$_2$ is A or I; X$_3$ is I or F; X$_4$ is E; X$_5$ is K or R; X$_6$ is H or P; X$_7$ is L or T; X$_8$ is not N; and X$_9$ is V.

Disclosed herein, in certain embodiments, are polypeptides comprising: a signal-regulatory protein α (SIRP-α) D1 variant, wherein the SIRP-α D1 variant is a non-naturally occurring high affinity SIRP-α D1 domain, wherein the SIRP-α D1 variant binds to human CD47 with an affinity that is at least 10-fold greater than the affinity of a naturally occurring D1 domain; and an Fc domain monomer, wherein the Fc domain monomer is linked to a second polypeptide comprising a second Fc domain monomer to form an Fc domain, wherein the Fc domain has ablated or reduced effector function. In some embodiments, the non-naturally occurring high affinity SIRP-α D1 domain comprises an amino acid mutation at residue 80.

Disclosed herein, in certain embodiments, are polypeptides comprising a signal-regulatory protein α (SIRP-α) D1 variant, wherein the SIRP-α D1 variant binds CD47 from a first species with a $K_D$ less than 250 nM; and wherein the SIRP-α D1 variant binds CD47 from a second species with a $K_D$ less than 250 nM; and the $K_D$ for CD47 from the first species and the $K_D$ for CD47 from the second species are within 100 fold of each other; wherein the first species and the second species are selected from the group consisting of: human, rodent, and non-human primate. In some embodiments, the SIRP-α D1 variant binds CD47 from at least 3 different species. In some embodiments, the non-human primate is cynomolgus monkey.

Disclosed herein, in certain embodiments, are polypeptides comprising: (a) a signal-regulatory protein α (SIRP-α) D1 domain that binds human CD47 with a $K_D$ less than 250 nM; and (b) an Fc domain monomer linked to the N-terminus or the C-terminus of the SIRP-α D1 domain, wherein the polypeptide does not cause acute anemia in rodents and non-human primates. In some embodiments, the polypeptide is a non-naturally occurring variant of a human SIRP-α. In some embodiments, administration of the polypeptide in vivo results in hemoglobin reduction by less than 50% during the first week after administration. In some embodiments, administration of the polypeptide in humans results in hemoglobin reduction by less than 50% during the first week after administration. In some embodiments, the polypeptide further comprises at least one Fc variant, wherein the Fc variant is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc variant is a human IgG1 Fc region consisting of mutations L234A, L235A, G237A, and N297A. In some embodiments, the Fc variant is a human IgG2 Fc region consisting of mutations A330S, P331S and N297A. In some embodiments, the Fc variant is a human IgG4 Fc region comprising mutations S228P, E233P, F234V, L235A, delG236, and N297A.

Disclosed herein, in certain embodiments, are methods of treating an individual having a disease or disorder, the method comprising administering to the subject a polypeptide disclosed herein. In some embodiments, the polypeptide comprises a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92. In some embodiments, the polypeptide comprises a signal-regulatory protein α (SIRP-α) D1 variant, wherein the SIRP-α D1 variant comprises the amino acid sequence, EEX$_1$X$_2$QX$_3$IQPDKX$_4$VX$_5$VAAGEX$_6$X$_7$X$_8$LX$_9$CTX$_{10}$TSLX$_{11}$ PVGPIQWFRGAGPX$_{12}$RX$_{13}$LIYNQX$_{14}$X$_{15}$GX$_{16}$FPRVT TVSX$_{17}$X$_{18}$TX$_{19}$RX$_{20}$NMDFX$_{21}$IX$_{22}$IX$_{23}$X$_{24}$ITX$_{25}$ADA GTYYCX$_{26}$KX$_{27}$RKGSPDX$_{28}$X$_{29}$EX$_{30}$KSGAGTELSVR X$_{31}$KPS (SEQ ID NO: 47), wherein X$_1$ is E, or G; X$_2$ is L, I, or V; X$_3$ is V, L, or I; X$_4$ is S, or F; X$_5$ is L, or S; X$_6$ is S, or T; X$_7$ is A, or V; X$_8$ is I, or T; X$_9$ is H, R, or L; X$_{10}$ is A, V, I, or L; X$_{11}$ is I, T, S, or F; X$_{12}$ is A, or G; X$_{13}$ is E, V, or L; X$_{14}$ is K, or R; X$_{15}$ is E, or Q; X$_{16}$ is H, P, or R; X$_{17}$ is D, or E; X$_{18}$ is S, L, T, or G; X$_{19}$ is K, or R; X$_{20}$ is E, or N; X$_{21}$ is S, or P; X$_{22}$ is S, or R; X$_{23}$ is S, or G; X$_{24}$ is any amino acid; X$_{25}$ is any amino acid; X$_{26}$ is V, or I; X$_{27}$ is F, L, or V; X$_{28}$ is D or absent; X$_{29}$ is T, or V; X$_{30}$ is F, or V; and X$_{31}$ is A, or G; and wherein the SIRP-α D1 variant has at least two amino acid substitutions relative to a wild-type SIRP-α D1 domain having a sequence according to any one of SEQ ID NOs: 1 to 10; and an Fc variant comprising an Fc domain dimer having two Fc domain monomers, wherein each Fc domain monomer independently is (i) a human IgG1 Fc region comprising a N297A mutation; (ii) a human IgG1 Fc region comprising L234A, L235A, and G237A mutations; (iii) a human IgG1 Fc region comprising L234A, L235A, G237A, and N297A mutations; (iv) a human IgG2 Fc region comprising a N297A mutation; (v) a human IgG2 Fc region comprising A330S and P331S mutations; (vi) a human IgG2 Fc region comprising A330S, P331S, and N297A mutations; (vii) a human IgG4 Fc region comprising S228P, E233P, F234V, L235A, and delG236 mutations; or (viii) a human IgG4 Fc region comprising S228P, E233P, F234V, L235A, delG236, and N297A mutations. In some embodiments, the polypeptide comprises an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the polypeptide comprises a signal-regulatory protein α (SIRP-α) D1 variant, wherein the SIRP-α D1 variant is a non-naturally occurring high affinity SIRP-α D1 domain, wherein the SIRP-α D1 variant binds to human CD47 with an affinity that is at least 10-fold greater than the affinity of a naturally occurring D1 domain; and an Fc domain monomer, wherein the Fc domain monomer is linked to a second polypeptide comprising a second Fc domain monomer to form an Fc domain, wherein the Fc domain has ablated or reduced effector function. In some embodiments, the non-naturally occurring high affinity SIRP-α D1 domain comprises an amino acid mutation at residue 80. In some embodiments, the polypeptide comprises a signal-regulatory protein α (SIRP-α) D1 variant, wherein the SIRP-α D1 variant binds CD47 from a first species with a K$_D$ less than 250 nM; and wherein the SIRP-α D1 variant binds CD47 from a second species with a K$_D$ less than 250 nM; and the K$_D$ for CD47 from the first species and the K$_D$ for CD47 from the second species are within 100 fold of each other; wherein the first species and the second species are selected from the group consisting of: human, rodent, and non-human primate. In some embodiments, the polypeptide comprises (a) a signal-regulatory protein α (SIRP-α) D1 domain that binds human CD47 with a K$_D$ less than 250 nM; and (b) an Fc domain monomer linked to the N-terminus or the C-terminus of the SIRP-α D1 domain, wherein the polypeptide does not cause acute anemia in rodents and non-human primates. In some embodiments, the disease or disorder is a cancer, an autoimmune disease, or an inflammatory disease. In some embodiments, the disease or disorder is a cancer, and the cancer is selected from solid tumor cancer, hematological cancer, acute myeloid leukemia, chronic lymphocytic leukemia, chronic myeloid leukemia, acute lymphoblastic leukemia, non-Hodgkin lymphoma, Hodgkin lymphoma, multiple myeloma, bladder cancer, pancreatic cancer, cervical cancer, endometrial cancer, lung cancer, bronchus cancer, liver cancer, ovarian cancer, colon and rectal cancer, stomach cancer, gastric cancer, gallbladder cancer, gastrointestinal stromal tumor cancer, thyroid cancer, head and neck cancer, oropharyngeal cancer, esophageal cancer, melanoma, non-melanoma skin cancer, Merkel cell carcinoma, virally induced cancer, neuroblastoma, breast cancer, prostate cancer, renal cancer, renal cell cancer, renal pelvis cancer, leukemia, lymphoma, sarcoma, glioma, brain tumor, and carcinoma. In some embodiments, the disease or disorder is an autoimmune disease or an inflammatory disease, and the autoimmune disease or the inflammatory disease is selected from multiple sclerosis, rheumatoid arthritis, a spondyloarthropathy, systemic lupus erythematosus, an antibody-mediated inflammatory or autoimmune disease, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, and inflammatory autoimmune myositis. In some embodiments, the SIRP-α D1 variant has a sequence according to any one of SEQ ID NOs: 78-85, 98-104, 107-113, 116-122, 135-137, or 152-159. In some embodiments, the method further comprises administering at least one additional agent. In some embodiments, the at least one additional agent is an antibody, tumor associated antigen, or a non-antibody therapeutic. In some embodiments, at least two additional agents are administered. In some embodiments, the at least two additional agents comprise two antibodies. In some embodiments, the at least two additional agents comprise an antibody and a tumor associated antigen. In some embodiments, the at least one additional agent is an antibody. In some embodiments, the antibody is a human IgG1 isotype antibody. In some embodiments, the antibody is a human IgG2 isotype antibody. In some embodiments, the antibody is a human IgG4 isotype antibody. In some embodiments, the antibody is selected from an anti-HER2 antibody, anti-CD20 antibody, anti-CD19 antibody, anti-CS1 antibody, anti-CD38 antibody, anti-EGFR antibody, anti-PD1 antibody, anti-OX40 antibody, anti-PD-1 antibody, anti-PD-L1 antibody, anti-CD274 antibody, anti-CTLA-4 antibody, anti-CD137 antibody, anti-4-1BB antibody, anti-B7-H3 antibody, anti-FZD7 antibody, anti-CD27 antibody, anti-CCR4 antibody, anti-CD38 antibody, anti-CSF1R antibody, anti-CSF antibody, anti-CD30 antibody, anti-BAFF antibody, anti-VEGF antibody, or anti-VEGFR2 antibody. In some embodiments, the antibody is selected from an anti-HER2 antibody, anti-CD20 antibody, anti-CD19 antibody, anti-CS1 antibody, anti-CD38 antibody, anti-PD-1 antibody, anti-RANKL antibody, or anti-PD-L1 antibody. In some embodiments, the at least one additional agent is at least one antibody and the antibody is selected from cetuximab, necitumumab, pembrolizumab, nivolumab, pidilizumab, MEDI0680, MED16469, atezolizumab, avelumab, durvalumab, MEDI6383, RG7888, ipilimumab, tremelimumab, urelumab, PF-05082566, enoblituzumab, vantictumab, varlilumab, mogamalizumab, SAR650984, daratumumab, trastuzumab, trastuzumab emtansine, pertuzumab, elotuzumab, rituximab, ofatumumab, obinutuzumab, RG7155, FPA008, panitumumab, brentuximab vedotin, MSB0010718C, belimumab, bevacizumab, denosumab, panitumumab, ramucirumab, necitumumab, nivolumab, pembrolizumab, avelumab, atezolizumab, durvalumab, MEDI0680, pidilizumab, or BMS-93659. In some embodiments, the antibody is trastuzumab. In some embodiments, the SIRP-α D1 variant has a sequence according to any one of SEQ ID NOs: 78-85, 98-104, 107-113, 116-122, 135-137, or 152-159. In some embodiments, the antibody is rituximab. In some embodiments, the SIRP-α D1 variant has a sequence according to any one of SEQ ID NOs: 78-85, 98-104, 107-113, 116-122, 135-137, or 152-159. In some embodiments, the antibody is cetuximab. In some embodiments, the SIRP-α D1 variant has a sequence according to any one of SEQ ID NOs: 78-85, 98-104, 107-113, 116-122, 135-137, or 152-159. In some embodiments, the antibody is daratumumab. In some embodiments, the SIRP-α D1 variant has a sequence according to any one of SEQ ID NOs: 78-85, 98-104, 107-113, 116-122, 135-137, or 152-159. In some embodiments, the antibody is belimumab. In some embodiments, the SIRP-α D1 variant has a sequence according to any one of SEQ ID NOs: 78-85, 98-104, 107-113, 116-122, 135-137, or 152-159. In some embodiments, n the antibody is bevacizumab. In some embodiments, the SIRP-α D1 variant has a sequence according to any one of SEQ ID NOs: 78-85, 98-104, 107-113, 116-122, 135-137, or 152-159. In some embodiments, the antibody is denosumab. In some embodiments, the SIRP-α D1 variant has a sequence according to any one of SEQ ID NOs: 78-85, 98-104, 107-113, 116-122, 135-137, or 152-159. In some embodiments, the antibody is pantimumab. In some embodiments, the SIRP-α D1 variant has a sequence according to any one of SEQ ID NOs: 78-85, 98-104, 107-113, 116-122, 135-137, or 152-159. In some embodiments, the antibody is ramucirumab. In some embodiments, the SIRP-α D1 variant has a sequence according to any one of SEQ ID NOs: 78-85, 98-104, 107-113, 116-122, 135-137, or 152-159. In some embodiments, the antibody is necitumumab. In some embodiments, the SIRP-α D1 variant has a sequence according to any one of SEQ ID NOs: 78-85, 98-104, 107-113, 116-122, 135-137, or 152-159. In some embodiments, the antibody is nivolumab. In some embodiments, the SIRP-α D1 variant has a sequence according to any one of SEQ ID NOs: 78-85, 98-104, 107-113, 116-122, 135-137, or 152-159. In some embodiments, the antibody is pembrolizumab. In some embodiments, the SIRP-α D1 variant has a sequence according to any one of SEQ ID NOs: 78-85, 98-104, 107-113, 116-122, 135-137, or 152-159. In some embodiments, the antibody is avelumab. In some embodiments, the SIRP-α D1 variant has a sequence according to any one of SEQ ID NOs: 78-85, 98-104, 107-113, 116-122, 135-137, or 152-159. In some embodiments, the antibody is atezolizumab. In some embodiments, the SIRP-α D1 variant has a sequence according to any one of SEQ ID NOs: 78-85, 98-104, 107-113, 116-122, 135-137, or 152-159. In some embodiments, the antibody is durvalumab. In some embodiments, the SIRP-α D1 variant has a sequence according to any one of SEQ ID NOs: 78-85, 98-104, 107-113, 116-122, 135-137, or 152-159. In some embodiments, the antibody is MEDI0680. In some embodiments, the SIRP-α D1 variant has a sequence according to any one of SEQ ID NOs: 78-85, 98-104, 107-113, 116-122, 135-137, or 152-159. In some embodiments, the antibody is pidilizumab. In some embodiments, the SIRP-α D1 variant has a sequence according to any one of SEQ ID NOs: 78-85, 98-104, 107-113, 116-122, 135-137, or 152-159. In some embodiments, the antibody is BMS-93659. In some embodiments, the SIRP-α D1 variant has a sequence according to any one of SEQ ID NOs: 78-85, 98-104, 107-113, 116-122, 135-137, or 152-159. In some embodiments, the at least one additional agent is a tumor associated antigen and the tumor associated antigen elicits an immune response. In some embodiments, the at least one additional agent is an antibody and the antibody targets a HLA/peptide or MHC/peptide complex. In some embodiments, the antibody targets a HLA/peptide or MHC/peptide complex comprising NY-ESO-1/LAGE1, SSX-2, MAGE family (MAGE-A3), gp100/pmel17, Melan-A/MART-1, gp75/TRP1, tyrosinase, TRP2, CEA, PSA, TAG-72, Immature laminin receptor, MOK/RAGE-1, WT-1, Her2/neu, EphA3, SAP-1, BING-4, Ep-CAM, MUC1, PRAME, survivin, Mesothelin, BRCA1/2 (mutated), CDK4, CML66, MART-2, p53 (mutated), Ras (mutated), β-catenin (mutated), TGF-βRII (mutated), HPV E6, or E7. In some embodiments, the antibody is ESK1, RL1B, Pr20, or 3.2G1.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
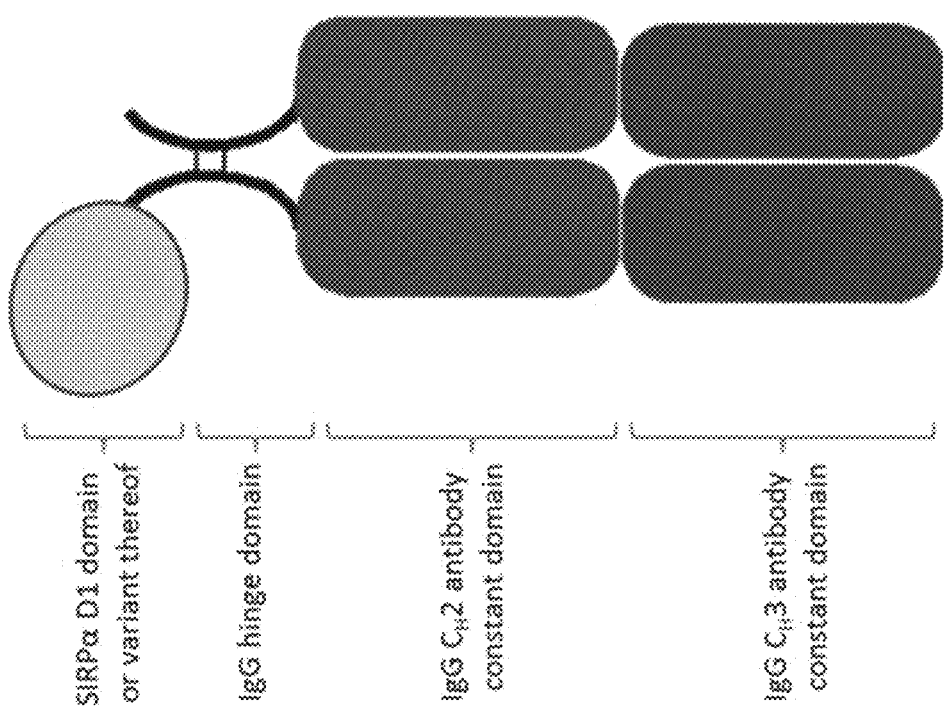
FIG. 1 is an illustration of a SIRP-α construct including a SIRP-α D1 domain or variant thereof joined to a first Fc domain monomer, which forms an Fc domain with a second Fc domain monomer.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description or the claims, such terms are intended to be inclusive in a manner similar to the term "comprising."

As used herein, the term "antibody" refers to intact antibodies; antibody fragments, provided that they exhibit the desired biological activity (e.g. epitope binding); monoclonal antibodies; polyclonal antibodies; monospecific antibodies; multi-specific antibodies (e.g., bispecific antibodies); and antibody-like proteins.

As used herein, the term "antibody variable domain" refers to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs).

As used herein, the term "linker" refers to a linkage between two elements, e.g., protein domains. In some embodiments, a linker can be a covalent bond or a spacer. The term "spacer" refers to a moiety (e.g., a polyethylene glycol (PEG) polymer) or an amino acid sequence (e.g., a 1-200 amino acid sequence) occurring between two polypeptides or polypeptide domains to provide space or flexibility (or both space and flexibility) between the two polypeptides or polypeptide domains. In some embodiments, an amino acid spacer is part of the primary sequence of a polypeptide (e.g., joined to the spaced polypeptides or polypeptide domains via the polypeptide backbone).

As used herein, the term "therapeutically effective amount" refers to an amount of a polypeptide or a pharmaceutical composition containing a polypeptide described herein, e.g., a polypeptide having a SIRP-α D1 domain or variant thereof, that is sufficient and effective in achieving a desired therapeutic effect in treating a patient having a disease, such as a cancer, e.g., solid tumor or hematological cancer. In some embodiments, a therapeutically effective amount of polypeptide will avoid adverse side effects.

As used herein, the term "pharmaceutical composition" refers to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with the polypeptide. In some embodiments, the pharmaceutical composition is in tablet or capsule form for oral administration or in aqueous form for intravenous or subcutaneous administration, for example by injection.

As used herein, the terms "subject," "individual," and "patient" are used interchangeably to refer to a vertebrate, for example, a mammal. Mammals include, but are not limited to, murines, simians, humans, farm animals, sport animals, and pets. Tissues, cells, and their progeny of a biological entity obtained in vivo or cultured in vitro are also encompassed. None of the terms entail supervision of a medical professional.

As used herein, the term "affinity" or "binding affinity" refers to the strength of the binding interaction between two molecules. Generally, binding affinity refers to the strength of the sum total of non-covalent interactions between a molecule and its binding partner, such as a high affinity SIRP-α D1 variant and CD47. Unless indicated otherwise, binding affinity refers to intrinsic binding affinity, which reflects a 1:1 interaction between members of a binding pair. The binding affinity between two molecules is commonly described by the dissociation constant ($K_D$) or the association constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. In some embodiments, the $K_D$ of two interacting molecules is determined using known methods and techniques, e.g., surface plasmon resonance (SPR). $K_D$ can be calculated as the ratio of $k_{off}/k_{on}$.

As used herein, the term "$K_D$ less than" refers to a numerically smaller $K_D$ value and an increasing binding affinity relative to the recited $K_D$ value. As used herein, the term "$K_D$ greater than" refers to a numerically larger $K_D$ value and a decreasing binding affinity relative to the recited $K_D$ value.

As used herein, the term "acute anemia" refers to a decrease of red blood cell mass or hemoglobin of 30% during the first five days after administration of a compound or treatment.

I. Signal-Regulatory Protein α (SIRP-α) D1 Domain and Variants Thereof

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Signal-regulatory protein α ("SIRP-α" or "SIRP-alpha") is a transmembrane glycoprotein belonging to the Ig superfamily that is widely expressed on the membrane of myeloid cells. SIRP-α interacts with CD47, a protein broadly expressed on many cell types in the body. The interaction of SIRP-α with CD47 prevents engulfment of "self" cells, which can otherwise be recognized by the immune system. It has been observed that high CD47 expression on tumor cells can act, in acute myeloid leukemia and several solid tumor cancers, as a negative prognostic factor for survival.

Native SIRP-α comprises 3 highly homologous immunoglobulin (Ig)-like extracellular domains—D1, D2, and D3. The SIRP-α D1 domain ("D1 domain") refers to the membrane distal, extracellular domain of SIRP-α and mediates binding of SIRP-α to CD47. As used herein, the term "SIRP-α polypeptide" refers to any SIRP-α polypeptide or fragment thereof that is capable of binding to CD47. There are at least ten variants of wild-type human SIRP-α. Table 1 shows the amino acid sequences of the D1 domains of the ten naturally occurring wild-type human SIRP-α D1 domain variants (SEQ ID NOs: 1-10). In some embodiments, a SIRP-α polypeptide comprises a SIRP-α D1 domain. In some embodiments, a SIRP-α polypeptide comprises a wild-type D1 domain, such as those provided in SEQ ID NOs: 1-10. In some embodiments, a SIRP-α polypeptide includes a D2 or D3 domain (or both a D2 and a D3 domain) (Table 3) of a wild-type human SIRP-α.

TABLE 1

Sequences of Wild-Type SIRP-a D1 Domains

| SEQ ID NO: | Description | Amino Acid Sequence |
|---|---|---|
| 1 | Wild-type D1 domain variant 1 | EEELQVIQPDKSVLVAAGETATLRCTATSLIPVGPI QWFRGAGPGRELIYNQKEGHFPRVTTVSDLTKRN NMDFSIRIGNITPADAGTYYCVKFRKGSPDDVEFK SGAGTELSVRAKPS |
| 2 | Wild-type D1 domain variant 2 | EEELQVIQPDKSVSVAAGESAILHCTVTSLIPVGPIQ WFRGAGPARELIYNQKEGHFPRVTTVSESTKREN MDFSISISNITPADAGTYYCVKFRKGSPDTEFKSGA GTELSVRAKPS |
| 3 | Wild-type D1 domain variant 3 | EEELQVIQPDKSVSVAAGESAILLCTVTSLIPVGPIQ WFRGAGPARELIYNQKEGHFPRVTTVSESTKREN MDFSISISNITPADAGTYYCVKFRKGSPDTEFKSGA GTELSVRAKPS |
| 4 | Wild-type D1 domain variant 4 | EEGLQVIQPDKSVSVAAGESAILHCTATSLIPVGPI QWFRGAGPGRELIYNQKEGHFPRVTTVSDLTKRN NMDFSIRIGNITPADAGTYYCVKFRKGSPDDVEFK SGAGTELSVRAKPS |
| 5 | Wild-type D1 domain variant 5 | EEELQVIQPDKFVLVAAGETATLRCTATSLIPVGPI QWFRGAGPGRELIYNQKEGHFPRVTTVSDLTKRN NMDFSIRIGNITPADAGTYYCVKFRKGSPDDVEFK SGAGTELSVRAKPS |
| 6 | Wild-type D1 domain variant 6 | EEELQVIQPDKSVLVAAGETATLRCTATSLIPVGPI QWFRGAGPGRELIYNQKEGHFPRVTTVSDLTKRN NMDFPIRIGNITPADAGTYYCVKFRKGSPDDVEFK SGAGTELSVRAKPS |
| 7 | Wild-type D1 domain variant 7 | EEELQVIQPDKSVSVAAGESAILHCTVTSLIPVGPIQ WFRGAGPARELIYNQKEGHFPRVTTVSESTKREN MDFSISISNITPADAGTYYCVKFRKGSPDTEFKSGA GTELSVRGKPS |

TABLE 1-continued

Sequences of Wild-Type SIRP-a D1 Domains

| SEQ ID NO: | Description | Amino Acid Sequence |
|---|---|---|
| 8 | Wild-type D1 domain variant 8 | EEELQVIQPDKSVLVAAGETATLRCTATSLIPVGPI QWFRGAGPARELIYNQKEGHFPRVTTVSESTKREN MDFSISISNITPADAGTYYCVKFRKGSPDTEFKSGA GTELSVRAKPS |
| 9 | Wild-type D1 domain variant 9 | EEELQVIQPDKSVLVAAGETATLRCTATSLIPVGPI QWFRGAGPGRELIYNQKEGHFPRVTTVSDLTKRN NMDFSIRISNITPADAGTYYCVKFRKGSPDDVEFKS GAGTELSVRAKPS |
| 10 | Wild-type D1 domain variant 10 | EEELQVIQPDKSVSVAAGESAILHCTVTSLIPVGPIQ WFRGAGPARELIYNQKEGHFPRVTTVSESTKREN MDFSISISNITPADAGTYYCVKFRKGSPDTEFKSGA GTELSVRAKPS |
| 11 | Wild-type pan-D1 domain | EEX$_1$LQVIQPDKX$_2$VX$_3$VAAGEX$_4$AX$_5$LX$_6$CTX$_7$TSLI PVGPIQWFRGAGPX$_8$RELIYNQKEGHFPRVTTVSX$_9$ X$_{10}$TKRX$_{11}$NMDFX$_{12}$IX$_{13}$IX$_{14}$NITPADAGTYYCVKFR KGSX$_{15}$X$_{16}$DX$_{17}$EFKSGAGTELSVRX$_{18}$KPS |
| | Amino acid substitutions relative to SEQ ID NO: 11 | X$_1$ is E or G; X$_2$ is S or F; X$_3$ is L or S; X$_4$ is T or S; X$_5$ is T or I; X$_6$ is R, H, or L; X$_7$ is A or V; X$_8$ is G or A; X$_9$ is D or E; X$_{10}$ is L or S; X$_{11}$ is N or E or D; X$_{12}$ is S or P; X$_{13}$ is R or S; X$_{14}$ is G or S; X$_{15}$ is P or absent; X$_{16}$ is D or P; X$_{17}$ is V or T; and X$_{18}$ is A or G |

As used herein, the terms "high affinity SIRP-α D1 variant," "high affinity SIRP-α variant," or "SIRP-α D1 variant" refers to a polypeptide comprising a SIRP-α D1 domain or a CD47-binding portion of a SIRP-α polypeptide that has a higher affinity to CD47 than wild-type SIRP-α. A high affinity SIRP-α D1 variant comprises at least one amino acid substitution, deletion, or insertion (or a combination thereof) relative to a wild-type SIRP-α.

In some embodiments, high affinity SIRP-α D1 variants disclosed herein comprise a SIRP-α D1 domain or variant thereof. In some embodiments, a high affinity SIRP-α D1 variant comprises one or more amino acid substitutions, insertions, additions, or deletions relative to a wild-type D1 domain shown in SEQ ID NOs: 1-10. Table 2 lists exemplary amino acid substitutions in each SIRP-α D1 domain variant (SEQ ID NOs: 13-22). In some embodiments, the SIRP-α D1 domain polypeptide or high affinity SIRP-α D1 variant comprises a fragment of the D1 domain. In some embodiments, the SIRP-α polypeptide fragment or high affinity SIRP-α variant fragment comprises an amino acid sequence of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. In some embodiments, the SIRP-α D1 domain fragments retain the ability to bind to CD47.

In some embodiments, a polypeptide of the disclosure comprising a high affinity SIRP-α D1 variant binds with higher binding affinity to CD47 than a wild-type human SIRP-α D1 domain. In some embodiments, the high affinity SIRP-α D1 variant binds to human CD47 with at least 1-fold (e.g., at least 1.5-fold, 2-fold, 2.5-fold, 3-fold, 3.5-fold, 4-fold, 5-fold or greater than 5-fold) affinity than the affinity of a naturally occurring D1 domain. In some embodiments, the high affinity SIRP-α D1 variant binds to human CD47 with at least 1-fold (e.g., at least 10-fold, 100-fold, 1000-fold or greater than 1000-fold) affinity than the affinity of a naturally occurring D1 domain.

As used herein, the term "optimized affinity" or "optimized binding affinity" refers to an optimized strength of the binding interaction between a polypeptide disclosed herein, including a high affinity SIRP-α D1 variant, and CD47. For example, in some embodiments, the polypeptide binds primarily or with higher affinity to CD47 on cancer cells and does not substantially bind or binds with lower affinity to CD47 on non-cancer cells. In some embodiments, the binding affinity between the polypeptide and CD47 is optimized such that the interaction does not cause clinically relevant toxicity or decreases toxicity compared to a variant which binds with maximal affinity. In some embodiments, in order to achieve an optimized binding affinity between a polypeptide provided herein and CD47, the polypeptide including a high affinity SIRP-α D1 variant is developed to have a lower binding affinity to CD47 than which is maximally achievable. In some embodiments, the high affinity SIRP-α variants disclosed herein cross react with rodent, non-human primate (NHP), and human CD47.

As used herein, the term "immunogenicity" refers to the property of a protein (e.g., a therapeutic protein) which causes an immune response in the host as though it is a foreign antigen. The immunogenicity of a protein can be assayed in vitro in a variety of different ways, such as through in vitro T-cell proliferation assays.

As used herein, the term "minimal immunogenicity" refers to an immunogenicity of a protein (e.g., a therapeutic protein) that has been modified, e.g., through amino acid substitutions, to be lower (e.g., at least 10%, 25%, 50%, or 100% lower) than the immunogenicity before the amino acid substitutions are introduced (e.g., an unmodified protein). In some embodiments, a protein (e.g., a therapeutic protein) is modified to have minimal immunogenicity and causes no or very little host immune response even though it is a foreign antigen.

In some embodiments, the high affinity SIRP-α D1 variant has minimal immunogenicity. In some embodiments, a SIRP-α polypeptide of the disclosure administered to a subject has the same amino acid sequence as that of the SIRP-α polypeptide in a biological sample of the subject, except for amino acid changes which increase affinity of the SIRP-α D1 variant. In some embodiments, the polypeptide variants disclosed herein lower the risk of side effects compared to anti-CD47 antibodies or wild-type SIRP-α. In some embodiments, the polypeptide variants disclosed herein lower the risk of anemia compared to anti-CD47 antibodies or wild-type SIRP-α. In some embodiments, the polypeptide variants disclosed herein do not cause acute anemia in rodent or non-human primates (NHP) studies.

Table 2 lists specific amino acid substitutions in a high affinity SIRP-α D1 variant relative to each D1 domain sequence. In some embodiments, a high affinity SIRP-α D1 variant includes one or more (e.g., two, three, four, five, six, seven, eight, nine, ten, eleven, twelve, thirteen, fourteen or more) of the substitutions listed in Table 2. In some embodiments, a high affinity SIRP-α D1 variant includes at most fourteen amino acid substitutions relative to a wild-type D1 domain. In some embodiments, a high affinity SIRP-α D1 variant includes at most ten amino acid substitutions relative to a wild-type D1 domain. In some embodiments, a high affinity SIRP-α D1 variant includes at most seven amino acid substitutions relative to a wild-type D1 domain. In some embodiments, a high affinity SIRP-α D1 variant of the disclosure has at least 90% (e.g., at least 92%, 95%, 97% or greater than 97%) amino acid sequence identity to a sequence of a wild-type D1 domain.

In some embodiments, a high affinity SIRP-α D1 variant is a chimeric high affinity SIRP-α D1 variant that includes a portion of two or more wild-type D1 domains or variants thereof (e.g., a portion of one wild-type D1 domain or variant thereof and a portion of another wild-type D1 domain or variant thereof). In some embodiments, a chimeric high affinity SIRP-α D1 variant includes at least two portions (e.g., three, four, five or more portions) of wild-type D1 domains or variants thereof, wherein each of the portions is from a different wild-type D1 domain. In some embodiments, a chimeric high affinity SIRP-α D1 variant further includes one or more amino acid substitutions listed in Table 2.

TABLE 2

Amino Acid Substitutions in a High Affinity SIRP-a D1 Variant

| SEQ ID NO: | Description | Amino Acid Sequence |
|---|---|---|
| 13 | D1 domain v1 | EEEX$_1$QX$_2$IQPDKSVLVAAGETX$_3$TLRCTX$_4$TSLX$_5$PV GPIQWFRGAGPGRX$_6$LIYNQX$_7$X$_8$GX$_9$FPRVTTVSDX$_{10}$ TX$_{11}$RNNMDFSIRIGNITPADAGTYYCX$_{12}$KX$_{13}$RKGS PDDVEX$_{14}$KSGAGTELSVRAKPS |
| — | Amino acid substitutions relative to SEQ ID NO: 13 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = V, I; X$_{13}$ = F, L, V; X$_{14}$ = F, V |
| 14 | D1 domain v2 | EEEX$_1$QX$_2$IQPDKSVSVAAGESX$_3$ILHCTX$_4$TSLX$_5$PVG PIQWFRGAGPARX$_6$LIYNQX$_7$X$_8$GX$_9$FPRVTTVSEX$_{10}$T X$_{11}$RENMDFSISISNITPADAGTYYCX$_{12}$KX$_{13}$RKGSPD TEX$_{14}$KSGAGTELSVRAKPS |
| — | Amino acid substitutions relative to SEQ ID NO: 14 | X$_1$ = L, I, V; X$_2$ = V, L, I; X$_3$ = A, V; X$_4$ = V, I, L; Xs = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = V, I; X$_{13}$ = F, L, V; X$_{14}$ = F, V |
| 15 | D1 domain v3 | EEEX$_1$QX$_2$IQPDKSVSVAAGESX$_3$ILLCTX$_4$TSLX$_5$PVG PIQWFRGAGPARX$_6$LIYNQX$_7$X$_8$GX$_9$FPRVTTVSEX$_{10}$T X$_{11}$RENMDFSISISNITPADAGTYYCX$_{12}$KX$_{13}$RKGSPD TEX$_{14}$KSGAGTELSVRAKPS |
| — | Amino acid substitutions relative to SEQ ID NO: 15 | X$_1$ = L, I, V; X$_2$ = V, L, I; X$_3$ = A, V; X$_4$ = V, I, L; Xs = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = V, I; X$_{13}$ = F, L, V; X$_{14}$ = F, V |
| 16 | D1 domain v4 | EEGX$_1$QX$_2$IQPDKSVSVAAGESX$_3$ILHCTX$_4$TSLX$_5$PVG PIQWFRGAGPGRX$_6$LIYNQX$_7$X$_8$GX$_9$FPRVTTVSDX$_{10}$ TX$_{11}$RNNMDFSIRIGNITPADAGTYYCX$_{12}$KX$_{13}$RKGSP DDVEX$_{14}$KSGAGTELSVRAKPS |
| — | Amino acid substitutions relative to SEQ ID NO: 16 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = V, I; X$_{13}$ = F, L, V; X$_{14}$ = F, V |
| 17 | D1 domain v5 | EEEX$_1$QX$_2$IQPDKFVLVAAGETX$_3$TLRCTX$_4$TSLX$_5$PV GPIQWFRGAGPGRX$_6$LIYNQX$_7$X$_8$GX$_9$FPRVTTVSDX$_{10}$ TX$_{11}$RNNMDFSIRIGNITPADAGTYYCX$_{12}$KX$_{13}$RKGS PDDVEX$_{14}$KSGAGTELSVRAKPS |

TABLE 2-continued

Amino Acid Substitutions in a High Affinity SIRP-a D1 Variant

| SEQ ID NO: | Description | Amino Acid Sequence |
|---|---|---|
| — | Amino acid substitutions relative to SEQ ID NO: 17 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = V, I; $X_{13}$ = F, L, V; $X_{14}$ = F, V |
| 18 | D1 domain v6 | EEE$X_1$Q$X_2$IQPDKSVLVAAGET$X_3$TLRCT$X_4$TSL$X_5$PVGPIQWFRGAGPGR$X_6$LIYNQ$X_7$$X_8$G$X_9$FPRVTTVSD$X_{10}$T$X_{11}$RNNMDFPIRIGNITPADAGTYYC$X_{12}$K$X_{13}$RKGSPDDVE$X_{14}$KSGAGTELSVRAKPS |
| — | Amino acid substitutions relative to SEQ ID NO: 18 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = V, I; $X_{13}$ = F, L, V; $X_{14}$ = F, V |
| 19 | D1 domain v7 | EEE$X_1$Q$X_2$IQPDKSVSVAAGES$X_3$ILHCT$X_4$TSL$X_5$PVGPIQWFRGAGPAR$X_6$LIYNQ$X_7$$X_8$G$X_9$FPRVTTVSE$X_{10}$T$X_{11}$RENMDFSISISNITPADAGTYYC$X_{12}$K$X_{13}$RKGSPDTE$X_{14}$KSGAGTELSVRGKPS |
| — | Amino acid substitutions relative to SEQ ID NO: 19 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_r$ = E, Q; $X_9$ = H, P, R; $X_{10}$ = S, T, G; $X_{11}$ = K, R; $X_{12}$ = V, I; $X_{13}$ = F, L, V; $X_{14}$ = F, V |
| 20 | D1 domain v8 | EEE$X_1$Q$X_2$IQPDKSVLVAAGET$X_3$TLRCT$X_4$TSL$X_5$PVGPIQWFRGAGPAR$X_6$LIYNQ$X_7$$X_8$G$X_9$FPRVTTVSE$X_{10}$T$X_{11}$RENMDFSISISNITPADAGTYYC$X_{12}$K$X_{13}$RKGSPDTE$X_{14}$KSGAGTELSVRAKPS |
| — | Amino acid substitutions relative to SEQ ID NO: 20 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = V, I; $X_{13}$ = F, L, V; $X_{14}$ = F, V |
| 21 | D1 domain v9 | EEE$X_1$Q$X_2$IQPDKSVLVAAGET$X_3$TLRCT$X_4$TSL$X_5$PVGPIQWFRGAGPGR$X_6$LIYNQ$X_7$$X_8$G$X_9$FPRVTTVSD$X_{10}$T$X_{11}$RNNMDFSIRISNITPADAGTYYC$X_{12}$K$X_{13}$RKGSPDDVE$X_{14}$KSGAGTELSVRAKPS |
| — | Amino acid substitutions relative to SEQ ID NO: 21 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = V, I; $X_{13}$ = F, L, V; $X_{14}$ = F, V |
| 22 | D1 domain v10 | EEE$X_1$Q$X_2$IQPDKSVSVAAGES$X_3$ILHCT$X_4$TSL$X_5$PVGPIQWFRGAGPAR$X_6$LIYNQ$X_7$$X_8$G$X_9$FPRVTTVSE$X_{10}$T$X_{11}$RENMDFSISISNITPADAGTYYC$X_{12}$K$X_{13}$RKGSPDTE$X_{14}$KSGAGTELSVRAKPS |
| — | Amino acid substitutions relative to SEQ ID NO: 22 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = V, I; $X_{13}$ = F, L, V; $X_{14}$ = F, V |
| 23 | Pan D1 domain | EE$X_1$$X_2$Q$X_3$IQPDK$X_4$V$X_5$VAAGE$X_6$$X_7$$X_8$L$X_9$CT$X_{10}$TSL$X_{11}$PVGPIQWFRGAGP$X_{12}$R$X_{13}$LIYNQ$X_{14}$$X_{15}$G$X_{16}$FPRVTTVS$X_{17}$$X_{18}$T$X_{19}$R$X_{20}$NMDF$X_{21}$I$X_{22}$I$X_{23}$NITPADAGTYYC$X_{24}$K$X_{25}$RKGSPD$X_{26}$$X_{27}$E$X_{28}$KSGAGTELSVR$X_{29}$KPS |
| — | Amino acid substitutions relative to SEQ ID NO: 23 | $X_1$ = E, G; $X_2$ = L, I, V; $X_3$ = V, L, I; $X_4$ = S, F; $X_5$ = L, S; $X_6$ = S, T; $X_7$ = A, V; $X_8$ = I, T; $X_9$ = H, R; $X_{10}$ = A, V, I, L; $X_{11}$ = I, T, S, F; $X_{12}$ = A, G; $X_{13}$ = E, V, L; $X_{14}$ = K, R; $X_{15}$ = E, Q; $X_{16}$ = H, P, R; $X_{17}$ = D, E; $X_{18}$ = S, L, T, G; $X_{19}$ = K, R; $X_{20}$ = E, D; $X_{21}$ = S, P; $X_{22}$ = S, R; $X_{23}$ = S, G; $X_{24}$ = V, I; $X_{25}$ = F, L, V; $X_{26}$ = D or absent; $X_{27}$ = T, V; $X_{28}$ = F, V; and $X_{29}$ = A, G |

In some embodiments, a polypeptide includes a SIRP-α D1 variant having a sequence of: EEE$X_1$Q$X_2$IQPDKSVLVAAGET$X_3$TLRCT$X_4$TSL$X_5$PVGPIQWFRGAGPGR$X_6$LIYNQ$X_7$$X_8$G$X_9$FPRVTTVSD$X_{10}$T$X_{11}$RNNMDFSIRIGNITPADAGTYYC$X_{12}$K$X_{13}$RKGSPDDVE$X_{14}$KSGAGTELSVRAKPS (SEQ ID NO: 13), wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is L, T, or G; $X_{11}$ is K or R; $X_{12}$ is V or I; $X_{13}$ is F, L, or V; and $X_{14}$ is F or V; and wherein the variant has at least one amino acid substitution relative to a wild-type SIRP-α D1 domain having the sequence of SEQ ID NO: 1.

In some embodiments, a polypeptide includes a SIRP-α D1 variant having a sequence of: EEGX$_1$QX$_2$IQPDKSVSVAAGESX$_3$ILHCTX$_4$TSLX$_5$PVGPIQWFRGAGPGRX$_6$LIYNQX$_7$X$_8$GX$_9$FPRVTTVSDX$_{10}$TX$_{11}$RNNMDFSIRIGNITPADAGTYYCX$_{12}$KX$_{13}$RKGSPDDVEX$_{14}$KSGAGTELSVRAKPS (SEQ ID NO: 16), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 4.

In some embodiments, a polypeptide includes a SIRP-α D1 variant having a sequence of: EEEX$_1$QX$_2$IQPDKFVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFSIRIGNITPADAGTYYCX$_{12}$KX$_{13}$RKGSPDDVEX$_{14}$KSGAGTELSVRAKPS (SEQ ID NO: 17), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 5.

In some embodiments, a polypeptide includes a SIRP-α D1 variant having a sequence of: EEEX$_1$QX$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFPIRIGNITPADAGTYYCX$_{12}$KX$_{13}$RKGSPDDVEX$_{14}$KSGAGTELSVRAKPS (SEQ ID NO: 18), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 6.

In some embodiments, a polypeptide includes a SIRP-α D1 variant having a sequence of: EEEX$_1$QX$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFSIRISNITPADAGTYYCX$_{12}$KX$_{13}$RKGSPDDVEX$_{14}$KSGAGTELSVRAKPS (SEQ ID NO: 21), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 9.

In any of the aforementioned embodiments, a polypeptide includes a high affinity SIRP-α D1 variant having a sequence of any one of SEQ ID NOs: 13, 16-18, and 21, wherein X$_1$ is L, I, or V. In any of the aforementioned embodiments, X$_2$ is V, L, or, I. In any of the aforementioned embodiments, X$_3$ is A or V. In any of the aforementioned embodiments, X$_4$ is A, I, or L. In any of the aforementioned embodiments, X$_5$ is I, T, S, or F. In any of the aforementioned embodiments, X$_6$ is E, V, or L. In any of the aforementioned embodiments, X$_7$ is K or R. In any of the aforementioned embodiments, X$_8$ is E or Q. In any of the aforementioned embodiments, X$_9$ is H, P, or R. In any of the aforementioned embodiments, X$_{10}$ is L, T, or G. In any of the aforementioned embodiments, X$_{11}$ is K or R. In any of the aforementioned embodiments, X$_{12}$ is V or I. In any of the aforementioned embodiments, X$_{13}$ is F, L, V. In any of the aforementioned embodiments, X$_{14}$ is F or V. In some embodiments, the polypeptide of this aspect of the disclosure includes no more than six amino acid substitutions relative to the wild-type SIRP-α D1 domain having the sequence of any one of SEQ ID NOs: 1, 4-6, and 9.

In some embodiments, the polypeptide binds CD47 with at least 10-fold greater binding affinity than the wild-type SIRP-α D1 domain having the sequence of any one of SEQ ID NOs: 1, 4-6, and 9. In some embodiments, the polypeptide binds CD47 with at least 100-fold greater binding affinity than the wild-type SIRP-α D1 domain having the sequence of any one of SEQ ID NOs: 1, 4-6, and 9. In some embodiments, the polypeptide binds CD47 with at least 1000-fold greater binding affinity than the wild-type SIRP-α D1 domain having the sequence of any one of SEQ ID NOs: 1, 4-6, and 9. In some embodiments, a SIRP-α D1 variant polypeptide or fragment thereof binds to CD47 with a K$_D$ less than 1×10$^{-8}$M less than 5×10$^{-8}$ M, less than 1×10$^{-9}$M, less 5×10$^{-10}$ M, less than 1×10$^{-10}$M or less than 1×10$^{-11}$ M. In some embodiments, a SIRP-α D1 variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRP-α D1 variant having a sequence of: EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRAKPS (SEQ ID NO: 14), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 2.

In some embodiments, a polypeptide includes a SIRP-α D1 variant having a sequence of: EEEX$_1$QX$_2$IQPDKSVSVAAGESX$_3$ILLCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRAKPS (SEQ ID NO: 15), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 3.

In some embodiments, a polypeptide includes a SIRP-α D1 variant having a sequence of: EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRGKPS (SEQ ID NO: 19), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 7.

In some embodiments, a polypeptide includes a SIRP-α D1 variant having a sequence of: EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRAKPS (SEQ ID NO: 22), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 10.

In any of the aforementioned embodiments in this aspect of the disclosure, the polypeptide has the sequence of any one of SEQ ID NOs: 14, 15, 19, and 22, wherein X$_1$ is L, I, or V. In any of the aforementioned embodiments, X$_2$ is V, L, or, I. In any of the aforementioned embodiments, X$_3$ is A or V. In any of the aforementioned embodiments, X$_4$ is V, I, or L. In any of the aforementioned embodiments, X$_5$ is I, T, S, or F. In any of the aforementioned embodiments, X$_6$ is E, V, or L. In any of the aforementioned embodiments, X$_7$ is K or R. In any of the aforementioned embodiments, X$_8$ is E or Q. In any of the aforementioned embodiments, X$_9$ is H, P, or R. In any of the aforementioned embodiments, X$_{10}$ is S, T, or G. In any of the aforementioned embodiments, X$_{11}$ is K or R. In any of the aforementioned embodiments, X$_{12}$ is V or I. In any of the aforementioned embodiments, X$_{13}$ is F, L, or V. In any of the aforementioned embodiments, X$_{14}$ is F or V. In some embodiments, the polypeptide of this aspect of the disclosure includes no more than six amino acid substitutions relative to the wild-type SIRP-α D1 domain having the sequence of any one of SEQ ID NOs: 2, 3, 7, and 10.

In some embodiments, the polypeptide binds CD47 with at least 10-fold greater binding affinity than the wild-type SIRP-α D1 domain having the sequence of any one of SEQ ID NOs: 2, 3, 7, and 10. In some embodiments, the polypeptide binds CD47 with at least 100-fold greater binding affinity than the wild-type SIRP-α D1 domain having the sequence of any one of SEQ ID NOs: 2, 3, 7, and 10. In some embodiments, the polypeptide binds CD47 with at least 1000-fold greater binding affinity than the wild-type SIRP-α D1 domain having the sequence of any one of SEQ ID NOs: 2, 3, 7, and 10. In some embodiments, a SIRP-α D1 variant polypeptide or fragment thereof binds to CD47 with a K$_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRP-α D1 variant having a sequence of: EEEX$_1$QX$_2$IQPDKSVLVAAGETX$_3$TLRCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRAKPS (SEQ ID NO: 20), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant has at least one amino acid substitution relative to a wild-type SIRP-α D1 domain having the sequence of SEQ ID NO: 8.

In some embodiments, the polypeptide has the sequence of SEQ ID NO: 20, wherein X$_1$ is L, I, or V. In any of the aforementioned embodiments in this aspect of the disclosure, X$_2$ is V, L, or, I. In any of the aforementioned embodiments, X$_3$ is A or V. In any of the aforementioned embodiments, X$_4$ is A, I, or L. In any of the aforementioned embodiments, X$_5$ is I, T, S, or F. In any of the aforementioned embodiments, X$_6$ is E, V, or L. In any of the aforementioned embodiments, X$_7$ is K or R. In any of the aforementioned embodiments, X$_8$ is E or Q. In any of the aforementioned embodiments, X$_9$ is H, P, or R. In any of the aforementioned embodiments, X$_{10}$ is S, T, or G. In any of the aforementioned embodiments, X$_{11}$ is K or R. In any of the aforementioned embodiments, X$_{12}$ is V or I. In any of the aforementioned embodiments, X$_{13}$ is F, L, or V. In any of the aforementioned embodiments, X$_{14}$ is F or V. In some embodiments, the polypeptide of this aspect of the disclosure includes no more than six amino acid substitutions relative to the wild-type SIRP-α D1 domain having the sequence of SEQ ID NO: 8.

In some embodiments, the polypeptide binds CD47 with at least 10-fold greater binding affinity than the wild-type SIRP-α D1 domain having the sequence of SEQ ID NO: 8. In some embodiments, the polypeptide binds CD47 with at least 100-fold greater binding affinity than the wild-type SIRP-α D1 domain having the sequence of SEQ ID NO: 8. In some embodiments, the polypeptide binds CD47 with at least 1000-fold greater binding affinity than the wild-type SIRP-α D1 domain having the sequence of SEQ ID NO: 8. In some embodiments, a SIRP-α D1 variant polypeptide or fragment thereof binds to CD47 with a K$_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRP-α D1 variant having a sequence of: EEX$_1$X$_2$QX$_3$IQPDKX$_4$VX$_5$VAAGEX$_6$X$_7$X$_8$LX$_9$CTX$_{10}$TSLX$_{11}$PVGPIQWFRGAGPX$_{12}$RX$_{13}$LIYNQX$_{14}$X$_{15}$GX$_{16}$FPRVTTVSX$_{17}$X$_{18}$TX$_{19}$RX$_{20}$NMDFX$_{21}$IX$_{22}$IX$_{23}$NITPADAGTYYCX$_{24}$KX$_{25}$RKGSPDX$_{26}$X$_{27}$EX$_{28}$KSGAGTELSVRX$_{29}$KPS (SEQ ID NO: 23), wherein X$_1$ is E or G; X$_2$ is L, I, or V; X$_3$ is V, L, or, I; X$_4$ is S or F; X$_5$ is L or S; X$_6$ is S or T; X$_7$ is A or V; X$_8$ is I or T; X$_9$ is H or R; X$_{10}$ is A, V, I, or L; X$_{11}$ is I, T, S, or F; X$_{12}$ is A or G; X$_{13}$ is E, V, or L; X$_{14}$ is K or R; X$_{15}$ is E or Q; X$_{16}$ is H, P, or R; X$_{17}$ is D or E; X$_{18}$ is S, L, T, or G; X$_{19}$ is K or R; X$_{20}$ is E or D; X$_{21}$ is S or P; X$_{22}$ is S or R; X$_{23}$ is S or G; X$_{24}$ is V or I; X$_{25}$ is F, L, V; X$_{26}$ is D or absent; X$_{27}$ is T or V; X$_{28}$ is F or V; and X$_{29}$ is A or G; and wherein the variant has at least one amino acid substitution relative to a wild-type SIRP-α D1 domain having the sequence of any one of SEQ ID NOs: 1-10.

In any of the aforementioned embodiments in this aspect of the disclosure, X$_2$ is L, I, or V. In any of the aforementioned embodiments, X$_3$ is V, L, or, I. In any of the aforementioned embodiments, X$_4$ is S or F. In any of the aforementioned embodiments, X$_5$ is L or S. In any of the aforementioned embodiments, X$_6$ is S or T. In any of the aforementioned embodiments, $X_7$ is A or V. In any of the aforementioned embodiments, $X_8$ is I or T. In any of the aforementioned embodiments, $X_9$ is H or R. In any of the aforementioned embodiments, $X_{10}$ is A, V, I, or L. In any of the aforementioned embodiments, $X_{11}$ is I, T, S, or F. In any of the aforementioned embodiments, $X_{12}$ is A or G. In any of the aforementioned embodiments, $X_{13}$ is E, V, or L. In any of the aforementioned embodiments, $X_{14}$ is K or R. In any of the aforementioned embodiments, $X_{15}$ is E or Q. In any of the aforementioned embodiments, $X_{16}$ is H, P, or R. In any of the aforementioned embodiments, $X_{17}$ is D or E. In any of the aforementioned embodiments, $X_{18}$ is S, L, T, or G. In any of the aforementioned embodiments, $X_{19}$ is K or R. In any of the aforementioned embodiments, $X_{20}$ is E or D. In any of the aforementioned embodiments, $X_{21}$ is S or P. In any of the aforementioned embodiments, $X_{22}$ is S or R. In any of the aforementioned embodiments, $X_{23}$ is S or G. In any of the aforementioned embodiments, $X_{24}$ is V or I. In any of the aforementioned embodiments, $X_{25}$ is F, L, V. In any of the aforementioned embodiments, $X_{26}$ is D or absent. In any of the aforementioned embodiments, $X_{27}$ is T or V. In any of the aforementioned embodiments, $X_{28}$ is F or V. In any of the aforementioned embodiments, $X_{29}$ is A or G. In some embodiments, the polypeptide of this aspect of the disclosure includes no more than six amino acid substitutions relative to the wild-type SIRP-α D1 domain having the sequence of any one of SEQ ID NOs: 1-10.

In some embodiments, the polypeptide binds CD47 with at least 10-fold greater binding affinity than the wild-type SIRP-α D1 domain having the sequence of any one of SEQ ID NOs: 1-10. In some embodiments, the polypeptide binds CD47 with at least 100-fold greater binding affinity than the wild-type SIRP-α D1 domain having the sequence of any one of SEQ ID NOs: 1-10. In some embodiments, the polypeptide binds CD47 with at least 1000-fold greater binding affinity than the wild-type SIRP-α D1 domain having the sequence of any one of SEQ ID NOs: 1-10. In some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide of the disclosure including a high affinity SIRP-α D1 variant further comprises a D2 domain having the sequence of SEQ ID NO: 24, a D3 domain having the sequence of SEQ ID NO: 25, or a D2 domain having the sequence of SEQ ID NO: 24 and a D3 domain having the sequence of SEQ ID NO: 25 of a wild-type human SIRP-α as shown in Table 3. In some embodiments, the high affinity SIRP-α D1 variant further comprises a fragment or variant of a D2 domain or a fragment or variant of a D3 domain. In some embodiments, the high affinity SIRP-α D1 variant further comprises a fragment or variant of a D2 domain and a fragment or variant of a D3 domain. In some embodiments, a high affinity SIRP-α D1 variant is joined to a D2 or D3 domain by way of a linker. In some embodiments, a high affinity SIRP-α D1 variant is joined to a D2 and D3 domain by way of a linker.

TABLE 3

Amino Acid Sequences of SIRP-α D2 and D3 Domains

| SEQ ID NO: | Description | Amino Acid Sequence |
|---|---|---|
| 24 | SIRP-α D2 domain | APVVSGPAARATPQHTVSFTC ESHGFSPRDITLKWFKNGNEL SDFQTNVDPVGESVSYSIHST AKVVLTREDVHSQVICEVAHV TLQGDPLRGTANLSETIR |
| 25 | SIRP-α D3 domain | VPPTLEVTQQPVRAENQVNVT CQVRKFYPQRLQLTWLENGNV SRTETASTVTENKDGTYNWMS WLLVNVSAHRDDVKLTCQVEH DGQPAVSKSHDLKVS |

In some embodiments, a polypeptide of the disclosure including a high affinity SIRP-α D1 variant is attached to an Fc domain monomer, a human serum albumin (HSA) or variant thereof, a serum-binding protein or peptide, or an organic molecule, e.g., a polymer (e.g., a PEG polymer), in order to improve the pharmacokinetic properties of the polypeptide, e.g., increase serum half-life. In some embodiments, a high affinity SIRP-α D1 variant is attached to an Fc domain monomer that is unable to dimerize. In some embodiments, Fc domain monomers, HSA proteins, serum-binding proteins or peptides, and organic molecules such as a PEG serve to increase the serum half-life of the polypeptides described herein. In some embodiments, a polypeptide of the disclosure including a high affinity SIRP-α D1 variant does not include the sequence of any one of SEQ ID NOs: 26-36 shown in Table 4.

TABLE 4

| SEQ ID NO: | Amino Acid Sequence |
|---|---|
| 26 | EEELQVIQPDKSVSVAAGESAILHCTI TSLIPVGPIQWFRGAGPARELIYNQRE GHFPRVTTVSETTRRENMDFSISISNI TPADAGTYYCVKFRKGSPDTEVKSGAG TELSVRAKPS |
| 27 | EEEVQVIQPDKSVSVAAGESAILHCTL TSLIPVGPIQWFRGAGPARVLIYNQRQ GHFPRVTTVSEGTRRENMDFSISISNI TPADAGTYYCIKFRKGSPDTEFKSGAG TELSVRAKPS |
| 28 | EEEVQIIQPDKSVSVAAGESVILHCTI TSLTPVGPIQWFRGAGPARLLIYNQRE GPFPRVTTVSETTRRENMDFSISISNI TPADAGTYYCVKLRKGSPDTEFKSGAG TELSVRAKPS |
| 29 | EEELQIIQPDKSVSVAAGESAILHCTI TSLSPVGPIQWFRGAGPARVLIYNQRQ GPFPRVTTVSEGTKRENMDFSISISNI TPADAGTYYCIKLRKGSPDTEFKSGAG TELSVRAKPS |
| 30 | EEEIQVIQPDKSVSVAAGESVIIHCTV TSLFPVGPIQWFRGAGPARVLIYNQRQ GRFPRVTTVSEGTKRENMDFSISISNI TPADAGTYYCVKVRKGSPDTEVKSGAG TELSVRAKPS |

TABLE 4-continued

| SEQ ID NO: | Amino Acid Sequence |
|---|---|
| 31 | EEEVQIIQPDKSVSVAAGESIILHCTV<br>TSLFPVGPIQWFRGAGPARVLIYNQRE<br>GRFPRVTTVSEGTRRENMDFSISISNI<br>TPADAGTYYCIKLRKGSPDTEFKSGAG<br>TELSVRAKPS |
| 32 | EEEVQLIQPDKSVSVAAGESAILHCTV<br>TSLFPVGPIQWFRGAGPARVLIYNQRE<br>GPFPRVTTVSEGTKRENMDFSISISNI<br>TPADAGTYYCIKFRKGSPDTEVKSGAG<br>TELSVRAKPS |
| 33 | EEELQIIQPDKSVLVAAGETATLRCTI<br>TSLFPVGPIQWFRGAGPGRVLIYNQRQ<br>GPFPRVTTVSDTTKRNNMDFSIRIGNI<br>TPADAGTYYCIKFRKGSPDDVEFKSGA<br>GTELSVRAKPS |
| 34 | EEELQIIQPDKSVSVAAGESAILHCTI<br>TSLFPVGPIQWFRGAGPARLLIYNQRQ<br>GPFPRVTTVSETTKRENMDFSISISNI<br>TPADAGTYYCVKFRKGSPDTEFKSGAG<br>TELSVRAKPS |
| 35 | EEEVQIIQPDKSVSVAAGESAILHCTI<br>TSLFPVGPIQWFRGAGPARVLIYNQKQ<br>GPFPRVTTISETTRRENMDFSISISNI<br>TPADAGTYYCIKFRKGSPDTEFKSGAG<br>TELSVRAKPS |
| 36 | EEELQIIQPDKSVSVAAGESAILHCTI<br>TSLTPVGPIQWFRGAGPARVLIYNQRQ<br>GPFPRVTTVSEGTRRENMDFSISISNI<br>TPADAGTYYCIKFRKGSPDTEVKSGAG<br>TELSVRAKPS |

In some embodiments, the polypeptides and polypeptide constructs described herein are utilized in vitro for binding assays, such as immune assays. For example, in some embodiments, the polypeptides and polypeptide constructs described herein are utilized in liquid phase or bound to a solid phase carrier. In some embodiments, polypeptides utilized for immunoassays are detectably labeled in various ways.

In some embodiments, polypeptides and polypeptide constructs described herein are bound to various carriers and used to detect the presence of specific antigen expressing cells. Examples of carriers include glass, polystyrene, polypropylene, polyethylene, dextran, nylon, amylases, natural and modified celluloses, polyacrylamides, agaroses, and magnetite. The nature of the carrier can be either soluble or insoluble.

Various different labels and methods of labeling are known. Examples of labels include enzymes, radioisotopes, fluorescent compounds, colloidal metals, chemiluminescent compounds, and bio-luminescent compounds. Various techniques for binding labels to polypeptides disclosed herein are available.

In some embodiments, the polypeptides are coupled to low molecular weight haptens. These haptens are then specifically detected by means of a second reaction. For example, in some embodiments, the hapten biotin is used with avidin or the haptens dinitrophenol, pyridoxal, or fluorescein are detected with specific anti-hapten antibodies (e.g., anti-dinitrophenol antibodies, anti-pyridoxal antibodies, and anti-fluorescein antibodies respectively).

II. High Affinity SIRP-α D1 Domains with Altered Glycosylation

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, a polypeptide in a composition disclosed herein comprises a high affinity SIRP-α D1 variant that has reduced or minimal glycosylation. The D1 domain of each of the ten wild-type human SIRP-α proteins (SEQ ID NOs: 1-10 in Table 1) contains a single potential N-linked glycosylation site at amino acid N80 in the sequence N80ITP. Expression of a SIRP-α D1 domain in Chinese Hamster Ovary (CHO) cells results in a major band of 16 kDa (non-glycosylated) and a minor band of higher molecular weight that was removed by Endo Hf. Endo Hf is a recombinant protein fusion of Endoglycosidase H and maltose binding protein. Endo Hf cleaves within the chitobiose core of high mannose and some hybrid oligosaccharides from N-linked glycoproteins. This implies that a proline at amino acid position 83 can reduce the efficiency of glycosylation, leading to a protein with different degrees of glycosylation and therefore heterogeneity. For drug development, heterogeneity can give rise to challenges in process development. Therefore, to investigate the possibility of generating homogenous, non-glycosylated forms of high affinity SIRP-α D1 variants, in some embodiments, amino acid N80 of a SIRP-α D1 variant is mutated to Ala. In some embodiments, to make a non-glycosylated, high affinity SIRP-α D1 variant, amino acid N80 in a high affinity SIRP-α D1 variant is replaced by any amino acid, including any naturally and non-naturally occurring amino acid, e.g., N80A and N80Q. In some embodiments, a high affinity SIRP-α D1 variant comprises an N80A mutation and at least 1 additional mutation (e.g., at least 2, 3, 4, 5, 6, 7, 8, 9, or 10 additional mutations or more). In some embodiments, the additional mutation is in the CD47 binding site. In some embodiments, the additional mutation is in the hydrophobic core of the D1 domain.

In some embodiments, a polypeptide in a composition disclosed herein includes a high affinity SIRP-α D1 variant that has increased glycosylation relative to a wild-type SIRP-α D1 domain. Another option to increase homogeneity of the final product is to enhance the efficiency of glycosylation at amino acid N80 and generate high affinity SIRP-α D1 variants with increased glycosylation relative to a wild-type. In some embodiments, the amino acid P83 in the sequence NITP83 affects the degree of glycosylation at amino acid N80. In some embodiments, changing P83 to any amino acid increases the efficiency of glycosylation at N80. In some embodiments, amino acid P83 in a high affinity SIRP-α D1 variant is replaced by any amino acid, including naturally and non-naturally amino acids, e.g., P83V, P83A, P83I, and P83L. In some embodiments, a polypeptide of the disclosure is expressed in a cell that is optimized not to glycosylate proteins that are expressed by such cell, for example by genetic engineering of the cell line (e.g., genetically engineered yeast or mammalian host) or modifications of cell culture conditions such as addition of kifunensine or by using a naturally non-glycosylating host such as a prokaryote (E. coli, etc.).

Table 5 lists specific amino acid substitutions in a high affinity SIRP-α D1 variant relative to each D1 domain variant sequence. In some embodiments, a high affinity SIRP-α D1 variant includes one or more (e.g., two, three, four, five, six, seven, eight, nine, ten, eleven, twelve, thirteen, fourteen or more) of the substitutions listed in Table 5. In some embodiments, the SIRP-α D1 variants are not glycosylated or are minimally glycosylated. In some embodiments, the SIRP-α D1 variants are fully glycosylated or almost fully glycosylated. In some embodiments, a high affinity SIRP-α D1 variant includes at most fourteen amino acid substitutions relative to a wild-type D1 domain. In some embodiments, a high affinity SIRP-α D1 variant includes at most ten amino acid substitutions relative to a wild-type D1 domain. In some embodiments, a high affinity SIRP-α D1 variant includes at most seven amino acid substitutions relative to a wild-type D1 domain. In some embodiments, a high affinity SIRP-α D1 variant of the disclosure has at least 90% (e.g., at least 92%, 95%, 97% or greater than 97%) amino acid sequence identity to a sequence of a wild-type D1 domain.

In some embodiments, a high affinity SIRP-α D1 variant is a chimeric high affinity SIRP-α D1 variant that includes a portion of two or more wild-type D1 domains or variants thereof (e.g., a portion of one wild-type D1 domain or variant thereof and a portion of another wild-type D1 domain or variant thereof). In some embodiments, a chimeric high affinity SIRP-α D1 variant includes at least two portions (e.g., three, four, five or more portions) of wild-type D1 domains or variants thereof, wherein each of the portions is from a different wild-type D1 domain. In some embodiments, a chimeric high affinity SIRP-α D1 variant further includes one or more amino acid substitutions listed in Table 5.

TABLE 5

Amino Acid Substitutions in a High Affinity SIRP-α D1 Variant

| SEQ ID NO: | Description | Amino Acid Sequence |
|---|---|---|
| 37 | D1 domain v1 | EEEX$_1$QX$_2$IQPDKSVLVAAGETX$_3$TLRCTX$_4$TSLX$_5$PV GPIQWFRGAGPGRX$_6$LIYNQX$_7$X$_8$GX$_9$FPRVTTVSDX$_10$ TX$_{11}$RNNMDFSIRIGX$_{12}$ITX$_{13}$ADAGTYYCX$_{14}$KX$_{15}$RK GSPDDVEX$_{16}$KSGAGTELSVRAKPS |
| — | Amino acid substitutions relative to SEQ ID NO: 37 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 38 | D1 domain v2 | EEEX$_1$QX$_2$IQPDKSVSVAAGESX$_3$ILHCTX$_4$TSLX$_5$PVG PIQWFRGAGPARX$_6$LIYNQX$_7$X$_8$GX$_9$FPRVTTVSEX$_{10}$T X$_{11}$RENMDFSISISX$_{12}$ITX$_{13}$ADAGTYYCX$_{14}$KX$_{15}$RKGS PDTEX$_{16}$KSGAGTELSVRAKPS |
| — | Amino acid substitutions relative to SEQ ID NO: 38 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$p = H, P, R; X$_{10}$ = S, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 39 | D1 domain v3 | EEEX$_1$QX$_2$IQPDKSVSVAAGESX$_3$ILLCTX$_4$TSLX$_5$PVG PIQWFRGAGPARX$_6$LIYNQX$_7$X$_8$GX$_9$FPRVTTVSEX$_{10}$T X$_{11}$RENMDFSISISX$_{12}$ITX$_{13}$ADAGTYYCX$_{14}$KX$_{15}$RKGS PDTEX$_{16}$KSGAGTELSVRAKPS |
| — | Amino acid substitutions relative to SEQ ID NO: 39 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 40 | D1 domain v4 | EEGX$_1$QX$_2$IQPDKSVSVAAGESX$_3$ILHCTX$_4$TSLX$_5$PVG PIQWFRGAGPGRX$_6$LIYNQX$_7$X$_8$GX$_9$FPRVTTVSDX$_{10}$ TX$_{11}$RNNMDFSIRIGX$_{12}$ITX$_{13}$ADAGTYYCX$_{14}$KX$_{15}$RK GSPDDVEX$_{16}$KSGAGTELSVRAKPS |
| — | Amino acid substitutions relative to SEQ ID NO: 40 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 41 | D1 domain v5 | EEEX$_1$QX$_2$IQPDKFVLVAAGETX$_3$TLRCTX$_4$TSLX$_5$PV GPIQWFRGAGPGRX$_6$LIYNQX$_7$X$_8$GX$_9$FPRVTTVSDX$_{10}$ TX$_{11}$RNNMDFSIRIGX$_{12}$ITX$_{13}$ADAGTYYCX$_{14}$KX$_{15}$RK GSPDDVEX$_{16}$KSGAGTELSVRAKPS |

TABLE 5-continued

Amino Acid Substitutions in a High Affinity SIRP-α D1 Variant

| SEQ ID NO: | Description | Amino Acid Sequence |
|---|---|---|
| — | Amino acid substitutions relative to SEQ ID NO: 41 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 42 | D1 domain v6 | EEEX$_1$QX$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFPIRIGX$_{12}$ITX$_{13}$ADAGTYYCX$_{14}$KX$_{15}$RKGSPDDVEX$_{16}$KSGAGTELSVRAKPS |
| — | Amino acid substitutions relative to SEQ ID NO: 42 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 43 | D1 domain v7 | EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISX$_{12}$ITX$_{13}$ADAGTYYCX$_{14}$KX$_{15}$RKGSPDTEX$_{16}$KSGAGTELSVRGKPS |
| — | Amino acid substitutions relative to SEQ ID NO: 43 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 44 | D1 domain v8 | EEEX$_1$QX$_2$IQPDKSVLVAAGETX$_3$TLRCTX$_4$TSLX$_5$PVGPIQWFRGAGPARX$_6$LIYNQX$_7$X$_8$GX$_9$FPRVTTVSEX$_{10}$TX$_{11}$RENMDFSISISX$_{12}$ITX$_{13}$ADAGTYYCX$_{14}$KX$_{15}$RKGSPDTEX$_{16}$KSGAGTELSVRAKPS |
| — | Amino acid substitutions relative to SEQ ID NO: 44 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 45 | D1 domain v9 | EEEX$_1$QX$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFSIRISX$_{12}$ITX$_{13}$ADAGTYYCX$_{14}$KX$_{15}$RKGSPDDVEX$_{16}$KSGAGTELSVRAKPS |
| — | Amino acid substitutions relative to SEQ ID NO: 45 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 46 | D1 domain v10 | EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISX$_{12}$ITX$_{13}$ADAGTYYCX$_{14}$KX$_{15}$RKGSPDTEX$_{16}$,KSGAGTELSVRAKPS |
| — | Amino acid substitutions relative to SEQ ID NO: 46 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 47 | Pan D1 domain | EEX$_1$X$_2$QX$_3$IQPDKX$_4$VX$_5$VAAGEX$_6$X$_7$X$_8$LX$_9$CTX$_{10}$TSLX$_{11}$PVGPIQWFRGAGPX$_{12}$RX$_{13}$LIYNQX$_{14}$X$_{15}$GX$_{16}$FPRVTTVSX$_{17}$X$_{18}$TX$_{19}$RX$_{20}$NMDFX$_{21}$IX$_{22}$IX$_{23}$X$_{24}$ITX$_{25}$ADAGTYYCX$_{26}$KX$_{27}$RKGSPDX$_{28}$X$_{29}$EX$_{30}$KSGAGTELSVRX$_{31}$KPS |
| — | Amino acid substitutions relative to SEQ ID NO: 47 | $X_1$ = E, G; $X_2$ = L, I, V; $X_3$ = V, L, I; $X_4$ = S, F; $X_5$ = L, S; $X_6$ = S, T; $X_7$ = A, V; $X_8$ = I, T; $X_9$ = H, R, L; $X_{10}$ = A, V, I, L; $X_{11}$ = I, T, S, F; $X_{12}$ = A, G; $X_{13}$ = E, V, L; $X_{14}$ = K, R; $X_{15}$ = E, Q; $X_{16}$ = H, P, R; $X_{16}$ = D, E; $X_{18}$ = S, L, T, G; $X_{19}$ = K, R; $X_{20}$ = E, N; $X_{21}$ = S, P; $X_{22}$ = S, R; $X_{23}$ = S, G; $X_{24}$ = any amino acid; $X_{25}$ = any amino acid; $X_{26}$ = V, I; $X_{27}$ = F, L, V; $X_{28}$ = D or absent; $X_{29}$ = T, V; $X_{30}$ = F, V; and $X_{31}$ = A, G |
| 48 | Pan D1 domain | EEELQX$_1$IQPDKSVX$_2$VAAGEX$_3$AX$_4$LX$_5$CTX$_6$TSLX$_7$PVGPIQWFRGAGPX$_8$RX$_9$LIYNQX$_{10}$X$_{11}$GX$_{12}$FPRVTTVSX$_{13}$X$_{14}$TKRX$_{15}$NMDFSIX$_{16}$IX$_{17}$X$_{18}$ITPADAGTYYCX$_{19}$KFRKGX$_{20}$X$_{21}$X$_{22}$DX$_{23}$EFKSGAGTELSVRAKPS |

TABLE 5 -continued

Amino Acid Substitutions in a High Affinity SIRP-α D1 Variant

| SEQ ID NO: | Description | Amino Acid Sequence |
|---|---|---|
| — | Amino acid substitutions relative to SEQ ID NO: 48 | $X_1$ = V, I; $X_2$ = L, S; $X_3$ = T, S; $X_4$ = T, I; $X_5$ = R, H; $X_6$ = A, V, I; $X_7$ = I, R, Y, K, F; $X_8$ = G, A; $X_9$ = E, V; $X_{10}$ = K, R; $X_{11}$ = E, D, Q; $X_{12}$ = H, P; $X_{13}$ = D, E; $X_{14}$ = S, L, T; $X_{15}$ = N, E; $X_{16}$ = R, S; $X_{17}$ = G, S; $X_{18}$ = N, A; $X_{19}$ = V, I; $X_{20}$ = S, I, M; $X_{21}$ = P or absent; $X_{22}$ = D, P; and $X_{23}$ = V, T |
| 49 | Pan D1 domain | EEELQX$_1$IQPDKSVLVAAGETATLRCTX$_2$TSLX$_3$PVGP IQWFRGAGPGRX$_4$LIYNQX$_5$X$_6$GX$_7$FPRVTTVSDX$_8$TK RNNMDFSIRIGX$_9$ITPADAGTYYCX$_{10}$KFRKGSPDDV EFKSGAGTELSVRAKPS |
| — | Amino acid substitutions relative to SEQ ID NO: 49 | $X_1$ = V, I, L; $X_2$ = A, I, V, L; $X_3$ = I, F, S, T; $X_4$ = E, V, L; $X_5$ = K, R; $X_6$ = E, Q; $X_7$ = H, P, R; $X_8$ = L, T, S, G; $X_9$ = A; and $X_{10}$ = V, I |
| 50 | Pan D1 domain | EEELQX$_1$IQPDKSVSVAAGESAILHCTX$_2$TSLX$_3$PVGPI QWFRGAGPARX$_4$LIYNQX$_5$X$_6$GX$_7$FPRVTTVSEX$_8$TK RENMDFSISISX$_9$ITPADAGTYYCX$_{10}$KFRKGSPDTEF KSGAGTELSVRAKPS |
| — | Amino acid substitutions relative to SEQ ID NO: 50 | $X_1$ = V, I; $X_2$ = V, I; $X_3$ = I, F; $X_4$ = E, V; $X_5$ = K, R; $X_6$ = E, Q; $X_7$ = H, P; $X_8$ = S, T; $X_9$ = N, A; and $X_{10}$ = V, I |
| 51 | Pan D1 domain | EEELQX$_1$IQPDKSVLVAAGETATLRCTX$_2$TSLX$_3$PVGP IQWFRGAGPGRX$_4$LIYNQX$_5$EGX$_6$FPRVTTVSDX$_7$TK RNNMDFSIRIGX$_8$ITPADAGTYYCX$_9$KFRKGSPDDVE FKSGAGTELSVRAKPS |
| — | Amino acid substitutions relative to SEQ ID NO: 51 | $X_1$ = V, I; $X_2$ = A, I; $X_3$ = I, F; $X_4$ = E, V; $X_5$ = K, R; $X_6$ = H, P; $X_7$ = L, T; $X_8$ = N, A; and $X_9$ = V, I |
| 52 | Pan D1 domain | EEELQX$_1$IQPDKSVLVAAGETATLRCTX$_2$TSLX$_3$PVGP IQWFRGAGPRELIYNQX$_4$EGX$_5$FPRVTTVSDX$_6$TKR NNMDFSIRIGX$_7$ITPADAGTYYCVKFRKGSPDDVEF KSGAGTELSVRAKPS |
| — | Amino acid substitutions relative to SEQ ID NO: 52 | $X_1$ = V, L, I; $X_2$ = A, I, L; $X_3$ = I, T, S, F; $X_4$ = K, R; $X_5$ = H, P, R; $X_6$ = L, T, G; and $X_7$ = N, A |
| 212 | Pan D1 domain | EEELQX$_1$IQPDKSVSVAAGESAILHCTX$_2$TSLX$_3$PVGPI QWFRGAGPARELIYNQX$_4$EGX$_5$FPRVTTVSEX$_6$TKRE NMDFSISISX$_7$ITPADAGTYYCVKFRKGSPDTEFKSG AGTELSVRAKPS |
| — | Amino acid substitutions relative to SEQ ID NO: 212 | $X_1$ = V, L, I; $X_2$ = V, I, L; $X_3$ = I, T, S, F; $X_4$ = K, R; $X_5$ = H, P, R; $X_6$ = S, T, G; and $X_7$ = N, A |
| 217 | Pan D1 domain | EEELQX$_1$IQPDKSVLVAAGETATLRCTX$_2$TSLX$_3$PVGP IQWFRGAGPGRX$_4$LIYNQX$_5$X$_6$GX$_7$FPRVTTVSDX$_8$TK RNNMDFSIRIGX$_9$X$_{10}$X$_{11}$X$_{12}$ADAGTYYCX$_{13}$KFRKGSP DDVEFKSGAGTELSVRAKPS |
| — | Amino acid substitutions relative to SEQ ID NO: 217 | $X_1$ = V, L, or I; $X_2$ = A, V, L, or I; $X_3$ = I, S, T, or F; $X_4$ = E, L, or V; $X_5$ = K or R; $X_6$ = E or Q; $X_7$ = H, R or P; $X_8$ = S, G, L or T; $X_9$ = any amino acid; $X_{10}$ = any amino acid; $X_{11}$ = any amino acid; $X_{12}$ = any amino acid; and $X_{13}$ = V or I |
| 218 | Pan D1 domain | EEELQX$_1$IQPDKSVLVAAGETATLRCTX$_2$TSLX$_3$PVGP IQWFRGAGPGRX$_4$LIYNQX$_5$X$_6$GX$_7$FPRVTTVSDX$_8$TK RNNMDFSIRIGX$_9$ITX$_{10}$ADAGTYYCX$_{11}$KFRKGSPDD VEFKSGAGTELSVRAKPS |
| — | Amino acid substitutions relative to SEQ ID NO: 218 | $X_1$ = V, L or I; $X_2$ = A, V, L, or I; $X_3$ = I, S, T or F; $X_4$ = E, L, or V; $X_5$ = K or R; $X_6$ = E or Q; $X_7$ = H, R or P; $X_8$ = S, G, L, or T; $X_9$ = N; $X_{10}$ = any amino acid other than P; and $X_{11}$ = V or I |

In some embodiments, a polypeptide includes a SIRP-α D1 variant having a sequence of: EEEX$_1$QX$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFSIRIGX$_{12}$ITX$_{13}$ADAGTYYCX$_{14}$KX$_{15}$RKGSPDDVEX$_{16}$KSGAGTELSVRAKPS (SEQ ID NO: 37), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant has at least one amino acid substitution relative to a wild-type SIRP-α D1 domain having the sequence of SEQ ID NO: 1.

In some embodiments, a polypeptide includes a SIRP-α D1 variant having a sequence of: EEGX$_1$QX$_2$IQPDKSVSVAAGESX$_3$ILHCTX$_4$TSLX$_5$PVGPIQWFRGAGPGRX$_6$LIYNQX$_7$X$_8$GX$_9$FPRVTTVSDX$_{10}$TX$_{11}$RNNMDFSIRIGX$_{12}$ITX$_{13}$ADAGTYYCX$_{14}$KX$_{15}$RKGSPDDVEX$_{16}$KSGAGTELSVRAKPS (SEQ ID NO: 40), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant has at least one amino acid substitution relative to a wild-type SIRP-α D1 domain having the sequence of SEQ ID NO: 4.

In some embodiments, a polypeptide includes a SIRP-α D1 variant having a sequence of: EEEX$_1$QX$_2$IQPDKFVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFSIRIGX$_{12}$ITX$_{13}$ADAGTYYCX$_{14}$KX$_{15}$RKGSPDDVEX$_{16}$KSGAGTELSVRAKPS (SEQ ID NO: 41), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant has at least one amino acid substitution relative to a wild-type SIRP-α D1 domain having the sequence of SEQ ID NO: 5.

In some embodiments, a polypeptide includes a SIRP-α D1 variant having a sequence of: EEEX$_1$Q X$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFPIRIGX$_{12}$ITXDADAGTYYCX$_{14}$KX$_{15}$RKGSPDDVEX$_{16}$KSGAGTELSVRAKPS (SEQ ID NO: 42), and wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant has at least one amino acid substitution relative to a wild-type SIRP-α D1 domain having the sequence of SEQ ID NO: 6.

In some embodiments, a polypeptide includes a SIRP-α D1 variant having a sequence of: EEEX$_1$Q X$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFSIRISX$_{12}$ITX$_{13}$ADAGTYYCX$_{14}$KX$_{15}$RKGSPDDVEX$_{16}$KSGAGTELSVRAKPS (SEQ ID NO: 45), and wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant has at least one amino acid substitution relative to a wild-type SIRP-α D1 domain having the sequence of SEQ ID NO: 9.

In any of the aforementioned embodiments in this aspect of the disclosure, a polypeptide includes a SIRP-α D1 variant having a sequence of any one of SEQ ID NOs: 37, 40-42, and 45, wherein X$_1$ is L, I, or V. In any of the aforementioned embodiments, X$_2$ is V, L, or, I. In any of the aforementioned embodiments, X$_3$ is A or V. In any of the aforementioned embodiments, X$_4$ is A, I, or L. In any of the aforementioned embodiments, X$_5$ is I, T, S, or F. In any of the aforementioned embodiments, X$_6$ is E, V, or L. In any of the aforementioned embodiments, X$_7$ is K or R. In any of the aforementioned embodiments, X$_8$ is E or Q. In any of the aforementioned embodiments, X$_9$ is H, P, or R. In any of the aforementioned embodiments, X$_{10}$ is L, T, or G. In any of the aforementioned embodiments, X$_{11}$ is K or R. In any of the aforementioned embodiments, X$_{12}$ is N, A, C, D, E, F, G, H, I, K, L, M, P, Q, R, S, T, V, W, or Y. In any of the aforementioned embodiments, X$_{13}$ is P, A, C, D, E, F, G, H, I, K, L, M, N, Q, R, S, T, V, W, or Y. In any of the aforementioned embodiments, X$_{14}$ is V or I. In any of the aforementioned embodiments, X$_{15}$ is F, L, V. In any of the aforementioned embodiments, X$_{16}$ is F or V.

In some embodiments, a polypeptide provided herein includes no more than ten amino acid substitutions relative to the wild-type SIRP-α D1 domain having the sequence of any one of SEQ ID NOs: 1, 4-6, and 9. In some embodiments, the polypeptide provided herein includes no more than seven amino acid substitutions relative to the wild-type SIRP-α D1 domain having the sequence of any one of SEQ ID NOs: 1, 4-6, and 9.

In some embodiments, the polypeptide binds CD47 with at least 10-fold greater binding affinity than the wild-type SIRP-α D1 domain having the sequence of any one of SEQ ID NOs: 1, 4-6, and 9. In some embodiments, the polypeptide binds CD47 with at least 100-fold greater binding affinity than the wild-type SIRP-α D1 domain having the sequence of any one of SEQ ID NOs: 1, 4-6, and 9. In some embodiments, the polypeptide binds CD47 with at least 1000-fold greater binding affinity than the wild-type SIRP-α D1 domain having the sequence of any one of SEQ ID NOs: 1, 4-6, and 9. In some embodiments, a SIRP-α D1 variant polypeptide or fragment thereof binds to CD47 with a K$_D$ less than $1 \times 10^{-8}$ M, less than $5 \times 10^{-9}$ M, less than $1 \times 10^{-9}$ M, less $5 \times 10^{-10}$ M, less than $1 \times 10^{-10}$ M or less than $1 \times 10^{-11}$ M. In some embodiments, a SIRP-α D1 variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRP-α D1 variant having a sequence of: EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISX$_{12}$ITX$_{13}$ADAGTYYCX$_{14}$KX$_{15}$RKGSPDTEX$_{16}$KSGAGTELSVRAKPS (SEQ ID NO: 38), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q;

$X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant has at least one amino acid substitution relative to a wild-type SIRP-α D1 domain having the sequence of SEQ ID NO: 2.

In some embodiments, a polypeptide includes a SIRP-α D1 variant having a sequence of: EEEX$_1$QX$_2$IQPDKSVSVAAGESX$_3$ILLCTX$_4$TSLX$_5$PVGPIQWFRG AGPARX$_6$LIYNQX$_7$X$_8$GX$_9$FPRVTTVSEX$_{10}$TX$_{11}$RENM DFSISISX$_{12}$ITX$_{13}$ADAGTYYCX$_{14}$KX$_{15}$RKGSPDTEX$_{16}$ KSGAGTELSVRAKPS (SEQ ID NO: 39), wherein $X_1$ is L, I, or V; $X_2$ is V, L, or, I; $X_3$ is A or V; $X_4$ is V, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant has at least one amino acid substitution relative to a wild-type SIRP-α D1 domain having the sequence of SEQ ID NO: 3.

In some embodiments, a polypeptide includes a SIRP-α D1 variant having a sequence of: EEEX$_1$QX$_2$IQPDKSVSVAAGESX$_3$ILHCTX$_4$TSLX$_5$PVGPIQWFRG AGPARX$_6$LIYNQX$_7$X$_8$GX$_9$FPRVTTVSEX$_{10}$TX$_{11}$RENM DFSISISX$_{12}$ITX$_{13}$ADAGTYYCX$_{14}$KX$_{15}$RKGSPDTEX$_{16}$ KSGAGTELSVRGKPS (SEQ ID NO: 43), wherein $X_1$ is L, I, or V; $X_2$ is V, L, or, I; $X_3$ is A or V; $X_4$ is V, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant has at least one amino acid substitution relative to a wild-type SIRP-α D1 domain having the sequence of SEQ ID NO: 7.

In some embodiments, a polypeptide includes a SIRP-α D1 variant having a sequence of: EEEX$_1$QX$_2$IQPDKSVSVAAGESX$_3$ILHCTX$_4$TSLX$_5$PVGPIQWFRG AGPARX$_6$LIYNQX$_7$X$_8$GX$_9$FPRVTTVSEX$_{10}$TX$_{11}$RENM DFSISISX$_{12}$ITX$_{13}$ADAGTYYCX$_{14}$KX$_{15}$RKGSPDTEX$_{16}$ KSGAGTELSVRAKPS (SEQ ID NO: 46), wherein $X_1$ is L, I, or V; $X_2$ is V, L, or, I; $X_3$ is A or V; $X_4$ is V, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant has at least one amino acid substitution relative to a wild-type SIRP-α D1 domain having the sequence of SEQ ID NO: 10.

In any of the aforementioned embodiments in this aspect of the disclosure, a polypeptide includes a SIRP-α D1 variant having a sequence of any one of SEQ ID NOs: 38, 39, 43, and 46, wherein $X_1$ is L, I, or V. In any of the aforementioned embodiments, $X_2$ is V, L, or, I. In any of the aforementioned embodiments, $X_3$ is A or V. In any of the aforementioned embodiments, $X_4$ is V, I, or L. In any of the aforementioned embodiments, $X_5$ is I, T, S, or F. In any of the aforementioned embodiments, $X_6$ is E, V, or L. In any of the aforementioned embodiments, $X_7$ is K or R. In any of the aforementioned embodiments, $X_8$ is E or Q. In any of the aforementioned embodiments, $X_9$ is H, P, or R. In any of the aforementioned embodiments, $X_{10}$ is S, T, or G. In any of the aforementioned embodiments, $X_{11}$ is K or R. In any of the aforementioned embodiments, $X_{12}$ is N, A, C, D, E, F, G, H, I, K, L, M, P, Q, R, S, T, V, W, or Y. In any of the aforementioned embodiments, $X_{13}$ is P, A, C, D, E, F, G, H, I, K, L, M, N, Q, R, S, T, V, W, or Y. In any of the aforementioned embodiments, $X_{14}$ is V or I. In any of the aforementioned embodiments, $X_{15}$ is F, L, or V. In any of the aforementioned embodiments, $X_{16}$ is F or V.

In some embodiments, a polypeptide includes a SIRP-α D1 variant having no more than ten amino acid substitutions relative to the wild-type SIRP-α D1 domain having the sequence of any one of SEQ ID NOs: 2, 3, 7, and 10. In some embodiments, a polypeptide includes a SIRP-α D1 variant having no more than seven amino acid substitutions relative to the wild-type SIRP-α D1 domain having the sequence of any one of SEQ ID NOs: 2, 3, 7, and 10.

In some embodiments, the polypeptide binds CD47 with at least 10-fold greater binding affinity than the wild-type SIRP-α D1 domain having the sequence of any one of SEQ ID NOs: 2, 3, 7, and 10. In some embodiments, the polypeptide binds CD47 with at least 100-fold greater binding affinity than the wild-type SIRP-α D1 domain having the sequence of any one of SEQ ID NOs: 2, 3, 7, and 10. In some embodiments, the polypeptide binds CD47 with at least 1000-fold greater binding affinity than the wild-type SIRP-α D1 domain having the sequence of any one of SEQ ID NOs: 2, 3, 7, and 10. In some embodiments, a SIRP-α D1 variant polypeptide or fragment thereof binds to CD47 with a $K_D$ less than $1 \times 10^{-8}$ M, less than $5 \times 10^{-9}$ M, less than $1 \times 10^{-9}$ M, less $5 \times 10^{-10}$ M, less than $1 \times 10^{-10}$ M or less than $1 \times 10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRP-α D1 variant having a sequence of: EEEX$_1$QX$_2$IQPDKSVLVAAGETX$_3$TLRCTX$_4$TSLX$_5$PVGPIQWFRG AGPARX$_6$LIYNQX$_7$X$_8$GX$_9$FPRVTTVSEX$_{10}$TX$_{11}$RENM DFSISISX$_{12}$ITX$_{13}$ADAGTYYCX$_{14}$KX$_{15}$RKGSPDTEX$_{16}$ KSGAGTELSVRAKPS (SEQ ID NO: 44), wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant has at least one amino acid substitution relative to a wild-type SIRP-α D1 domain having the sequence of SEQ ID NO: 8.

In some embodiments, the polypeptide has the sequence of SEQ ID NO: 44, wherein $X_1$ is L, I, or V. In any of the aforementioned embodiments in this aspect of the disclosure, $X_2$ is V, L, or, I. In any of the aforementioned embodiments, $X_3$ is A or V. In any of the aforementioned embodiments, $X_4$ is A, I, or L. In any of the aforementioned embodiments, $X_5$ is I, T, S, or F. In any of the aforementioned embodiments, $X_6$ is E, V, or L. In any of the aforementioned embodiments, $X_7$ is K or R. In any of the aforementioned embodiments, $X_8$ is E or Q. In any of the aforementioned embodiments, $X_9$ is H, P, or R. In any of the aforementioned embodiments, $X_{10}$ is S, T, or G. In any of the aforementioned embodiments, $X_{11}$ is K or R. In any of the aforementioned embodiments, $X_{12}$ is N, A, C, D, E, F, G, H, I, K, L, M, P, Q, R, S, T, V, W, or Y. In any of the aforementioned embodiments, $X_{13}$ is P, A, C, D, E, F, G, H, I, K, L, M, N, Q, R, S, T, V, W, or Y. In any of the aforementioned embodiments, $X_{14}$ is V or I. In any of the aforementioned embodiments, $X_{15}$ is F, L, or V. In any of the aforementioned embodiments, $X_{16}$ is F or V.

In some embodiments, a polypeptide includes a SIRP-α D1 variant having no more than ten amino acid substitutions relative to the wild-type SIRP-α D1 domain having the sequence of SEQ ID NO: 8. In some embodiments, a polypeptide includes a SIRP-α D1 variant having no more than seven amino acid substitutions relative to the wild-type SIRP-α D1 domain having the sequence of SEQ ID NO: 8.

In some embodiments, the polypeptide binds CD47 with at least 10-fold greater binding affinity than the wild-type SIRP-α D1 domain having the sequence of SEQ ID NO: 8. In some embodiments, the polypeptide binds CD47 with at least 100-fold greater binding affinity than the wild-type SIRP-α D1 domain having the sequence of SEQ ID NO: 8. In some embodiments, the polypeptide binds CD47 with at least 1000-fold greater binding affinity than the wild-type SIRP-α D1 domain having the sequence of SEQ ID NO: 8. In some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRP-α D1 variant having a sequence of: EEX$_1$X$_2$QX$_3$IQPDKX$_4$VX$_5$VAAGEX$_6$X$_7$X$_8$LX$_9$CTX$_{10}$TS LX$_{11}$PVGPIQWFRGAGPX$_{12}$RX$_{13}$LIYNQX$_{14}$X$_{15}$GX$_{16}$FP RVTTVSX$_{17}$X$_{18}$TX$_{19}$RX$_{20}$NMDFX$_{21}$IX$_{22}$IX$_{23}$X$_{24}$ITX$_{25}$ ADAGTYYCX$_{26}$KX$_{27}$RKGSPDX$_{28}$X$_{29}$EX$_{30}$KSGAGTEL SVRX$_{31}$KPS (SEQ ID NO: 47), wherein $X_1$ is E or G; $X_2$ is L, I, or V; $X_3$ is V, L, or, I; $X_4$ is S or F; $X_5$ is L or S; $X_6$ is S or T; $X_7$ is A or V; $X_8$ is I or T; $X_9$ is H or R; $X_{10}$ is A, V, I, or L; $X_{11}$ is I, T, S, or F; $X_{12}$ is A or G; $X_{13}$ is E, V, or L; $X_{14}$ is K or R; $X_{15}$ is E or Q; $X_{16}$ is H, P, or R; $X_{17}$ is D or E; $X_{18}$ is S, L, T, or G; $X_{19}$ is K or R; $X_{20}$ is E or N; $X_{21}$ is S or P; $X_{22}$ is S or R; $X_{23}$ is S or G; $X_{24}$ is any amino acid; $X_{25}$ is any amino acid; $X_{26}$ is V or I; $X_{27}$ is F, L, V; $X_{28}$ is D or absent; $X_{29}$ is T or V; $X_{30}$ is F or V; and $X_{31}$ is A or G; and wherein the variant has at least one amino acid substitution relative to a wild-type SIRP-α D1 domain having the sequence of any one of SEQ ID NOs: 1-10.

In some embodiments, the polypeptide has the sequence of SEQ ID NO: 47, wherein $X_1$ is E or G. In any of the aforementioned embodiments in this aspect of the disclosure, $X_2$ is L, I, or V. In any of the aforementioned embodiments, $X_3$ is V, L, or, I. In any of the aforementioned embodiments, $X_4$ is S or F. In any of the aforementioned embodiments, $X_5$ is L or S. In any of the aforementioned embodiments, $X_6$ is S or T. In any of the aforementioned embodiments, $X_7$ is A or V. In any of the aforementioned embodiments, $X_8$ is I or T. In any of the aforementioned embodiments, $X_9$ is H or R. In any of the aforementioned embodiments, $X_{10}$ is A, V, I, or L. In any of the aforementioned embodiments, $X_{11}$ is I, T, S, or F. In any of the aforementioned embodiments, $X_{12}$ is A or G. In any of the aforementioned embodiments, $X_{13}$ is E, V, or L. In any of the aforementioned embodiments, $X_{14}$ is K or R. In any of the aforementioned embodiments, $X_{15}$ is E or Q. In any of the aforementioned embodiments, $X_{16}$ is H, P, or R. In any of the aforementioned embodiments, $X_{17}$ is D or E. In any of the aforementioned embodiments, $X_{18}$ is S, L, T, or G. In any of the aforementioned embodiments, $X_{19}$ is K or R. In any of the aforementioned embodiments, $X_{20}$ is E or N. In any of the aforementioned embodiments, $X_{21}$ is S or P. In any of the aforementioned embodiments, $X_{22}$ is S or R. In any of the aforementioned embodiments, $X_{23}$ is S or G. In any of the aforementioned embodiments, $X_{24}$ is N, A, C, D, E, F, G, H, I, K, L, M, P, Q, R, S, T, V, W, or Y. In any of the aforementioned embodiments, $X_{25}$ is P, A, C, D, E, F, G, H, I, K, L, M, N, Q, R, S, T, V, W, or Y. In any of the aforementioned embodiments, $X_{26}$ is V or I. In any of the aforementioned embodiments, $X_{27}$ is F, L, V. In any of the aforementioned embodiments, $X_{28}$ is D or absent. In any of the aforementioned embodiments, $X_{29}$ is T or V. In any of the aforementioned embodiments, $X_{30}$ is F or V. In any of the aforementioned embodiments, $X_{31}$ is A or G.

In some embodiments, the polypeptide of this aspect of the disclosure includes no more than ten amino acid substitutions relative to the wild-type SIRP-α D1 domain having the sequence of any one of SEQ ID NOs: 1-10. In some embodiments, the polypeptide of this aspect of the disclosure includes no more than seven amino acid substitutions relative to the wild-type SIRP-α D1 domain having the sequence of any one of SEQ ID NOs: 1-10.

In some embodiments, the polypeptide binds CD47 with at least 10-fold greater binding affinity than the wild-type SIRP-α D1 domain having the sequence of any one of SEQ ID NOs: 1-10. In some embodiments, the polypeptide binds CD47 with at least 100-fold greater binding affinity than the wild-type SIRP-α D1 domain having the sequence of any one of SEQ ID NOs: 1-10. In some embodiments, the polypeptide binds CD47 with at least 1000-fold greater binding affinity than the wild-type SIRP-α D1 domain having the sequence of any one of SEQ ID NOs: 1-10. In some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRP-α D1 variant having a sequence of:
EEELQX$_1$IQPDKSVX$_2$VAAGEX$_3$AX$_4$LX$_5$CTX$_6$TSLX$_7$ PVGPIQWFRGAGPX$_8$RX$_9$LIYNQX$_{10}$X$_{11}$GX$_{12}$FPRVTTV SX$_{13}$X$_{14}$TKRX$_{15}$NMDFSIX$_{16}$IX$_{17}$X$_{18}$ITPADAGTYYC X$_{19}$KFRKGX$_{20}$X$_{21}$X$_{22}$DX$_{23}$EFKSGAGTELSVRAKPS (SEQ ID NO: 48), wherein $X_1$ is V or I; $X_2$ is L or S; $X_3$ is T or S; $X_4$ is T or I; $X_5$ is R or H; $X_6$ is A, V, or I; $X_7$ is I, R, Y, K or F; $X_8$ is G or A; $X_9$ is E or V; $X_{10}$ is K or R; $X_{11}$ is E, D or Q; $X_{12}$ is H or P; $X_{13}$ is D or E; $X_{14}$ is S, L or T; $X_{15}$ is N or E; $X_{16}$ is R or S; $X_{17}$ is G or S; $X_{18}$ is N or A; $X_{19}$ is V or I; $X_{20}$ is S, I or M; $X_{21}$ is P or absent; $X_{22}$ is D or P; and $X_{23}$ is V or T, or a fragment thereof.

In another aspect, the disclosure features a polypeptide including a SIRP-α D1 variant having a sequence of: EEELQX$_1$IQPDKSVLVAAGETATLRCTX$_2$TSLX$_3$PVGP IQWFRGAGPGRX$_4$LIYNQX$_5$X$_6$GX$_7$FPRVTTVSDX$_8$T KRNNMDFSIRIGX$_9$ITPADAGTYYCX$_{10}$KFRKGSPDD VEFKSGAGTELSVRAKPS (SEQ ID NO: 49), wherein $X_1$ is V, L, or I; $X_2$ is A, I, V, or L; $X_3$ is I, F, S, or T; $X_4$ is E, V, or L; $X_5$ is K or R; $X_6$ is E or Q; $X_7$ is H, P, or R; $X_8$ is L, T, S, or G; $X_9$ is A; and $X_{10}$ is V or I; and wherein the variant has at least one amino acid substitution relative to a wild-type SIRP-α D1 domain having the sequence of any one of SEQ ID NO: 1.

In some embodiments, the polypeptide has the sequence of SEQ ID NO: 49, wherein $X_1$ is V, L or I. In any of the aforementioned embodiments in this aspect of the disclosure, $X_2$ is A, I, V, or L. In any of the aforementioned embodiments, $X_3$ is I, F, S, or T. In any of the aforementioned embodiments, $X_4$ is E, V, or L. In any of the aforementioned embodiments, $X_5$ is K or R. In any of the aforementioned embodiments, $X_6$ is E or Q. In any of the aforementioned embodiments, $X_7$ is H, P, or R. In any of the aforementioned embodiments, $X_8$ is L, T, S or G. In any of the aforementioned embodiments, $X_9$ is A. In any of the aforementioned embodiments, $X_{10}$ is V or I.

In some embodiments, the polypeptide has a high affinity SIRP-α D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 49, wherein each of $X_1$, $X_2$, $X_3$, $X_4$, $X_5$, $X_6$, $X_7$, $X_8$, $X_9$, and $X_{10}$ are not a wild-type amino acid.

In some embodiments, the polypeptide of this aspect of the disclosure includes no more than ten amino acid substitutions relative to the wild-type SIRP-α D1 domain having the sequence of any one of SEQ ID NO: 1. In some embodiments, the polypeptide of this aspect of the disclosure includes no more than seven amino acid substitutions relative to the wild-type SIRP-α D1 domain having the sequence of any one of SEQ ID NO: 1.

In some embodiments, the polypeptide binds CD47 with at least 10-fold greater binding affinity than the wild-type SIRP-α D1 domain having the sequence of any one of SEQ ID NO: 1. In some embodiments, the polypeptide binds CD47 with at least 100-fold greater binding affinity than the wild-type SIRP-α D1 domain having the sequence of any one of SEQ ID NO: 1. In some embodiments, the polypeptide binds CD47 with at least 1000-fold greater binding affinity than the wild-type SIRP-α D1 domain having the sequence of any one of SEQ ID NO: 1. In some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRP-α D1 variant having a sequence of: EEELQX$_1$IQPDKSVSVAAGESAILHCTX$_2$TSLX$_3$PVGPI QWFRGAGPARX$_4$LIYNQX$_5$X$_6$GX$_7$FPRVTTVSEX$_8$TKR ENMDFSISISX$_9$ITPADAGTYYCX$_{10}$KFRKGSPDTEFKS GAGTELSVRAKPS, (SEQ ID NO: 50), wherein $X_1$ is V or I; $X_2$ is V or I; $X_3$ is I or F; $X_4$ is E or V; $X_5$ is K or R; $X_6$ is E or Q; $X_7$ is H or P; $X_8$ is S or T; $X_9$ is N or A; and $X_{10}$ V or I; and wherein the variant has at least one amino acid substitution relative to a wild-type SIRP-α D1 domain having the sequence of any one of SEQ ID NO: 2.

In some embodiments, the polypeptide has the sequence of SEQ ID NO: 50, wherein $X_1$ is V or I. In any of the aforementioned embodiments in this aspect of the disclosure, $X_2$ is V or I. In any of the aforementioned embodiments, $X_3$ is I or F. In any of the aforementioned embodiments, $X_4$ is E or V. In any of the aforementioned embodiments, $X_5$ is K or R. In any of the aforementioned embodiments, $X_6$ is E or Q. In any of the aforementioned embodiments, $X_7$ is H or P. In any of the aforementioned embodiments, $X_8$ is S or T. In any of the aforementioned embodiments, $X_9$ is N or A. In any of the aforementioned embodiments, $X_{10}$ is V or I.

In some embodiments, the polypeptide has a high affinity SIRP-α D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 50, wherein each of $X_1$, $X_2$, $X_3$, $X_4$, $X_5$, $X_6$, $X_7$, $X_8$, $X_9$, and $X_{10}$ is not a wild-type amino acid.

In some embodiments, the polypeptide of this aspect of the disclosure includes no more than ten amino acid substitutions relative to the wild-type SIRP-α D1 domain having the sequence of any one of SEQ ID NO: 2. In some embodiments, the polypeptide of this aspect of the disclosure includes no more than seven amino acid substitutions relative to the wild-type SIRP-α D1 domain having the sequence of any one of SEQ ID NO: 2.

In some embodiments, the polypeptide binds CD47 with at least 10-fold greater binding affinity than the wild-type SIRP-α D1 domain having the sequence of any one of SEQ ID NO: 2. In some embodiments, the polypeptide binds CD47 with at least 100-fold greater binding affinity than the wild-type SIRP-α D1 domain having the sequence of any one of SEQ ID NO: 2. In some embodiments, the polypeptide binds CD47 with at least 1000-fold greater binding affinity than the wild-type SIRP-α D1 domain having the sequence of any one of SEQ ID NO: 2. In some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRP-α D1 variant having a sequence of: EEELQX$_1$IQPDKSVLVAAGETATLRCTX$_2$TSLX$_3$PVGPI QWFRGAGPGRX$_4$LIYNQX$_5$EGX$_6$FPRVTTVSDX$_7$TKR NNMDFSIRIGX$_8$ITPADAGTYYCX$_9$KFRKGSPDDVEFK SGAGTELSVRAKPS (SEQ ID NO: 51), wherein $X_1$ is V or I; $X_2$ is A or I; $X_3$ is I or F; $X_4$ is E or V; $X_5$ is K or R; $X_6$ is H or P; $X_7$ is L or T; $X_8$ is N or A; and $X_9$ is V or I; and wherein the variant has at least one amino acid substitution relative to a wild-type SIRP-α D1 domain having the sequence of any one of SEQ ID NO: 1.

In some embodiments, the polypeptide has the sequence of SEQ ID NO: 51, wherein $X_1$ is V or I. In any of the aforementioned embodiments in this aspect of the disclosure, $X_2$ is A or I. In any of the aforementioned embodiments, $X_3$ is I or F. In any of the aforementioned embodiments, $X_4$ is E or V. In any of the aforementioned embodiments, $X_5$ is K or R. In any of the aforementioned embodiments, $X_6$ is H or P. In any of the aforementioned embodiments, $X_7$ is L or T. In any of the aforementioned embodiments, $X_8$ is N or A. In any of the aforementioned embodiments, $X_9$ is V or I. In some embodiments, $X_4$ is not V.

In some embodiments, the polypeptide has the sequence of SEQ ID NO: 51, wherein $X_8$ is A. In any of the aforementioned embodiments in this aspect of the disclosure, $X_8$ is A and $X_1$ is V or I. In any of the aforementioned embodiments in this aspect of the disclosure, $X_8$ is A and $X_2$ is A or I. In any of the aforementioned embodiments, $X_8$ is A and $X_3$ is I or F. In any of the aforementioned embodiments, $X_8$ is A and $X_4$ is E or V. In some embodiments, $X_4$ is not V. In any of the aforementioned embodiments, $X_8$ is A and $X_5$ is K or R. In any of the aforementioned embodiments, $X_8$ is A and $X_6$ is H or P. In any of the aforementioned embodiments, $X_8$ is A and $X_7$ is A or V. In any of the aforementioned embodiments, $X_8$ is A and $X_9$ is V or I.

In some embodiments, the polypeptide has the sequence of SEQ ID NO: 51, wherein $X_8$ is A. In any of the aforementioned embodiments in this aspect of the disclosure, $X_8$ is A and $X_1$ is I. In any of the aforementioned embodiments in this aspect of the disclosure, $X_8$ is A and $X_2$ is I. In any of the aforementioned embodiments, $X_8$ is A and $X_3$ is F. In any of the aforementioned embodiments, $X_8$ is A and $X_4$ is V. In any of the aforementioned embodiments, $X_8$ is A and $X_5$ is R. In any of the aforementioned embodiments, $X_8$ is A and $X_6$ is P. In any of the aforementioned embodiments, $X_8$ is A and $X_7$ is T. In any of the aforementioned embodiments, $X_8$ is A and $X_9$ is I.

In some embodiments, the polypeptide has a high affinity SIRP-α D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 51, wherein each of $X_1$, $X_2$, $X_3$, $X_4$, $X_5$, $X_6$, $X_7$, $X_8$, and $X_9$ is not a wild-type amino acid.

In some embodiments, the polypeptide of this aspect of the disclosure includes no more than ten amino acid substitutions relative to the wild-type SIRP-α D1 domain having the sequence of any one of SEQ ID NO: 1. In some embodiments, the polypeptide of this aspect of the disclosure includes no more than seven amino acid substitutions relative to the wild-type SIRP-α D1 domain having the sequence of any one of SEQ ID NO: 1.

In some embodiments, the polypeptide binds CD47 with at least 10-fold greater binding affinity than the wild-type SIRP-α D1 domain having the sequence of any one of SEQ ID NO: 1. In some embodiments, the polypeptide binds CD47 with at least 100-fold greater binding affinity than the wild-type SIRP-α D1 domain having the sequence of any one of SEQ ID NOs: 1. In some embodiments, the polypeptide binds CD47 with at least 1000-fold greater binding affinity than the wild-type SIRP-α D1 domain having the sequence of any one of SEQ ID NO: 1. In some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRP-α D1 variant having a sequence of:
EEELQX$_1$IQPDKSVLVAAGETATLRCTX$_2$TSLX$_3$PVGPI QWFRGAGPGRELIYNQX$_4$EGX$_5$FPRVTTVSDX$_6$TKRN NMDFSIRIGX$_7$ITPADAGTYYCVKFRKGSPDDVEFKS GAGTELSVRAKPS (SEQ ID NO: 222), wherein $X_1$ is V, L, or I; $X_2$ is A, I, or L; $X_3$ is I, T, S, or F; $X_4$ is K or R; $X_5$ is H or P; $X_6$ is L, T, or G; $X_7$ is N or A; and wherein the variant has at least one amino acid substitution relative to a wild-type SIRP-α D1 domain having a sequence according to SEQ ID NO: 1.

In some embodiments, the polypeptide has the sequence of SEQ ID NO: 222, wherein $X_1$ is V, L, or I. In any of the aforementioned embodiments in this aspect of the disclosure, $X_2$ is A, I, or L. In any of the aforementioned embodiments, $X_3$ is I, T, S, or F. In any of the aforementioned embodiments, $X_4$ is K or R. In any of the aforementioned embodiments, $X_5$ is H or P. In any of the aforementioned embodiments, $X_6$ is L, T, or G. In any of the aforementioned embodiments, $X_7$ is N or A.

In some embodiments, the polypeptide has the sequence of SEQ ID NO: 222, wherein $X_1$ is V or I. In any of the aforementioned embodiments in this aspect of the disclosure, $X_2$ is A or I. In any of the aforementioned embodiments, $X_3$ is I or F. In any of the aforementioned embodiments, $X_4$ is K or R. In any of the aforementioned embodiments, $X_5$ is H or P. In any of the aforementioned embodiments, $X_6$ is L or T. In any of the aforementioned embodiments, $X_7$ is N or A.

In some embodiments, the polypeptide has the sequence of SEQ ID NO: 222, wherein $X_7$ is A. In any of the aforementioned embodiments in this aspect of the disclosure, $X_7$ is A and $X_1$ is V or I. In any of the aforementioned embodiments in this aspect of the disclosure, $X_7$ is A and $X_2$ is A or I. In any of the aforementioned embodiments, $X_7$ is A and $X_3$ is I or F. In any of the aforementioned embodiments, $X_7$ is A and $X_4$ is K or R. In any of the aforementioned embodiments, $X_7$ is A and $X_5$ is H or P. In any of the aforementioned embodiments, $X_7$ is A and $X_6$ is L or T.

In some embodiments, the polypeptide has the sequence of SEQ ID NO: 222, wherein $X_7$ is A. In any of the aforementioned embodiments in this aspect of the disclosure, $X_7$ is A and $X_1$ is I. In any of the aforementioned embodiments in this aspect of the disclosure, $X_7$ is A and $X_2$ is I. In any of the aforementioned embodiments, $X_7$ is A and $X_3$ is F. In any of the aforementioned embodiments, $X_7$ is A and $X_4$ is R. In any of the aforementioned embodiments, $X_7$ is A and $X_5$ is P. In any of the aforementioned embodiments, $X_7$ is A and $X_6$ is T.

In some embodiments, the polypeptide has a high affinity SIRP-α D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 222, wherein each of $X_1$, $X_2$, $X_3$, $X_4$, $X_5$, $X_6$, and $X_7$ is not a wild-type amino acid.

In some embodiments, the polypeptide of this aspect of the disclosure includes no more than ten amino acid substitutions relative to the wild-type SIRP-α D1 domain having the sequence of any one of SEQ ID NO: 1. In some embodiments, the polypeptide of this aspect of the disclosure includes no more than seven amino acid substitutions relative to the wild-type SIRP-α D1 domain having the sequence of any one of SEQ ID NO: 1.

In some embodiments, the polypeptide binds CD47 with at least 10-fold greater binding affinity than the wild-type SIRP-α D1 domain having the sequence of any one of SEQ ID NO: 1. In some embodiments, the polypeptide binds CD47 with at least 100-fold greater binding affinity than the wild-type SIRP-α D1 domain having the sequence of any one of SEQ ID NO: 1. In some embodiments, the polypeptide binds CD47 with at least 1000-fold greater binding affinity than the wild-type SIRP-α D1 domain having the sequence of any one of SEQ ID NO: 1. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRP-α D1 variant polypeptides and fragments thereof bind to CD47 with a higher affinity than a SIRP-α polypeptide binds to CD47. For example, in some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRP-α D1 variant having a sequence of: EEELQX$_1$IQPDKSVSVAAGESAILHCTX$_2$TSLX$_3$PVGPI QWFRGAGPARELIYNQX$_4$EGX$_5$FPRVTTVSEX$_6$TKRE NMDFSISISX$_7$ITPADAGTYYCVKFRKGSPDTEFKSGA GTELSVRAKPS (SEQ ID NO: 212), wherein X$_1$ is V, L, or I; X$_2$ is V, I, or L; X$_3$ is I, T, S, or F; X$_4$ is K or R; X$_5$ is H, P, or R; X$_6$ is S, T, of G; X$_7$ is N or A; and wherein the variant has at least one amino acid substitution relative to a wild-type SIRP-α D1 domain having the sequence of any one of SEQ ID NO: 2.

In some embodiments, the polypeptide has the sequence of SEQ ID NO: 212, wherein X$_1$ is V, L, or I. In any of the aforementioned embodiments in this aspect of the disclosure, X$_2$ is V, I, or L. In any of the aforementioned embodiments, X$_3$ is I, T, S, or F. In any of the aforementioned embodiments, X$_4$ is K or R. In any of the aforementioned embodiments, X$_5$ is H or P. In any of the aforementioned embodiments, X$_6$ is S, T, or G. In any of the aforementioned embodiments, X$_7$ is N or A.

In some embodiments, the polypeptide has the sequence of SEQ ID NO: 212, wherein X$_1$ is V or I. In any of the aforementioned embodiments in this aspect of the disclosure, X$_2$ is V or I. In any of the aforementioned embodiments, X$_3$ is I or F. In any of the aforementioned embodiments, X$_4$ is K or R. In any of the aforementioned embodiments, X$_5$ is H or P. In any of the aforementioned embodiments, X$_6$ is S or T. In any of the aforementioned embodiments, X$_7$ is N or A.

In some embodiments, the polypeptide has the sequence of SEQ ID NO: 212, wherein X$_7$ is A. In any of the aforementioned embodiments in this aspect of the disclosure, X$_7$ is A and X$_1$ is V or I. In any of the aforementioned embodiments in this aspect of the disclosure, X$_7$ is A and X$_2$ is V or I. In any of the aforementioned embodiments, X$_7$ is A and X$_3$ is I or F. In any of the aforementioned embodiments, X$_7$ is A and X$_4$ is K or R. In any of the aforementioned embodiments, X$_7$ is A and X$_5$ is H or P. In any of the aforementioned embodiments, X$_7$ is A and X$_6$ is S or T.

In some embodiments, the polypeptide has the sequence of SEQ ID NO: 212, wherein X$_7$ is A. In any of the aforementioned embodiments in this aspect of the disclosure, X$_7$ is A and X$_1$ is I. In any of the aforementioned embodiments in this aspect of the disclosure, X$_7$ is A and X$_2$ is I. In any of the aforementioned embodiments, X$_7$ is A and X$_3$ is F. In any of the aforementioned embodiments, X$_7$ is A and X$_4$ is R. In any of the aforementioned embodiments, X$_7$ is A and X$_5$ is P. In any of the aforementioned embodiments, X$_7$ is A and X$_6$ is T.

In some embodiments, the polypeptide has a high affinity SIRP-α D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 212, wherein each of X$_1$, X$_2$, X$_3$, X$_4$, X$_5$, X$_6$, and X$_7$ is not a wild-type amino acid.

In some embodiments, the polypeptide of this aspect of the disclosure includes no more than ten amino acid substitutions relative to the wild-type SIRP-α D1 domain having the sequence of any one of SEQ ID NO: 2. In some embodiments, the polypeptide of this aspect of the disclosure includes no more than seven amino acid substitutions relative to the wild-type SIRP-α D1 domain having the sequence of any one of SEQ ID NO: 2.

In some embodiments, the polypeptide binds CD47 with at least 10-fold greater binding affinity than the wild-type SIRP-α D1 domain having the sequence of any one of SEQ ID NO: 2. In some embodiments, the polypeptide binds CD47 with at least 100-fold greater binding affinity than the wild-type SIRP-α D1 domain having the sequence of any one of SEQ ID NO: 2. In some embodiments, the polypeptide binds CD47 with at least 1000-fold greater binding affinity than the wild-type SIRP-α D1 domain having the sequence of any one of SEQ ID NO: 2. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRP-α D1 variant polypeptides and fragments thereof bind to CD47 with a higher affinity than a SIRP-α polypeptide binds to CD47. For example, in some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M less than $1\times10^{-10}$ M or less than $1\times10^{-10}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

Described herein, in some embodiments, is a polypeptide comprising a SIRP-α D1 variant having a sequence according to: EEELQX$_1$IQPDKSVLVAAGETATL RCTX$_2$TSLX$_3$PVGPIQWFRGAGPGRX$_4$LIYNQX$_5$X$_6$GX$_7$ FPRVTTVSDX$_8$TKRNNMDFSIRIGX$_9$X$_{10}$X$_{11}$X$_{12}$ADAGT YYCX$_{13}$KFRKGSPDDVEFKSGAGTELSVRAKPS (SEQ ID NO: 218), wherein X$_1$ is V, L, or I; X$_2$ is A, V, L, or I; X$_3$ is I, S, T, or F; X$_4$ is E, L, or V; X$_5$ is K or R; X$_6$ is E or Q; X$_7$ is H, R, or P; X$_8$ is S,G, L, or T; X$_9$ is any amino acid; X$_{10}$ is any amino acid; X$_{11}$ is any amino acid; X$_{12}$ is any amino acid; and X$_{13}$ is V or I; and wherein the SIRP-α D1 variant has at least two amino acid substitutions relative to a wild-type SIRP-α D1 domain having a sequence according to SEQ ID NO: 1.

In some embodiments, the polypeptide has the sequence of SEQ ID NO: 212, wherein X$_1$, wherein X$_9$ is A. In any of the aforementioned embodiments in this aspect of the disclosure, $X_9$ is N. In any of the aforementioned embodiments in this aspect of the disclosure $X_{10}$ is I. In any of the aforementioned embodiments in this aspect of the disclosure $X_9$ is N and $X_{10}$ is P. In any of the aforementioned embodiments in this aspect of the disclosure $X_9$ is N and $X_{11}$ is any amino acid other than S, T, or C. In any of the aforementioned embodiments in this aspect of the disclosure $X_{11}$ is T. In any of the aforementioned embodiments in this aspect of the disclosure $X_{11}$ is an amino acid other than T. In any of the aforementioned embodiments in this aspect of the disclosure $X_{12}$ is P. In any of the aforementioned embodiments in this aspect of the disclosure $X_9$ is N and $X_{12}$ is any amino acid other than P.

Described herein, in some embodiments, is a polypeptide comprising a SIRP-α D1 variant having a sequence according to: EEELQX$_1$IQPDKSVLVAAGETATLRCTX$_2$TSLX$_3$PVGPIQWFRGAGPGRX$_4$LIYNQX$_5$X$_6$GX$_7$FPRVTTVSDX$_8$TKRNNMDFSIRIGX$_9$ITX$_{10}$ADAGTYYCX$_{11}$KFRKGSPDDVEFKSGAGTELSVRAKPS (SEQ ID NO: 219), wherein $X_1$ is V, L, or I; $X_2$ is A, V, L, or I; $X_3$ is I, S, T, or F; $X_4$ is E, L, or V; $X_5$ is K or R; $X_6$ is E or Q; $X_7$ is H, R, or P; $X_8$ is S, G, L, or T; $X_9$ is N; $X_{10}$ is any amino acid other than P; and $X_{11}$ is V or I; and wherein the SIRP-α D1 variant has at least two amino acid substitutions relative to a wild-type SIRP-α D1 domain having a sequence according to SEQ ID NO: 1.

In another aspect of the disclosure, compositions are disclosed herein which include a SIRP-α D1 variant polypeptide having the amino acid sequence of SEQ ID NO: 48, or a fragment thereof. In some embodiments, the SIRP-α D1 variant polypeptide or fragment thereof binds to CD47 with a higher affinity compared to the affinity that a SIRP-α polypeptide binds to the CD47. In some embodiments, the SIRP-α D1 variant polypeptide binds to CD47 with a $K_D$ less than $1\times10^{-8}$ M, or less than $1\times10^{-9}$ M, less than $1\times10^{-10}$ M or less than $1\times10^{-11}$ M. In some embodiments, the above-mentioned SIRP-α D1 variant polypeptides are attached or fused to a second polypeptide. In some embodiments, the second polypeptide includes, without limitation, an Fc polypeptide, an Fc variant, an HSA polypeptide, an albumin peptide, a PEG polymer or a fragment of the foregoing.

Without limiting the foregoing, in some embodiments, a SIRP-α D1 variant polypeptide is selected from any one of SEQ ID NOs: 53-87 and 213 shown in Table 6.

TABLE 6

SIRP-α Variant Polypeptides

| SEQ ID NO: | Amino Acid Sequence |
|---|---|
| 53 | EEELQIIQPDKSVSVAAGESAILHCTITSLFPVGPIQWFRGAGPARVLIYNQRQGPFPRVTTVSETTKRENMDFSISISNITPADAGTYYCIKFRKGSPDTEFKSGAGTELSVRAKPS |
| 54 | EEELQVIQPDKSVSVAAGESAILHCTVTSLFPVGPIQWFRGAGPARELIYNQRQGPFPRVTTVSESTKRENMDFSISISNITPADAGTYYCVKFRKGSPDTEFKSGAGTELSVRAKPS |
| 55 | EEELQVIQPDKSVSVAAGESAILHCTITSLFPVGPIQWFRGAGPARVLIYNQRQGPFPRVTTVSETTKRENMDFSISISNITPADAGTYYCIKFRKGSPDTEFKSGAGTELSVRAKPS |
| 56 | EEELQIIQPDKSVSVAAGESAILHCTVTSLFPVGPIQWFRGAGPARVLIYNQRQGPFPRVTTVSETTKRENMDFSISISNITPADAGTYYCIKFRKGSPDTEFKSGAGTELSVRAKPS |
| 57 | EEELQIIQPDKSVSVAAGESAILHCTITSLIPVGPIQWFRGAGPARVLIYNQRQGPFPRVTTVSETTKRENMDFSISISNITPADAGTYYCIKFRKGSPDTEFKSGAGTELSVRAKPS |
| 58 | EEELQIIQPDKSVSVAAGESAILHCTITSLFPVGPIQWFRGAGPARELIYNQRQGPFPRVTTVSETTKRENMDFSISISNITPADAGTYYCIKFRKGSPDTEFKSGAGTELSVRAKPS |
| 59 | EEELQIIQPDKSVSVAAGESAILHCTITSLFPVGPIQWFRGAGPARVLIYNQKQGPFPRVTTVSETTKRENMDFSISISNITPADAGTYYCIKFRKGSPDTEFKSGAGTELSVRAKPS |
| 60 | EEELQIIQPDKSVSVAAGESAILHCTITSLFPVGPIQWFRGAGPARVLIYNQREGPFPRVTTVSETTKRENMDFSISISNITPADAGTYYCIKFRKGSPDTEFKSGAGTELSVRAKPS |
| 61 | EEELQIIQPDKSVSVAAGESAILHCTITSLFPVGPIQWFRGAGPARVLIYNQRQGHFPRVTTVSETTKRENMDFSISISNITPADAGTYYCIKFRKGSPDTEFKSGAGTELSVRAKPS |
| 62 | EEELQIIQPDKSVSVAAGESAILHCTITSLFPVGPIQWFRGAGPARVLIYNQRQGPFPRVTTVSESTKRENMDFSISISNITPADAGTYYCIKFRKGSPDTEFKSGAGTELSVRAKPS |
| 63 | EEELQIIQPDKSVSVAAGESAILHCTITSLFPVGPIQWFRGAGPARVLIYNQRQGPFPRVTTVSETTKRENMDFSISISNITPADAGTYYCVKFRKGSPDTEFKSGAGTELSVRAKPS |

TABLE 6-continued

SIRP-α Variant Polypeptides

| SEQ ID NO: | Amino Acid Sequence |
|---|---|
| 64 | EEELQVIQPDKSVSVAAGESAILHCTVTSLIPVGPIQWFRGAGPARELIYNQREGPFPRVTTVSESTKRENMDFSISISNITPADAGTYYCVKFRKGSPDTEFKSGAGTELSVRAKPS |
| 65 | EEELQVIQPDKSVSVAAGESAILHCTVTSLFPVGPIQWFRGAGPARELIYNQREGPFPRVTTVSESTKRENMDFSISISNITPADAGTYYCVKFRKGSPDTEFKSGAGTELSVRAKPS |
| 66 | EEELQVIQPDKSVSVAAGESAILHCTITSLFPVGPIQWFRGAGPARELIYNQREGPFPRVTTVSESTKRENMDFSISISNITPADAGTYYCVKFRKGSPDTEFKSGAGTELSVRAKPS |
| 67 | EEELQVIQPDKSVSVAAGESAILHCTITSLFPVGPIQWFRGAGPARELIYNQREGPFPRVTTVSETTKRENMDFSISISNITPADAGTYYCVKFRKGSPDTEFKSGAGTELSVRAKPS |
| 68 | EEELQIIQPDKSVSVAAGESAILHCTITSLFPVGPIQWFRGAGPARELIYNQREGPFPRVTTVSESTKRENMDFSISISNITPADAGTYYCVKFRKGSPDTEFKSGAGTELSVRAKPS |
| 69 | EEELQVIQPDKSVSVAAGESAILHCTITSLIPVGPIQWFRGAGPARELIYNQREGPFPRVTTVSESTKRENMDFSISISNITPADAGTYYCVKFRKGSPDTEFKSGAGTELSVRAKPS |
| 70 | EEELQIIQPDKSVSVAAGESAILHCTITSLFPVGPIQWFRGAGPARELIYNQREGPFPRVTTVSETTKRENMDFSISISNITPADAGTYYCVKFRKGSPDTEFKSGAGTELSVRAKPS |
| 71 | EEELQVIQPDKSVLVAAGETATLRCTATSLFPVGPIQWFRGAGPGRELIYNQRQGPFPRVTTVSDLTKRNNMDFSIRIGNITPADAGTYYCVKFRKGSPDDVEFKSGAGTELSVRAKPS |
| 72 | EEELQIIQPDKSVLVAAGETATLRCTITSLFPVGPIQWFRGAGPGRELIYNQREGPFPRVTTVSDLTKRNNMDFSIRIGNITPADAGTYYCVKFRKGSPDDVEFKSGAGTELSVRAKPS |
| 73 | EEELQVIQPDKSVLVAAGETATLRCTITSLFPVGPIQWFRGAGPGRELIYNQREGPFPRVTTVSDTTKRNNMDFSIRIGNITPADAGTYYCVKFRKGSPDDVEFKSGAGTELSVRAKPS |
| 74 | EEELQIIQPDKSVLVAAGETATLRCTITSLFPVGPIQWFRGAGPGRELIYNQREGPFPRVTTVSDTTKRNNMDFSIRIGNITPADAGTYYCVKFRKGSPDDVEFKSGAGTELSVRAKPS |
| 75 | EEELQVIQPDKSVLVAAGETATLRCTITSLFPVGPIQWFRGAGPGRELIYNQREGPFPRVTTVSDLTKRNNMDFSIRIGNITPADAGTYYCVKFRKGSPDDVEFKSGAGTELSVRAKPS |
| 76 | EEELQVIQPDKSVLVAAGETATLRCTATSLFPVGPIQWFRGAGPGRELIYNQREGPFPRVTTVSDLTKRNNMDFSIRIGNITPADAGTYYCVKFRKGSPDDVEFKSGAGTELSVRAKPS |
| 77 | EEELQIIQPDKSVLVAAGETATLRCTITSLFPVGPIQWFRGAGPGRVLIYNQRQGPFPRVTTVSDTTKRNNMDFSIRIGNITPADAGTYYCIKFRKGSPDDVEFKSGAGTELSVRAKPS |
| 78 | EEELQIIQPDKSVLVAAGETATLRCTITSLFPVGPIQWFRGAGPGRVLIYNQRQGPFPRVTTVSDTTKRNNMDFSIRIGAITPADAGTYYCIKFRKGSPDDVEFKSGAGTELSVRAKPS |
| 79 | EEELQVIQPDKSVLVAAGETATLRCTATSLFPVGPIQWFRGAGPGRELIYNQRQGPFPRVTTVSDLTKRNNMDFSIRIGAITPADAGTYYCVKFRKGSPDDVEFKSGAGTELSVRAKPS |
| 80 | EEELQIIQPDKSVLVAAGETATLRCTITSLFPVGPIQWFRGAGPGRVLIYNQREGPFPRVTTVSDTTKRNNMDFSIRIGAITPADAGTYYCIKFRKGSPDDVEFKSGAGTELSVRAKPS |
| 81 | EEELQVIQPDKSVLVAAGETATLRCTATSLFPVGPIQWFRGAGPGRELIYNQREGPFPRVTTVSDLTKRNNMDFSIRIGAITPADAGTYYCVKFRKGSPDDVEFKSGAGTELSVRAKPS |
| 82 | EEELQVIQPDKSVLVAAGETATLRCTITSLFPVGPIQWFRGAGPGRELIYNQREGPFPRVTTVSDLTKRNNMDFSIRIGAITPADAGTYYCVKFRKGSPDDVEFKSGAGTELSVRAKPS |

TABLE 6-continued

SIRP-α Variant Polypeptides

| SEQ ID NO: | Amino Acid Sequence |
|---|---|
| 83 | EEELQIIQPDKSVLVAAGETATLRCTITSLFPVGPIQWFRGAGPGRELIYNQ REGPFPRVTTVSDLTKRNNMDFSIRIGAITPADAGTYYCVKFRKGSPDDVE FKSGAGTELSVRAKPS |
| 84 | EEELQVIQPDKSVLVAAGETATLRCTITSLFPVGPIQWFRGAGPGRELIYN QREGPFPRVTTVSDTTKRNNMDFSIRIGAITPADAGTYYCVKFRKGSPDD VEFKSGAGTELSVRAKPS |
| 85 | EEELQIIQPDKSVLVAAGETATLRCTITSLFPVGPIQWFRGAGPGRELIYNQ REGPFPRVTTVSDTTKRNNMDFSIRIGAITPADAGTYYCVKFRKGSPDDVE FKSGAGTELSVRAKPS |
| 86 | EEELQIIQPDKSVLVAAGETATLRCTITSLFPVGPIQWFRGAGPGRVLIYNQ RQGPFPRVTTVSDTTKRNNMDFSIRIGNITPADAGTYYCIKFRKGSPDDVE FKSGAGTELSVRAKPS |
| 87 | EEELQVIQPDKSVLVAAGETATLRCTATSLIPVGPIQWFRGAGPGRELIYN QKEGHFPRVTTVSDLTKRNNMDFSIRIGNITPADAGTYYCVKFRKGSPDD VEFKSGAGTELSVRAKPS |
| 213 | EEELQVIQPDKSVLVAAGETATLRCTATSLFPVGPIQWFRGAGPGRELIYN QRQGPFPRVTTVSDLTKRNNMDFSIRIGNITVADAGTYYCVKFRKGSPDD VEFKSGAGTELSVRAKPS |

In some embodiments, the polypeptide includes a high affinity SIRP-α D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 6.

In some embodiments, the polypeptide includes a high affinity SIRP-α D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NOs: 80, 81, or 85 in Table 6.

III. Fc Domain Variants and Fusion Constructs

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Antibodies that target cell surface antigens can trigger immunostimulatory and effector functions that are associated with Fc receptor (FcR) engagement on immune cells. There are a number of Fc receptors that are specific for particular classes of antibodies, including IgG (gamma receptors), IgE (eta receptors), IgA (alpha receptors) and IgM (mu receptors). Binding of the Fc region to Fc receptors on cell surfaces can trigger a number of biological responses including phagocytosis of antibody-coated particles (antibody-dependent cell-mediated phagocytosis, or ADCP), clearance of immune complexes, lysis of antibody-coated cells by killer cells (antibody-dependent cell-mediated cytotoxicity, or ADCC) and, release of inflammatory mediators, placental transfer, and control of immunoglobulin production. Additionally, binding of the C1 component of complement to antibodies can activate the complement system. Activation of complement can be important for the lysis of cellular pathogens. However, the activation of complement can also stimulate the inflammatory response and can also be involved in autoimmune hypersensitivity or other immunological disorders. Variant Fc regions with reduced or ablated ability to bind certain Fc receptors are useful for developing therapeutic antibodies and Fc-fusion polypeptide constructs which act by targeting, activating, or neutralizing ligand functions while not damaging or destroying local cells or tissues.

In some embodiments, a SIRP-α D1 polypeptide construct comprises a non-naturally occurring high affinity SIRP-α D1 variant linked to an Fc domain monomer which forms an Fc domain having ablated or reduced effector function.

In some embodiments, a Fc domain monomer refers to a polypeptide chain that includes second and third antibody constant domains (e.g., CH2 and CH3). In some embodiments, an Fc domain monomer also includes a hinge domain. In some embodiments, the Fc domain monomer is of any immunoglobulin antibody isotype, including IgG, IgE, IgM, IgA, and IgD. Additionally, in some embodiments, an Fc domain monomer is of any IgG subtype (e.g., IgG1, IgG2, IgG2a, IgG2b, IgG2c, IgG3, and IgG4). In some embodiments, Fc domain monomers include as many as ten changes from a wild-type Fc domain monomer sequence (e.g., 1-10, 1-8, 1-6, 1-4 amino acid substitutions, additions or insertions, deletions, or combinations thereof) that alter the interaction between an Fc domain and an Fc receptor.

As used herein, the term "Fc domain" refers to a dimer of two Fc domain monomers. In a wild-type Fc domain, two Fc domain monomers dimerize by the interaction between the two CH3 antibody constant domains, as well as one or more disulfide bonds that form between the hinge domains of the two dimerized Fc domain monomers. In some embodiments, an Fc domain is mutated to lack effector functions, for example a "dead Fc domain." In some embodiments, each of the Fc domain monomers in an Fc domain includes amino acid substitutions in the CH2 antibody constant domain to reduce the interaction or binding between the Fc domain and an Fc receptor, such as an Fcγ receptor (FcγR), an Fcα receptor (FcαR), or an Fcε (FcεR).

In some embodiments, a high affinity SIRP-α D1 variant (e.g., any of the variants described in Tables 2, 5, and 6) is fused to an Fc domain monomer of an immunoglobulin or a fragment of an Fc domain monomer. In some embodiments, an Fc domain monomer of an immunoglobulin or a fragment of an Fc domain monomer is capable of forming an Fc domain with another Fc domain monomer. In some embodiments, an Fc domain monomer of an immunoglobulin or a fragment of an Fc domain monomer is not capable of forming an Fc domain with another Fc domain monomer. In some embodiments, an Fc domain monomer or a fragment of an Fc domain is fused to a polypeptide of the disclosure to increase serum half-life of the polypeptide. In some embodiments, an Fc domain monomer or a fragment of an Fc domain monomer fused to a polypeptide of the disclosure dimerizes with a second Fc domain monomer to form an Fc domain which binds an Fc receptor, or alternatively, an Fc domain monomer binds to an Fc receptor. In some embodiments, an Fc domain or a fragment of the Fc domain fused to a polypeptide to increase serum half-life of the polypeptide does not induce any immune system-related response.

In some embodiments, a SIRP-α polypeptide or construct provided herein includes a SIRP-α D1 domain or variant thereof joined to a first Fc domain monomer and an antibody variable domain joined to a second Fc domain monomer, in which the first and second Fc domain monomers combine to form an Fc domain (e.g., a heterodimeric Fc domain). An Fc domain is the protein structure that is found at the C-terminus of an immunoglobulin. An Fc domain includes two Fc domain monomers that are dimerized by the interaction between the CH3 antibody constant domains. A wild-type Fc domain forms the minimum structure that binds to an Fc receptor, e.g., FcγRI, FcγRIIa, FcγRIIb, FcγRIIIa, FcγRIIIb, and FcγRIV.

The Fc domain is not involved directly in binding an antibody to its target, but can be involved in various effector functions, such as participation of the antibody in antibody-dependent cellular toxicity. In some embodiments, the Fc domain in a SIRP-α polypeptide or construct of the disclosure comprise amino acid substitutions, additions or insertions, deletions, or any combinations thereof that lead to decreased effector function such as decreased antibody-dependent cell-mediated cytotoxicity (ADCC), decreased complement-dependent cytolysis (CDC), decreased antibody-dependent cell-mediated phagocytosis (ADCP), or any combinations thereof. In some embodiments, the SIRP-α polypeptides or constructs of the disclosure are characterized by decreased binding (e.g., minimal binding or absence of binding) to a human Fc receptor and decreased binding (e.g., minimal binding or absence of binding) to complement protein C1q. In some embodiments, the SIRP-α constructs of the disclosure are characterized by decreased binding (e.g., minimal binding or absence of binding) to human FcγRI, FcγRIIA, FcγRIIB, FcγRIIIB, or any combinations thereof, and C1q. To alter or reduce an antibody-dependent effector function, such as ADCC, CDC, ADCP, or any combinations thereof, in some embodiments, the Fc domains in SIRP-α constructs of the disclosure are of the IgG class and comprise one or more amino acid substitutions at E233, L234, L235, G236, G237, D265, D270, N297, E318, K320, K322, A327, A330, P331, or P329 (numbering according to the EU index of Kabat (Sequences of Proteins of Immunological Interest, 5th Ed. Public Health Service, National Institutes of Health, Bethesda, Md. (1991))).

In some embodiments, polypeptide constructs comprising a non-native Fc region described herein exhibit reduced or ablated binding to at least one of Fcγ receptors CD16a, CD32a, CD32b, CD32c, and CD64 as compared to a polypeptide construct comprising a native Fc region. In some cases, the polypeptide constructs described herein exhibit reduced or ablated binding to CD16a, CD32a, CD32b, CD32c, and CD64 Fcγ receptors.

CDC refers to a form of cytotoxicity in which the complement cascade is activated by the complement component C1q binding to antibody Fc. In some embodiments, polypeptide constructs comprising a non-native Fc region described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising a non-native Fc region as described herein exhibit reduced CDC as compared to a polypeptide construct comprising a wild-type Fc region. In some embodiments, polypeptide constructs comprising a non-native Fc region as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising a non-natural Fc variant as described herein exhibit negligible CDC as compared to a polypeptide construct comprising a wild-type Fc region.

In some embodiments, the Fc variants herein are minimally glycosylated or have reduced glycosylation relative to a wild-type sequence. In some embodiments, deglycosylation is accomplished with a mutation of N297A, or by mutating N297 to any amino acid which is not N. In some embodiments, deglycosylation is accomplished by disrupting the motif N-Xaa1-Xaa2-Xaa3, wherein N=asparagine; Xaa1=any amino acid except P (proline); Xaa2=T (threonine), S (serine) or C (cysteine); and Xaa3=any amino acid except P (proline). In one embodiment, the N-Xaa1-Xaa2-Xaa3 motif refers to residues 297-300 as designated according to Kabat et al., 1991. In some embodiments, a mutation to any one or more of N, Xaa1, Xaa2, or Xaa3 results in deglycosylation of the Fc variant.

In some embodiments, variants of antibody IgG constant regions (e.g., Fc variants) possess a reduced capacity to specifically bind Fcγ receptors or have a reduced capacity to induce phagocytosis. In some embodiments, variants of antibody IgG constant regions (e.g., Fc variants) possess a reduced capacity to specifically bind Fcγ receptors and have a reduced capacity to induce phagocytosis. For example, in some embodiments, an Fc domain is mutated to lack effector functions, typical of a "dead" Fc domain. For example, in some embodiments, an Fc domain includes specific amino acid substitutions that are known to minimize the interaction between the Fc domain and an Fcγ receptor. In some embodiments, an Fc domain monomer is from an IgG1 antibody and includes one or more of amino acid substitutions L234A, L235A, G237A, and N297A (as designated according to the EU numbering system per Kabat et al., 1991). In some embodiments, one or more additional mutations are included in such IgG1 Fc variant. Non-limiting examples of such additional mutations for human IgG1 Fc variants include E318A and K322A. In some instances, a human IgG1 Fc variant has up to 12, 11, 10, 9, 8, 7, 6, 5 or 4 or fewer mutations in total as compared to wild-type human IgG1 sequence. In some embodiments, one or more additional deletions are included in such IgG1 Fc variant. For example, in some embodiments, the C-terminal lysine of the Fc IgG1 heavy chain constant region provided in SEQ ID NO: 88 in Table 7 is deleted, for example to increase the homogeneity of the polypeptide when the polypeptide is produced in bacterial or mammalian cells. In some instances, a human IgG1 Fc variant has up to 12, 11, 10, 9, 8, 7, 6, 5 or 4 or fewer deletions in total as compared to wild-type human IgG1 sequence. In some embodiments, a IgG1 Fc variant has a sequence according to any one of SEQ ID NO: 135, SEQ ID NO: 136, or SEQ ID NO: 137.

In some embodiments, an Fc domain monomer is from an IgG2 or IgG4 antibody and includes amino acid substitutions A330S, P331S, or both A330S and P331S. The aforementioned amino acid positions are defined according to Kabat, et al. (1991). The Kabat numbering of amino acid residues can be determined for a given antibody by alignment at regions of homology of the sequence of the antibody with a "standard" Kabat numbered sequence. In some embodiments, the Fc variant comprises a human IgG2 Fc sequence comprising one or more of A330S, P331S and N297A amino acid substitutions (as designated according to the EU numbering system per Kabat, et al. (1991). In some embodiments, one or more additional mutations are included in such IgG2 Fc variants. Non-limiting examples of such additional mutations for human IgG2 Fc variant include V234A, G237A, P238S, V309L and H268A (as designated according to the EU numbering system per Kabat et al. (1991)). In some instances, a human IgG2 Fc variant has up to 12, 11, 10, 9, 8, 7, 6, 5, 4, 3 or fewer mutations in total as compared to wild-type human IgG2 sequence. In some embodiments, one or more additional deletions are included in such IgG2 Fc variant. For example, in some embodiments, the C-terminal lysine of the Fc IgG2 heavy chain constant region provided in SEQ ID NO: 89 in Table 7 is deleted, for example to increase the homogeneity of the polypeptide when the polypeptide is produced in bacterial or mammalian cells. In some instances, a human IgG2 Fc variant has up to 12, 11, 10, 9, 8, 7, 6, 5 or 4 or fewer deletions in total as compared to wild-type human IgG2 sequence.

When the Fc variant is an IgG4 Fc variant, in some embodiments, such Fc variant comprises a S228P mutation (as designated according to Kabat, et al. (1991)). In some instances, a human IgG4 Fc variant has up to 12, 11, 10, 9, 8, 7, 6, 5, 4, 3, 2 or 1 mutation(s) in total as compared to wild-type human IgG4 sequence.

In some embodiments, the Fc variant includes at least one of the mutations L234A, L235A, G237A or N297A of an IgG1 Fc region or at least one of the mutations A330S, P331S or N297A of an IgG2 Fc region. In some embodiments, the Fc variant includes at least two of the mutations L234A, L235A, G237A or N297A of an IgG1 Fc region or at least two of the mutations A330S, P331S or N297A of an IgG2 Fc region. In some embodiments, the Fc variant includes at least three of the mutations L234A, L235A, G237A or N297A of an IgG1 Fc region or consists of the mutations A330S, P331S and N297A of an IgG2 Fc region. In some embodiments, the Fc variant consists of the mutations L234A, L235A, G237A and N297A.

In some embodiments, the Fc variant exhibits reduced binding to an Fc receptor of the subject compared to the wild-type human IgG Fc region. In some embodiments, the Fc variant exhibits ablated binding to an Fc receptor of the subject compared to the wild-type human IgG Fc region. In some embodiments, the Fc variant exhibits a reduction of phagocytosis compared to the wild-type human IgG Fc region. In some embodiments, the Fc variant exhibits ablated phagocytosis compared to the wild-type human IgG Fc region.

SEQ ID NO: 88 and SEQ ID NO: 89 provide amino acid sequences of Fc IgG1 and IgG2 heavy chain constant regions. In some embodiments, an Fc variant is any variant of SEQ ID NOs: 90-95 as shown in Table 7.

TABLE 7

Amino Acid Sequences of Fc Variants

| SEQ ID NO: | Amino Acid Sequence |
|---|---|
| 88 | EPKSCDKTHTCPPCPAPELLGGPSVFLFPPKPKDTLMISRTP EVTCVVVDVSHEDPEVKFNWYVDGVEVHNAKTKPREEQYNST YRVVSVLTVLHQDWLNGKEYKCKVSNKALPAPIEKTISKAKG QPREPQVYTLPPSREEMTKNQVSLTCLVKGFYPSDIAVEWES NGQPENNYKTTPPVLDSDGSFFLYSKLTVDKSRWQQGNVFSC SVMHEALHNHYTQKSLSLSPGK |
| 89 | STKGPSVFPLAPCSRSTSESTAALGCLVKDYFPEPVTVSWNS GALTSGVHTFPAVLQSSGLYSLSSVVTVPSSSLGTQTYTCNV DHKPSNTKVDKTVERKCCVECPPCPAPPVAGPSVFLFPPKPK DTLMISRTPEVTCVVVDVSHEDPEVQFNWYVDGVEVHNAKTK PREEQFNSTFRVVSVLTVVHQDWLNGKEYKCKVSNKGLPAPI EKTISKTKGQPREPQVYTLPPSREEMTKNQVSLTCLVKGFYP SDIAVEWESNGQPENNYKTTPPMLDSDGSFFLYSKLTVDKSR WQQGNVFSCSVMHEALHNHYTQKSLSLSPGK |
| 90 | DKTHTCPPCPAPEAAGAPSVFLFPPKPKDTLMISRTPEVTCV VVDVSHEDPEVKFNWYVDGVEVHNAKTKPREEQYASTYRVVS VLTVLHQDWLNGKEYKCKVSNKALPAPIEKTISKAKGQPREP QVYTLPPSREEMTKNQVSLTCLVKGFYPSDIAVEWESNGQPE NNYKTTPPVLDSDGSFFLYSKLTVDKSRWQQGNVFSCSVMHE ALHNHYTQKSLSLSPGK |
| 91 | DKTHTCPPCPAPEAAGAPSVFLFPPKPKDTLMISRTPEVTCV VVDVSHEDPEVKFNWYVDGVEVHNAKTKPREEQYASTYRVVS VLTVLHQDWLNGKEYKCKVSNKALPAPIEKTISKAKGQPREP QVYTLPPSREEMTKNQVSLTCLVKGFYPSDIAVEWESNGQPE NNYKTTPPVLDSDGSFFLYSKLTVDKSRWQQGNVFSCSVMHE ALHNHYTQKSLSLSPG |
| 92 | VECPPCPAPPVAGPSVFLFPPKPKDTLMISRTPEVTCVVVDV SHEDPEVQFNWYVDGVEVHNAKTKPREEQFASTFRVVSVLTV VHQDWLNGKEYKCKVSNKGLPSSIEKTISKTKGQPREPQVYT LPPSREEMTKNQVSLTCLVKGFYPSDIAVEWESNGQPENNYK TTPPMLDSDGSFFLYSKLTVDKSRWQQGNVFSCSVMHEALHN HYTQKSLSLSPGK |
| 93 | VECPPCPAPPVAGPSVFLFPPKPKDTLMISRTPEVTCVVVDV SHEDPEVQFNWYVDGVEVHNAKTKPREEQFASTFRVVSVLTV VHQDWLNGKEYKCKVSNKGLPSSIEKTISKTKGQPREPQVYT LPPSREEMTKNQVSLTCLVKGFYPSDIAVEWESNGQPENNYK TTPPMLDSDGSFFLYSKLTVDKSRWQQGNVFSCSVMHEALHN HYTQKSLSLSPG |
| 94 | ERKSSVECPPCPAPPVAGPSVFLFPPKPKDTLMISRTPEVTC VVVDVSHEDPEVQFNWYVDGVEVHNAKTKPREEQFASTFRVV SVLTVVHQDWLNGKEYKCKVSNKGLPSSIEKTISKTKGQPRE PQVYTLPPSREEMTKNQVSLTCLVKGFYPSDIAVEWESNGQP ENNYKTTPPMLDSDGSFFLYSKLTVDKSRWQQGNVFSCSVMF IEALHNHYTQKSLSLSPGK |
| 95 | ERKSSVECPPCPAPPVAGPSVFLFPPKPKDTLMISRTPEVTC VVVDVSHEDPEVQFNWYVDGVEVHNAKTKPREEQFASTFRVV SVLTVVHQDWLNGKEYKCKVSNKGLPSSIEKTISKTKGQPRE PQVYTLPPSREEMTKNQVSLTCLVKGFYPSDIAVEWESNGQP ENNYKTTPPMLDSDGSFFLYSKLTVDKSRWQQGNVFSCSVMH EALHNHYTQKSLSLSPG |

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc variant as described herein exhibit reduced ADCC or ADCP as compared to a polypeptide construct comprising a wild-type Fc region. In some embodiments, polypeptide constructs comprising an Fc variant as described herein exhibit at least a 5%, 10%, 15%, 20%, 30%, 40%, 50%, 60%, 70%, 80%, 90% or greater reduction in ADCC or ADCP compared to a polypeptide construct comprising a wild-type Fc region. In some embodiments, polypeptide constructs comprising an Fc variant as described herein exhibit ablated ADCC or ADCP as compared to a polypeptide construct comprising a wild-type Fc region.

Complement-directed cytotoxicity, which is also referred to herein as CDC, refers to a form of cytotoxicity in which the complement cascade is activated by the complement component C1q binding to antibody Fc. In some embodiments, polypeptide constructs comprising an Fc variant as described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising an Fc variant as described herein exhibit reduced CDC as compared to a polypeptide construct comprising a wild-type Fc region. In some embodiments, polypeptide constructs comprising an Fc variant as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising an Fc variant as described herein exhibit negligible CDC as compared to a polypeptide construct comprising a wild-type Fc region.

Fc variants herein include those that exhibit reduced binding to an Fcγ receptor compared to the wild-type human IgG Fc region. For example, in some embodiments, an Fc variant exhibits binding to an Fcγ receptor that is less than the binding exhibited by a wild-type human IgG Fc region to an Fcγ receptor, as described in the Examples. In some instances, an Fc variant has reduced binding to an Fcγ receptor by a factor of 10%, 20% 30%, 40%, 50%, 60%, 70%, 80%, 90%, 95%, 96%, 97%, 98%, 99% or 100% (fully ablated effector function). In some embodiments, the reduced binding is for any one or more Fcγ receptor, e.g., CD16a, CD32a, CD32b, CD32c, or CD64.

In some instances, the Fc variants disclosed herein exhibit a reduction of phagocytosis compared to its wild-type human IgG Fc region. Such Fc variants exhibit a reduction in phagocytosis compared to its wild-type human IgG Fc region, wherein the reduction of phagocytosis activity is e.g., by a factor of 10%, 20%, 30%, 40%, 50%, 60%, 70%, 80%, 90%, 95%, 96%, 97%, 98%, 99% or 100%. In some instances, an Fc variant exhibits ablated phagocytosis compared to its wild-type human IgG Fc region.

In some embodiments, the Fc variants disclosed herein are coupled to one or more fusion partners. In some cases the fusion partner is a therapeutic moiety. In some cases, the fusion partner is selected to enable targeting of an expressed protein, purification, screening, display, and the like. In some embodiments, the fusion partner also affects the degree of binding to Fc receptors or the degree of phagocytosis reduction. As described herein, in some embodiments, when an Fc variant is coupled to a fusion partner, it forms a polypeptide construct as described below.

In some embodiments, fusion partners are linked to the Fc variant sequence via a linker sequence. In some embodiments, the linker sequence generally comprises a small number of amino acids, such as less than ten amino acids, although longer linkers are also utilized. In some cases, the linker has a length less than 10, 9, 8, 7, 6, or 5 amino acids or shorter. In some cases, the linker has a length of at least 10, 11, 12, 13, 14, 15, 20, 25, 30, or 35 amino acids or longer. Optionally, in some embodiments, a cleavable linker is employed.

In some embodiments, a fusion partner is a targeting or signal sequence that directs an Fc variant protein and any associated fusion partners to a desired cellular location or to the extracellular media. In some embodiments, certain signaling sequences target a protein to be either secreted into the growth media, or into the periplasmic space, located between the inner and outer membrane of the cell. In some embodiments, a fusion partner is a sequence that encodes a peptide or protein that enables purification or screening. Such fusion partners include, but are not limited to, polyhistidine tags (His-tags) (for example His6 (SEQ ID NO: 223) and His10 (SEQ ID NO: 224)) or other tags for use with Immobilized Metal Affinity Chromatography (IMAC) systems (e.g., Ni+2 affinity columns), GST fusions, MBP fusions, Strep-tag, the BSP biotinylation target sequence of the bacterial enzyme BirA, and epitope tags which are targeted by antibodies (for example c-myc tags, flag-tags, and the like).

In some embodiments, such tags are useful for purification, for screening, or both. For example, in some embodiments, an Fc variant is purified using a His-tag by immobilizing it to a Ni+2 affinity column, and then after purification the same His-tag is used to immobilize the antibody to a Ni+2 coated plate to perform an ELISA or other binding assay as described elsewhere herein. In some embodiments, a fusion partner enables the use of a selection method to screen Fc variants as described herein.

Various fusion partners that enable a variety of selection methods are available. For example, by fusing the members of an Fc variant library to the gene III protein, phage display can be employed. In some embodiments, fusion partners enable Fc variants to be labeled. Alternatively, in some embodiments, a fusion partner binds to a specific sequence on the expression vector, enabling the fusion partner and associated Fc variant to be linked covalently or noncovalently with the nucleic acid that encodes them.

In some embodiments, when a fusion partner is a therapeutic moiety, the therapeutic moiety is, e.g., a peptide, a protein, an antibody, a siRNA, or a small molecule. Non-limiting examples of therapeutic antibodies that are coupled to the Fc variants of the present disclosure include, but are not limited to antibodies that recognize CD47. Non-limiting examples of therapeutic polypeptides that are coupled to the Fc variants of the present disclosure include, but are not limited to, CD47 binding polypeptides, including SIRP-α polypeptides. In such instances, the CD47 binding polypeptide is attached or fused to an Fc variant of the disclosure.

Examples of CD47 binding polypeptides include, but are not limited to, anti-CD47 antibodies or fragments thereof, and ligands of CD47 such as SIRP-α or a fragment thereof. Additional examples of CD47 binding polypeptides include, but are not limited to naturally-occurring forms of SIRP-α as well as mutants thereof.

In some embodiments, disclosed herein is a polypeptide comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain monomers are identical (i.e., homodimer). In some embodiments, the Fc domain monomers are different (i.e., heterodimer). In some embodiments, at least one of the Fc domain monomers in an Fc domain dimer is a human IgG1 Fc region consisting of mutations L234A, L235A, G237A, and N297A. In some embodiments, at least one of the Fc domain monomers in an Fc domain dimer is a human IgG2 Fc region consisting of mutations A330S, P331S and N297A. In some embodiments, the Fc variant exhibits ablated or reduced binding to an Fcγ receptor compared to the wild-type version of the human IgG Fc region. In some embodiments, the Fc variant exhibits ablated or reduced binding to CD16a, CD32a, CD32b, CD32c, and CD64 Fcγ receptors compared to the wild-type version of the human IgG Fc region. In some embodiments, the Fc variant exhibits ablated or reduced binding to C1q compared to the wild-type version of the human IgG Fc fusion. In some embodiments, at least one of the Fc domain monomers in an Fc domain dimer is a human IgG4 Fc region comprising mutations S228P, E233P, F234V, L235A, delG236, and N297A. In some embodiments, the Fc variant exhibits ablated or reduced binding to a Fcγ receptor compared to the wild-type human IgG4 Fc region. In some embodiments, the Fc variant exhibits ablated or reduced binding to CD16a and CD32b Fcγ receptors compared to the wild-type version of its human IgG4 Fc region. In some embodiments, the Fc variant binds to an Fcγ receptor with a $K_D$ greater than about $5\times10^{-6}$ M.

In some embodiments, the Fc variant further comprises a CD47 binding polypeptide. In some embodiments, the Fc variant exhibits ablated or reduced binding to an Fcγ receptor compared to a wild-type version of a human IgG Fc region. In some embodiments, the CD47 binding polypeptide does not cause acute anemia in rodents and non-human primates. In some embodiments, the CD47 binding polypeptide does not cause acute anemia in humans.

In some embodiments, the CD47 binding polypeptide is a signal-regulatory protein α (SIRP-α) polypeptide or a fragment thereof. In some embodiments, the SIRP-α polypeptide comprises a SIRP-α D1 variant comprising the amino acid sequence, EEELQX$_1$IQPDKSVLVAAGETATLRCTX$_2$TSLX$_3$PVGPI QWFRGAGPGRX$_4$LIYNQX$_5$EGX$_6$FPRVTTVSDX$_7$TKR NNMDFSIRIGX$_8$ITPADAGTYYCX$_9$KFRKGSPDDVEF KSGAGTELSVRAKPS (SEQ ID NO: 221), wherein X$_1$ is V or I; X$_2$ is A or I; X$_3$ is I or F; X$_4$ is E or V; X$_5$ is K or R; X$_6$ is H or P; X$_7$ is L or T; X$_8$ is any amino acid other than N; and X$_9$ is V or I. In some embodiments, the SIRP-α polypeptide comprises a SIRP-α D1 variant wherein X$_1$ is V or I; X$_2$ is A or I; X$_3$ is I or F; X$_4$ is E; X$_5$ is K or R; X$_6$ is H or P; X$_7$ is L or T; X$_8$ is not N; and X$_9$ is V.

In some embodiments, disclosed herein, is a polypeptide comprising: a SIRP-α D1 variant, wherein the SIRP-α D1 variant is a non-naturally occurring high affinity SIRP-α D1 domain, wherein the SIRP-α D1 variant binds to human CD47 with an affinity that is at least 10-fold greater than the affinity of a naturally occurring D1 domain; and an Fc domain monomer, wherein the Fc domain monomer is linked to a second polypeptide comprising a second Fc domain monomer to form an Fc domain, wherein the Fc domain has ablated or reduced effector function. In some embodiments, the non-naturally occurring high affinity SIRP-α D1 domain comprises an amino acid mutation at residue 80.

In some embodiments, disclosed herein, is a SIRP-α D1 variant, wherein the SIRP-α D1 variant binds CD47 from a first species with a KD less than 250 nM; and wherein the SIRP-α D1 variant binds CD47 from a second species with a KD less than 250 nM; and the KD for CD47 from the first species and the KD for CD47 from the second species are within 100 fold of each other; wherein the first species and the second species are selected from the group consisting of: human, rodent, and non-human primate. In some embodiments, the SIRP-α D1 variant binds CD47 from at least 3 different species. In some embodiments, the non-human primate is cynomolgus monkey.

In some embodiments, disclosed herein, is a polypeptide comprising (a) a SIRP-α D1 domain that binds human CD47 with a KD less than 250 nM; and (b) an Fc domain monomer linked to the N-terminus or the C-terminus of the SIRP-α D1 domain, wherein the polypeptide does not cause acute anemia in rodents and non-human primates. In some embodiments, the polypeptide is a non-naturally occurring variant of a human SIRP-α. In some embodiments, administration of the polypeptide in vivo results in hemoglobin reduction by less than 50% during the first week after administration. In some embodiments, administration of the polypeptide in humans results in hemoglobin reduction by less than 50% during the first week after administration. In some embodiments, the polypeptide further comprises at least one Fc variant, wherein the Fc variant comprises an Fc domain monomer selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain monomer is a human IgG1 Fc region consisting of mutations L234A, L235A, G237A, and N297A. In some embodiments, the Fc domain monomer is a human IgG2 Fc region consisting of mutations A330S, P331S and N297A.

The SIRP-α constructs of the disclosure include a SIRP-α domain or variant thereof that has its C-terminus joined to the N-terminus of an Fc domain monomer by way of a linker using conventional genetic or chemical means, e.g., chemical conjugation. In some embodiments, a linker (e.g., a spacer) is inserted between the polypeptide and the Fc domain monomer. In some embodiments, a polypeptide of the disclosure including a high affinity SIRP-α D1 variant is fused to an Fc domain monomer that is incapable of forming a dimer. In some embodiments, a polypeptide of the disclosure is fused to an Fc domain monomer that is capable of forming a dimer, e.g., a heterodimer, with another Fc domain monomer. In some embodiments, a polypeptide of the invention is fused to an Fc domain monomer and this fusion protein forms a homodimer. In some embodiments, a polypeptide of the disclosure is fused to a first Fc domain monomer and a different protein or peptide (e.g., an antibody variable region) is fused to a second Fc domain monomer. In some embodiments, a SIRP-α D1 domain or variant thereof is joined to a first Fc domain monomer and a therapeutic protein (e.g., a cytokine, an interleukin, an antigen, a steroid, an anti-inflammatory agent, or an immunomodulatory agent) is joined to a second Fc domain monomer. In some embodiments, the first and second Fc domain monomers form a heterodimer.

Without the limiting the foregoing, in some embodiments, a SIRP-α D1 variant polypeptide (e.g., any of the variants described in Tables 2, 5, and 6) is fused to an Fc polypeptide or Fc variant polypeptide, such as an Fc domain monomer. Examples of polypeptides comprising a SIRP-α D1 variant polypeptide and a fused Fc variant polypeptide include, but are not limited to, SEQ ID NOS: 96-137, 214, and 216 shown in Table 8.

TABLE 8

Polypeptides Comprising SIRP-α D1 Variants Fused to Fc Variants

| SEQ ID NO: | Amino Acid Sequence |
|---|---|
| 96 | EEELQIIQPDKSVLVAAGETATLRCTITSLFPVGPIQWFRGAGPGRVLIY NQRQGPFPRVTTVSDTTKRNNMDFSIRIGNITPADAGTYYCIKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 97 | EEELQVIQPDKSVLVAAGETATLRCTATSLFPVGPIQWFRGAGPGRELIY NQRQGPFPRVTTVSDLTKRNNMDFSIRIGNITPADAGTYYCVKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 98 | EEELQIIQPDKSVLVAAGETATLRCTITSLFPVGPIQWFRGAGPGRVLIY NQRQGPFPRVTTVSDTTKRNNMDFSIRIGAITPADAGTYYCIKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 99 | EEELQVIQPDKSVLVAAGETATLRCTATSLFPVGPIQWFRGAGPGRELIY NQRQGPFPRVTTVSDLTKRNNMDFSIRIGAITPADAGTYYCVKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMFIEALFINHYTQKSLSLSPGK |
| 100 | EEELQVIQPDKSVLVAAGETATLRCTATSLFPVGPIQWFRGAGPGRELIY NQREGPFPRVTTVSDLTKRNNMDFSIRIGAITPADAGTYYCVKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 101 | EEELQVIQPDKSVLVAAGETATLRCTITSLFPVGPIQWFRGAGPGRELIY NQREGPFPRVTTVSDLTKRNNMDFSIRIGAITPADAGTYYCVKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMFIEALHNHYTQKSLSLSPGK |
| 102 | EEELQIIQPDKSVLVAAGETATLRCTITSLFPVGPIQWFRGAGPGRELIY NQREGPFPRVTTVSDLTKRNNMDFSIRIGAITPADAGTYYCVKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 103 | EEELQVIQPDKSVLVAAGETATLRCTITSLFPVGPIQWFRGAGPGRELIY NQREGPFPRVTTVSDTTKRNNMDFSIRIGAITPADAGTYYCVKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |

TABLE 8-continued

Polypeptides Comprising SIRP-α D1 Variants Fused to Fc Variants

| SEQ ID NO: | Amino Acid Sequence |
|---|---|
| 104 | EEELQIIQPDKSVLVAAGETATLRCTITSLFPVGPIQWFRGAGPGRELIY NQREGPFPRVTTVSDTTKRNNMDFSIRIGAITPADAGTYYCVKFRKGSPD DVEFKSGAGTELSVRAKPSDKTHTCPPCPAPEAAGAPSVFLFPPKPKDTL MISRTPEVTCVVVDVSHEDPEVKFNWYVDGVEVHNAKTKPREEQYASTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 105 | EEELQIIQPDKSVLVAAGETATLRCTITSLFPVGPIQWFRGAGPGRVLIYN QRQGPFPRVTTVSDTTKRNNMDFSIRIGNITPADAGTYYCIKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALFINHYTQKSLSLSPGK |
| 106 | EEELQVIQPDKSVLVAAGETATLRCTATSLFPVGPIQWFRGAGPGRELIYN QRQGPFPRVTTVSDLTKRNNMDFSIRIGNITPADAGTYYCVKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALHNHYTQKSLSLSPGK |
| 107 | EEELQIIQPDKSVLVAAGETATLRCTITSLFPVGPIQWFRGAGPGRVLIYN QRQGPFPRVTTVSDTTKRNNMDFSIRIGAITPADAGTYYCIKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALHNHYTQKSLSLSPGK |
| 108 | EEELQVIQPDKSVLVAAGETATLRCTATSLFPVGPIQWFRGAGPGRELIYN QRQGPFPRVTTVSDLTKRNNMDFSIRIGAITPADAGTYYCVKFRKGSPDDV EFKSGAGTELSVRAKPSVECPPCPAPPVAGPSVFLFPPKPKDTLMISRTPE VTCVVVDVSHEDPEVQFNWYVDGVEVFTNAKTKPREEQFASTFRVVSVLTV VHQDWLNGKEYKCKVSNKGLPSSIEKTISKTKGQPREPQVYTLPPSREEMT KNQVSLTCLVKGFYPSDIAVEWESNGQPENNYKTTPPMLDSDGSFFLYSKL TVDKSRWQQGNVFSCSVMHEALHNHYTQKSLSLSPGK |
| 109 | EEELQVIQPDKSVLVAAGETATLRCTATSLFPVGPIQWFRGAGPGRELIYN QREGPFPRVTTVSDLTKRNNMDFSIRIGAITPADAGTYYCVKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALHNHYTQKSLSLSPGK |
| 110 | EEELQVIQPDKSVLVAAGETATLRCTITSLFPVGPIQWFRGAGPGRELIYN QREGPFPRVTTVSDLTKRNNMDFSIRIGAITPADAGTYYCVKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALHNHYTQKSLSLSPGK |
| 111 | EEELQIIQPDKSVLVAAGETATLRCTITSLFPVGPIQWFRGAGPGRELIYN QREGPFPRVTTVSDLTKRNNMDFSIRIGAITPADAGTYYCVKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALHNHYTQKSLSLSPGK |
| 112 | EEELQVIQPDKSVLVAAGETATLRCTITSLFPVGPIQWFRGAGPGRELIYN QREGPFPRVTTVSDTTKRNNMDFSIRIGAITPADAGTYYCVKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALHNHYTQKSLSLSPGK |

TABLE 8-continued

Polypeptides Comprising SIRP-α D1 Variants Fused to Fc Variants

| SEQ ID NO: | Amino Acid Sequence |
|---|---|
| 113 | EEELQIIQPDKSVLVAAGETATLRCTITSLFPVGPIQWFRGAGPGRELIYN QREGPFPRVTTVSDTTKRNNMDFSIRIGAITPADAGTYYCVKFRKGSPDDV EFKSGAGTELSVRAKPSVECPPCPAPPVAGPSVFLFPPKPKDTLMISRTPE VTCVVVDVSHEDPEVQFNWYVDGVEVHNAKTKPREEQFASTFRVVSVLTVV HQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSKLT VDKSRWQQGNVFSCSVMHEALHNHYTQKSLSLSPGK |
| 114 | EEELQIIQPDKSVLVAAGETATLRCTITSLFPVGPIQWFRGAGPGRVLIYN QRQGPFPRVTTVSDTTKRNNMDFSIRIGNITPADAGTYYCIKFRKGSPDDV EFKSGAGTELSVRAKPSERKSSVECPPCPAPPVAGPSVFLFPPKPKDTLMI SRTPEVTCVVVDVSHEDPEVQFNWYVDGVEVHNAKTKPREEQFASTFRVVS VLTVVHQDWLNGKEYKCKVSNKGLPSSIEKTISKTKGQPREPQVYTLPPSR EEMTKNQVSLTCLVKGFYPSDIAVEWESNGQPENNYKTTPPMLDSDGSFFL YSKLTVDKSRWQQGNVFSCSVMHEALHNHYTQKSLSLSPGK |
| 115 | EEELQVIQPDKSVLVAAGETATLRCTATSLFPVGPIQWFRGAGPGRELIYN QRQGPFPRVTTVSDLTKRNNMDFSIRIGNITPADAGTYYCVKFRKGSPDDV EFKSGAGTELSVRAKPSERKSSVECPPCPAPPVAGPSVFLFPPKPKDTLMI SRTPEVTCVVVDVSHEDPEVQFNWYVDGVEVHNAKTKPREEQFASTFRVVS VLTVVHQDWLNGKEYKCKVSNKGLPSSIEKTISKTKGQPREPQVYTLPPSR EEMTKNQVSLTCLVKGFYPSDIAVEWESNGQPENNYKTTPPMLDSDGSFFL YSKLTVDKSRWQQGNVFSCSVMHEALHNHYTQKSLSLSPGK |
| 116 | EEELQIIQPDKSVLVAAGETATLRCTITSLFPVGPIQWFRGAGPGRVLIYN QRQGPFPRVTTVSDTTKRNNMDFSIRIGAITPADAGTYYCIKFRKGSPDDV EFKSGAGTELSVRAKPSERKSSVECPPCPAPPVAGPSVFLFPPKPKDTLMI SRTPEVTCVVVDVSHEDPEVQFNWYVDGVEVHNAKTKPREEQFASTFRVVS VLTVVHQDWLNGKEYKCKVSNKGLPSSIEKTISKTKGQPREPQVYTLPPSR EEMTKNQVSLTCLVKGFYPSDIAVEWESNGQPENNYKTTPPMLDSDGSFFL YSKLTVDKSRWQQGNVFSCSVMHEALHNHYTQKSLSLSPGK |
| 117 | EEELQVIQPDKSVLVAAGETATLRCTATSLFPVGPIQWFRGAGPGRELIYN QRQGPFPRVTTVSDLTKRNNMDFSIRIGAITPADAGTYYCVKFRKGSPDDV EFKSGAGTELSVRAKPSERKSSVECPPCPAPPVAGPSVFLFPPKPKDTLMI SRTPEVTCVVVDVSHEDPEVQFNWYVDGVEVHNAKTKPREEQFASTFRVVS VLTVVHQDWLNGKEYKCKVSNKGLPSSIEKTISKTKGQPREPQVYTLPPSR EEMTKNQVSLTCLVKGFYPSDIAVEWESNGQPENNYKTTPPMLDSDGSFFL YSKLTVDKSRWQQGNVFSCSVMHEALFTNHYTQKSLSLSPGK |
| 118 | EEELQVIQPDKSVLVAAGETATLRCTATSLFPVGPIQWFRGAGPGRELIYN QREGPFPRVTTVSDLTKRNNMDFSIRIGAITPADAGTYYCVKFRKGSPDDV EFKSGAGTELSVRAKPSERKSSVECPPCPAPPVAGPSVFLFPPKPKDTLMI SRTPEVTCVVVDVSHEDPEVQFNWYVDGVEVHNAKTKPREEQFASTFRVVS VLTVVHQDWLNGKEYKCKVSNKGLPSSIEKTISKTKGQPREPQVYTLPPSR EEMTKNQVSLTCLVKGFYPSDIAVEWESNGQPENNYKTTPPMLDSDGSFFL YSKLTVDKSRWQQGNVFSCSVMHEALFINHYTQKSLSLSPGK |
| 119 | EEELQVIQPDKSVLVAAGETATLRCTITSLFPVGPIQWFRGAGPGRELIYN QREGPFPRVTTVSDLTKRNNMDFSIRIGAITPADAGTYYCVKFRKGSPDDV EFKSGAGTELSVRAKPSERKSSVECPPCPAPPVAGPSVFLFPPKPKDTLMI SRTPEVTCVVVDVSHEDPEVQFNWYVDGVEVHNAKTKPREEQFASTFRVVS VLTVVHQDWLNGKEYKCKVSNKGLPSSIEKTISKTKGQPREPQVYTLPPSR EEMTKNQVSLTCLVKGFYPSDIAVEWESNGQPENNYKTTPPMLDSDGSFFL YSKLTVDKSRWQQGNVFSCSVMHEALHNHYTQKSLSLSPGK |
| 120 | EEELQIIQPDKSVLVAAGETATLRCTITSLFPVGPIQWFRGAGPGRELIYN QREGPFPRVTTVSDLTKRNNMDFSIRIGAITPADAGTYYCVKFRKGSPDDV EFKSGAGTELSVRAKPSERKSSVECPPCPAPPVAGPSVFLFPPKPKDTLMI SRTPEVTCVVVDVSHEDPEVQFNWYVDGVEVHNAKTKPREEQFASTFRVVS VLTVVHQDWLNGKEYKCKVSNKGLPSSIEKTISKTKGQPREPQVYTLPPSR EEMTKNQVSLTCLVKGFYPSDIAVEWESNGQPENNYKTTPPMLDSDGSFFL YSKLTVDKSRWQQGNVFSCSVMHEALHNHYTQKSLSLSPGK |
| 121 | EEELQVIQPDKSVLVAAGETATLRCTITSLFPVGPIQWFRGAGPGRELIYN QREGPFPRVTTVSDTTKRNNMDFSIRIGAITPADAGTYYCVKFRKGSPDDV EFKSGAGTELSVRAKPSERKSSVECPPCPAPPVAGPSVFLFPPKPKDTLMI SRTPEVTCVVVDVSHEDPEVQFNWYVDGVEVFINAKTKPREEQFASTFRVV SVLTVVHQDWLNGKEYKCKVSNKGLPSSIEKTISKTKGQPREPQVYTLPPS REEMTKNQVSLTCLVKGFYPSDIAVEWESNGQPENNYKTTPPMLDSDGSFF LYSKLTVDKSRWQQGNVFSCSVMHEALHNHYTQKSLSLSPGK |

TABLE 8-continued

Polypeptides Comprising SIRP-α D1 Variants
Fused to Fc Variants

| SEQ ID NO: | Amino Acid Sequence |
|---|---|
| 122 | EEELQIIQPDKSVLVAAGETATLRCTITSLFPVGPIQWFRGAGPGRELIYN
QREGPFPRVTTVSDTTKRNNMDFSIRIGAITPADAGTYYCVKFRKGSPDDV
EFKSGAGTELSVRAKPSERKSSVECPPCPAPPVAGPSVFLFPPKPKDTLMI
SRTPEVTCVVVDVSHEDPEVQFNWYVDGVEVHNAKTKPREEQFASTFRVVS
VLTVVHQDWLNGKEYKCKVSNKGLPSSIEKTISKTKGQPREPQVYTLPPSR
EEMTKNQVSLTCLVKGFYPSDIAVEWESNGQPENNYKTTPPMLDSDGSFFL
YSKLTVDKSRWQQGNVFSCSVMHEALHNHYTQKSLSLSPGK |
| 123 | EEELQIIQPDKSVLVAAGETATLRCTITSLFPVGPIQWFRGAGPGRVLIYN
QRQGPFPRVTTVSDTTKRNNMDFSIRIGNITPADAGTYYCIKFRKGSPDDV
EFKSGAGTELSVRAKPSDKTHTCPPCPAPELLGGPSVFLFPPKPKDTLMIS
RTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK |
| 124 | EEELQIIQPDKSVLVAAGETATLRCTITSLFPVGPIQWFRGAGPGRVLIYN
QRQGPFPRVTTVSDTTKRNNMDFSIRIGNITPADAGTYYCIKFRKGSPDDV
EFKSGAGTELSVRAKPSDKTHTCPPCPAPEAAGAPSVFLFPPKPKDTLMIS
RTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLY
SKLTVDKSRWQQGNVFSCSVMHEALHNHYTQKSLSLSPGK |
| 125 | EEELQIIQPDKSVLVAAGETATLRCTITSLFPVGPIQWFRGAGPGRVLIYN
QRQGPFPRVTTVSDTTKRNNMDFSIRIGNITPADAGTYYCIKFRKGSPDDV
EFKSGAGTELSVRAKPSDKTHTCPPCPAPELLGGPSVFLFPPKPKDTLMIS
RTPEVTCVVVDVSHEDPEVKFNWYVDGVEVHNAKTKPREEQYASTYRVVS
VLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK |
| 126 | EEELQIIQPDKSVLVAAGETATLRCTITSLFPVGPIQWFRGAGPGRVLIYN
QRQGPFPRVTTVSDTTKRNNMDFSIRIGNITPADAGTYYCIKFRKGSPDDV
EFKSGAGTELSVRAKPSERKCCVECPPCPAPPVAGPSVFLFPPKPKDTLMI
SRTPEVTCVVVDVSHEDPEVQFNWYVDGVEVHNAKTKPREEQFNSTFRVV
SVLTVVHQDWLNGKEYKCKVSNKGLPAPIEKTISKTKGQPREPQVYTLPP
SREEMTKNQVSLTCLVKGFYPSDIAVEWESNGQPENNYKTTPPMLDSDG
SFFLYSKLTVDKSRWQQGNVFSCSVMHEALHNHYTQKSLSLSPGK |
| 127 | EEELQIIQPDKSVLVAAGETATLRCTITSLFPVGPIQWFRGAGPGRVLIYN
QRQGPFPRVTTVSDTTKRNNMDFSIRIGNITPADAGTYYCIKFRKGSPDDV
EFKSGAGTELSVRAKPSERKCCVECPPCPAPPVAGPSVFLFPPKPKDTLMI
SRTPEVTCVVVDVSHEDPEVQFNWYVDGVEVFINAKTKPREEQFNSTFRVV
SVLTVVHQDWLNGKEYKCKVSNKGLPSSIEKTISKTKGQPREPQVYTLPP
SREEMTKNQVSLTCLVKGFYPSDIAVEWESNGQPENNYKTTPPMLDSDG
SFFLYSKLTVDKSRWQQGNVFSCSVMHEALHNHYTQKSLSLSPGK |
| 128 | EEELQIIQPDKSVLVAAGETATLRCTITSLFPVGPIQWFRGAGPGRVLIYN
QRQGPFPRVTTVSDTTKRNNMDFSIRIGNITPADAGTYYCIKFRKGSPDDV
EFKSGAGTELSVRAKPSERKCCVECPPCPAPPVAGPSVFLFPPKPKDTLMI
SRTPEVTCVVVDVSHEDPEVQFNWYVDGVEVHNAKTKPREEQFASTFRVV
SVLTVVHQDWLNGKEYKCKVSNKGLPAPIEKTISKTKGQPREPQVYTLPP
SREEMTKNQVSLTCLVKGFYPSDIAVEWESNGQPENNYKTTPPMLDSDG
SFFLYSKLTVDKSRWQQGNVFSCSVMFIEALHNHYTQKSLSLSPGK |
| 129 | EEELQIIQPDKSVLVAAGETATLRCTITSLFPVGPIQWFRGAGPGRVLIYN
QRQGPFPRVTTVSDTTKRNNMDFSIRIGNITPADAGTYYCIKFRKGSPDDV
EFKSGAGTELSVRAKPSERKCCVECPPCPAPPVAGPSVFLFPPKPKDTLMI
SRTPEVTCVVVDVSHEDPEVQFNWYVDGVEVHNAKTKPREEQFASTFRVV
SVLTVVHQDWLNGKEYKCKVSNKGLPSSIEKTISKTKGQPREPQVYTLPP
SREEMTKNQVSLTCLVKGFYPSDIAVEWESNGQPENNYKTTPPMLDSDG
SFFLYSKLTVDKSRWQQGNVFSCSVMHEALHNHYTQKSLSLSPGK |
| 130 | EEELQVIQPDKSVSVAAGESAILHCTVTSLIPVGPIQWFRGAGPARELIYN
QKEGHFPRVTTVSESTKRENMDFSISISNITPADAGTYYCVKFRKGSPDTE
FKSGAGTELSVRAKPSESKYGPPCPSCPAPEFLGGPSVFLFPPKPKDTLMI
SRTPEVTCVVVDVSQEDPEVQFNWYVDGVEVHNAKTKPREEQFNSTYRVV
SVLTVLFIQDWLNGKEYKCKVSNKGLPSSIEKTISKAKGQPREPQVYTLPP
SQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK |

TABLE 8-continued

Polypeptides Comprising SIRP-α D1 Variants Fused to Fc Variants

| SEQ ID NO: | Amino Acid Sequence |
|---|---|
| 131 | EEELQIIQPDKSVLVAAGETATLRCTITSLFPVGPIQWFRGAGPGRELIYN<br>QREGPFPRVTTVSDTTKRNNMDFSIRIGAITPADAGTYYCVKFRKGSPDDV<br>EFKSGAGTELSVRAKPSESKYGPPCPPCPAPEFLGGPSVFLFPPKPKDTLM<br>ISRTPEVTCVVVDVSQEDPEVQFNWYVDGVEVHNAKTKPREEQFNSTYRV<br>VSVLTVLFIQDWLNGKEYKCKVSNKGLPSSIEKTISKAKGQPREPQVYTLP<br>PSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGK |
| 132 | EEELQIIQPDKSVLVAAGETATLRCTITSLFPVGPIQWFRGAGPGRELIYN<br>QREGPFPRVTTVSDTTKRNNMDFSIRIGAITPADAGTYYCVKFRKGSPDDV<br>EFKSGAGTELSVRAKPSESKYGPPCPPCPAPEFEGGPSVFLFPPKPKDTLM<br>ISRTPEVTCVVVDVSQEDPEVQFNWYVDGVEVFTNAKTKPREEQFNSTYRV<br>VSVLTVLHQDWLNGKEYKCKVSNKGLPSSIEKTISKAKGQPREPQVYTLP<br>PSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGK |
| 133 | EEELQIIQPDKSVLVAAGETATLRCTITSLFPVGPIQWFRGAGPGRELIYN<br>QREGPFPRVTTVSDTTKRNNMDFSIRIGAITPADAGTYYCVKFRKGSPDDV<br>EFKSGAGTELSVRAKPSESKYGPPCPPCPAPPVAGPSVFLFPPKPKDTLMI<br>SRTPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>sqeemtknqvsltclvkgfypsdiavewesngQpennykttppvldsdgs<br>FFLYSRLTVDKSRWQEGNVFSCSVMHEALHNHYTQKSLSLSLGK |
| 134 | EEELQIIQPDKSVLVAAGETATLRCTITSLFPVGPIQWFRGAGPGRVLIYN<br>QRQGPFPRVTTVSDTTKRNNMDFSIRIGNITPADAGTYYCIKFRKGSPDDV<br>EFKSGAGTELSVRAKPSAAAPPCPPCPAPEFLGGPSVFLFPPKPKDTLMIS<br>RTPEVTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSF<br>FLYSRLTVDKSRWQEGNVFSCSVMHEALHNHYTQKSLSLSPGK |
| 135 | EEELQVIQPDKSVLVAAGETATLRCTATSLFPVGPIQWFRGAGPGRELIY<br>NQREGPFPRVTTVSDLTKRNNMDFSIRIGAITPADAGTYYCVKFRKGSPD<br>DVEFKSGAGTELSVRAKPSDKTHTCPPCPAPEAAGAPSVFLFPPKPKDTL<br>MISRTPEVTCVVVDVSHEDPEVKFNWYVDGVEVHNAKTKPREEQYASTYR<br>VVSVLTVLHQDWLNGKEYKCKVSNKALPAPIEKTISKAKGQPREPQVYTL<br>PPSREEMTKNQVSLTCLVKGFYPSDIAVEWESNGQPENNYKTTPPVLDSD<br>GSFFLYSKLTVDKSRWQQGNVFSCSVMHEALITNHYTQKSLSLSPG |
| 136 | EEELQIIQPDKSVLVAAGETATLRCTITSLFPVGPIQWFRGAGPGRELIY<br>NQREGPFPRVTTVSDTTKRNNMDFSIRIGAITPADAGTYYCVKFRKGSPD<br>DVEFKSGAGTELSVRAKPSDKTHTCPPCPAPEAAGAPSVFLFPPKPKDTL<br>MISRTPEVTCVVVDVSHEDPEVKFNWYVDGVEVHNAKTKPREEQYASTYR<br>VVSVLTVLHQDWLNGKEYKCKVSNKALPAPIEKTISKAKGQPREPQVYTL<br>PPSREEMTKNQVSLTCLVKGFYPSDIAVEWESNGQPENNYKTTPPVLDSD<br>GSFFLYSRLTVDKSRWQQGNVFSCSVMHEALHNHYTQKSLSLSPG |
| 137 | EEELQIIQPDKSVLVAAGETATLRCTITSLFPVGPIQWFRGAGPGRVLIY<br>NQREGPFPRVTTVSDTTKRNNMDFSIRIGAITPADAGTYYCIKFRKGSPD<br>DVEFKSGAGTELSVRAKPSDKTHTCPPCPAPEAAGAPSVFLFPPKPKDTL<br>MISRTPEVTCVVVDVSHEDPEVKFNWYVDGVEVHNAKTKPREEQYASTYR<br>VVSVLTVLHQDWLNGKEYKCKVSNKALPAPIEKTISKAKGQPREPQVYTL<br>PPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| 214 | EEELQVIQPDKSVLVAAGETATLRCTATSLFPVGPIQWFRGAGPGRELIY<br>NQREGPFPRVTTVSDLTKRNNMDFSIRIGAITPADAGTYYCVKFRKGSPD<br>DVEFKSGAGTELSVRAKPSERKSSVECPPCPAPPVAGPSVFLFPPKPKDT<br>LMISRTPEVTCVVVDVSHEDPEVQFNWYVDGVEVHNAKTKPREEQFASTF<br>RVVSVLTVVHQDWLNGKEYKCKVSNKGLPSSIEKTISKTKGQPREPQVYT<br>LPPSREEMTKNQVSLTCLVKGFYPSDIAVEWESNGQPENNYKTTPPMLDS<br>DGSFFLYSKLTVDKSRWQQGNVFSCSVMHEALHNHYTQKSLSLSPG |
| 216 | EEELQIIQPDKSVLVAAGETATLRCTITSLFPVGPIQWFRGAGPGRVLIY<br>NQRQGPFPRVTTVSDTTKRNNMDFSIRIGNITPADAGTYYCIKFRKGSPD<br>DVEFKSGAGTELSVRAKPSDKTHTCPPCPAPELLGGPSVFLFPPKPKDTL<br>MISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTL<br>PPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |

In some embodiments, the polypeptide comprises a high affinity SIRP-α D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 8.

In some embodiments, the polypeptide comprises a high affinity SIRP-α D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NOs: 98-104, 107-113, 116-122, or 135-137 in Table 8.

In some embodiments, the polypeptide comprises (a) a signal-regulatory protein α (SIRP-α) D1 variant, wherein the SIRP-α D1 variant comprises the amino acid sequence, EEX$_1$X$_2$QX$_3$IQPDKX$_4$VX$_5$VAAGEX$_6$X$_7$X$_8$LX$_9$CTX$_{10}$TSL X$_{11}$PVGPIQWFRGAGPX$_{12}$RX$_{13}$LIYNQX$_{14}$X$_{15}$GX$_{16}$FPR VTTVSX$_{17}$X$_{18}$TX$_{19}$RX$_{20}$NMDFX$_{21}$IX$_{22}$IX$_{23}$X$_{24}$ITX$_{25}$AD AGTYYCX$_{26}$KX$_{27}$RKGSPDX$_{28}$X$_{29}$EX$_{30}$KSGAGTELSV RX$_{31}$KPS (SEQ ID NO: 47), wherein X$_1$ is E, or G; X$_2$ is L, I, or V; X$_3$ is V, L, or I; X$_4$ is S, or F; X$_5$ is L, or S; X$_6$ is S, or T; X$_7$ is A, or V; X$_8$ is I, or T; X$_9$ is H, R, or L; X$_{10}$ is A, V, I, or L; X$_{11}$ is I, T, S, or F; X$_{12}$ is A, or G; X$_{13}$ is E, V, or L; X$_{14}$ is K, or R; X$_{15}$ is E, or Q; X$_{16}$ is H, P, or R; X$_{17}$ is D, or E; X$_{18}$ is S, L, T, or G; X$_{19}$ is K, or R; X$_{20}$ is E, or N; X$_{21}$ is S, or P; X$_{22}$ is S, or R; X$_{23}$ is S, or G; X$_{24}$ is any amino acid; X$_{25}$ is any amino acid; X$_{26}$ is V, or I; X$_{27}$ is F, L, or V; X$_{28}$ is D or absent; X$_{29}$ is T, or V; X$_{30}$ is F, or V; and X$_{31}$ is A, or G; and wherein the SIRP-α D1 variant has at least two amino acid substitutions relative to a wild-type SIRP-α D1 domain having a sequence according to any one of SEQ ID NOs: 1 to 10; and (b) an Fc variant comprising an Fc domain dimer having two Fc domain monomers, wherein each Fc domain monomer independently is (i) a human IgG1 Fc region comprising a N297A mutation; (ii) a human IgG1 Fc region comprising L234A, L235A, and G237A mutations; (iii) a human IgG1 Fc region comprising L234A, L235A, G237A, and N297A mutations; (iv) a human IgG2 Fc region comprising a N297A mutation; (v) a human IgG2 Fc region comprising A330S and P331S mutations; (vi) a human IgG2 Fc region comprising A330S, P331S, and N297A mutations; (vii) a human IgG4 Fc region comprising S228P, E233P, F234V, L235A, and delG236 mutations; or (viii) a human IgG4 Fc region comprising S228P, E233P, F234V, L235A, delG236, and N297A mutations.

In some embodiments, the polypeptide comprises a SIRP-α D1 variant wherein the SIRP-α D1 variant comprises an amino acid sequence according to SEQ ID NO: 47; an Fc variant comprising an Fc domain dimer having two Fc domain monomers, wherein one of the Fc domain monomers in the Fc domain dimer comprises a human IgG1 Fc region comprising L234A, L235A, G237A, and N297A mutations.

Dimerization of Fc Domain Monomers

In some embodiments, a SIRP-α D1 variant polypeptide (e.g., any of the variants described in Tables 2, 5, and 6) is fused to a first Fc domain monomer either at the N-terminus or at the C-terminus. In some embodiments, the first Fc domain monomer is incapable of forming an Fc domain or a dimer. In some embodiments, the first Fc domain monomer combines with a second Fc domain monomer to form an Fc domain or a dimer. In some embodiments, the first and second Fc domain monomers include amino acid substitutions that promote heterodimerization between the first and second domain monomers.

In some embodiments, each of the two Fc domain monomers in an Fc domain includes amino acid substitutions that promote the heterodimerization of the two monomers. In some embodiments, a SIRP-α construct is formed, for example, from a first subunit including a SIRP-α D1 variant polypeptide fused to a first Fc domain monomer and a second subunit including a second Fc domain monomer (e.g., without a SIRP-α D1 variant polypeptide or any other polypeptide). In some embodiments, a construct has a single SIRP-α D1 variant polypeptide linked to an Fc domain (e.g., single arm). In some embodiments, a construct has two SIRP-α D1 variant polypeptides linked to an Fc domain (e.g., double arm). In some embodiments, a SIRP-α D1 variant having a K$_D$ of about 500 nM is particularly useful in a double arm construct. In some embodiments, a SIRP-α D1 variant having a K$_D$ of about 50 nM is particularly useful in a double arm construct. In some embodiments, a SIRP-α D1 variant having a K$_D$ of about 5 nM is useful in a double arm construct and a single arm construct. In some embodiments, a SIRP-α D1 variant having a K$_D$ of about 500 pM is useful in a double arm construct and a single arm construct. In some embodiments, a SIRP-α D1 variant having a K$_D$ of about 100 pM is useful in a double arm construct and a single arm construct. In some embodiments, a SIRP-α D1 variant having a K$_D$ of about 50 pM is useful in a double arm construct and a single arm construct. In some embodiments, a SIRP-α D1 variant having a K$_D$ of about 10 pM is useful in a double arm construct and a single arm construct.

In some embodiments, heterodimerization of Fc domain monomers is promoted by introducing different, but compatible, substitutions in the two Fc domain monomers, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain monomer and involved in the dimerization of two Fc domain monomers. In some embodiments, a hole in one CH3 antibody constant domain is created to accommodate a knob in another CH3 antibody constant domain, such that the knob and hole amino acids act to promote or favor the heterodimerization of the two Fc domain monomers. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain monomer includes the knob mutation T366W and the other Fc domain monomer includes hole mutations T366S, L358A, and Y407V. In some embodiments, a polypeptide of the disclosure including a high affinity SIRP-α D1 variant is fused to an Fc domain monomer including the knob mutation T366W to limit unwanted knob-knob homodimer formation. Examples of knob-into-hole amino acid pairs are included, without limitation, in Table 9 and examples of knob-into-hole Fc variants and SIRP-α-Fc fusions are provided in Table 10.

TABLE 9

Knob-into-Hole Amino Acid Pairs

| Fc domain monomer 1 | Y407T | Y407A | F405A | T394S | T366S L358A Y407V | T394W Y407T | T394S Y407A | T366W T394S |
|---|---|---|---|---|---|---|---|---|
| Fc domain monomer 2 | T366Y | T366W | T394W | F405W | T366W | T366Y F405A | T366W F405W | F405W Y407A |

TABLE 10

Examples of Fc Variants and SIRP-α - Fc Fusions

| SEQ ID NO: | Amino Acid Sequence |
|---|---|
| 138 | EEELQIIQPDKSVLVAAGETATLRCTITSLFPVGPIQWFRGAGPGR VLIYNQRQGPFPRVTTVSDTTKRNNMDFSIRIGAITPADAGTYYCI KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 139 | DKTHTCPPCPAPEAAGAPSVFLFPPKPKDTLMISRTPEVTCVVVDV SHEDPEVKFNWYVDGVEVHNAKTKPREEQYASTYRVVSVLTVLHQD WLNGKEYKCKVSNKALPAPIEKTISKAKGQPREPQVYTLPPSREEM TKNQVSLSCAVKGFYPSDIAVEWESNGQPENNYKTTPPVLDSDGSF FLVSKLTVDKSRWQQGNVFSCSVMHEALHNHYTQKSLSLSPGK |
| 140 | EEELQIIQPDKSVLVAAGETATLRCTITSLFPVGPIQWFRGAGPGR VLIYNQRQGPFPRVTTVSDTTKRNNMDFSIRIGAITPADAGTYYCI KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLSCAVKGFYPSDI AVEWESNGQPENNYKTTPPVLDSDGSFFLVSKLTVDKSRWQQGNVF SCSVMHEALHNHYTQKSLSLSPGK |
| 141 | DKTHTCPPCPAPEAAGAPSVFLFPPKPKDTLMISRTPEVTCVVVDV SHEDPEVKFNWYVDGVEVHNAKTKPREEQYASTYRVVSVLTVLHQD WLNGKEYKCKVSNKALPAPIEKTISKAKGQPREPQVYTLPPSREEM TKNQVSLWCLVKGFYPSDIAVEWESNGQPENNYKTTPPVLDSDGSF FLYSKLTVDKSRWQQGNVFSCSVMHEALHNHYTQKSLSLSPGK |
| 142 | EEELQIIQPDKSVLVAAGETATLRCTITSLFPVGPIQWFRGAGPGR ELIYNQREGPFPRVTTVSDTTKRNNMDFSIRIGAITPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 143 | EEELQIIQPDKSVLVAAGETATLRCTITSLFPVGPIQWFRGAGPGR ELIYNQREGPFPRVTTVSDTTKRNNMDFSIRIGAITPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLSCAVKGFYPSDI AVEWESNGQPENNYKTTPPVLDSDGSFFLVSKLTVDKSRWQQGNVF SCSVMHEALHNHYTQKSLSLSPGK |
| 145 | EEELQIIQPDKSVLVAAGETATLRCTITSLFPVGPIQWFRGAGPGR ELIYNQREGPFPRVTTVSDTTKRNNMDFSIRIGAITPADAGTYYCV KFRKGSPDDVEFKSGAGTELSVRAKPSEKTHTCPECPAPEAAGAPS VFLEPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLTCEVKGFYPSDI AVEWESNGQPENNYKTTPPVLDSDGSFFLYSKLTVDKSRWQQGNVF SCSVMHEALHNHYTQKSLSLSPGK |
| 146 | EEELQVIQPDKSVLVAAGETATLRCTATSLFPVGPIQWFRGAGPGR ELIYNQRQGPFPRVTTVSDLTKRNNMDFSIRIGNITPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYNSTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 147 | DKTHTCPPCPAPEAAGAPSVFLEPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLSCAVKGFYPSDIAVEWESNGQPENNYKTTPPVLDSDGSF FLVSKLTVDKSRWQQGNVFSCSVMHEALHNHYTQKSLSLSPGK |
| 148 | EEELQVIQPDKSVLVAAGETATLRCTATSLFPVGPIQWFRGAGPGR ELIYNQRQGPFPRVTTVSDLTKRNNMDFSIRIGNITPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYNSTYRVVSVLTVLHQDWLNGKEYKCKVSNKALPAP IEKTISKAKGQPREPQVYTLPPSREEMTKNQVSLSCAVKGFYPSDI AVEWESNGQPENNYKTTPPVLDSDGSFFLVSKLTVDKSRWQQGNVF SCSVMHEALHNHYTQKSLSLSPGK |
| 149 | DKTHTCPPCPAPEAAGAPSVFLEPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLWCLVKGFYPSDIAVEWESNGQPENNYKTTPPVLDSDGSF FLYSKLTVDKSRWQQGNVFSCSVMHEALHNHYTQKSLSLSPGK |

In addition to the knob-into-hole strategy, in some embodiments, electrostatic steering is also used to control the dimerization of Fc domain monomers. Electrostatic steering refers to the utilization of favorable electrostatic interactions between oppositely charged amino acids in peptides, protein domains, and proteins to control the formation of higher ordered protein molecules. In particular, to control the dimerization of Fc domain monomers using electrostatic steering, one or more amino acid residues that make up the CH3-CH3 interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In some embodiments, a negatively-charged amino acid in the interface is replaced with a positively-charged amino acid. In some embodiments, the charged amino acids are introduced to one of the interacting CH3 antibody constant domains, or both. In some embodiments, introducing charged amino acids to the interacting CH3 antibody constant domains of the two Fc domain monomers promotes the selective formation of heterodimers of Fc domain monomers as controlled by the electrostatic steering effects resulting from the interaction between charged amino acids. Examples of electrostatic steering amino acid pairs are included, without limitation, in Table 11.

TABLE 11

| | Electrostatic Steering Amino Acid Pairs | | | | | | | | | |
|---|---|---|---|---|---|---|---|---|---|---|
| Fc domain monomer 1 | K409D | K409D | K409E | K409E | K392D | K392D | K392E | K392E | K409D K392D | K370E K409D K439E |
| Fc domain monomer 2 | D399K | D399R | D399K | D399R | D399K | D399R | D399K | D399R | D399K D356K | D356K E357K D399K |

Other methods used to control the heterodimerization of Fc domain monomers, especially in the context of constructing a bispecific antibody, are available.

In some embodiments, a first Fc domain monomer and a second Fc domain monomer each includes one or more of the following amino acid substitutions: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1.

In some embodiments an Fc domain monomer comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; or (b) (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region. In some embodiments an Fc domain monomer comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; and (b) further comprises (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region.

In some embodiments, the first and second Fc domain monomers include different amino acid substitutions. In some embodiments, the first Fc domain monomer includes T366W. In some embodiments, the second Fc domain monomer includes T366S, L368A, and Y407V. In some embodiments, the first Fc domain monomer includes D399K. In some embodiments, the second Fc domain monomer includes K409D.

IV. Serum Albumin

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Fusion to serum albumins can improve the pharmacokinetics of protein pharmaceuticals, and in some embodiments, polypeptides of the disclosure, including a high affinity SIRP-α D1 variant described herein, is joined with a serum albumin.

Serum albumin is a globular protein that is abundant in blood in mammals. Serum albumin is produced in the liver and can constitute about half of the blood serum proteins. It is monomeric and soluble in the blood. Some of the most crucial functions of serum albumin include transporting hormones, fatty acids, and other proteins in the body, buffering pH, and maintaining osmotic pressure needed for proper distribution of bodily fluids between blood vessels and body tissues. In preferred embodiments, serum albumin is human serum albumin (HSA). In some embodiments, an HSA is joined to the C-terminus of the polypeptide of the disclosure to increase the serum half-life of the polypeptide. In some embodiments, the N-terminus of an HSA is joined to the C-terminus of the polypeptide of the disclosure. In some embodiments, a HSA is joined, either directly or through a linker, to the C-terminus of the polypeptide. In some embodiments, an HSA is joined, either directly or through a linker, to the N-terminus of the polypeptide.

In some embodiments, a human serum albumin comprises the sequence of amino acids (aa) 25-609 of UniProt ID NO: P02768 (SEQ ID NO: 12) as shown in Table 12. In some embodiments, the HSA joined to a high affinity SIRP-α D1 variant (e.g., any SIRP-α D1 variant described in Tables 2, 5, and 6) includes amino acids 25-609 (SEQ ID NO: 12) of the sequence of UniProt ID NO: P02768. In some embodiments, the HSA includes C34S or K573P substitutions, relative to SEQ ID NO: 12. In some embodiments, the HSA includes C34S and K573P substitutions, relative to SEQ ID NO: 12.

TABLE 12

Sequence of HSA

| SEQ ID NO: | Description | Amino Acid Sequence |
|---|---|---|
| 12 | UniProt ID NO: P02768, AA 25-609 | DAHKSEVAHRFKDLGEENFKALVLIAFAQYLQQCP FEDHVKLVNEVTEFAKTCVADESAENCDKSLHTLF GDKLCTVATLRETYGEMADCCAKQEPERNECFLQ HKDDNPNLPRLVRPEVDVMCTAFHDNEETFLKKY LYEIARRHPYFYAPELLFFAKRYKAAFTECCQAAD KAACLLPKLDELRDEGKASSAKQRLKCASLQKFGE RAFKAWAVARLSQRFPKAEFAEVSKLVTDLTKVH TECCHGDLLECADDRADLAKYICENQDSISSKLKE CCEKPLLEKSHCIAEVENDEMPADLPSLAADFVES KDVCKNYAEAKDVFLGMFLYEYARRHPDYSVVLLL RLAKTYETTLEKCCAAADPHECYAKVFDEFKPLVE EPQNLIKQNCELFEQLGEYKFQNALLVRYTKKVPQ VSTPTLVEVSRNLGKVGSKCCKHPEAKRMPCAED YLSVVLNQLCVLHEKTPVSDRVTKCCTESLVNRRP CFSALEVDETYVPKEFNAETFTFHADICTLSEKER QIKKQTALVELVKHKPKATKEQLKAVMDDFAAFVE KCCKADDKETCFAEEGKKLVAASQAALGL |

In some embodiments, a serum albumin is fused genetically to a polypeptide of the disclosure or joined to the polypeptide through chemical means, e.g., chemical conjugation. In some embodiments, a spacer is inserted between the polypeptide and the HSA. Some examples of spacers are described in detail elsewhere herein. In some embodiments, a spacer is A or AAAL SEQ ID NO: 178). In some embodiments, the fusion of an HSA in a polypeptide of the disclosure leads to prolonged retention of the polypeptide as well as increases in half-life.

Polypeptides comprising a SIRP-α D1 variant polypeptide and a fused HSA include, but are not limited to, SEQ ID NOS: 150-159 provided in Table 13.

TABLE 13

Polypeptides Comprising SIRP-α Variants Fused to HSA

| SEQ ID NO: | Amino Acid Sequence |
|---|---|
| 150 | EEELQIIQPDKSVLVAAGETATLRCTITSLFPVGPIQWFRGAGPGR VLIYNQRQGPFPRVTTVSDTTKRNNMDFSIRIGNITPADAGTYYCI KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 151 | EEELQVIQPDKSVLVAAGETATLRCTATSLFPVGPIQWFRGAGPGR ELIYNQRQGPFPRVTTVSDLTKRNNMDFSIRIGNITPADAGTYYCV KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 152 | EEELQIIQPDKSVLVAAGETATLRCTITSLFPVGPIQWFRGAGPGR VLIYNQRQGPFPRVTTVSDTTKRNNMDFSIRIGAITPADAGTYYCI KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 153 | EEELQVIQPDKSVLVAAGETATLRCTATSLFPVGPIQWFRGAGPGR ELIYNQRQGPFPRVTTVSDLTKRNNMDFSIRIGAITPADAGTYYCV KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 154 | EEELQIIQPDKSVLVAAGETATLRCTITSLFPVGPIQWFRGAGPGR VLIYNQREGPFPRVTTVSDTTKRNNMDFSIRIGAITPADAGTYYCI KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 155 | EEELQVIQPDKSVLVAAGETATLRCTATSLFPVGPIQWFRGAGPGR ELIYNQREGPFPRVTTVSDLTKRNNMDFSIRIGAITPADAGTYYCV KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD |

| SEQ ID NO: | Amino Acid Sequence |
|---|---|
| | LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 156 | EEELQVIQPDKSVLVAAGETATLRCTITSLFPVGPIQWFRGAGPGR ELIYNQREGPFPRVTTVSDLTKRNNMDFSIRIGAITPADAGTYYCV KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 157 | EEELQIIQPDKSVLVAAGETATLRCTITSLFPVGPIQWFRGAGPGR ELIYNQREGPFPRVTTVSDLTKRNNMDFSIRIGAITPADAGTYYCV KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 158 | EEELQVIQPDKSVLVAAGETATLRCTITSLFPVGPIQWFRGAGPGR ELIYNQREGPFPRVTTVSDTTKRNNMDFSIRIGAITPADAGTYYCV KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |
| 159 | EEELQIIQPDKSVLVAAGETATLRCTITSLEPVGPIQWFRGAGPGR ELIYNQREGPFPRVTTVSDTTKRNNMDFSIRIGAITPADAGTYYCV KFRKGSPDDVEFKSGAGTELSVRAKPSDAHKSEVAHRFKDLGEENF KALVLIAFAQYLQQSPFEDHVKLVNEVTEFAKTCVADESAENCDKS LHTLFGDKLCTVATLRETYGEMADCCAKQEPERNECFLQHKDDNPN LPRLVRPEVDVMCTAFHDNEETFLKKYLYEIARRHPYFYAPELLFF AKRYKAAFTECCQAADKAACLLPKLDELRDEGKASSAKQRLKCASL QKFGERAFKAWAVARLSQRFPKAEFAEVSKLVTDLTKVHTECCHGD LLECADDRADLAKYICENQDSISSKLKECCEKPLLEKSHCIAEVEN DEMPADLPSLAADFVESKDVCKNYAEAKDVFLGMFLYEYARRHPDY SVVLLLRLAKTYETTLEKCCAAADPHECYAKVFDEFKPLVEEPQNL IKQNCELFEQLGEYKFQNALLVRYTKKVPQVSTPTLVEVSRNLGKV GSKCCKHPEAKRMPCAEDYLSVVLNQLCVLHEKTPVSDRVTKCCTE SLVNRRPCFSALEVDETYVPKEFNAETFTFHADICTLSEKERQIKK QTALVELVKHKPKATKEQLKAVMDDFAAFVEKCCKADDKETCFAEE GKKLVAASQAALGL |

In some embodiments, the polypeptide includes a high affinity SIRP-α D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 13.

In some embodiments, the polypeptide includes a high affinity SIRP-α D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 154, 155, and 159 in Table 13.

V. Albumin-Binding Peptide

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Binding to serum proteins can improve the pharmacokinetics of protein pharmaceuticals, and in particular, in some embodiments, the polypeptides described herein are fused with serum protein-binding peptides or proteins.

As used herein, the term "albumin-binding peptide" refers to an amino acid sequence of about 12 to 16 amino acids that has affinity for and functions to bind a serum albumin protein. In some embodiments, an albumin-binding peptide originates from human, mouse, or rat.

In some embodiments, a polypeptide of the disclosure including a high affinity SIRP-α D1 variant (e.g., any variant provided in Tables 2, 5, and 6) is fused to an albumin-binding peptide that displays binding activity to serum albumin to increase the half-life of the polypeptide. Various albumin-binding peptides that can be used in the methods and compositions described here are available. In some embodiments, the albumin binding peptide includes the sequence DICLPRWGCLW (SEQ ID NO: 160). In some embodiments, an albumin-binding peptide is fused genetically to a polypeptide of the disclosure or attached to the polypeptide through chemical means, e.g., chemical conjugation.

In some embodiments, a linker (e.g., a spacer) is inserted between the polypeptide and the albumin-binding peptide to allow for additional structural and spatial flexibility of the fusion protein. Specific linkers (e.g., a spacer) and their amino acid sequences are described in detail further herein. In some embodiments, an albumin-binding peptide is fused to the N- or C-terminus of a polypeptide of the disclosure. In one example, the N-terminus of the albumin-binding peptide is directly fused to the C-terminus of a polypeptide of the disclosure through a peptide bond. In another example, the C-terminus of the albumin-binding peptide is directly fused to the N-terminus of a polypeptide of the disclosure through a peptide bond. In some embodiments, the fusion of an albumin-binding peptide to a polypeptide of the disclosure leads to prolonged retention of the polypeptide through its binding to serum albumin.

VI. Polyethylene Glycol (PEG) Polymer

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, a polypeptide including a high affinity SIRP-α D1 domain (e.g., any variant provided in Tables 2, 5, and 6) is fused to a polymer (e.g., polyethylene glycol, PEG). In some embodiments, the attachment of a polymer to a protein pharmaceutical "masks" the protein pharmaceutical from the host's immune system. In addition, in some embodiments, certain polymers, such as hydrophilic polymers, provide water solubility to hydrophobic proteins and drugs. For example, in some embodiments, such polymers include PEG, polysialic acid chain, and PAS chain molecules. In some embodiments, a polymer such as PEG, is covalently attached to a cysteine substitution or addition in the polypeptide. In some embodiments, the cysteine substitution in the polypeptide is I7C, A16C, S20C, T20C, A45C, G45C, G79C, S79C, or A84C, relative to the sequence of any one of the sequences provided in Tables 2, 5, and 6. In some embodiments, the addition of a cysteine residue in the polypeptide is introduced using peptide synthesis, genetic modification, molecular cloning, or any combinations thereof. In some embodiments, the polymer, for example PEG, is attached to the cysteine residue using cysteine-maleimide conjugation. In some embodiments, a polymer such as PEG, is covalently attached to the polypeptide including a high affinity SIRP-α D1 variant either at the N- or C-terminus or at an internal location, using conventional chemical methods such as chemical conjugation.

VII. Bispecific Construct

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, a polypeptide having a high affinity SIRP-α D1 variant (e.g., any of the variants provided in Tables 2, 5, and 6) comprises a bispecific construct. A bispecific construct refers to a construct that has two target-interacting domains. In some embodiments, a bispecific construct includes an Fc domain and two target-interacting domains: (1) a SIRP-α D1 domain or variant thereof (e.g., any of the variants provided in Tables 2, 5, and 6) and (2) an antibody variable domain. In some embodiments, a bispecific construct includes a first polypeptide and a second polypeptide. In some embodiments, the first polypeptide has the formula A-L-B, wherein A includes a SIRP-α D1 domain or variant thereof, L is a linker, and B includes a first Fc domain monomer. In some embodiments, the second polypeptide has the formula A'-L'-B', wherein A' includes an antibody variable domain, L' is a linker; and B' includes a second Fc domain monomer. In some embodiments, the orientation of the first and second polypeptides is B-L-A and B'-L'-A', respectively. In some embodiments, the first and second Fc domain monomers combine to form the Fc domain in the bispecific construct. In some embodiments, a bispecific construct is of any immunoglobulin antibody isotypes (e.g., IgG, IgE, IgM, IgA, and IgD). A variant of a SIRP-α D1 domain includes the D1 domain of a wild-type human SIRP-α and one or more amino acid substitutions relative to the wild-type D1 domains (e.g., any SIRP-α D1 variant as described in Tables 2, 5, and 6). In some embodiments, a SIRP-α D1 variant binds with higher binding affinity to CD47 than does a wild-type human SIRP-α D1 domain. In some embodiments, the antibody variable domain in a bispecific construct targets a cell antigen (e.g., a cell antigen on a cancer cell).

An antibody variable domain refers to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs). The variable domain of the antibody can confer on the antibody the ability to bind to specific antigens. Many different antibody variable domain molecules can be constructed. In some embodiments, the antibody variable domain molecules used includes, but is not limited to, single-chain Fv.

In some embodiments, the antibody variable domain in a bispecific construct targets a cell antigen (e.g., a cell antigen on a cancer cell or on an immune cell). Some proteins are expressed at higher levels in cancer cells than in non-cancer cells. For example, a cancer antigen is a protein that is expressed preferentially by cancer cells (e.g., it is expressed at higher levels on cancer cells than on non-cancer cells) and in some instances it is expressed solely by cancer cells. In some embodiments, proteins, e.g., proteins expressed by cancer cells, that are targeted by an antibody variable domain forming an Fc domain with a high affinity SIRP-α domain or variant thereof include, but are not limited to: 5T4, AGS-16, ALK1, ANG-2, B7-H3, B7-H4, c-fms, c-Met, CA6, CD123, CD19, CD20, CD22, EpCAM, CD30, CD32b, CD33, CD37, CD38, CD40, CD52, CD70, CD74, CD79b, CD98, CEA, CEACAM5, CLDN18.2, CLDN6, CS1, CXCR4, DLL-4, EGFR, EGP-1, ENPP3, EphA3, ETBR, FGFR2, fibronectin, FR-alpha, GCC, GD2, glypican-3, GPNMB, HER-2, HER3, HLA-DR, ICAM-1, IGF-1R, IL-3R, LIV-1, mesothelin, MUC16, MUC1, NaPi2b, Nectin-4, Notch 2, Notch 1, PD-L1, PD-L2, PDGFR-a, PS, PSMA, SLTRK6, STEAP1, TEM1, VEGFR, CD25, CD27L, DKK-1, or CSF-1R. In some embodiments, the antibody variable domain in the bispecific construct is not engineered to bind a human protein.

In some embodiments, each of the first and second Fc domain monomers in the Fc domain of the bispecific construct includes one or more amino acid substitutions that promote the heterodimerization of the first and second Fc domain monomers. Methods of promoting heterodimerization of Fc domain monomers are described in detail further herein, see, e.g., knob-into-hole strategy and electrostatic steering strategy.

In some embodiments, the Fc domain of the bispecific construct is mutated to lack one or more effector functions, typical of a "dead Fc domain." In some embodiments, the Fc domain of the bispecific construct is from an IgG1 antibody and includes amino acid substitutions L14A, L15A, and G17A, relative to the sequence of SEQ ID NO: 161 (Table 14) to reduce the interaction or binding between the Fc domain and an Fcγ receptor. In some embodiments, an Fc domain monomer is from an IgG1 antibody and includes one or more of amino acid substitutions L234A, L235A, G237A, and N297A (as designated according to the EU numbering system per Kabat et al., 1991. In some embodiments, the Fc variants described herein are minimally glycosylated or have reduced glycosylation. In some embodiments, deglycosylation is accomplished with a mutation of N297A, or by mutating N297 to any amino acid which is not N (as designated according to the EU numbering system per Kabat, et al. (1991)). In some embodiments, the bispecific construct is designed such that it has preferential binding to proteins (e.g., receptors such as Fc receptors) expressed by different cell types. Studies have demonstrated that amino acid substitutions in the hinge, constant domains (e.g., CH2 and CH3 constant domains), or hinge and constant domains of an antibody can efficiently alter the binding affinities of the antibody towards specific receptors (e.g., Fc receptors) expressed on different types of cells (e.g., regulatory T-cells and effector T-cells). IgG2 having amino acid substitutions A111S and P112S (relative to SEQ ID NO: 162, Table 14) display significantly reduced binding to FcγRIIIa 131 H compared to wild-type IgG2. In some embodiments, the Fc variants herein are minimally glycosylated or have reduced glycosylation. In some embodiments, deglycosylation is accomplished with a mutation of N297A, or by mutating N297 to any amino acid which is not N (as designated according to the EU numbering system per Kabat, et al. (1991)). In some embodiments, a bispecific construct includes an Fc domain of the IgG2 or IgG4 subclass. In some embodiments, a bispecific construct including an Fc domain of an IgG2 subclass includes amino acid substitutions A111S and P112S, relative to SEQ ID NO: 162 (Table 14). In some embodiments, the Fc variant comprises a human IgG2 Fc sequence comprising one or more of A330S, P331S and N297A amino acid substitutions (as designated according to the EU numbering system per Kabat, et al. (1991)).

TABLE 14

IgG Amino Acid Sequences

| SEQ ID NO: | Amino Acid Sequence |
|---|---|
| 161 | DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPG |
| 162 | ERKCCVECPPCPAPPVAGPSVFLFPPKPKDTLMISRTPEVTCVVVD VSHEDPEVQFNWYVDGVEVHNAKTKPREEQFNSTFRVVSVLTVVHQ DWLNGKEYKCKVSNKGLPAPIEKTISKTKGQPREPQVYTLPPSREE MTKNQVSLTCLVKGFYPSDIAVEWESNGQPENNYKTTPPMLDSDGS FFLYSKLTVDKSRWQQGNVFSCSVMHEALHNHYTQKSLSLSPGK |

Figure 2:
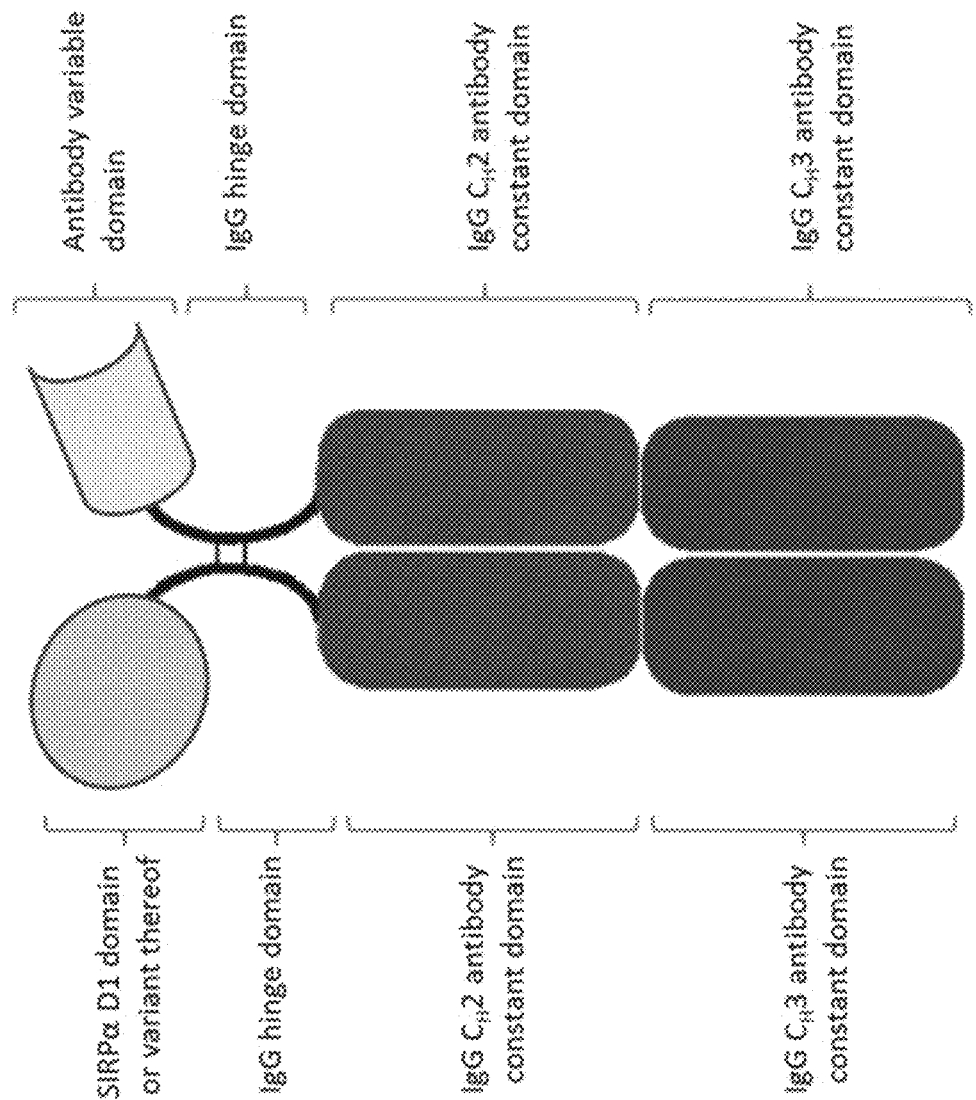
FIG. 2 is an illustration of a SIRP-α construct including a SIRP-α D1 domain or variant thereof joined to a first Fc domain monomer and an antibody variable domain joined to a second Fc domain monomer, wherein the first Fc domain monomer and the second Fc domain monomer combine to form an Fc domain.
Figure 3:
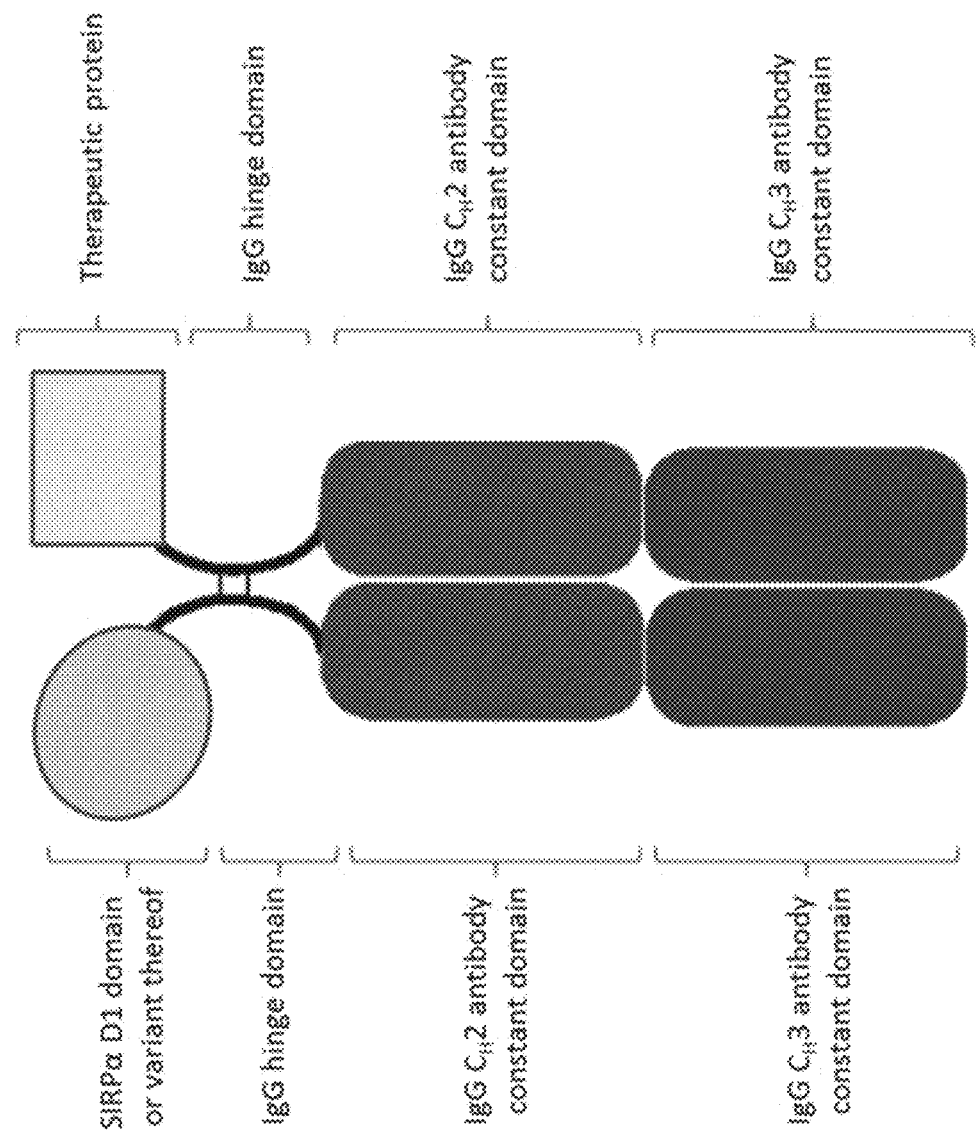
FIG. 3 is an illustration of a SIRP-α construct including a SIRP-α D1 domain or variant thereof joined to a first Fc domain monomer and a therapeutic protein joined to a second Fc domain monomer, wherein the first Fc domain monomer and the second Fc domain monomer combine to form an Fc domain.
Figures 4A, 4B:
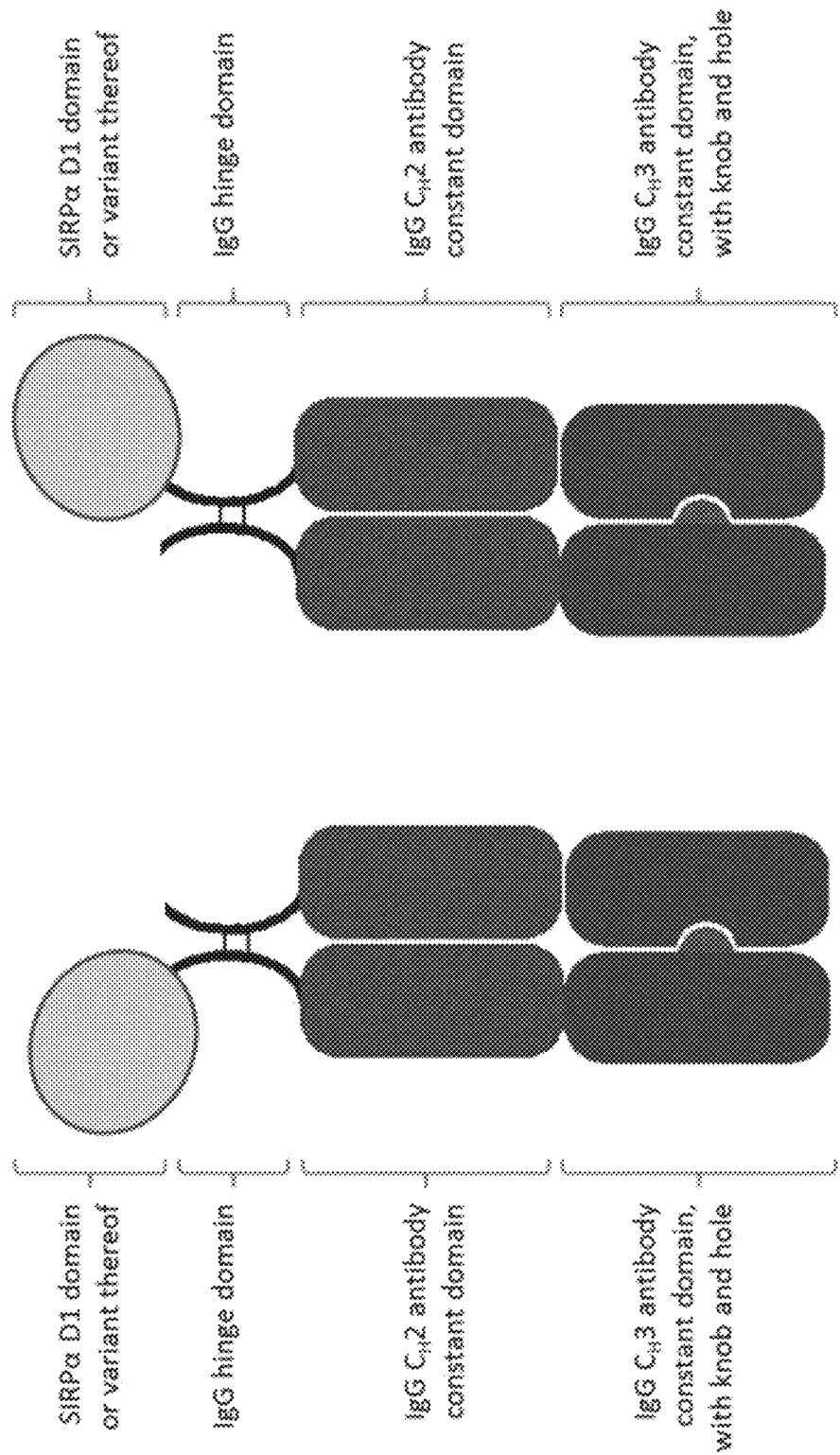
FIG. 4A is an illustration of a SIRP-α construct including a SIRP-α D1 domain or variant thereof joined to a first Fc domain monomer having a knob mutation, which forms an Fc domain with a second Fc domain monomer having a hole mutation.
FIG. 4B is an illustration of a SIRP-α construct including a SIRP-α D1 domain or variant thereof joined to a first Fc domain monomer having a hole mutation, which forms an Fc domain with a second Fc domain monomer having a knob mutation.
Figure 5B:
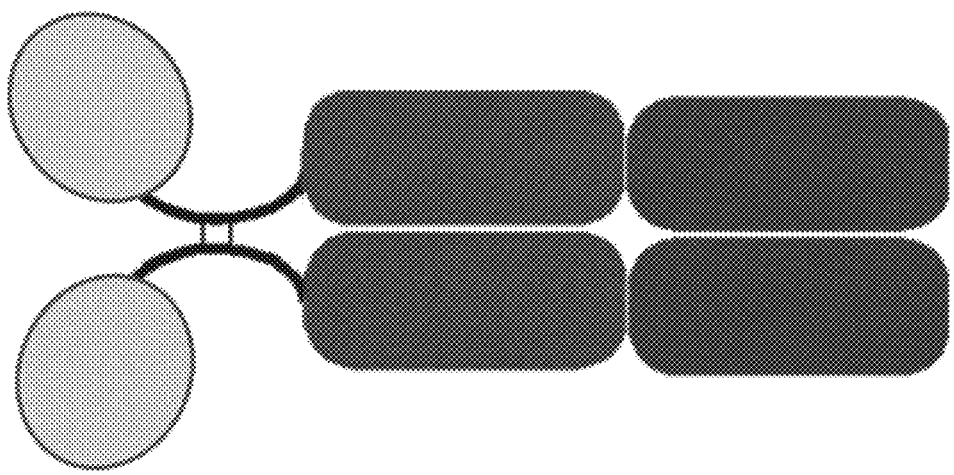
FIG. 5B is an illustration of a SIRP-α construct which is a homodimer of the construct illustrated in FIG. 5A.
Figure 5A:
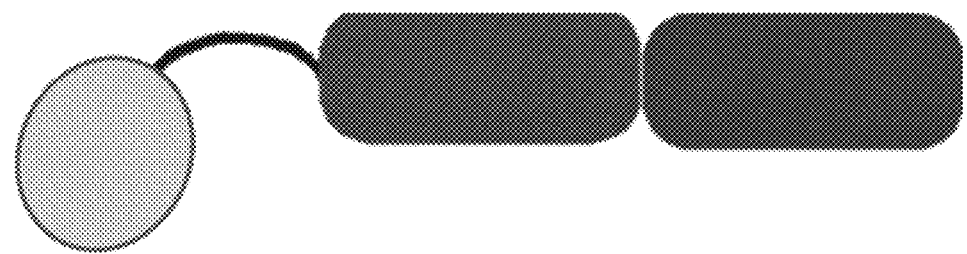
FIG. 5A is an illustration of a SIRP-α construct including a SIRP-α D1 domain or variant thereof joined to an Fc domain monomer.

An example of a SIRP-α construct comprising a SIRP-α D1 domain or variant thereof joined to a first Fc domain monomer by way of a linker and a second Fc domain monomer, in which the first and second Fc domain monomers combine to form an Fc domain is shown in FIG. 1. In some embodiments, there is no protein or antibody variable domain attached to the second Fc monomer. In some embodiments, a SIRP-α construct includes a SIRP-α D1 domain or variant thereof joined to a first Fc domain monomer by way of a linker and an antibody variable domain joined to a second Fc domain monomer by way of a linker, in which the first and second Fc domain monomers combine to form an Fc domain (as shown in FIG. 2). In some embodiments, a SIRP-α construct includes a SIRP-α D1 domain or variant thereof joined to a first Fc domain monomer by way of a linker and a therapeutic protein (e.g., a cytokine, an interleukin, an antigen, a steroid, an anti-inflammatory agent, or an immunomodulatory agent) joined to a second Fc domain monomer by way of a linker, in which the first and second Fc domain monomers combine to form an Fc domain (as shown in FIG. 3). In some embodiments, each of the two Fc domain monomers in the Fc domain of the SIRP-α constructs described previously (e.g., the SIRP-α constructs as shown in FIGS. 1-3), include amino acid substitutions that promote the heterodimerization of the two monomers. Different strategies (e.g., knob-into-hole strategy, electrostatic steering strategy) and Fc domain amino acid substitutions that promote the heterodimerization of two Fc domain monomers are described in detail herein. For example, FIG. 4A illustrates a SIRP-α construct having a SIRP-α D1 domain or variant thereof joined to an Fc domain monomer including a knob mutation, e.g., T366W, to limit unwanted knob-knob homodimer formation. FIG. 4B illustrates a SIRP-α construct having a having a SIRP-α D1 domain or variant thereof joined to an Fc domain monomer including hole mutations, e.g., T366S, L358A, and Y407V. In some embodiments, similar Fc domain heterodimerization strategies are applied to the Fc domains in the constructs described in FIGS. 2 and 3. In some embodiments, a SIRP-α construct includes a fusion protein of a SIRP-α D1 domain or variant thereof joined to an Fc domain monomer (as shown in FIG. 5A). In some embodiments, this fusion protein forms a homodimer (as shown in FIG. 5B).

Fc variants of the disclosure coupled with a fusion partner preferably exhibit reduced or ablated binding to at least one of Fcγ receptors CD16a, CD32a, CD32b, CD32c, and CD64 as compared to a similar polypeptide construct comprising the native or wild-type (non-mutated) antibody Fc region. In some cases, the Fc variant or fusion partner described herein exhibits reduced or ablated binding to the CD16a, CD32a, CD32b, CD32c, and CD64 Fcγ receptors.

In some embodiments, Fc variants of the disclosure coupled with a fusion partner exhibit reduced binding to complement component C1q and CDC compared to a similar polypeptide construct comprising the native or wild-type (non-mutated) Fc region. In some cases, the Fc variant exhibits at least a 5%, 10%, 15%, 20%, 30%, 40%, 50%, 60%, 70%, 80%, 90% or greater reduction in C1q binding compared to a polypeptide construct comprising a wild-type Fc region. In some cases, the Fc variant exhibits reduced CDC compared to a polypeptide construct comprising the native or wild-type (non-mutated) Fc region. In some embodiments, the Fc variant exhibits at least a 5%, 10%, 15%, 20%, 30%, 40%, 50%, 60%, 70%, 80%, 90% or greater reduction in CDC compared to a polypeptide construct comprising a wild-type Fc region.

VIII. Linkers

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In the present disclosure, a linker is used to describe a linkage or connection between polypeptides or protein domains or associated non-protein moieties. In some embodiments, a linker is a linkage or connection between an Fc domain monomer, an albumin-binding peptide, or an HSA, and a high affinity SIRP-α D1 variant. In some embodiments, the linker connects the C-terminus of the SIRP-α D1 variant and the N-terminus of the Fc domain monomer, the albumin-binding peptide, or the HSA, such that the two polypeptides are joined to each other in tandem series.

In some embodiments, a linker is a simple covalent bond, e.g., a peptide bond, a synthetic polymer such as a polyethylene glycol (PEG) polymer, or any kind of bond created from a chemical reaction, e.g. chemical conjugation. When a linker is a peptide bond, in some embodiments, the carboxylic acid group at the C-terminus of one protein domain reacts with the amino group at the N-terminus of another protein domain in a condensation reaction to form a peptide bond. In some embodiments, the peptide bond is formed from synthetic means through a conventional organic chemistry reaction, or by natural production from a host cell, wherein a nucleic acid molecule encoding the DNA sequences of both proteins (e.g., an Fc domain monomer and a high affinity SIRP-α D1 variant) in tandem series can be directly transcribed and translated into a contiguous polypeptide encoding both proteins by the necessary molecular machineries (e.g., DNA polymerase and ribosome) in the host cell.

When a linker is a synthetic polymer (e.g., a PEG polymer), in some embodiments, the polymer is functionalized with reactive chemical functional groups at each end to react with the terminal amino acids at the connecting ends of two proteins.

When a linker (except peptide bond mentioned above) is made from a chemical reaction, in some embodiments, chemical functional groups (e.g., amine, carboxylic acid, ester, azide, or other functional groups), are attached synthetically to the C-terminus of one protein and the N-terminus of another protein, respectively. In some embodiments, the two functional groups then react through synthetic chemistry means to form a chemical bond, thus connecting the two proteins together.

Spacers

In the present disclosure, in some embodiments, a linker between an Fc domain monomer, an albumin-binding peptide, or an HSA, and a polypeptide of the disclosure, is an amino acid spacer including about 1-200 amino acids. Suitable peptide spacers include peptide linkers containing flexible amino acid residues such as glycine and serine. Examples of linker sequences are provided in Table 15. In some embodiments, a spacer contains motifs, e.g., multiple or repeating motifs, of GS, GG, GGS, GGG, GGGGS (SEQ ID NO: 163), GGSG (SEQ ID NO: 164), or SGGG (SEQ ID NO: 165). In some embodiments, a spacer contains 2 to 12 amino acids including motifs of GS, e.g., GS, GSGS (SEQ ID NO: 166), GSGSGS (SEQ ID NO: 167), GSGSGSGS (SEQ ID NO: 168), GSGSGSGSGS (SEQ ID NO: 169), or GSGSGSGSGSGS (SEQ ID NO: 170). In some embodiments, a spacer contains 3 to 12 amino acids including motifs of GGS, e.g., GGS, GGSGGS (SEQ ID NO: 171), GGSGGSGGS (SEQ ID NO: 172), and GGSGGSGGSGGS (SEQ ID NO: 173). In some embodiments, a spacer contains 4 to 12 amino acids including motifs of GGSG (SEQ ID NO: 164), e.g., GGSG (SEQ ID NO: 164), GGSGGGSG (SEQ ID NO: 174), or GGSGGGSGGGSG (SEQ ID NO: 175). In some embodiments, a spacer contains motifs of GGGGS (SEQ ID NO: 163), e.g., GGGGSGGGGSGGGGS (SEQ ID NO: 176). In some embodiments, a spacer contains amino acids other than glycine and serine, e.g., AAS (SEQ ID NO: 177), AAAL (SEQ ID NO: 178), AAAK (SEQ ID NO: 179), AAAR (SEQ ID NO: 180), EGKSSGSGSESKST (SEQ ID NO: 181), GSAGSAAGSGEF (SEQ ID NO: 182), AEAAAKEAAAKA (SEQ ID NO: 183), KESGSVSSEQLAQFRSLD (SEQ ID NO: 184), GGGGAGGGG (SEQ ID NO: 185), GENLYFQSGG (SEQ ID NO: 186), SACYCELS (SEQ ID NO: 187), RSIAT (SEQ ID NO: 188), RPACKIPNDLKQKVMNH (SEQ ID NO: 189), GGSAGGSGSGSSGGSSGASGTGTAGGTGSGSGTGSG (SEQ ID NO: 190), AAANSSIDLISVPVDSR (SEQ ID NO: 191), or GGSGGGSEGGGSEGGGSEGGGSEGGGSEG GGSGGGS (SEQ ID NO: 192).

In some embodiments, a spacer contains motifs, e.g., multiple or repeating motifs, of EAAAK (SEQ ID NO: 193). In some embodiments, a spacer contains motifs, e.g., multiple or repeating motifs, of proline-rich sequences such as (XP)n, in which X is any amino acid (e.g., A, K, or E) and n is from 1-5, and PAPAP (SEQ ID NO: 194).

TABLE 15

Linker Sequences

| SEQ ID NO: | Amino Acid Sequence |
|---|---|
| 163 | GGGGS |
| 164 | GGSG |
| 165 | SGGG |
| 166 | GSGS |
| 167 | GSGSGS |
| 168 | GSGSGSGS |
| 169 | GSGSGSGSGS |
| 170 | GSGSGSGSGSGS |
| 171 | GGSGGS |
| 172 | GGSGGSGGS |
| 173 | GGSGGSGGSGGS |
| 174 | GGSGGGSG |
| 175 | GGSGGGSGGGSG |
| 176 | GGGGSGGGGSGGGGS |
| 177 | AAS |
| 178 | AAAL |
| 179 | AAAK |
| 180 | AAAR |
| 181 | EGKSSGSGSESKST |
| 182 | GSAGSAAGSGEF |
| 183 | AEAAAKEAAAKA |
| 184 | KESGSVSSEQLAQFRSLD |
| 185 | GGGGAGGGG |
| 186 | GENLYFQSGG |
| 187 | SACYCELS |
| 188 | RSIAT |
| 189 | RPACKIPNDLKQKVMNH |
| 190 | GGSAGGSGSGSSGGSSGASGTGTAGGTGSGSGTGSG |
| 191 | AAANSSIDLISVPVDSR |
| 192 | GGSGGGSEGGGSEGGGSEGGGSEGGGSEGGGSGGGS |
| 193 | EAAAK |
| 194 | PAPAP |

In some embodiments, the length of the peptide spacer and the amino acids used is adjusted depending on the two proteins involved and the degree of flexibility desired in the final protein fusion polypeptide. In some embodiments, the length of the spacer is adjusted to ensure proper protein folding and avoid aggregate formation. In some embodiments, a spacer such as a spacer between an HSA and a polypeptide disclosed herein, is A or AAAL (SEQ ID NO: 178).

IX. Vectors, Host Cells, and Protein Production

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, the polypeptides of the disclosure are produced from a host cell. A host cell refers to a vehicle that includes the necessary cellular components, e.g., organelles, needed to express the polypeptides and fusion polypeptides described herein from their corresponding nucleic acids. In some embodiments, the nucleic acids are included in nucleic acid vectors introduced into the host cell by transformation, transfection, electroporation, calcium phosphate precipitation, direct microinjection, infection, etc. In some embodiments, the choice of nucleic acid vectors depend on the host cell to be used. In some embodiments, host cells are of either prokaryotic (e.g., bacterial) or eukaryotic (e.g., mammalian) origin.

In some embodiments, a polypeptide, for example a polypeptide construct comprising a SIRP-α D1 variant (e.g., any variant provided in Tables 2, 5, and 6) and a fusion partner such as an Fc variant, HSA, and an albumin binding peptide, are produced by culturing a host cell transformed with a nucleic acid, preferably an expression vector, containing a nucleic acid encoding the polypeptide construct (e.g., Fc variant, linker, and fusion partner) under the appropriate conditions to induce or cause expression of the polypeptide construct. In some embodiments, the conditions appropriate for expression varies with the expression vector and the host cell chosen. In some embodiments, a wide variety of appropriate host cells are used, including, but not limited to, mammalian cells, bacteria, insect cells, and yeast. For example, a variety of cell lines that find use in the present disclosure are described in the ATCC® cell line catalog, available from the American Type Culture Collection. In some embodiments, Fc variants of this disclosure are expressed in a cell that is optimized not to glycosylate proteins that are expressed by such cell, either by genetic engineering of the cell line or modifications of cell culture conditions such as addition of kifunensine or by using a naturally non-glycosylating host such as a prokaryote (*E. coli*, etc.), and in some cases, modification of the glycosylation sequence in the Fc is not be needed.

Nucleic Acid Vector Construction and Host Cells

A nucleic acid sequence encoding the amino acid sequence of a polypeptide of the disclosure can be prepared by a variety of methods. These methods include, but are not limited to, oligonucleotide-mediated (or site-directed) mutagenesis and PCR mutagenesis. In some embodiments, a nucleic acid molecule encoding a polypeptide of the disclosure is obtained using standard techniques, e.g., gene synthesis. Alternatively, a nucleic acid molecule encoding a wild-type SIRP-α D1 domain is mutated to include specific amino acid substitutions using standard techniques, e.g., QuikChange™ mutagenesis. In some cases, nucleic acid molecules are synthesized using a nucleotide synthesizer or PCR techniques.

In some embodiments, the nucleic acids that encode a polypeptide construct, for example a polypeptide construct comprising a SIRP-α D1 variant (e.g., any variant provided in Tables 2, 5, and 6) and a fusion partner such as an Fc variant, HSA, and an albumin binding peptide, are incorporated into an expression vector in order to express the protein. A variety of expression vectors can be utilized for protein expression. Expression vectors can comprise self-replicating, extra-chromosomal vectors or vectors which integrate into a host genome. A vector can also include various components or elements. For example, in some embodiments, the vector components include, but are not limited to, transcriptional and translational regulatory sequences such as a promoter sequence, a ribosomal binding site, a signal sequence, transcriptional start and stop sequences, translational start and stop sequences, 3' and 5' untranslated regions (UTRs), and enhancer or activator sequences; an origin of replication; a selection marker gene; and the nucleic acid sequence encoding the polypeptide of interest, and a transcription termination sequence. In some embodiments, expression vectors comprise a protein operably linked with control or regulatory sequences, selectable markers, any fusion partners, additional elements, or any combinations thereof. The term "operably linked" means that the nucleic acid is placed into a functional relationship with another nucleic acid sequence. Generally, these expression vectors include transcriptional and translational regulatory nucleic acid operably linked to the nucleic acid encoding the Fc variant, and are typically appropriate to the host cell used to express the protein. A selection gene or marker, such as, but not limited to, an antibiotic resistance gene or fluorescent protein gene, can be used to select for host cells containing the expression vector, for example by antibiotic or fluorescence expression. Various selection genes are available.

In some embodiments, the components or elements of a vector are optimized such that expression vectors are compatible with the host cell type. Expression vectors which find use in the present disclosure include, but are not limited to, those which enable protein expression in mammalian cells, bacteria, insect cells, yeast, and in in vitro systems.

In some embodiments, mammalian cells are used as host cells to produce polypeptides of the disclosure. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In some embodiments, E. coli cells are used as host cells to produce polypeptides of the disclosure. Examples of E. coli strains include, but are not limited to, E. coli 294 (ATCC® 31,446), E. coli λ1776 (ATCC® 31,537, E. coli BL21 (DE3) (ATCC® BAA-1025), and E. coli RV308 (ATCC® 31,608).

Different host cells have characteristic and specific mechanisms for the posttranslational processing and modification of protein products (e.g., glycosylation). In some embodiments, appropriate cell lines or host systems are chosen to ensure the correct modification and processing of the polypeptide expressed. Once the vectors are introduced into host cells for protein production, host cells are cultured in conventional nutrient media modified as appropriate for inducing promoters, selecting transformants, or amplifying the genes encoding the desired sequences.

In some embodiments, a polypeptide construct, for example a polypeptide construct comprising a SIRP-α D1 variant (e.g., any variant provided in Tables 2, 5, and 6) and a fusion partner such as an Fc variant, HSA, and an albumin binding peptide, are expressed in mammalian expression systems, including systems in which the expression constructs are introduced into the mammalian cells using virus such as retrovirus or adenovirus. In some embodiments, human, mouse, rat, hamster, or primate cells are utilized. Suitable cells also include known research cells, including but not limited to Jurkat T cells, NIH3T3, CHO, COS, and 293 cells. Alternately, in some embodiments, proteins are expressed in bacterial cells. Bacterial expression systems are well known in the art, and include Escherichia coli (E. coli), Bacillus subtilis, Streptococcus cremoris, and Streptococcus lividans. In some cases, polypeptide constructs comprising Fc variants are produced in insect cells such as but not limited to Sf9 and Sf21 cells or yeast cells such as but not limited to organisms from the genera Saccharomyces, Pichia, Kluyveromyces, Hansenula and Yarrowia. In some cases, polypeptide constructs comprising Fc variants are expressed in vitro using cell free translation systems. In vitro translation systems derived from both prokaryotic (e.g., E. coli) and eukaryotic (e.g., wheat germ, rabbit reticulocytes) cells are available and, in some embodiments, chosen based on the expression levels and functional properties of the protein of interest. For example, as appreciated by those skilled in the art, in vitro translation is required for some display technologies, for example ribosome display. In addition, in some embodiments, the Fc variants are produced by chemical synthesis methods such as, but not limited to, liquid-phase peptide synthesis and solid-phase peptide synthesis. In the case of in vitro transcription using a non-glycosylating system such as bacterial extracts, the Fc will not be glycosylated even in presence of the natural glycosylation site and therefore inactivation of the Fc will be equivalently obtained.

In some embodiments, a polypeptide construct includes non-natural amino acids, amino acid analogues, amino acid mimetics, or any combinations thereof that function in a manner similar to the naturally occurring amino acids. Naturally encoded amino acids generally refer to the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, e.g., a carbon that is bound to a hydrogen, a carboxyl group, an amino group, and an R group, such as, homoserine, norleucine, methionine sulfoxide, methionine methyl sulfonium. In some embodiments, such analogs have modified R groups (such as, norleucine) or modified peptide backbones, but generally retain the same basic chemical structure as a naturally occurring amino acid.

Protein Production, Recovery, and Purification

In some embodiments, host cells used to produce polypeptides of the disclosure are grown in media suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. In some embodiments, host cells are cultured at suitable temperatures, such as from about 20° C. to about 39° C., e.g., from about 25° C. to about 37° C., preferably 37° C., and CO2 levels, such as about 5% to 10%. In some embodiments, the pH of the medium is from about pH 6.8 to pH 7.4, e.g., pH 7.0, depending mainly on the host organism. If an inducible promoter is used in the expression vector, protein expression can be induced under conditions suitable for the activation of the promoter.

In some embodiments, protein recovery involves disrupting the host cell, for example by osmotic shock, sonication, or lysis. Once the cells are disrupted, cell debris is removed by centrifugation or filtration. The proteins can then be further purified. In some embodiments, a polypeptide of the disclosure is purified by various methods of protein purification, for example, by chromatography (e.g., ion exchange chromatography, affinity chromatography, and size-exclusion column chromatography), centrifugation, differential solubility, or by any other standard technique for the purification of proteins. For example, in some embodiments, the protein is isolated and purified by appropriately selecting and combining affinity columns such as Protein A column (e.g., POROS Protein A chromatography) with chromatography columns (e.g., POROS HS-50 cation exchange chromatography), filtration, ultra-filtration, de-salting and dialysis procedures. In some embodiments, a polypeptide is conjugated to marker sequences, such as a peptide to facilitate purification. An example of a marker amino acid sequence is a hexa-histidine peptide (His6-tag (SEQ ID NO: 223)), which can bind to a nickel-functionalized agarose affinity column with micromolar affinity. As an alternative, a hemagglutinin "HA" tag, which corresponds to an epitope derived from the influenza hemagglutinin protein can be used.

In some embodiments, polypeptides of the disclosure, for example a polypeptide construct comprising a SIRP-α D1 variant (e.g., any variant provided in Tables 2, 5, and 6) and a fusion partner such as an Fc variant, HSA, and an albumin binding peptide, are produced by the cells of a subject (e.g., a human), e.g., in the context of gene therapy, by administrating a vector such as a viral vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding a polypeptide of the disclosure. The vector, once inside a cell of the subject (e.g., by transformation, transfection, electroporation, calcium phosphate precipitation, direct microinjection, infection, etc) can be used for the expression of a polypeptide disclosed herein. In some cases, the polypeptide is secreted from the cell. In some embodiments, if treatment of a disease or disorder is the desired outcome, no further action is required. In some embodiments, if collection of the protein is desired, blood is collected from the subject and the protein purified from the blood by various methods.

X. Pharmaceutical Compositions and Preparations

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

The disclosure features pharmaceutical compositions that include polypeptides described herein, such as polypeptides having a high affinity SIRP-α D1 variant. In some embodiments, a pharmaceutical composition of the disclosure includes a polypeptide of the disclosure as the therapeutic protein. In some embodiments, a pharmaceutical composition of the disclosure including a polypeptide described herein is used in combination with other agents or compositions (e.g., therapeutic agents, biologics, small molecules, or any combinations thereof) in a therapy. In some embodiments, one or more additional therapeutically active agents, such as for example a small molecule, chemical compound or a biological compound such as polynucleotides and polypeptides including, but not limited to, siRNA, short polypeptides, and antibodies with therapeutic activity, are optionally formulated in pharmaceutical compositions of polypeptides described herein. In some embodiments, formulations of polypeptide constructs described herein are prepared for storage by mixing a polypeptide construct described herein having the desired degree of purity with optional, pharmaceutically acceptable carriers, excipients or stabilizers in the form of lyophilized formulations or aqueous solutions. In some embodiments, a pharmaceutical composition of the disclosure includes a nucleic acid molecule (DNA or RNA, e.g., mRNA) encoding a polypeptide of the disclosure, or a vector containing such a nucleic acid molecule.

Acceptable carriers, excipients, or stabilizers in a pharmaceutical composition are preferably nontoxic to recipients at the dosages and concentrations administered. In some embodiments, acceptable carriers, excipients, and stabilizers include buffers such as phosphate, citrate, HEPES, TAE, and other organic acids; antioxidants such as ascorbic acid and methionine; preservatives (e.g., hexamethonium chloride; octadecyldimethylbenzyl ammonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (e.g., less than about 10 residues) polypeptides; proteins such as human serum albumin, gelatin, dextran, and immunoglobulins; hydrophilic polymers such as polyvinylpyrrolidone; amino acids such as glycine, glutamine, histidine, and lysine; monosaccharides, disaccharides, and other carbohydrates such as glucose, mannose, sucrose, and sorbitol; chelating agents such as EDTA sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g., Zn-protein complexes); non-ionic surfactants such as TWEEN™, PLURONICS™, and polyethylene glycol (PEG); or any combinations thereof.

In some embodiments, pharmaceutical compositions that comprise polypeptides described herein are in a water-soluble form, such as being present as pharmaceutically acceptable salts, which is meant to include both acid and base addition salts. The term "pharmaceutically acceptable acid addition salt" refers to those salts that retain the biological effectiveness of the free bases and that are not otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. The term "pharmaceutically acceptable base addition salts" includes those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This can be accomplished by filtration through sterile filtration membranes or other methods.

In some embodiments, pharmaceutical compositions of the disclosure are administered parenterally in the form of an injectable formulation. In some embodiments, pharmaceutical compositions for injection are formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), and F-12 medium). Various formulation methods are available.

In some embodiments, the polypeptides described herein are formulated as immunoliposomes. A liposome is a small vesicle comprising various types of lipids, phospholipids or surfactants that is useful for delivery of a therapeutic agent to a mammal. Liposomes containing the antibody or Fc fusion can be prepared by various methods known in the art. In some embodiments, the components of the liposome are arranged in a bilayer formation, similar to the lipid arrangement of biological membranes. In some embodiments, liposomes are generated by the reverse phase evaporation method with a lipid composition comprising phosphatidylcholine, cholesterol and PEG-derivatized phosphatidylethanolamine (PEG-PE). In some embodiments, liposomes are extruded through filters of defined pore size to yield liposomes with the desired diameter. In some embodiments, a chemotherapeutic agent or other therapeutically active agent is optionally contained within the liposome.

In some embodiments, polypeptide constructs described herein and other therapeutically active agents are entrapped in microcapsules prepared by methods including, but not limited to, coacervation techniques, interfacial polymerization (for example using hydroxymethylcellulose or gelatin-microcapsules, or poly-(methylmethacrylate) microcapsules), colloidal drug delivery systems (for example, liposomes, albumin microspheres, microemulsions, nanoparticles and nanocapsules), and macroemulsions.

In some embodiments, sustained-release preparations are prepared. Suitable examples of sustained-release preparations include semipermeable matrices of solid hydrophobic polymer, which matrices are in the form of shaped articles, e.g., films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers such as the LUPRON DEPOT™ (which are injectable microspheres composed of lactic acid-glycolic acid copolymer and leuprolide acetate), poly-D-(–)-3-hydroxybutyric acid, and Pro-Lease® (commercially available from Alkermes), which is a microsphere-based delivery system composed of the desired bioactive molecule incorporated into a matrix of poly-DL-lactide-co-glycolide (PLG). Some sustained-release formulations enable release of molecules over a few months, e.g., one to six months, while other formulations release pharmaceutical compositions of the disclosure for shorter time periods, e.g., days to weeks.

In some embodiments, the concentration of the polypeptide described herein in a pharmaceutical formulation varies from about 0.1 to 100 weight %. In some cases, the concentration of the polypeptide described herein is in the range of 0.003 to 1.0 molar. In some cases, the concentration of the polypeptide in a pharmaceutical formulation varies from about 5 mg/mL to about 50 mg/mL (e.g., from about 10 mg/mL to about 40 mg/mL or from about 20 mg/mL to about 30 mg/mL). In some embodiments, in order to treat a patient, a therapeutically effective dose of a polypeptide described herein is administered. The term "therapeutically effective dose" refers to a dose that produces the effects for which it is administered. The exact dose will depend on the purpose of the treatment. In some embodiments, dosages range from 0.01 to 100 mg/kg of body weight or greater, for example 0.1, 1, 5, 10, 15, 20, 25, 30, 35, 40, 45 or 50 mg/kg of body weight. In some embodiments, adjustments for polypeptide construct degradation, systemic versus localized delivery, and rate of new protease synthesis, as well as the age, body weight, general health, sex, diet, time of administration, drug interaction and the severity of the condition is necessary.

In some embodiments, the compositions and formulations described herein are administered to a subject in need thereof. In some embodiments, such administration is carried out in vivo. In some embodiments, such administration is carried out ex vivo. In some embodiments, administration of the pharmaceutical composition comprising a polypeptide described herein, is done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance™ pulmonary delivery system commercially available from Inhale Therapeutics), vaginally, parenterally, rectally, or intraocularly. In some embodiments, the pharmaceutical composition is formulated accordingly depending upon the manner of introduction.

In some embodiments, the pharmaceutical composition for gene therapy is in an acceptable diluent, or includes a slow release matrix in which the gene delivery vehicle is imbedded. In some embodiments, vectors used as in vivo gene delivery vehicles include, but are not limited to, retroviral vectors, adenoviral vectors, poxviral vectors (e.g., vaccinia viral vectors, such as Modified Vaccinia Ankara), adeno-associated viral vectors, and alphaviral vectors.

XI. Routes, Dosage, and Administration

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, pharmaceutical compositions that include polypeptides of the disclosure as the therapeutic proteins are formulated for, e.g., intravenous administration, parenteral administration, subcutaneous administration, intramuscular administration, intra-arterial administration, intrathecal administration, or intraperitoneal administration. In some embodiments, the pharmaceutical composition is formulated for, or administered via, oral, nasal, spray, aerosol, rectal, or vaginal administration. For injectable formulations, various effective pharmaceutical carriers are available.

In some embodiments, a pharmaceutical composition that includes a nucleic acid molecule encoding a polypeptide of the disclosure or a vector containing such nucleic acid molecule is administered by way of gene delivery. Various methods of gene delivery are available. In some embodiments, vectors used for in vivo gene delivery and expression include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors. In some embodiments, mRNA molecules encoding polypeptides of the disclosure are administered directly to a subject.

The dosage of the pharmaceutical compositions of the disclosure depends on factors including the route of administration, the disease to be treated, and physical characteristics, e.g., age, weight, general health, of the subject. In some embodiments, the amount of a polypeptide of the disclosure contained within a single dose is an amount that effectively prevents, delays, or treats the disease without inducing significant toxicity. In some embodiments, a pharmaceutical composition of the disclosure includes a dosage of a polypeptide of the disclosure ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 50 mg/kg and, in a more specific embodiment, about 1 to about 30 mg/kg. In some embodiments, the dosage is adapted by a physician in accordance with the extent of the disease and different parameters of the subject.

In some embodiments, toxicity of therapeutic agents and polypeptides described herein is determined by standard pharmaceutical procedures in cell cultures or experimental animals, e.g., by determining the $LD_{50}$ (the dose lethal to 50% of the population) or the $LD_{100}$ (the dose lethal to 100% of the population). In some embodiments, the data obtained from these cell culture assays and animal studies is used in formulating a dosage range that is not toxic for use in human. The dosage of the proteins described herein lies preferably within a range of circulating concentrations that include the effective dose with little or no toxicity. In some embodiments, the dosage is varied within this range depending upon the dosage form employed and the route of administration utilized. In some embodiments, the exact formulation, route of administration and dosage is chosen by an individual physician in view of the patient's condition.

In some embodiments, the pharmaceutical compositions are administered in a manner compatible with the dosage formulation and in such amount as is therapeutically effective to result in an improvement or remediation of symptoms of a disease or disorder. In some embodiments, the pharmaceutical compositions are administered in a variety of dosage forms, e.g., intravenous dosage forms, subcutaneous dosage forms, and oral dosage forms (e.g., ingestible solutions, drug release capsules). Generally, therapeutic proteins are dosed at 0.1-100 mg/kg, e.g., 1-50 mg/kg. In some embodiments, pharmaceutical compositions that include a polypeptide of the disclosure are administered to a subject in need thereof, for example, one or more times (e.g., 1-10 times or more) daily, weekly, monthly, biannually, annually, or as medically necessary. Dosages can be provided in either a single or multiple dosage regimens. In some embodiments, the timing between administrations is decreased as the medical condition improves or increased as the health of the patient declines.

XII. Methods of Treatment

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Further disclosed herein, in some embodiments, are methods of treatment comprising administering polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

In some embodiments, the disclosure provides pharmaceutical compositions and methods of treatment that are used to treat patients who are suffering from diseases and disorders associated with SIRP-α or CD47 activity, such as cancers and immunological diseases (e.g., autoimmune diseases and inflammatory diseases). In some embodiments, the polypeptides described herein are administered to a subject in a method of increasing phagocytosis of a target cell (e.g., a cancer cell) in the subject. In some embodiments, the polypeptides are administered to a subject in a method to kill cancer cells in the subject. In some embodiments, the polypeptides are administered to a subject in a method of eliminating regulatory T-cells in the subject. In some embodiments, the polypeptides described herein are administered to a subject in a method of increasing hematopoietic stem cell engraftment in the subject, wherein the method includes modulating the interaction between SIRP-α and CD47 in the subject. In some embodiments, the polypeptides described herein are administered to a subject in a method of altering an immune response (e.g., suppressing the immune response) in the subject. In some embodiments, the foregoing methods are coupled with other methods for treating a disease. In some embodiments, disclosed herein, are a combination of a polypeptide (e.g., a SIRP-α D1 variant) and a second therapeutic agent. In some embodiments, the combination comprises a polypeptide (e.g., a SIRP-α D1 variant) and a second therapeutic agent, wherein the second therapeutic agent is an antibody. In some embodiments, the combination comprises a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody. In some embodiments, the combination comprises a polypeptide having a sequence according to any one of SEQ ID NOs: 78-85, 98-104, 107-113, 116-122, 135-137, or 152-159; and an antibody.

In some embodiments, the foregoing methods are employed with strategies for treating a disease wherein administration of a polypeptide is a therapeutic option. Non-limiting examples of the foregoing include use of an antibody or a protein fragment. For example, in some embodiments, an antibody or protein fragment is administered in combination with the Fc variant polypeptides disclosed herein. In some embodiments, the polypeptide constructs disclosed herein are used to improve the phagocytosis of other agents.

Methods of treatment include administering to a subject having a disease (e.g., cancer) (i) a polypeptide including a SIRP-α D1 variant and optionally (ii) an antibody. In some embodiments, before treating a disease (e.g., cancer) in a subject, the amino acid sequence(s) of SIRP-α in the subject are determined, for example, from each of the two alleles encoding the SIRP-α gene. In this method of treatment, the amino acid sequence(s) of SIRP-α polypeptides in a biological sample from the subject are first determined. The subject is then administered a therapeutically effective amount of a polypeptide of the disclosure. In some embodiments, the high affinity SIRP-α D1 variant administered has the same amino acid sequence as that of SIRP-α polypeptides in the biological sample of the subject, except for the introduction of amino acids changes which increase the affinity of the SIRP-α polypeptide to CD47. The high affinity SIRP-α D1 variant in the polypeptide preferably has minimal immunogenicity in the subject after the polypeptide is administered.

In some embodiments, an antibody is administered in addition to the polypeptides disclosed herein. In some embodiments, the antibody is co-administered with the polypeptide. In some embodiments, the antibody is administered simultaneously, for example in a pharmaceutical composition having both the polypeptide and the antibody. Alternatively, the antibody is administered either before or after the administration of the polypeptide. In some embodiments, the polypeptide and the antibody are administered substantially simultaneously (e.g., within one week, 6, 5, 4, 3, 2, 1 days, 12, 6, 3, 2, 1 hours of each other, or substantially simultaneously), followed by administering the antibody alone. In some embodiments, the antibody is administered first, followed by administering of the polypeptide and the antibody substantially simultaneously (i.e., within one week, 6, 5, 4, 3, 2, 1 days, 12, 6, 3, 2, 1 hours of each other, or substantially simultaneously).

An antibody co-administered or provided in a composition or method disclosed herein, refers to an antibody that targets a cell, such as a cancer cell or a cell of the immune system, such as a T-cell (e.g., a regulatory T-cell). An antibody can be of any immunoglobulin antibody isotypes, e.g., IgG, IgE, IgM, IgA, or IgD. In some embodiments, the antibody is a human IgG1 isotype antibody. In some embodiments, the antibody is a human IgG2 isotype antibody. In some embodiments, the antibody is a human IgG4 isotype antibody.

The term "antibody" herein is used in the broadest sense and encompasses various antibody structures, including but not limited to monoclonal antibodies, polyclonal antibodies, multi-specific antibodies (e.g., bispecific antibodies), antibody fragments, and antibody-like proteins so long as they exhibit the desired activity. "Antibody fragments" include a portion of an intact antibody, preferably the antigen binding or variable region of the intact antibody. Examples of antibody fragments include Fab, Fab', F(ab')2, and Fv fragments, diabodies, linear antibodies, single-chain antibody molecules, and multi-specific antibodies. Monoclonal antibody refers to an antibody obtained from a population of substantially homogeneous antibodies, e.g., individual antibodies in the population have the same primary sequence except for possible naturally occurring mutations that can be present in minor amounts. Monoclonal antibodies can be highly specific and directed against a single antigenic site (e.g., an epitope on a cancer antigen). In contrast to polyclonal antibody preparations which typically include different antibodies directed against different epitopes, each monoclonal antibody is generally directed against a single epitope on the antigen. The modifier "monoclonal" indicates the character of the antibody as being obtained from a substantially homogenous population of antibodies, and is not to be construed as requiring production of the antibody by any particular method. In some embodiments, an antibody in a composition of the present disclosure causes antibody-dependent cellular phagocytosis (ADCP) or antibody-dependent cellular cytotoxicity (ADCC). Non-limiting examples of diseases that are treated using such strategies include cancers such hematological cancers, for example leukemias (e.g., acute myeloid leukemia); immune disorders (e.g., to enhance a subject's impaired or diminished immune response, or alternately to limit a subject's over-active immune response); and pathogenic infections.

In some embodiments, the methods disclosed herein comprise administering a polypeptide described herein (e.g., a SIRP-a D1 variant) and an antibody that targets a cancer antigen. In some embodiments, a cancer antigen targeted by an antibody or antibody-like protein are exposed peptides derived from intracellular tumor-associated antigens (TAAs) in complex with human leukocyte antigen (HLA) class I molecules on the surface (also known as MHC/peptide complex). Non-limiting examples of such cancer antigens, e.g. peptides in complex with HLA molecules exposed on the surface of cancer cells, that are targeted by an antibody or anti-body-like proteins in a composition of the disclosure include: NY-ESO-1/LAGE1, SSX-2, MAGE family (MAGE-A3), gp100/pmel17, Melan-A/MART-1, gp75/TRP1, tyrosinase, TRP2, CEA, PSA, TAG-72, Immature laminin receptor, MOK/RAGE-1, WT-1, Her2/neu, EphA3, SAP-1, BING-4, Ep-CAM, MUC1, PRAME, survivin, Mesothelin, BRCA1/2 (mutated), CDK4, CML66, MART-2, p53 (mutated), Ras (mutated), β-catenin (mutated), TGF-βRII (mutated), HPV E6, E7. Examples of such antibodies include ESK1 (WT-1), RL1B (Her2-E75), Pr20 (PRAME), and 3.2G1 (hCGβ).

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody that targets a cancer antigen. In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody that targets NY-ESO-1/LAGE1, SSX-2, MAGE family (MAGE-A3), gp100/pmel17, Melan-A/MART-1, gp75/TRP1, tyrosinase, TRP2, CEA, PSA, TAG-72, Immature laminin receptor, MOK/RAGE-1, WT-1, Her2/neu, EphA3, SAP-1, BING-4, Ep-CAM, MUC1, PRAME, survivin, Mesothelin, BRCA1/2 (mutated), CDK4, CML66, MART-2, p53 (mutated), Ras (mutated), β-catenin (mutated), TGF-βRII (mutated), HPV E6, E7. In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is ESK1 (WT-1), RL1B (Her2-E75), Pr20 (PRAME), and 3.2G1 (hCGβ).

In some embodiments, the methods disclosed herein comprise administering a polypeptide having a sequence according to SEQ ID NOs: 78-85, 98-104, 107-113, 116-122, 135-137, or 152-159. and an antibody that targets a cancer antigen. In some embodiments, the methods disclosed herein comprise administering a polypeptide having a sequence according to any one of SEQ ID NOs: 78-85, 98-104, 107-113, 116-122, 135-137, or 152-159; and an antibody that targets NY-ESO-1/LAGE1, SSX-2, MAGE family (MAGE-A3), gp100/pmel17, Melan-A/MART-1, gp75/TRP1, tyrosinase, TRP2, CEA, PSA, TAG-72, Immature laminin receptor, MOK/RAGE-1, WT-1, Her2/neu, EphA3, SAP-1, BING-4, Ep-CAM, MUC1, PRAME, survivin, Mesothelin, BRCA1/2 (mutated), CDK4, CML66, MART-2, p53 (mutated), Ras (mutated), β-catenin (mutated), TGF-βRII (mutated), HPV E6, E7. In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is ESK1 (WT-1), RL1B (Her2-E75), Pr20 (PRAME), and 3.2G1 (hCGβ).

In some embodiments, an antibody targets cancer cells, for example, by binding to proteins expressed by cancer cells. Some proteins are expressed at higher levels in cancer cells than in non-cancer cells. For example, a cancer antigen is a protein that is expressed preferentially by cancer cells (e.g., it is expressed at higher levels in cancer cells than on non-cancer cells) and in some instances it is expressed solely by cancer cells. Non-limiting examples of proteins, e.g., proteins expressed by cancer cells, that are be targeted by an antibody in a composition of the disclosure include: 4-1BB, 5T4, AGS-16, ALK1, ANG-2, B7-H3, B7-H4, c-fms, c-Met, CA6, CCR4, CD123, CD19, CD20, CD22, CD27, EpCAM, CD30, CD32b, CD33, CD37, CD38, CD40, CD52, CD70, CD74, CD79b, CD98, CEA, CEACAM5, CLDN18.2, CLDN6, CS1, CTLA-4, CXCR4, DLL-4, EGFR, EGP-1, ENPP3, EphA3, ETBR, FGFR2, fibronectin, FR-alpha, Frizzled receptor, GCC, GD2, glypican-3, GPNMB, HER-2, HER3, HLA-DR, ICAM-1, IGF-1 R, IL-3R, LAG-3, LIV-1, mesothelin, MUC16, MUC1, NaPi2b, Nectin-4, Notch 2, Notch 1, OX40, PD-1, PD-L1, PD-L2, PDGFR-α, PS, PSMA, SLTRK6, STEAP1, TEM1, VEGFR, CD25, CD27L, DKK-1, CSF-1 R, or any combinations thereof. In some embodiments, the polypeptides described herein are administered in combination with a checkpoint inhibitor, such as an antibody inhibitor of CTLA-4 (e.g., ipilimumab, tremelimumab), PD-1 (e.g., nivolumab, Pidilizumab, MK3475 also known as pembrolizumab, BMS936559, and MPDL3280A), and LAG-3 (e.g., BMS986016).

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody that targets a protein expressed a by a cancer cell. In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody that targets 4-1BB, 5T4, AGS-16, ALK1, ANG-2, B7-H3, B7-H4, c-fms, c-Met, CA6, CCR4, CD123, CD19, CD20, CD22, CD27, EpCAM, CD30, CD32b, CD33, CD37, CD38, CD40, CD52, CD70, CD74, CD79b, CD98, CEA, CEACAM5, CLDN18.2, CLDN6, CS1, CTLA-4, CXCR4, DLL-4, EGFR, EGP-1, ENPP3, EphA3, ETBR, FGFR2, fibronectin, FR-alpha, Frizzled receptor, GCC, GD2, glypican-3, GPNMB, HER-2, HER3, HLA-DR, ICAM-1, IGF-1 R, IL-3R, LIV-1, mesothelin, MUC16, MUC1, NaPi2b, Nectin-4, Notch 2, Notch 1, OX40, PD-1, PD-L1, PD-L2, PDGFR-α, PS, PSMA, SLTRK6, STEAP1, TEM1, VEGFR, CD25, CD27L, DKK-1, CSF-1 R, or any combination thereof. In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is an antibody inhibitor of CTLA-4 (e.g., ipilimumab, tremelimumab), PD-1 (e.g., nivolumab, Pidilizumab, MK3475 also known as pembrolizumab, BMS936559, and MPDL3280A), or LAG-3 (e.g., BMS986016).

In some embodiments, the methods disclosed herein comprise administering a polypeptide having a sequence according to any one of SEQ ID NOs: 78-85, 98-104, 107-113, 116-122, 135-137, or 152-159; and an antibody that targets a protein expressed a by a cancer cell. In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody that targets 4-1BB, 5T4, AGS-16, ALK1, ANG-2, B7-H3, B7-H4, c-fms, c-Met, CA6, CCR4, CD123, CD19, CD20, CD22, CD27, EpCAM, CD30, CD32b, CD33, CD37, CD38, CD40, CD52, CD70, CD74, CD79b, CD98, CEA, CEACAM5, CLDN18.2, CLDN6, CS1, CTLA-4, CXCR4, DLL-4, EGFR, EGP-1, ENPP3, EphA3, ETBR, FGFR2, fibronectin, FR-alpha, Frizzled receptor, GCC, GD2, glypican-3, GPNMB, HER-2, HER3, HLA-DR, ICAM-1, IGF-1 R, IL-3R, LAG-3, LIV-1, mesothelin, MUC16, MUC1, NaPi2b, Nectin-4, Notch 2, Notch 1, OX40, PD-1, PD-L1, PD-L2, PDGFR-α, PS, PSMA, SLTRK6, STEAP1, TEM1, VEGFR, CD25, CD27L, DKK-1, CSF-1 R, or any combinations thereof. In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is an antibody inhibitor of CTLA-4 (e.g., ipilimumab, tremelimumab), PD-1 (e.g., nivolumab, pidilizumab, MK3475 also known as pembrolizumab, BMS936559, and MPDL3280A), or LAG-3 (e.g., BMS986016).

In some embodiments, the methods disclosed herein comprise administering a polypeptide described herein (e.g., a SIRP-a D1 variant) and an immuno-oncology antibody. In some embodiments, antibodies that are used in compositions of the disclosure include, but are not limited to: cetuximab, necitumumab, pembrolizumab, nivolumab, pidilizumab, MEDI0680, MED16469, atezolizumab, avelumab, durvalumab, MEDI6383, RG7888, ipilimumab, tremelimumab, urelumab, PF-05082566, enoblituzumab, vantictumab, varlilumab, mogamalizumab, SAR650984, daratumumab, trastuzumab, trastuzumab emtansine, pertuzumab, elotuzumab, rituximab, ofatumumab, obinutuzumab, RG7155, FPA008, panitumumab, brentuximab vedotin, MSB0010718C, belimumab, bevacizumab, denosumab, panitumumab, ramucirumab, necitumumab, nivolumab, pembrolizumab, avelumab, atezolizumab, durvalumab, MEDI0680, pidilizumab, or BMS-93659, anti-HER2 antibody, anti-CD20 antibody, anti-CD19 antibody, anti-CS1 antibody, anti-CD38 antibody, anti-EGFR antibody, anti-PD1 antibody, anti-RANKL antibody, anti-OX40 antibody, anti-PD-1 antibody, anti-PD-L1 antibody, anti-CD274 antibody, anti-CTLA-4 antibody, anti-CD137 antibody, anti-4-1BB antibody, anti-B7-H3 antibody, anti-FZD7 antibody, anti-CD27 antibody, anti-CCR4 antibody, anti-CD38 antibody, anti-CSF1R antibody, anti-CSF antibody, anti-CD30 antibody, anti-BAFF antibody, anti-VEGF antibody, or anti-VEGFR2 antibody. In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is, an anti-HER2 antibody, anti-CD20 antibody, anti-CD19 antibody, anti-CS1 antibody, anti-CD38 antibody, anti-EGFR antibody, anti-PD1 antibody, anti-RANKL antibody, anti-OX40 antibody, anti-PD-1 antibody, anti-PD-L1 antibody, anti-CD274 antibody, anti-CTLA-4 antibody, anti-CD137 antibody, anti-4-1BB antibody, anti-B7-H3 antibody, anti-FZD7 antibody, anti-CD27 antibody, anti-CCR4 antibody, anti-CD38 antibody, anti-CSF1R antibody, anti-CSF antibody, anti-CD30 antibody, anti-BAFF antibody, anti-VEGF antibody, or anti-VEGFR2 antibody. In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is cetuximab, necitumumab, pembrolizumab, nivolumab, pidilizumab, MEDI0680, MED16469, atezolizumab, avelumab, durvalumab, MEDI6383, RG7888, ipilimumab, tremelimumab, urelumab, PF-05082566, enoblituzumab, vantictumab, varlilumab, mogamalizumab, SAR650984, daratumumab, trastuzumab, trastuzumab emtansine, pertuzumab, elotuzumab, rituximab, ofatumumab, obinutuzumab, RG7155, FPA008, panitumumab, brentuximab vedotin, MSB0010718C, belimumab, bevacizumab, denosumab, panitumumab, ramucirumab, necitumumab, nivolumab, pembrolizumab, avelumab, atezolizumab, durvalumab, MEDI0680, pidilizumab, or BMS-93659.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is trastuzumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is rituximab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α

D1 domain at a residue selected from the group consisting of: residue 6, residue 27, residue 31, residue 47, residue 53, residue 54, residue 56, residue 66, and residue 92; and an antibody, wherein the antibody is cetuximab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is daratumumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is belimumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is bevacizumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is denosumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is pantimumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is ramucirumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is necitumumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is nivolumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is pembrolizumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is avelumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is atezolizumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is durvalumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is MEDI0680.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is pidilizumab.

In some embodiments, the methods disclosed herein comprise administering a polypeptide comprising a SIRP-α D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92; and an antibody, wherein the antibody is BMS-93659.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is, an anti-HER2 antibody, anti-CD20 antibody, anti-CD19 antibody, anti-CS1 antibody, anti-CD38 antibody, anti-EGFR antibody, anti-PD1 antibody, anti-RANKL antibody, anti-OX40 antibody, anti-PD-1 antibody, anti-PD-L1 antibody, anti-CD274 antibody, anti-CTLA-4 antibody, anti-CD137 antibody, anti-4-1BB antibody, anti-B7-H3 antibody, anti-FZD7 antibody, anti-CD27 antibody, anti-CCR4 antibody, anti-CD38 antibody, anti-CSF1R antibody, anti-CSF antibody, anti-CD30 antibody, anti-BAFF antibody, anti-VEGF antibody, or anti-VEGFR2 antibody. In some embodiments, the methods disclosed herein comprise administering a polypeptide having a sequence according to SEQ ID NOs: SEQ ID NOs: 78-85, 98-104, 107-113, 116-122, 135-137, or 152-159; and an antibody, wherein the antibody is cetuximab, necitumumab, pembrolizumab, nivolumab, pidilizumab, MEDI0680, MEDI6469, atezolizumab, avelumab, durvalumab, MEDI6383, RG7888, ipilimumab, tremelimumab, urelumab, PF-05082566, enoblituzumab, vantictumab, varlilumab, mogamalizumab, SAR650984, daratumumab, trastuzumab, trastuzumab emtansine, pertuzumab, elotuzumab, rituximab, ofatumumab, obinutuzumab, RG7155, FPA008, panitumumab, brentuximab vedotin, MSB0010718C, belimumab, bevacizumab, denosumab, panitumumab, ramucirumab, necitumumab, nivolumab, pembrolizumab, avelumab, atezolizumab, durvalumab, MEDI0680, pidilizumab, or BMS-93659.

In some embodiments, the methods disclosed herein comprise administering a polypeptide having a sequence according to any one of SEQ ID NOs: 78-85, 98-104, 107-113, 116-122, 135-137, or 152-159; and an antibody, wherein the antibody is trastuzumab.

In some embodiments, the methods disclosed herein comprise administering a polypeptide having a sequence according to any one of SEQ ID NOs: 7 SEQ ID NOs: 78-85, 98-104, 107-113, 116-122, 135-137, or 152-159; and an antibody, wherein the antibody is rituximab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is cetuximab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is daratumumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is belimumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is bevacizumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is denosumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is pantimumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is ramucirumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is necitumumab.

In some embodiments, the methods disclosed herein comprise a polypeptide having a sequence according to any one of SEQ ID NOs: SEQ ID NOs: 78-85, 98-104, 107-113, 116-122, 135-137, or 152-159; and an antibody, wherein the antibody is nivolumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is pembrolizumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is avelumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is atezolizumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is durvalumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is MEDI0680.

In some embodiments, the methods disclosed herein comprise a polypeptide having a sequence according to any one of SEQ ID NOs: SEQ ID NOs: 78-85, 98-104, 107-113, 116-122, 135-137, or 152-159; and an antibody, wherein the antibody is pidilizumab.

In some embodiments, the methods disclosed herein comprise administering a polypeptide having a sequence according to any one of SEQ ID NOs: SEQ ID NOs: 78-85, 98-104, 107-113, 116-122, 135-137, or 152-159; and an antibody, wherein the antibody is BMS-93659.

In some embodiments, the polypeptides disclosed herein enhance the anti-tumor activity of rituximab. In some embodiments, the polypeptides disclosed herein enhance the anti-tumor activity of rituximab in the Raji-NSG xenograft model. In some embodiments, the polypeptides disclosed herein enhance rituximab-mediated B-cell depletion in non-human primates (NHP).

In some embodiments, the polypeptides and pharmaceutical compositions of the disclosure are used in various cancer therapies. The cancers amenable to treatment according to the disclosure include, but are not limited to, solid tumor cancer, hematological cancer, acute myeloid leukemia, chronic lymphocytic leukemia, chronic myeloid leukemia, acute lymphoblastic leukemia, non-Hodgkin lymphoma, Hodgkin lymphoma, multiple myeloma, bladder cancer, pancreatic cancer, cervical cancer, endometrial cancer, lung cancer, bronchus cancer, liver cancer, ovarian cancer, colon and rectal cancer, stomach cancer, gastric cancer, gallbladder cancer, gastrointestinal stromal tumor cancer, thyroid cancer, head and neck cancer, oropharyngeal cancer, esophageal cancer, melanoma, non-melanoma skin cancer, Merkel cell carcinoma, virally induced cancer, neuroblastoma, breast cancer, prostate cancer, renal cancer, renal cell cancer, renal pelvis cancer, leukemia, lymphoma, sarcoma, glioma, brain tumor, and carcinoma. In some embodiments, cancerous conditions amenable to treatment according to the disclosure include metastatic cancers. In some embodiments, the cancer amenable to treatment according to the disclosure is a solid tumor or hematological cancer.

In some embodiments, an antibody targets cells of the immune system, such as T-cells, e.g., regulatory T-cells, by binding to proteins expressed by cells of the immune system. In some embodiments, the methods disclosed herein comprise administering a polypeptide described herein (e.g., a SIRP-a D1 variant) and an antibody that targets cells of the immune system. Examples of proteins expressed by cells of the immune system include, but are not limited to, 41BB, CD40, CD40L, CD163, CD206, CTLA4, PD1, TIM-3, BTLA, VISTA, LAG-3, CD28, OX40, GITR, CD137, CD27, HVEM, CCR4, CD25, CD103, KIrg1, Nrp 1, CD278, Gpr83, TIGIT, CD154, CD160, and PD1H. In some embodiments, an antibody is designed such that it has preferential binding to proteins (e.g., receptors) expressed by T-cells (e.g., regulatory T-cells) as compared to other cells of the immune system. In some embodiments, an antibody in a composition of the disclosure includes an Fc domain of the IgG1, IgG2 or IgG4 subclass.

In some embodiments, the methods of the disclosure include altering an immune response in a subject. The methods include administering the subject a polypeptide including a high affinity SIRP-α D1 variant and an antibody, thereby altering the immune response in the subject. In some embodiments, altering the immune response includes suppressing the immune response.

In some embodiments, the polypeptides and pharmaceutical compositions of the disclosure are used in various therapies to treat immunological diseases. Autoimmune diseases and inflammatory diseases amenable to treatment according to the disclosure include, but are not limited to, multiple sclerosis, rheumatoid arthritis, a spondyloarthropathy, systemic lupus erythematosus, an antibody-mediated inflammatory or autoimmune disease, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, and inflammatory autoimmune myositis.

In some embodiments, delivering a polypeptide to a cell involves contacting the cell with one or more of the compositions described herein.

Effective doses for such treatment options vary depending upon many different factors, including means of administration, target site, physiological state of the patient, whether the patient is human or an animal, other medications administered, and whether treatment is prophylactic or therapeutic. In some embodiments, the patient is a human, but nonhuman mammals are also be treated, e.g., companion animals such as dogs, cats, horses, etc., laboratory mammals such as rabbits, mice, rats, etc., and the like. In some embodiments, treatment dosages are titrated to optimize safety and efficacy.

In some embodiments, therapeutic dosage range from about 0.0001 to 100 mg/kg, and more usually 0.01 to 30 mg/kg, of the host body weight. In some embodiments, for example, dosages are 1 mg/kg body weight or 30 mg/kg body weight or within the range of 1-30 mg/kg. In some embodiments, an exemplary treatment regime entails administration once every week or once every two weeks or once a month or once every 3 to 6 months. In some embodiments, therapeutic agents and polypeptide constructs described herein are administered on multiple occasions. In some embodiments, intervals between single dosages are weekly, monthly or yearly. In some embodiments, intervals are also irregular as indicated by measuring blood levels of the therapeutic entity in the patient. Alternatively, the therapeutic agents or polypeptide constructs described herein are administered as a sustained release formulation, in which case less frequent administration is possible. In some embodiments, dosage and frequency varies depending on the half-life of the polypeptide in the patient.

In prophylactic applications, in some embodiments, a relatively low dosage is administered at relatively infrequent intervals over a long period of time. In some embodiments, patients continue to receive treatment for the rest of their lives. In other therapeutic applications, a relatively high dosage at relatively short intervals is required until progression of the disease is reduced or terminated, and preferably until the patient shows partial or complete amelioration of symptoms of disease. Thereafter, in some embodiments, the patent is administered a prophylactic regime.

As used herein, the terms "treatment", "treating", and the like, refer to administering an agent, or carrying out a procedure, for the purposes of obtaining an effect. In some embodiments, the effect is prophylactic in terms of completely or partially preventing a disease or symptom thereof. In some embodiments, the effect is therapeutic in terms of affecting a partial or complete cure for a disease or symptoms of the disease.

XIII. Kits

Disclosed herein, in some embodiments, are polypeptides comprising a signal-regulatory protein α (SIRP-α) D1 variant comprising a SIRP-α D1 domain, or a fragment thereof, having an amino acid mutation at residue 80 relative to a wild-type SIRP-α D1 domain; and at least one additional amino acid mutation relative to a wild-type SIRP-α D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Also provided are kits which include polypeptides described herein and instructions for use of the same. Optionally, the kits can further include at least one additional reagent. As a non-limiting example, a chemotherapeutic agent or anti-tumor antibody could serve as at least one additional agent. In some embodiments, kits include a label indicating the intended use of the contents of the kit. The term label includes any writing, or recorded material supplied on or with the kit, or which otherwise accompanies the kit.

In some embodiments, a kit includes (i) a polypeptide including a high affinity SIRP-α D1 variant; optionally (ii) an antibody; and (iii) instructions for administering (i) and (ii) (if provided) to a subject having a disease. In some embodiments, kits include (i) a polypeptide including a high affinity SIRP-α D1 variant; and (ii) instructions for administering (i) with an antibody, for example, an antibody that is not provided in the kit, to a subject having a disease. In some embodiments, kits include (i) an antibody; and (ii) instructions for administering (i) with a polypeptide including a high affinity SIRP-α D1 variant to a subject having a disease.

In some embodiments, the kits are used to treat a subject having cancer, such as solid tumor cancer, hematological cancer, acute myeloid leukemia, chronic lymphocytic leukemia, chronic myeloid leukemia, acute lymphoblastic leukemia, non-Hodgkin lymphoma, Hodgkin lymphoma, multiple myeloma, bladder cancer, pancreatic cancer, cervical cancer, endometrial cancer, lung cancer, bronchus cancer, liver cancer, ovarian cancer, colon and rectal cancer, stomach cancer, gastric cancer, gallbladder cancer, gastrointestinal stromal tumor cancer, thyroid cancer, head and neck cancer, oropharyngeal cancer, esophageal cancer, melanoma, non-melanoma skin cancer, Merkel cell carcinoma, virally induced cancer, neuroblastoma, breast cancer, prostate cancer, renal cancer, renal cell cancer, renal pelvis cancer, leukemia, lymphoma, sarcoma, glioma, brain tumor, carcinoma, or any combinations thereof. In some embodiments, the kits are used to treat a subject having a solid tumor cancer or a hematological cancer.

In some embodiments, the kits are used to treat a subject having immunological diseases. In some embodiments, the immunological disease is an autoimmune disease or an inflammatory disease, such as multiple sclerosis, rheumatoid arthritis, a spondyloarthropathy, systemic lupus erythematosus, an antibody-mediated inflammatory or autoimmune disease, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, inflammatory autoimmune myositis, or any combinations thereof.

EXAMPLES

Example 1

SIRP-α D1 Variant Polypeptides

Generating Polypeptides of the Disclosure

A polypeptide of the disclosure including a high affinity SIRP-α D1 variant is generated using conventional molecular cloning and protein expression techniques. Possible amino acid substitutions in a SIRP-α D1 variant relative to a wild-type SIRP-α D1 domain are listed in Tables 2 and 5. A nucleic acid molecule encoding a polypeptide of the disclosure is cloned into a vector optimized for expression in bacterial or mammalian cells using well known molecular biology techniques. After induction of protein expression, cells are collected and the expressed polypeptides are purified from the cell culture supernatant using affinity column chromatography. Purified polypeptides are then analyzed by SDS-PAGE, followed by Coomassie Blue staining to confirm the presence of protein bands of expected size.

Purified polypeptides are screened for binding to CD47 using available techniques in the art, such as phage display, yeast display, surface plasmon resonance (SPR), scintillation proximity assays, ELISA, ORIGEN immunoassay (IGEN), fluorescence quenching, fluorescence transfer, or any suitable bioassay. The desired polypeptides bind with higher affinity to CD47, e.g., human CD47, than a wild-type SIRP-α.

Binding Affinity of SIRP-α D1 Variant Polypeptides

In a series of experiments, polypeptides of wild-type SIRP-α D1 domains and high affinity SIRP-α D1 variants were generated using conventional molecular cloning and protein expression techniques. Binding to human CD47 was determined using SPR as follows: briefly, binding of human CD47 (R and D Systems, catalog number 4670-CD or in-house produced as monomeric extracellular domain, ECD) to wild-type SIRP-α and SIRP-α D1 variant polypeptides variants was analyzed on a Biacore T100 instrument (GE Healthcare) or Proteon XPR36 (Bio-rad, Hercules, Calif.) using phosphate buffered saline (PBS, pH 7.4) supplemented with 0.01% Tween-20 (PBST) as running buffer. 200 to 1000 RU of ligand were immobilized in 10 mM sodium acetate buffer (pH 4.5) on a Biacore chip CM4 sensor or Proteon GLC chip by standard amine coupling following manufacturer recommendations. Several concentrations of analyte (or SIRP-α D1 variant polypeptides), e.g., ranging from at least 0.1× to 10× KD value, were injected for two minutes with a flow rate 100 μL/min, followed by ten minutes of dissociation time. After each analyte injection, the surface was regenerated using a 2:1 mixture of Pierce IgG elution buffer (Life Technologies, catalog number 21004) and 4 M NaCl injected for 30 seconds. Complete regeneration of the surface was confirmed by baseline analysis and injecting the same analyte at the beginning and end of the experiment. All sensorgrams were double-referenced using reference surface and a buffer injection and fitted to 1:1 Langmuir. The analyte was primarily monomeric, either CD47 ECD or SIRP-α without Fc. Ligand on the chip can be either monomeric or an Fc fusion. Binding data is provided in Table 16. All SPR assays were performed at 25° C.

TABLE 16

SIRP-α Variant Polypeptide and Associated $K_D$ Values

| SEQ ID NO: | Human CD47 $K_D$ (M) |
|---|---|
| 2 | $0.5 \times 10^{-6}$ |
| 53 | $4.5 \times 10^{-10}$ |
| 54 | $2.7 \times 10^{-9}$ |
| 55 | $6.2 \times 10^{-10}$ |
| 56 | $2.0 \times 10^{-10}$ |
| 57 | $3.6 \times 10^{-10}$ |
| 58 | $1.6 \times 10^{-10}$ |
| 59 | $1.4 \times 10^{-8}$ |
| 60 | $3.8 \times 10^{-10}$ |
| 61 | $3.8 \times 10^{-10}$ |
| 62 | $1.3 \times 10^{-10}$ |
| 63 | $8.9 \times 10^{-11}$ |
| 64 | $5.45 \times 10^{-9}$ |
| 65 | $8.00 \times 10^{-10}$ |
| 66 | $4.70 \times 10^{-10}$ |
| 67 | $2.06 \times 10^{-10}$ |
| 68 | $2.51 \times 10^{-10}$ |
| 69 | $2.40 \times 10^{-9}$ |
| 71 | $4.94 \times 10^{-9}$ |
| 72 | $7.38 \times 10^{-10}$ |
| 73 | $4.48 \times 10^{-10}$ |
| 74 | $2.76 \times 10^{-10}$ |
| 75 | $1.33 \times 10^{-9}$ |
| 76 | $7.41 \times 10^{-9}$ |
| 77 | $1.14 \times 10^{-10}$ |
| 78 | $1.44 \times 10^{-11}$ |
| 79 | $2.17 \times 10^{-10}$ |
| 80 | $4.72 \times 10^{-11}$ |
| 85 | $1.19 \times 10^{-10}$ |

It has also been determined that having a glutamate or aspartate residue at position 54 improves the binding of SIRP-α D1 variant polypeptides to mouse CD47. As a non-limiting example, the SIRP-α D1 variant polypeptides identified in Table 17 below demonstrate high affinity binding to mouse CD47. The binding affinity to human CD47 of several SIRP-α D1 variant polypeptides was compared to the binding affinity to mouse CD47 using SPR as previously described, with mouse CD47 protein being used in place of human CD47 where appropriate. The results are presented in Table 18.

TABLE 17

SIRP-α Variant Polypeptide Sequences having Improved Binding to Mouse CD47

| SEQ ID NO: | Amino Acid Sequence |
|---|---|
| 195 | EEELQIIQPDKSVLVAAGETATLRCTMTSLFPVGPIQWFRGAGPGRELIYNQREGPFPRVTTVSDTTKRNNMDFSIRIGAITPADAGTYYCVKFRKGSPDDVEFKSGAGTELSVRAKPS |
| 196 | EEELQIIQPDKSVLVAAGETATLRCTITSLKPVGPIQWFRGAGPGRELIYNQREGPFPRVTTVSDTTKRNNMDFSIRIGAITPADAGTYYCVKFRKGSPDDVEFKSGAGTELSVRAKPS |
| 197 | EEELQIIQPDKSVLVAAGETATLRCTITSLRPVGPIQWFRGAGPGRELIYNQREGPFPRVTTVSDTTKRNNMDFSIRIGAITPADAGTYYCVKFRKGSPDDVEFKSGAGTELSVRAKPS |
| 198 | EEELQIIQPDKSVLVAAGETATLRCTITSLYPVGPIQWFRGAGPGRELIYNQREGPFPRVTTVSDTTKRNNMDFSIRIGAITPADAGTYYCVKFRKGSPDDVEFKSGAGTELSVRAKPS |
| 199 | EEELQIIQPDKSVLVAAGETATLRCTITSLFPVGPIQWFRGAGPGRELIYNQRDGPFPRVTTVSDTTKRNNMDFSIRIGAITPADAGTYYCVKFRKGSPDDVEFKSGAGTELSVRAKPS |
| 200 | EEELQIIQPDKSVLVAAGETATLRCTITSLFPVGPIQWFRGAGPGRELIYNQREGPFPRVTTVSDTTKRNNMDFSIRIGAITPADAGTYYCVKFRKGIPDDVEFKSGAGTELSVRAKPS |
| 201 | EEELQIIQPDKSVLVAAGETATLRCTITSLFPVGPIQWFRGAGPGRELIYNQREGPFPRVTTVSDTTKRNNMDFSIRIGAITPADAGTYYCVKFRKGMPDDVEFKSGAGTELSVRAKPS |
| 202 | EEELQIIQPDKSVLVAAGETATLRCTITSLFPVGPIQWFRGAGPGRELIYNQREGPFPRVTTVSDTTKRNNMDFSIRIGAITPADAGTYYCVKFRKGSPDVEFKSGAGTELSVRAKPS |
| 203 | EEELQIIQPDKSVLVAAGETATLRCTITSLFPVGPIQWFRGAGPGRELIYNQREGPFPRVTTVSDTTKRNNMDFSIRIGAITPADAGTYYCVKFRKGSSEPDVEFKSGAGTELSVRAKPS |
| 204 | EEELQIIQPDKSVLVAAGETATLRCTITSLRPVGPIQWFRGAGPGRELIYNQRDGPFPRVTTVSDTTKRNNMDFSIRIGAITPADAGTYYCVKFRKGSPDDVEFKSGAGTELSVRAKPS |
| 205 | EEELQIIQPDKSVLVAAGETATLRCTITSLRPVGPIQWFRGAGPGRELIYNQREGPFPRVTTVSDTTKRNNMDFSIRIGAITPADAGTYYCVKFRKGIPDDVEFKSGAGTELSVRAKPS |
| 206 | EEELQIIQPDKSVLVAAGETATLRCTITSLRPVGPIQWFRGAGPGRELIYNQRDGPFPRVTTVSDTTKRNNMDFSIRIGAITPADAGTYYCVKFRKGIPDDVEFKSGAGTELSVRAKPS |
| 207 | EEELQIIQPDKSVLVAAGETATLRCTITSLYPVGPIQWFRGAGPGRELIYNQRDGPFPRVTTVSDTTKRNNMDFSIRIGAITPADAGTYYCVKFRKGSPDDVEFKSGAGTELSVRAKPS |
| 208 | EEELQIIQPDKSVLVAAGETATLRCTITSLYPVGPIQWFRGAGPGRELIYNQREGPFPRVTTVSDTTKRNNMDFSIRIGAITPADAGTYYCVKFRKGIPDDVEFKSGAGTELSVRAKPS |
| 209 | EEELQIIQPDKSVLVAAGETATLRCTITSLYPVGPIQWFRGAGPGRELIYNQRDGPFPRVTTVSDTTKRNNMDFSIRIGAITPADAGTYYCVKFRKGIPDDVEFKSGAGTELSVRAKPS |
| 210 | EEELQIIQPDKSVLVAAGETATLRCTITSLFPVGPIQWFRGAGPGRELIYNQRDGPFPRVTTVSDTTKRNNMDFSIRIGAITPADAGTYYCVKFRKGIPDDVEFKSGAGTELSVRAKPS |

TABLE 18

Binding of SIRP-α Variant Polypeptides to Human and Mouse CD47

| SEQ ID NO: | $K_D$ (M) - Human | $K_D$ (M) - Mouse |
|---|---|---|
| 96 | $1.04 \times 10^{-11}$ | $3.32 \times 10^{-8}$ |
| 97 | $1.55 \times 10^{-9}$ | >100 nM |
| 100 | $2.69 \times 10^{-9}$ | $6.32 \times 10^{-8}$ |
| 104 | $9.19 \times 10^{-11}$ | $8.04 \times 10^{-9}$ |
| 86 | $1.44 \times 10^{-11}$ | $4.30 \times 10^{-8}$ |
| 85 | $8.23 \times 10^{-11}$ | $1.14 \times 10^{-8}$ |
| 204 | $3.49 \times 10^{-09}$ | $5.21 \times 10^{-9}$ |
| 206 | $5.26 \times 10^{-09}$ | $3.33 \times 10^{-9}$ |
| 209 | $4.46 \times 10^{-09}$ | $4.11 \times 10^{-9}$ |
| 210 | $6.79 \times 10^{-09}$ | $6.01 \times 10^{-9}$ |

It has also been determined that the N80A mutation, which can minimize or abrogate partial glycosylation present in certain SIRP-α D1 variant polypeptides, confers a functional benefit of increasing the homogeneity associated with SIRP-α D1 variant polypeptides containing such mutation. When SIRP-α variant polypeptides are expressed in *E. coli*, no glycosylation of N80 will occur due to lack of glycosylation system in *E. coli* compared to a mammalian system. Table 19 shows that effective binding between a SIRP-α D1 variant polypeptide produced in *E. coli* and human CD47 can still occur, thus demonstrating that deglycosylation does not affect the binding affinity with which SIRP-α D1 variants can still bind to CD47. In addition to the N80A mutation, deglycosylation can be accomplished by mutating N80 to any amino acid which is not N or by disrupting the motif N-Xaa1-Xaa2 wherein N=asparagine; Xaa1=any amino acid except P (proline); Xaa2=T (threonine), S (serine) or C (cysteine), wherein the motif refers to residues 80-82 of a SIRP-α D1 variant polypeptide. By mutating P83 to valine or other residue which is not P, increased glycosylation at N80 can occur and homogenously glycosylated SIRP-α D1 variant polypeptides can be generated.

Figure 18:
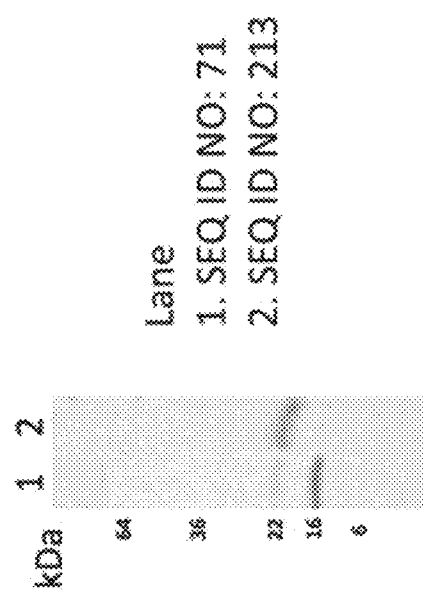
FIG. 18 exemplifies molecular weight analysis of a SIRP-α D1 variant having a P83V mutation.

The amino acid P83 can also affect the degree of glycosylation. Changing P83 to any amino acid can increase the efficiency of glycosylation at N80. A SIRP-α D1 variant having a valine (V) at position 83 (SEQ ID NO: 213) was expressed in HEK293FS mammalian cells. The size of the expressed protein was compared to a SIRP-α D1 variant having the wild-type amino acid residue (e.g., proline, P) at position 83 (SEQ ID NO: 71). Molecular weight analysis of the expressed protein on a protein gel (FIG. 18) shows that the variant having a P83V mutation (SEQ ID NO: 213, Lane 2) has a higher molecular weight (e.g., ~22 kDa) compared to the variant that is unmutated at position 83 (Lane 1). As shown in FIG. 18, when residue 83 is mutated to Val, the SIRP-α variant polypeptide expressed in a mammalian cell host is primarily a molecule at higher molecular weight (~22 kDa), indicating efficiency for glycosylation at N80 can be increased.

TABLE 19

Representative Binding Data for SIRP-α Variant Polypeptide Sequences having Various Glycosylation Profiles

| SEQ ID NO: | KD (M) | Expression system |
| --- | --- | --- |
| 53 | 4.5 × 10−10 | *E. coli* |
| 58 | 1.6 × 10−10 | *E. coli* |
| 60 | 3.8 × 10−10 | *E. coli* |
| 63 | 8.9 × 10−11 | *E. coli* |
| 55 | 6.2 × 10−10 | *E. coli* |
| 62 | 1.3 × 10−10 | *E. coli* |
| 57 | 3.6 × 10−10 | *E. coli* |
| 56 | 2.0 × 10−10 | *E. coli* |
| 61 | 3.8 × 10−10 | *E. coli* |
| 54 | 2.7 × 10−9 | *E. coli* |
| 59 | 1.4 × 10−8 | *E. coli* |
| 2 | 0.5 × 10−6 | *E. coli* |
| 53 | 5.2 × 10−10 | mammalian cell |
| 77 | 1.14 × 10−10 | mammalian cell |
| 74 | 2.76 × 10−10 | mammalian cell |
| 73 | 4.48 × 10−10 | mammalian cell |
| 72 | 7.38 × 10−10 | mammalian cell |
| 75 | 1.33 × 10−9 | mammalian cell |
| 71 | 4.94 × 10−9 | mammalian cell |
| 76 | 7.41 × 10−9 | mammalian cell |

Example 2

Generation of Single Arm and Bispecific SIRP-α Polypeptides

Figure 6:
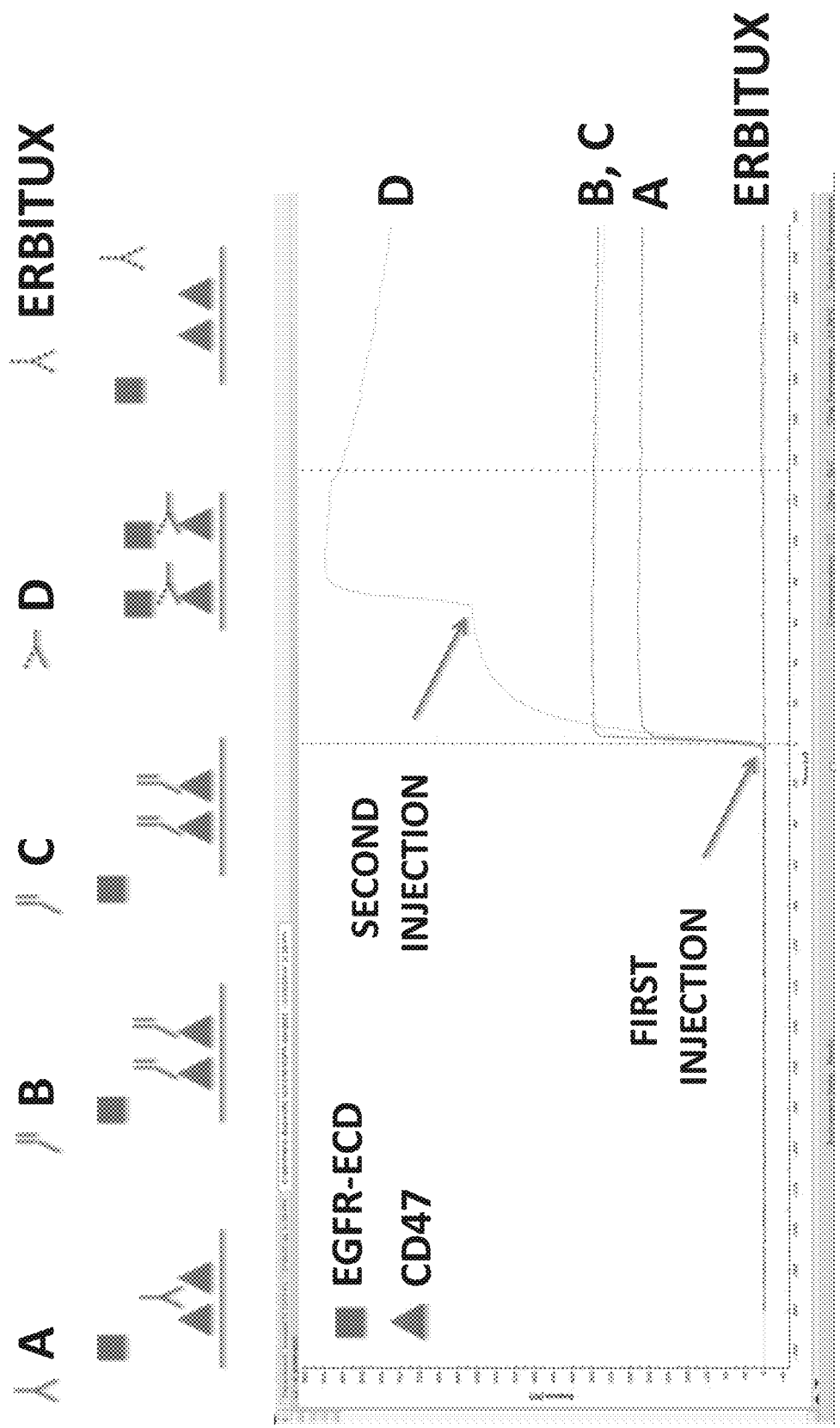
FIG. 6 exemplifies SPR binding data for monofunctional and bifunctional SIRP-α constructs including a SIRP-α D1 domain.

The ability of constructs comprising heterodimers of (i) a SIRP-α-Fc fusion protein and (ii) Fc domain monomer fused to a polypeptide, such as an antigen binding domain, to bind both CD47 and an antigen, e.g., EGFR, was determined by SPR as previously described in this example. The Fc fusion proteins for forming heterodimers are provided in Table 20. Three monofunctional (e.g., binding one target) SIRP-α-Fc fusions were tested. These fusion proteins are depicted as A, B, C in FIG. 6A. A first monofunctional SIRP-α-Fc fusion ("A") was a homodimer of SEQ ID NO: 136. Second and third monofunctional SIRP-α-Fc fusions were heterodimers of (i) a SIRP-α-Fc fusion and (ii) a Fc domain monomer without an additional polypeptide fused to it. These were generated using the Knob & Hole mutation engineering strategies depicted in FIGS. 4A and 4B. One monofunctional SIRP-α-Fc fusion ("B") was formed from heterodimerization of SEQ ID NO: 139 (an Fc variant) and SEQ ID NO: 142 (a SIRP-α-Fc fusion). Another monofunctional SIRP-α-Fc fusion ("C") was formed from heterodimerization of SEQ ID NO: 139 (an Fc variant) and SEQ ID NO: 138 (a SIRP-α Fc fusion). The bifunctional (e.g., binding two targets) SIRP-α-Fc fusion ("D") was formed from heterodimerization of SEQ ID NO: 127 (a SIRP-α Fc fusion) and SEQ ID NO: 144 (an antigen binding region of Erbitux linked to an Fc variant). SEQ ID NO: 220 represents the light chain of the Erbitux antibody.

TABLE 20

Amino Acid Sequences of Fc Fusion Proteins for Forming Heterodimers

| SEQ ID NO: | Amino Acid Sequence |
| --- | --- |
| 138 | EEELQIIQPDKSVLVAAGETATLRCTITSLFPVGPIQWFRGAGPGR VLIYNQRQGPFPRVTTVSDTTKRNNMDFSIRIGAITPADAGTYYCI KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 139 | DKTHTCPPCPAPEAAGAPSVFLFPPKPKDTLMISRTPEVTCVVVDV SHEDPEVKFNWYVDGVEVHNAKTKPREEQYASTYRVVSVLTVLHQD WLNGKEYKCKVSNKALPAPIEKTISKAKGQPREPQVYTLPPSREEM TKNQVSLSCAVKGFYPSDIAVEWESNGQPENNYKTTPPVLDSDGSF FLVSKLTVDKSRWQQGNVFSCSVMHEALHNHYTQKSLSLSPGK |
| 142 | EEELQIIQPDKSVLVAAGETATLRCTITSLFPVGPIQWFRGAGPGR ELIYNQREGPFPRVTTVSDTTKRNNMDFSIRIGAITPADAGTYYCV KFRKGSPDDVEFKSGAGTELSVRAKPSDKTHTCPPCPAPEAAGAPS VFLEPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 144 | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKKVEPKSCRKTHTCPR CPAPELLGGPSVFLFPPKPKDTLMISRTPEVTCVVVDVSHEDPEVK FNWYVDGVEVHNAKTKPREEQYASTYRVVSVLTVLHQDWLNGKEYK CKVSNKALPAPIEKTISKAKGQPREPQVYTLPPSREEMTKNQVSLT CLVKGFYPSDIAVEWESNGQPENNYKTTPPVLDSDGSFFLYSRLTV DKSRWQQGNVFSCSVMHEALHNHYTQKSLSLSPGK |
| 220 | DILLTQSPVILSVSPGERVSFSCRASQSIGTNIHWYQQRTNGSPRL LIKYASESISGIPSRFSGSGSGTDFTLSINSVESEDIADYYCQQNN NWPTTFGAGTKLELKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |

TABLE 20-continued

Amino Acid Sequences of Fc Fusion Proteins for Forming Heterodimers

| SEQ ID NO: | Amino Acid Sequence |
|---|---|
| 217 | EEELQIIQPDKSVLVAAGETATLRCTITSLFPVGPIQWFRGAGPGR ELIYNQREGPFPRVTTVSDTTKRNNMDFSIRIGAITPADAGTYYCV KFRKGSPDDVEFKSGAGTELSVRAKPSEKTHTCPECPAPEAAGAPS VFLEPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLTCEVKGFYPSDI AVEWESNGQPENNYKTTPPVLDSDGSFFLYSKLTVDKSRWQQGNVF SCSVMHEALHNHYTQKSLSLSPGK |

Briefly, CD47 was immobilized on a Proteon GLC chip by amine chemistry as described above. In a first injection, analytes (e.g., A, B, C, D, and Erbitux) were injected at 30 uL/min in PBST for 60 s at 100 nM and binding to the CD47 surface was determined by SPR. In a second, injection 100 nM EGFR-ECD (epidermal growth factor receptor extracellular domain produced in HEK293 cells) was injected and binding of EGFR-ECD to the CD47-bound analytes was measured. Erbitux did not bind CD47 on the chip and therefore it was not able to bind EGFR in the second injection as shown by the curve labeled "Erbitux" in FIG. 6B and illustrated in FIG. 6A. SIRP-α-Fc fusions (e.g., A, B, and C) did bind CD47 but did not bind EGFR in the second injection as shown by the curves labeled "A," "B," and "C" shown in FIG. 6B and illustrated in FIG. 6A. The monomeric proteins, or proteins with one SIRP-α D1 domain (e.g., B and C) higher resonance units than the dimeric protein (e.g., A) due to a higher amount of molecules bound to the same CD47 sites available on the chip as shown by the curves labeled "B" and "C", indicating binding to immobilized CD47 and negligible binding to EGFR-ECD (e.g., monofunctionality). Heterodimeric SIRP-α-Erbitux-Fc bound CD47 on the chip and was also able to bind EGFR-ECD in the second injection as shown by the curve labeled "D" in FIG. 6B, indicating binding to immobilized CD47 and binding of EGFR-ECD (e.g., bi-functionality).

Example 3

Testing Polypeptides with High Binding Affinity to CD47 in Mice

Genetically engineered mouse models of various cancers, e.g., solid tumor and hematological cancer, are used to test the binding of polypeptides of the disclosure to CD47. A polypeptide of the disclosure is injected in a mouse, which is dissected at the later time to detect the presence of the complex of the polypeptide and CD47. Antibodies specific to SIRP-α or CD47 are used in the detection.

Example 4

Testing Polypeptides for Immunogenicity

Polypeptides including a high affinity SIRP-α D1 variant are tested in immunogenicity assays. The polypeptides are tested both in silico and in vitro in T-cell proliferation assays, some of which are commercially available. Polypeptides which provoke a minimal immunogenicity reaction in an in vitro T-cell proliferation assay and display a greater binding affinity to CD47 than does wild-type SIRP-α are selected for further development.

Example 5

Testing Polypeptides for In Vivo Toxicity

Different polypeptides including different high affinity SIRP-α D1 variants which display various degrees of increased binding affinities to CD47 than does wild-type SIRP-α are injected into an animal cancer model (e.g., a mouse cancer model) to assay the effect of different binding affinities on toxicity in the organism. Non-human primate (NHP) can also be used to test high-affinity SIRP-α D1 variants, as the level of cross reactivity for non-human primate (NHP) CD47 and mouse CD47 may be different.

Example 6

Fcγ Receptor Binding of Fc Variants

In addition to their ability to modulate target function, therapeutic monoclonal antibodies and Fc containing fusion proteins are also capable of eliciting two primary immune effector mechanisms: antibody-dependent cell cytotoxicity (ADCC) and complement-dependent cytotoxicity (CDC). ADCC is mediated by Fc region binding to activating Fcγ receptors and polypeptide constructs comprising Fc variants described herein were tested for Fcγ receptor binding. As shown in Table 21 below, the polypeptide constructs demonstrated decreased binding to one or more Fcγ receptors as compared to a corresponding wild-type IgG Fc. With regard to IgG1, the mutations L234A, L235A, G237A, and N297A of an IgG1 Fc resulted in a severe loss of binding to Fcγ receptors CD16a, CD32a, CD32b, CD32c, and CD64 as compared to a wild-type IgG1, or a construct lacking one or more of these mutations. Accordingly, the mutations L234A, L235A, G237A (e.g., IgG1 AAA), along with aglycosylation or the deglycosylating mutation N297A results in complete loss of binding to the Fcγ receptors studied. Since Fcγ receptor binding is known to be important to phagocytosis, the mutations L234A, L235A, G237A, and N297A can result in reduction of phagocytosis of the construct comprising the Fc variant.

The following materials and methods were used in this example. Binding of human Fcγ receptors RI (CD64), RIIA (CD32a), RIIB/C (CD32b/c) and RIIIA (CD16a) (R & D Systems, catalog numbers 1257-FC-050, 1330-CD-050, 1875-CD-050 and 4325-FC-050 respectively) to Fc variant constructs was analyzed on a ProteOn XPR36 instrument (Bio-Rad, Hercules, Calif.) using phosphate buffered saline (PBS, pH 7.4) supplemented with 0.01% Tween-20 as running buffer. Approximately 400 Resonance Unit (RU) of minimally biotinylated Fc constructs were immobilized on flow cells of a NLC sensor chip (Bio-rad, Hercules, Calif.) by avidin-neutravidin interaction. Biotinylation was performed according to the manufacturer's instructions using Pierce EZ-Link Sulfo-NHS-LC-LC-Biotin and an equimolar ratio of linker:protein. Analytes (hFcγR) were injected in a "one-shot" kinetic mode at nominal concentrations of 0, 61, 185, 555, 1666, and 5000 nM. Association and dissociation times were monitored for 90 s and 600 s respectively. After each injection, the surface was regenerated using a 2:1 v/v mixture of Pierce IgG elution buffer (Life Technologies, catalog number 21004) and 4 M NaCl. Complete regeneration of the surface was confirmed by injecting the Fc variants at the beginning and end of the experiment. Biosensor data were double-referenced by subtracting the interspot data (containing no immobilized protein) from the reaction spot data (immobilized protein) and then subtracting the response of a buffer "blank" analyte injection from that of an analyte injection. Double-referenced data were fit to an equilibrium analysis using a simple binding isotherm. $K_D$,app. For Fc molecules with strong binding to hFcγRI, data were also fit globally to a simple Langmuir model and the $K_{D,app}$ value was calculated from the ratio of the apparent kinetic rate constants ($K_{D\ app}=k_{d,app}/k_{a,app}$)

As shown in Table 21, the mutations A330S, P331S, and N297A of an IgG2 Fc region resulted in a severe loss of binding to Fcγ receptors CD16a, CD32a, CD32b, CD32c, and CD64 as compared to a wild-type IgG or a construct lacking these mutations. Accordingly, the mutations A330S and P331S along with aglycosylation or the deglycosylating mutation N297A resulted in complete loss of binding to the Fcγ receptors studied. Since Fcγ receptor binding is known to be important to phagocytosis, the mutations A330S, P331S, and N297A are predicted to result in a reduction in phagocytosis of the Fc variant. Binding data for IgG4 and various mutations are also provided.

TABLE 21

Binding Data ($K_D$) for Fcγ Receptor Binding to Fc Variants.

| FC description | CD16a | CD32a | CD32b/c | CD64 |
|---|---|---|---|---|
| IgG1 | 370 nM | 400 nM | 2000 nM | 0.004 nM |
| IgG1_AAA | — | 2300 nM | — | 8000 nM |
| IgG1_N297A | — | — | — | 150 nM |
| IgG1_AAA_N297A | — | — | — | — |
| IgG2 | — | 420 nM | — | 700 nM |
| IgG2_A330S, P331S | — | 390 nM | — | 900 nM |
| IgG2_N297A | — | — | — | — |
| IgG2_A330S, P331S, N297A | — | — | — | — |
| IgG4 | 4100 nM | 720 nM | 710 nM | 1 nM |
| IgG4_S228P | 3000 nM | 810 nM | 850 nM | 1 nM |
| IgG4_S228P, L235E | 2400 nM | 1200 nM | 1100 nM | 60 nM |
| IgG4_S228P, E233P, F234V, L235A, delG236 | — | 1600 nM | — | 2100 nM |

An absence of binding is represented by "—"

Example 7

C1q Binding Determination of Fc Variants

Complement-dependent cytotoxicity (CDC) is mediated by complement protein C1q and activation of the complement cascade. Binding of various concentrations of C1q complement to various SIRP-α Fc constructs was determined by enzyme-linked immunosorbent assay (ELISA). SIRP-α Fc fusions were prepared at 5 µg/mL in PBS pH 7.4 and used to coat duplicate wells of Nunc Immulon 4HBX ELISA 96 well plates (using 50 µL/well) overnight at 4° C. The following day, plates were washed five times with wash buffer (PBS and 0.05% Tween-20) and incubated with 200 µL/well of blocking buffer (PBS and 0.5% BSA) for 1 hour at room temperature. Plates were washed five times and incubated for 2 hours at room temperature with 0, 0.13, 0.41, 1.23, 3.7, 11.1, 33.3, 100 µg/mL C1q in assay buffer (PBS, 0.5% BSA, 0.05% Tween-20, 0.25% CHAPS, 5 mM EDTA, and 0.35% NaCl). Plates were washed and incubated for 1 hour with 50 µl/well HRP Conjugated sheep-anti-human-C1q at 2.0 µg/mL in assay buffer. Plates were washed five times and incubated for ~10 minutes with TMB (1-Step Ultra TMB-ELISA, Thermo Sci. Cat. #34028). Finally, 50 µL/well Pierce/Thermo Sci. Stop Solution (0.16M sulfuric acid, cat. #N600) was added and plates were read at 450 nm absorbance with a 570 nm reference. Wells lacking SIRP-α-Fc fusion were run to control for non-specific binding of C1q or the HRP-conjugated detection antibody to the plate. Wells lacking C1q were run to control for non-specific binding of the HRP-conjugated detection antibody to a SIRP-α-Fc fusion or to the plate.

Figure 14:
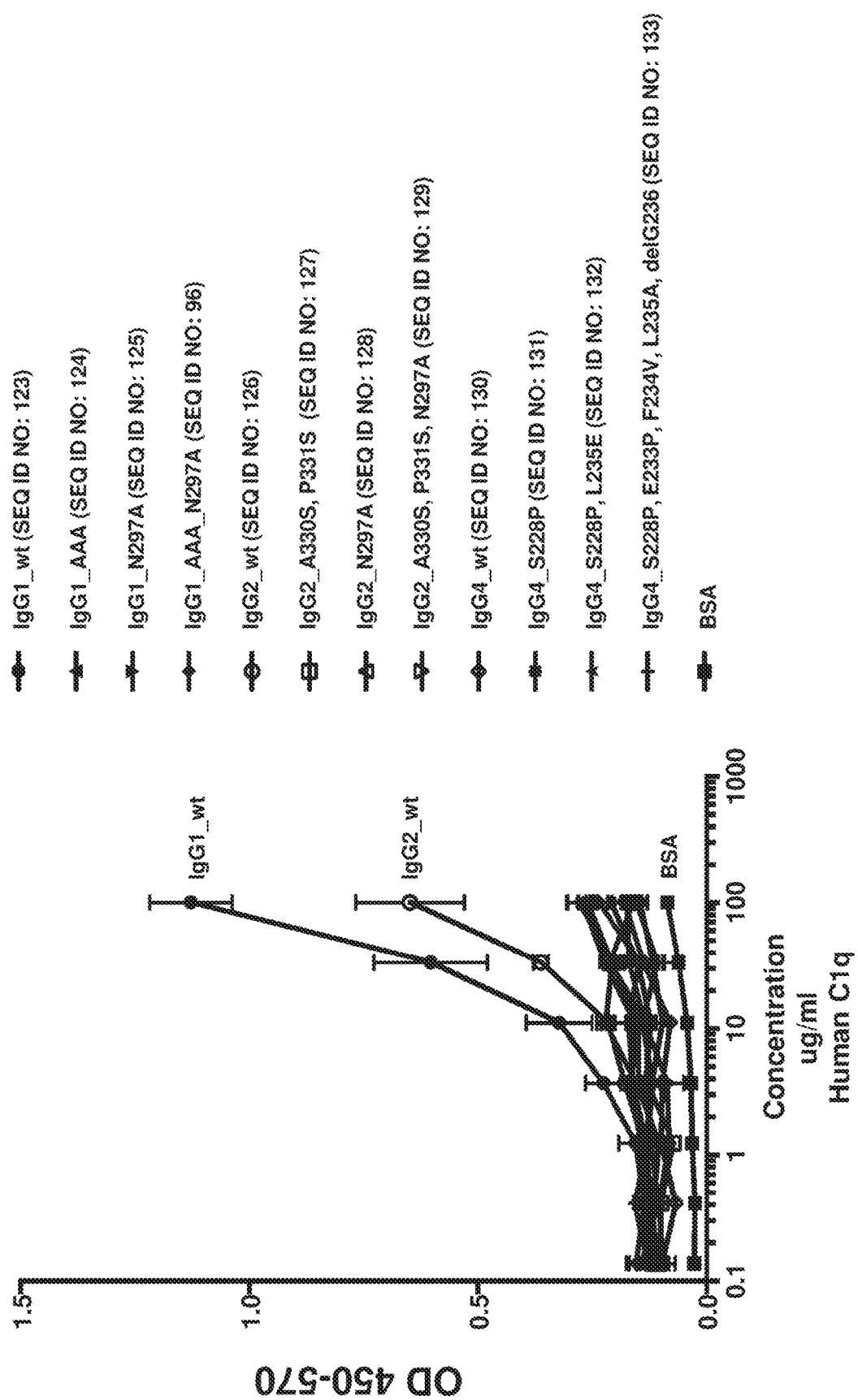
FIG. 14 exemplifies binding of various concentrations of C1q complement to SIRP-α-Fc fusions.

As shown in FIG. 14, both wildtype IgG1 (SEQ ID NO: 123) and wildtype IgG2 (SEQ ID NO: 126) bound C1q in a dose dependent manner. Conversely, IgG1 variants IgG1_AAA (SEQ ID NO: 124); IgG1_N297A (SEQ ID NO: 125); and IgG1_AAA_N297A (SEQ ID NO: 96) demonstrated significantly reduced and minimally detectable C1q binding activity. Likewise, IgG2 variants IgG2_A330S, P331S (SEQ ID NO: 127); IgG2_N297A (SEQ ID NO: 128); and IgG2_N297A, A330S, P331S (SEQ ID NO: 129) also demonstrated significantly reduced and minimally detectable C1q binding activity. This reduced and minimally detectable C1q binding activity of IgG1 and IgG2 variants were comparable to wildtype IgG4 (SEQ ID NO: 130), which does not to bind C1q.

Example 8

Production of Wild-Type Fc and Fc Variants

Using the methods described herein and in accordance with embodiments of the disclosure, the wild-type Fc polypeptides and Fc variants of Table 7 have been produced.

Example 9

Production of SIRP-α Variant and Fc Variant Polypeptides

Using the methods described herein and in accordance with embodiments of the disclosure, the following SIRP-α D1 variant-Fc variant polypeptides were produced as shown in Table 22 below. Binding to human CD47 was determined by the methodologies as described in Example 1.

TABLE 22

| CD47 Binding Affinity of SIRP-α Variant Fc Variant Polypeptides. | |
|---|---|
| SEQ ID NO: | $K_D$ (M) |
| 96 | $3.51 \times 10^{-11}$ |
| 97 | $1.09 \times 10^{-9}$ |
| 98 | $8.73 \times 10^{-11}$ |
| 99 | $8.95 \times 10^{-10}$ |
| 100 | $1.79 \times 10^{-9}$ |
| 101 | $8.90 \times 10^{-10}$ |
| 102 | $3.79 \times 10^{-10}$ |
| 103 | $2.56 \times 10^{-10}$ |
| 104 | $9.19 \times 10^{-11}$ |
| 105 | $3.16 \times 10^{-11}$ |
| 106 | $8.11 \times 10^{-10}$ |
| 107 | $2.19 \times 10^{-11}$ |
| 108 | $4.78 \times 10^{-10}$ |
| 109 | $2.15 \times 10^{-9}$ |
| 110 | $6.53 \times 10^{-10}$ |
| 111 | $3.15 \times 10^{-10}$ |
| 112 | $2.22 \times 10^{-10}$ |
| 113 | $1.32 \times 10^{-9}$ |
| 114 | $3.43 \times 10^{-11}$ |
| 115 | $4.98 \times 10^{-10}$ |
| 135 | $3.46 \times 10^{-9}$ |
| 136 | $1.19 \times 10^{-10}$ |

Example 10

Phagocytosis of SIRP-α-Fc Variants

To obtain quantitative measurements of phagocytosis, a phagocytosis assay was utilized in which primary human macrophages and GFP+ or CFSE-labeled tumor cells were co-cultured with Fc variant polypeptide constructs described herein. The following materials and methods were employed:

Culture of Tumor Cell Lines

DLD-1-GFP-Luciferase cells, MM1R, and N87 were maintained in growth medium comprising RPMI (Gibco) supplemented with 10% heat-inactivated Fetal Bovine Serum (Gibco), 1% penicillin/streptomycin (Gibco), and 1% Glutamax (Gibco). DLD-1-GFP-Luciferase and N87 cells were grown as adherent monolayers and MM1R cells were grown in suspension.

Derivation and Culture of Human Monocyte-Derived Macrophages

Whole blood buffy coats were diluted 1:2 with Phosphate Buffered Saline (PBS, Gibco). Diluted blood was split into two tubes and underlayed with 20 ml Ficoll-Paque Plus (GE Healthcare). Tubes were centrifuged for 30 minutes at 400×g. Peripheral blood mononuclear cells (PBMCs) were collected from the interface, washed twice by addition of 40 ml PBS, centrifuged for 10 minutes at 100×g, and resuspended in FACS buffer (PBS with 0.5% Bovine Serum Albumin (Gibco)). CD14+ monocytes were purified by negative selection using the Monocyte Isolation Kit II (Miltenyi Biotec) and LS columns (Miltenyi Biotec) according to the manufacturer's protocol. CD14+ monocytes were seeded into 15 cm tissue culture plates (Corning) at 10 million cells per dish in 25 ml differentiation medium comprised of IMDM (Gibco) supplemented with 10% human AB serum (Corning), 1% penicillin/streptomycin, and 1% Glutamax. Cells were cultured for seven to ten days.

In Vitro Phagocytosis Assays

DLD-1-GFP-Luciferase and N87 cells were detached from culture plates by washing twice with 20 ml PBS and incubation in 10 ml TrypLE Select (Gibco) for 10 minutes at 37° C. Cells were removed with a cell scraper (Corning), centrifuged, washed in PBS, and resuspended in IMDM. MM1R and N87 cells were labeled with the Celltrace CFSE Cell Proliferation kit (Thermo Fisher) according to the manufacturer's instructions and resuspended in IMDM. Macrophages were detached from culture plates by washing twice with 20 ml PBS and incubation in 10 ml TrypLE Select for 20 minutes at 37° C. Cells were removed with a cell scraper (Corning), washed in PBS, and resuspended in IMDM.

Phagocytosis assays were assembled in ultra-low attachment U-bottom 96 well plates (Corning) containing 100,000 DLD-1 GFP Luciferase, MM1R, or N87 cells, five-fold serial dilutions of SIRP-α-Fc variants from 1000 nM to 64 pM, and cetuximab (Absolute Antibody), daratumumab, or control antibody of the same isotype (Southern Biotech) at 1 µg/ml. Plates were preincubated 30 minutes at 37° C. in a humidified incubator with 5 percent carbon dioxide, then 50,000 macrophages were added. Plates were incubated two hours at 37° C. in a humidified incubator with 5 percent carbon dioxide. Cells were pelleted by centrifugation for five minutes at 400×g and washed in 250 µl FACS buffer. Macrophages were stained on ice for 15 minutes in 50 µl FACS buffer containing 10 µl human FcR Blocking Reagent (Miltenyi Biotec), 0.5 µl anti-CD33 BV421 (Biolegend), and 0.5 µl anti-CD206 APC-Cy7 (Biolegend). Cells were washed in 200 µl FACS buffer, washed in 250 µl PBS, and stained on ice for 30 minutes in 50 µl Fixable Viability Dye eFluor 506 (ebioscience) diluted 1:1000 in PBS. Cells were washed twice in 250 µl FACS buffer and fixed for 30 minutes on ice in 75 µl Cytofix (BD Biosciences). Cells were washed in 175 µl FACS buffer and resuspended in 75 µl FACS buffer. Cells were analyzed on a FACS Canto II (BD Biosciences), with subsequent data analysis by Flowjo 10.7 (Treestar). Dead cells were excluded by gating on the e506-negative population. Macrophages that had phagocytosed tumor cells were identified as cells positive for CD33, CD206, and GFP or CFSE. Five polypeptide constructs comprising SIRP-α D1 domain variants fused to respective Fc variants were tested for in vitro phagocytosis:

1)
(SEQ ID NO: 105)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPSVECPPCPAPPVAGPSVFLFPPKPKDTLMISR

TPEVTCVVVDVSHEDPEVQFNWYVDGVEVHNAKTKPREEQFASTFRVVSV

LTVVHQDWLNGKEYKCKVSNKGLPSSIEKTISKTKGQPREPQVYTLPPSR

EEMTKNQVSLTCLVKGFYPSDIAVEWESNGQPENNYKTTPPMLDSDGSFF

LYSKLTVDKSRWQQGNVFSCSVMHEALHNHYTQKSLSLSPGK 2)
(SEQ ID NO: 127)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPSERKCCVECPPCPAPPVAGPSVFLFPPKPKDT

LMISRTPEVTCVVVDVSHEDPEVQFNWYVDGVEVHNAKTKPREEQFNSTF

RVVSVLTVVHQDWLNGKEYKCKVSNKGLPSSIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK 3)
(SEQ ID NO: 96)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPSDKTHTCPPCPAPEAAGAPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK 4)
(SEQ ID NO: 124)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPSDKTHTCPPCPAPEAAGAPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK

-continued

```
                                          (SEQ ID NO: 134)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPSAAAPPCPPCPAPEFLGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSPGK
```

Results

Figure 7:
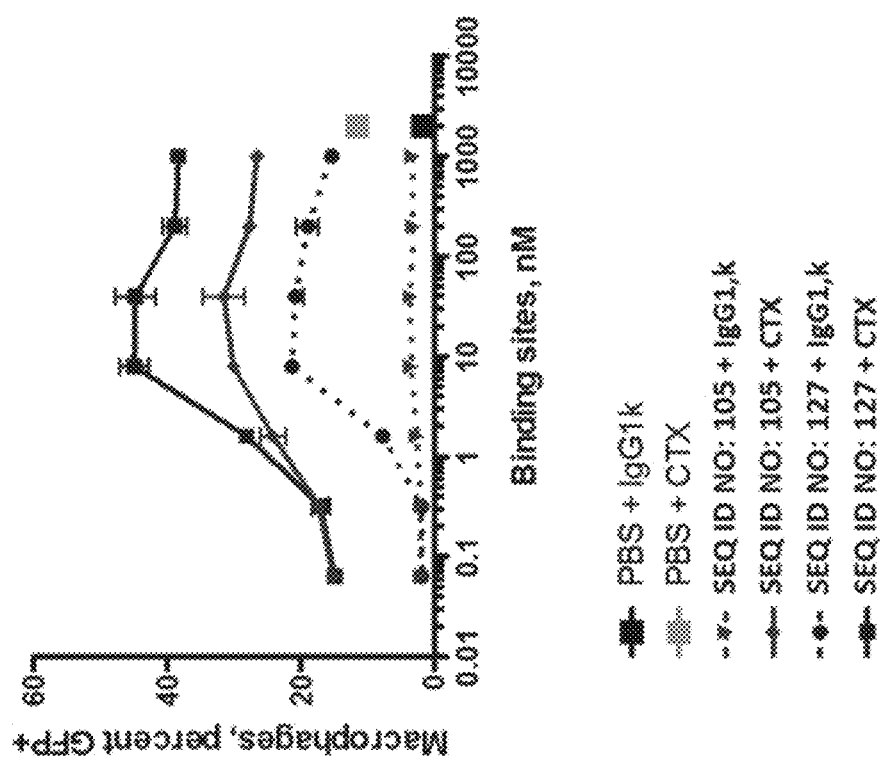
FIG. 7 exemplifies phagocytosis of DLD-1-GFP-Luciferase tumor cells by human monocyte-derived macrophages in the presence of varying concentrations of SIRP-α polypeptide constructs.

FIG. 7 shows phagocytosis of DLD-1-GFP-Luciferase tumor cells by human monocyte-derived macrophages in the presence of SEQ ID NO: 105 (Fc variant IgG2_A330S, P331S, N297A) and SEQ ID NO: 127 (Fc variant IgG2_A330S, P331S). In particular, FIG. 7 shows that SEQ ID NO: 105 (Fc variant IgG2_A330S, P331S, N297A) (in the presence or absence of a control antibody IgG1,k) has ablated phagocytosis in the phagocytosis assay as a single agent while it is able to increase cetuximab (CTX) phagocytosis (SEQ ID NO: 105+CTX). In contrast, a polypeptide with Fc variant IgG2_A330S, P331S (SEQ ID NO: 127+ IgG1,k) has measurable phagocytosis activity as a single agent. The percent of macrophages that phagocytosed tumor cells and are GFP$^+$ is indicated on the y-axis (FIG. 7). Concentration of CD47 binding sites from the addition of SEQ ID NO: 105 and SEQ ID NO: 127 is indicated on the x-axis. DLD-1-GFP-Luciferase cells and macrophages were incubated with the indicated concentrations of SEQ ID NO: 105, SEQ ID NO: 107 and CTX (1 ug/mL) and control antibody (IgG1, k). Cells were also incubated with PBS plus cetuximab (line labeled PBS+CTX) or a PBS plus a control antibody of the same isotype (line labeled PBS+IgG1k).

Figure 8:
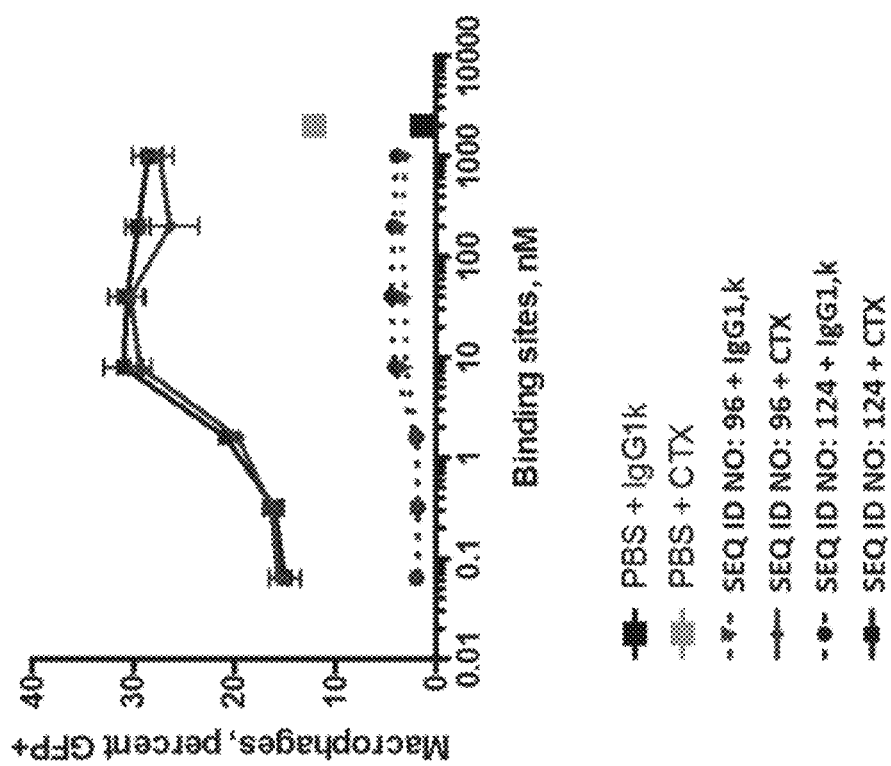
FIG. 8 exemplifies phagocytosis of DLD-1-GFP-Luciferase tumor cells by human monocyte-derived macrophages in the presence of varying concentrations of SIRP-α polypeptide constructs.

FIG. 8 shows phagocytosis of DLD-1-GFP-Luciferase tumor cells by human monocyte-derived macrophages in the presence of SEQ ID NO: 96 (Fc variant IgG1 L234A, L235A, G237A, N297A and SEQ ID NO: 124 (Fc variant IgG1 L234A, L235A, G237A). In particular, FIG. 8 shows that Fc variant IgG1 L234A, L235A, G237A, N297A (SEQ ID NO: 96) and Fc variant IgG1 L234A, L235A, G237A (SEQ ID NO: 124) have ablated phagocytosis in the phagocytosis assay as single agents. These are represented by lines labelled SEQ ID NO 96+IgG1, k and SEQ ID NO: 124+ IgG1,k respectively. Interestingly, both polypeptides SEQ ID NO: 96 and SEQ ID NO: 124 increased the phagocytosis of a tumor specific antibody, CTX. As shown in FIG. 8, the percent of macrophages that phagocytosed tumor cells and are GFP+ is indicated on the y-axis. Concentration of CD47 binding sites from addition of SEQ ID NO: 96 and SEQ ID NO: 124 is indicated on the x-axis. DLD-1-GFP-Luciferase cells and macrophages were incubated with CTX at 1 μg/mL and the indicated concentrations of SEQ ID NO: 96 (line labeled SEQ ID NO: 96+CTX) or SEQ ID NO: 124 (line labeled SEQ ID NO: 124+CTX). To identify nonspecific effects of cetuximab upon phagocytosis, cells were incubated with a control antibody of the same isotype as cetuximab and the indicated concentrations of SEQ ID NO: 96 (line labeled SEQ ID NO: 96+IgG1,k) or SEQ ID NO: 124 (line labeled SEQ ID NO: 124+IgG1,k). Cells were also incubated with PBS plus cetuximab (line labeled PBS+ CTX) or a PBS plus a control antibody of the same isotype (line labeled PBS+IgG1k).

Figure 9:
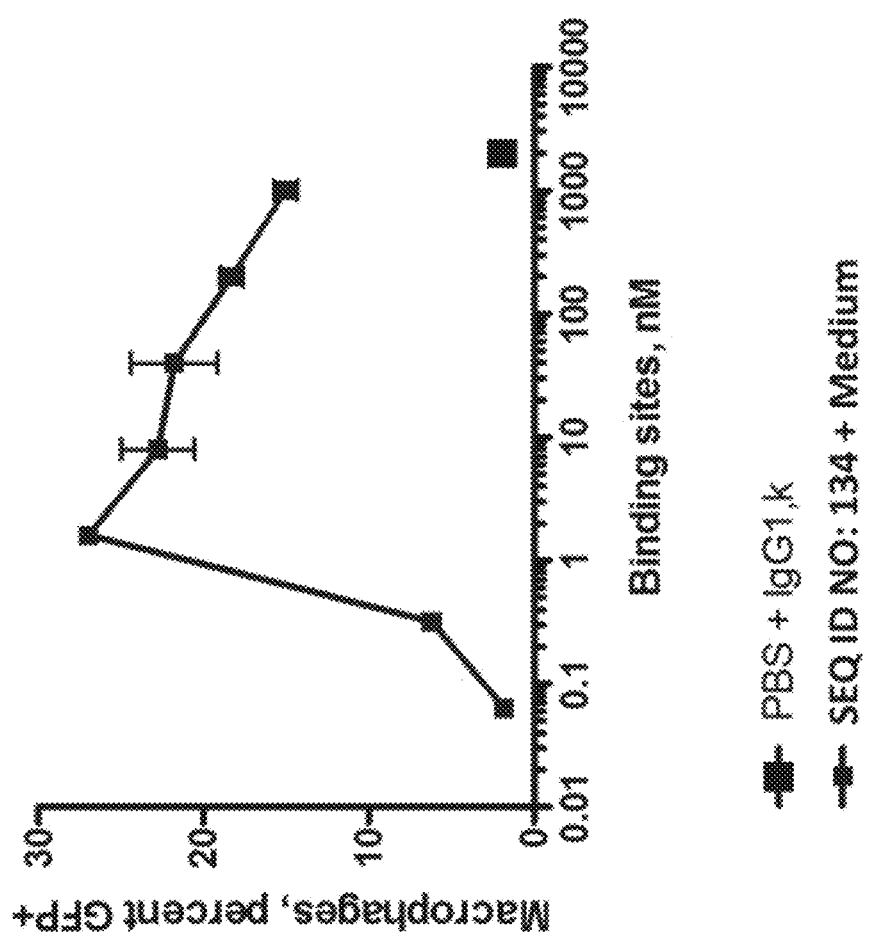
FIG. 9 exemplifies phagocytosis of DLD-1-GFP-Luciferase tumor cells by human monocyte-derived macrophages in the presence of varying concentrations of SIRP-α polypeptide constructs.

FIG. 9 shows phagocytosis of DLD-1-GFP-Luciferase tumor cells by human monocyte-derived macrophages in the presence of SEQ ID NO: 134 (Fc variant IgG4_S228P). In particular, FIG. 9 shows that the SEQ ID NO: 134 construct has considerable phagocytosis activity as a single agent in in vitro phagocytosis. As shown in FIG. 9, the percent of macrophages that phagocytosed tumor cells and are GFP+ is indicated on the y-axis. Concentration of CD47 binding sites from addition of SEQ ID NO: 134 is indicated on the x-axis. DLD-1-GFP-Luciferase cells and macrophages were incubated with the indicated concentrations of SEQ ID NO: 134 (line labeled SEQ ID NO: 134+Medium). Cells were also incubated with control antibody (IgG1, k; black square).

Example 11

Production of SIRP-α Variant and HSA Polypeptides

Additionally, using the methods described herein and in accordance with embodiments of the disclosure, SIRP-α D1 variant polypeptide was expressed by fusion to HSA polypeptides, as shown in Table 23 below. Binding to human CD47 was determined by the methodologies as described in Example 1.

TABLE 23

CD47 Binding Affinity of SIRP-α Variants Fused to HSA Polypeptides

| SEQ ID NO: | $K_D$ (M) |
|---|---|
| 150 | $4.53 \times 10^{-10}$ |
| 151 | $5.54 \times 10^{-9}$ |
| 152 | $2.78 \times 10^{-10}$ |
| 153 | $4.24 \times 10^{-9}$ |
| 154 | $2.35 \times 10^{-10}$ |
| 155 | $1.11 \times 10^{-8}$ |
| 157 | $2.15 \times 10^{-9}$ |
| 158 | $1.09 \times 10^{-9}$ |
| 159 | $7.6 \times 10^{-10}$ |

Example 12

Extended Half-Life Associated with SIRP-α Variant Polypeptides

Figure 10:
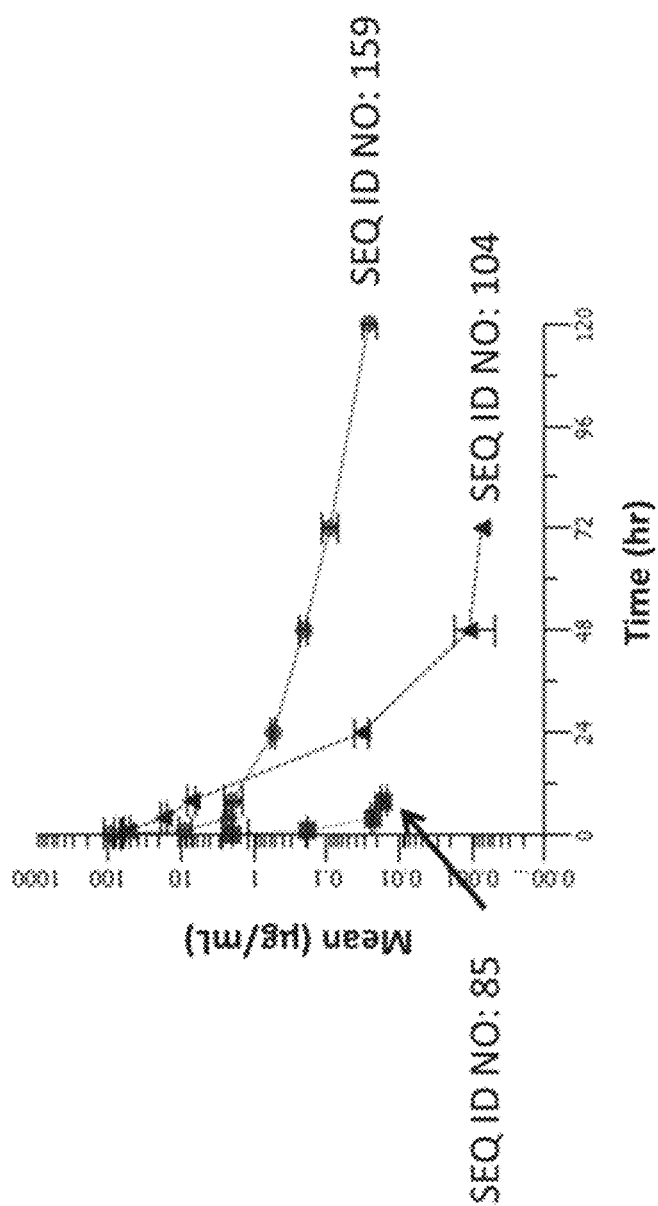
FIG. 10 exemplifies half-life stability of SIRP-α polypeptides over a defined time period.

As shown in Table 24 and FIG. 10, SIRP-α D1 variant polypeptides comprising Fc and HSA fusions can have an extended half-life compared to a SIRP-α D1 variant alone. For example, the SIRP-α D1 variant polypeptide fused to Fc as represented by SEQ ID NO: 104 and the SIRP-α D1 variant polypeptide fused to HSA as represented by SEQ ID NO: 159 have increased half-life relative to a SIRP-α D1 variant polypeptide which is not fused to an Fc or HSA as represented by SEQ ID NO: 85. The half-life extension can be attributed to the ability of SIRP-α D1 variant polypeptides which are fused to Fc and HSA to bind to FcRn, which may be associated with prolonged cycling.

TABLE 24

Half-life Measurements for Single Dose Treatments with SIRP-α Variant Polypeptides

| SEQ ID NO: | Dosage amount | Half-life (hour) |
|---|---|---|
| 104 | 10 mg/kg | 41.10 |
| 159 | 10 mg/kg | 24.54 |
| 85 | 10 mg/kg | 8.20 |

The methodologies used for this Example are as follows. Briefly, CD-1 male mice weighing approximately 25 grams were obtained from Harlan Labs, and were used for the single dose PK study of the compounds represented by SEQ ID NO: 104, SEQ ID NO: 159, and SEQ ID NO: 85. Each compound was formulated at a working dose of 5 mg/mL. The volume of the dose was adjusted based on the weight of each mouse, ensuring that each mouse was dosed at 1, 3 and 10 mg/kg. The compounds were administered intravenously via the mouse tail vein. Three mice were dosed for each time point at each dose level for each compound. After dosing, mice had blood withdrawn at the following 8 time points: 0.25, 1, 4, 8, 24, 48, 72 and 120 hrs. 500 µL of whole blood was collected into microtainer tubes by orbital bleed. Whole blood samples were rested for 30 minutes to allow serum separation. Samples were then centrifuged for 10 min at 4° C. at a RCF of 1000. Serum was then transferred to 0.5 mL tubes within 40 min of processing and kept frozen until analysis.

The data for SEQ ID NO: 104 was obtained using a human Fc ELISA protocol. Briefly, Immulon 4HBX ELISA 96 well plates were coated (Thermo Scientific cat. #3855) with 2 µg/ml, 100 µl/well of purified CD47 overnight at room temperature in 1× antigen coating buffer (Immuno-Chemistry Technologies, cat. #6248). Wells were washed 5 times with 200-300 µL/well 1× TBST (Tris-Buffered Saline+0.05% Tween-20) (Thermo Scientific 20×, cat. #28360). Wells were blocked with 200 µL/well 7.5% BSA in PBS (GIBCO, cat. #15260-037) for 1-2 hours. Wells were washed 5 times with 200-300 µL/well 1× TBST. 50 µL/well standard curve, Quality Controls (QCs) and unknown samples diluted in normal CD1 mouse serum diluted 1:4 in TBS was added. The standard curve, QCs and unknown samples were incubated at room temperature for 1 hour. Concentrations for standard curve were as follows: 0.2500 µg/mL; 0.1250 µg/mL; 0.0625 µg/mL; 0.0313 µg/mL; 0.0156 µg/mL; 0.0078 µg/mL; 0.0039 µg/mL; 0.0020 µg/mL; 0.0010 µg/mL; 0.0005 µg/mL; 0.00025 µg/mL; and 0.00000 µg/mL. Quality Controls (QCs) were frozen and aliquoted, and standard curve protein at a "high," "mid," and "low" concentrations on the linear curve of the standard curve which served as controls to ensure that the assay was working well were as follows: QC High=0.125 µg/ml; QC Mid=0.016 µg/ml; and QC Low=0.004 µg/ml.

Then, the wells were washed 5 times with 200-300 µL/well 1× TBST. 50 µL/well of 0.25 ug/mL Abbexa Goat anti-Human IgG Fc polyclonal antibody (11.6 mg/mL stock, Abbexa cat. #abx023511) diluted into 1× TBST+1% BSA was added and incubated for 1 hour at room temperature. Plates were washed 5 times with 200-300 µL/well 1× TBST. 50 µL/well of 0.125 µg/mL ZyMax/Invitrogen rabbit anti-goat IgG-HRP conjugated (Thermo Scientific, cat. #81-1620), diluted into TBST+1% BSA was added and incubated for 1 hour at room temperature. Wells were washed 6 times with 200-300 µL/well 1× TBST. The following steps and reagents were carried out at room temperature: 0 µL/well room temperature 1-Step Ultra TMB-ELISA (Thermo Scientific cat. #34028) was added and incubated 2-5 minutes at room temperature until color development was sufficient. 50 µL/well of room temperature Stop Solution (0.16M sulfuric acid, Thermo Scientific cat. #N600) was added immediately and mixed well. Plates were read immediately in a spectrophotometer at O.D. 450 and at O.D. 570. The O.D. 570 reading was a background reading which was subtracted from the O.D. 450 reading. Using a software program like Molecular Devices SoftMax Pro or Graph Pad Prism, the standard curve values were plotted using a 4 parameter fit curve and the concentrations of the unknown samples were interpolated from the standard curve using the software.

The data for SEQ ID NO: 85 was obtained using a His Tag ELISA protocol. Immulon 4HBX ELISA 96 well plates (Thermo Scientific cat. #3855) were coated with 2 µg/mL, 100 µL/well of purified CD47 overnight at room temperature in 1× antigen coating buffer (ImmunoChemistry Technologies, cat. #6248). Wells were washed 5 times with 200-300 µL/well using 1× TBST (Tris-Buffered Saline+0.05% Tween-20) (Thermo Scientific 20×, cat. #28360). Wells were blocked with 200 µL/well 7.5% BSA in PBS (GIBCO, cat. #15260-037) for 1-2 hours. Wells were washed 5 times with 200-300 µL/well 1× TBST. 50 µL/well standard curve, Quality Controls (QCs) and unknown samples diluted in normal CD1 mouse serum diluted 1:4 in TBS were added. The standard curve, QCs and unknown samples were incubated at room temperature for 1 hour. The standard curve concentrations were as follows: 0.12500 µg/mL; 0.06250 µg/mL; 0.03125 µg/mL; 0.01563 µg/mL; 0.00781 µg/mL; 0.00391 µg/mL; 0.00195 µg/mL; 0.00098 µg/mL; and 0.00000 µg/mL. Quality Controls (QCs) were frozen and aliquoted, and standard curve protein at a "high," "mid," and "low" concentration on the linear curve of the standard curve which served as controls to ensure that the assay was working well were as follows: QC High=0.02 µg/ml; QC Mid=0.01 µg/ml; and QC Low=0.005 µg/ml.

Thereafter, wells were washed 5 times with 200-300 µL/well 1× TBST. 50 µL/well of 0.2 µg/mL Abcam rabbit anti-6× His Tag-HRP conjugated polyclonal antibody (1 mg/mL stock, abcam cat. #ab1187) diluted into TBST+1% BSA was added and incubated for 1 hour at room temperature. Plates were washed 6 times with 200-300 uL/well 1× TBST. Thereafter, the following steps and agents were carried out at room temperature. 50 µL/well of room temperature 1-Step Ultra TMB-ELISA (Thermo Scientific cat. #34028) was added and incubated 3-5 minutes at room temperature until color development was sufficient. 50 µL/well of room temperature Stop Solution (0.16M sulfuric acid, Thermo Scientific cat. #N600) was immediately added and mixed well. Plates were read immediately in a spectrophotometer at O.D. 450 and at O.D. 570. The O.D. 570 reading was a background reading which was subtracted from the O.D. 450 reading. Using a software program such as Molecular Devices SoftMax Pro or Graph Pad Prism, the standard curve values were plotted using a 4 parameter fit curve and the concentrations of the unknown samples were interpolated from the standard curve using the software.

The data for SEQ ID NO: 159 was obtained using a HSA ELISA protocol. Immulon 4HBX ELISA 96 well plates (Thermo Scientific cat. #3855) were coated with 2 ug/ml, 100 ul/well of purified CD47 overnight at room temperature in 1× antigen coating buffer (ImmunoChemistry Technologies, cat. #6248). Wells were washed 5 times with 200-300 µL/well using 1× TBST (Tris-Buffered Saline+0.05% Tween-20) (Thermo Scientific 20×, cat. #28360). Wells were blocked with 200 µL/well Li-Cor Odyssey Blocking Buffer (TBS) (Li-Cor, cat. #927-50000) for 2 hours, and blocking buffers containing albumin were not used. Wells were washed 5 times with 200-300 µL/well 1× TBST. 50 uL/well standard curve, Quality Controls (QCs) and unknown samples diluted in normal CD1 mouse serum diluted 1:4 in TBS was added. The standard curve, QCs and unknown samples were incubated at room temperature for 1 hour.

The standard curve concentrations were as follows: 3.20 µg/ml; 1.60 µg/ml; 0.80 µg/ml; 0.40 µg/ml; 0.20 µg/ml; 0.10 µg/ml; 0.05 µg/ml; 0.025 µg/ml; and 0.00 µg/ml. Quality Controls (QCs) are frozen and aliquoted, and standard curve protein at a "high", "mid", and "low" concentrations on the linear part of the standard curve which served as controls to ensure that the assay was working well were as follows: QC High=0.6 µg/ml; QC Mid=0.3 µg/ml; QC Low=0.15 µg/ml, and QC Low=0.01 µg/ml.

Thereafter, wells were washed 5 times with 200-300 µL/well 1× TBST. 50 µL/well of 1 µg/ml Thermo Scientific/Pierce rabbit anti-HSA-HRP conjugated (Thermo Scientific cat. #PA1-26887) diluted into 1× TBST was added and incubated for 1 hour at room temperature. Plates were washed 6 times with 200-300 µL/well 1× TBST. Thereafter, the following steps and reagents were carried out at room temperature. 50 µL/well room temperature 1-Step Ultra TMB-ELISA substrate (Thermo Scientific, cat. #34028) was added and incubated 3-5 minutes at room temperature until color development was sufficient. 50 µl/well of room temperature TMB Stop Solution (0.16 M Sulfuric Acid solution, Thermo Scientific cat. #N600) was added and mixed well. Plates were read immediately in a spectrophotometer at O.D. 450 and at O.D. 570. The O.D. 570 reading was a background reading which was subtracted from the O.D. 450 reading. Using a software program such as Molecular Devices SoftMax Pro or Graph Pad Prism, the standard curve values were plotted using a 4 parameter fit curve and the concentrations of the unknown samples were interpolated from the standard curve using the software.

Example 13

Reduced Hemagglutination Demonstrated by SIRP-α Variant Polypeptides

Figure 11:
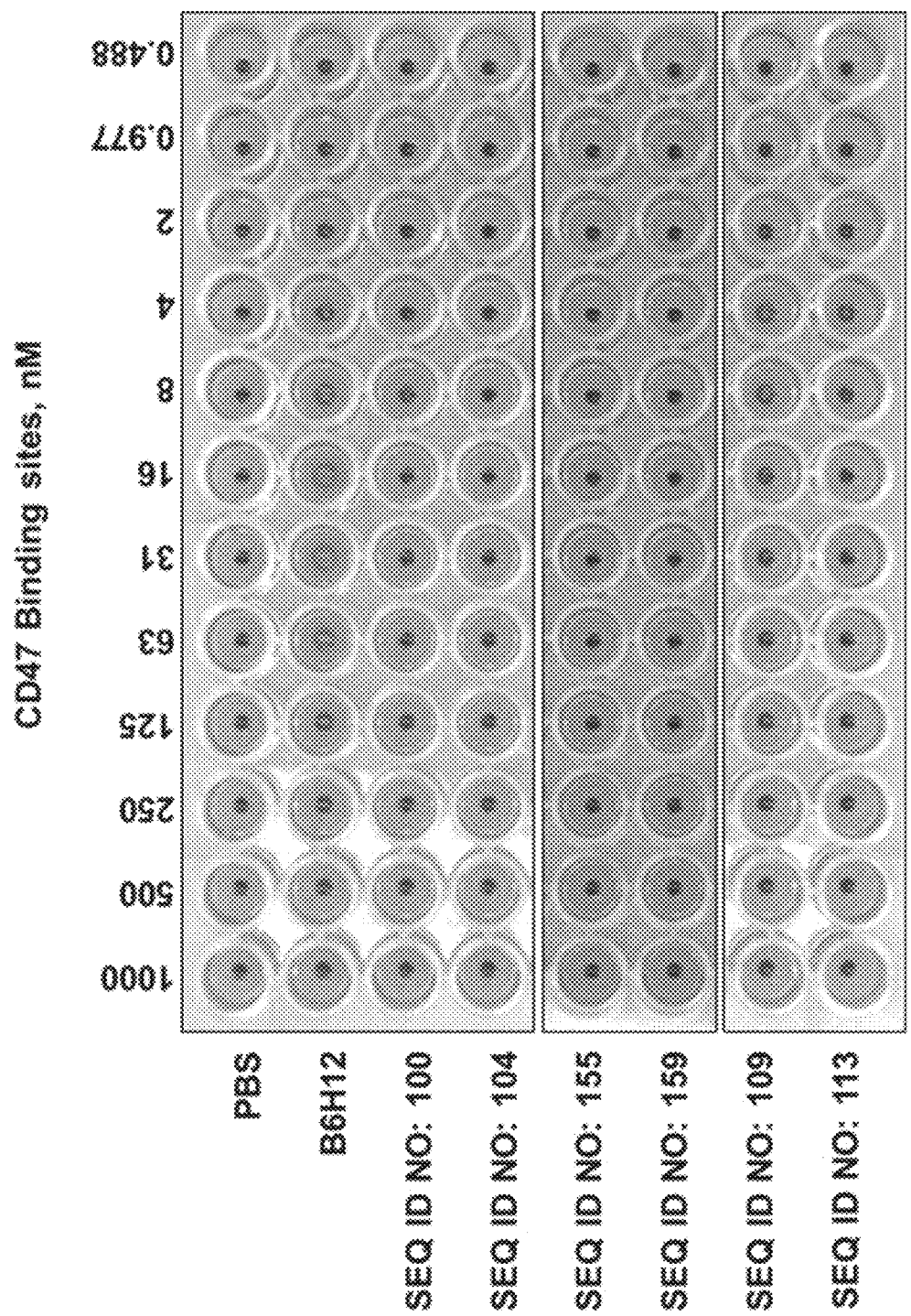
FIG. 11 exemplifies hemagglutination assay data for SIRP-α polypeptide constructs.

As shown in FIG. 11, SIRP-α D1 variant polypeptides demonstrated reduced or ablated hemagglutination. Specifically, when hemagglutination occurs, a diffused red coloration is present instead of a red dot, as is shown for the positive control B6H12. For the SIRP-α D1 variant polypeptides tested in FIG. 11, there was a reduction or ablation of hemagglutination.

The methodologies used for this Example were as follows: human whole blood buffy coats were received from the Stanford University Blood Center and diluted 1:2 with Phosphate Buffered Saline (PBS, Gibco). Diluted blood was split into two tubes and underlayed with 20 ml Ficoll-Paque Plus (GE Healthcare). Tubes were centrifuged for 30 minutes at 400×g. Supernatants were removed and the erythrocyte pellets were washed twice by addition of 30 mL of PBS and centrifugation at 3500 RPM. Thereafter, a hemagglutination assay was carried out as follows: human erythrocytes were diluted in PBS and transferred to 96 well polystyrene plates (Corning) at 4 million cells per well in a volume of 75 µL. Five-fold serial dilutions of the indicated proteins were added to wells in a volume of 75 µL PBS, with final concentration from 1000 nM to 0.488 nM. As a negative control, PBS alone was added to one row of wells. Erythrocytes settled to the well bottom, forming a small and well-defined pellet. As a positive control, cells were treated with the anti-CD47 antibody B6H12 (ebioscience). This antibody caused hemagglutination at concentrations between 8 and 63 nM, indicated by formation of a large and diffuse cell pellet. Among tested constructs, IgG2-based polypeptides (SEQ ID NO: 109 and SEQ ID NO: 113) caused slight hemagglutination at 4 and 8 nM. No hemagglutination was observed for all other polypeptide constructs (IgG1-based and HSA-based).

Example 14

Anti-Tumor Activity of SEQ ID NO: 211 in a Mouse Syngeneic Tumor Model

C57BL/6 mice (7- to 10-week-old female animals) obtained from Charles River Laboratory were used. Mouse colon adenocarcinoma cell line MC38 was recovered from frozen stocks and grown in RPMI 1640 containing 10% fetal bovine serum, penicillin-streptomycin, and L-glutamine. Cells were spun down and resuspended at a concentration of 2E+07 cells/mL in serum-free medium without additives. On Day −7 (i.e., 7 days before the projected staging day), the mice were implanted by subcutaneous injection into the left flank with 100 µL (2.0×10$^6$ cells) per mouse of the freshly prepared MC38 in phosphate buffered saline (PBS). When the tumors reached a mean volume of approximately 50 mm$^3$, fifty animals with established tumors and moderate body weights were randomized into 5 treatment groups (Group 1-5, n=10 mice each). Starting on Day 1, mice of Groups 1 to 5 were treated with vehicle (PBS), anti-mPD-L1 (Clone 10F.9G2, 200 µg), SEQ ID NO: 211 (200 µg), anti-mPD-L1 (200 µg)+SEQ ID NO: 211 (100 µg), or anti-mPD-L1 (200 µg)+SEQ ID NO: 211 (200 µg), respectively. Doses were by administered intraperitoneal (IP) injection of 0.05 mL/mouse on days 1, 4 and 7.

SEQ ID NO: 211 was generated by genetically fusing SED ID NO: 206 to a Fc domain monomer. SEQ ID NO: 206 contains mutations shown to improve binding to mouse CD47. The binding data is presented in Table 18.

6)
```
                                        SEQ ID NO: 211
EEELQIIQPDKSVLVAAGETATLRCTITSLRPVGPIQWFRGAGPGRELIY

NQRDGPFPRVTTVSDTTKRNNMDFSIRIGAITPADAGTYYCVKFRKGIPD

DVEFKSGAGTELSVRAKPSDKTHTCPPCPAPEAAGAPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK
```

Clinical observations and body weights were monitored throughout the study up to Day 42. Tumor sizes were measured two times per week, and at study completion, the perpendicular minor (width, W, and height, H) and major (length, L) dimensions were measured using microcalipers (Mitutoyo, Aurora, Ill.). Tumor volume (mm$^3$) was calculated using the formula for the volume of an ellipsoid sphere (L×W$^x$H/2). Study animals were subjected to humane sacrifice during the study when tumor volumes in individual animals exceeded (or approached) 2,500 mm$^3$. The number of animals remaining in the study up to Day 42 were used for a survival analysis.

Figure 12:
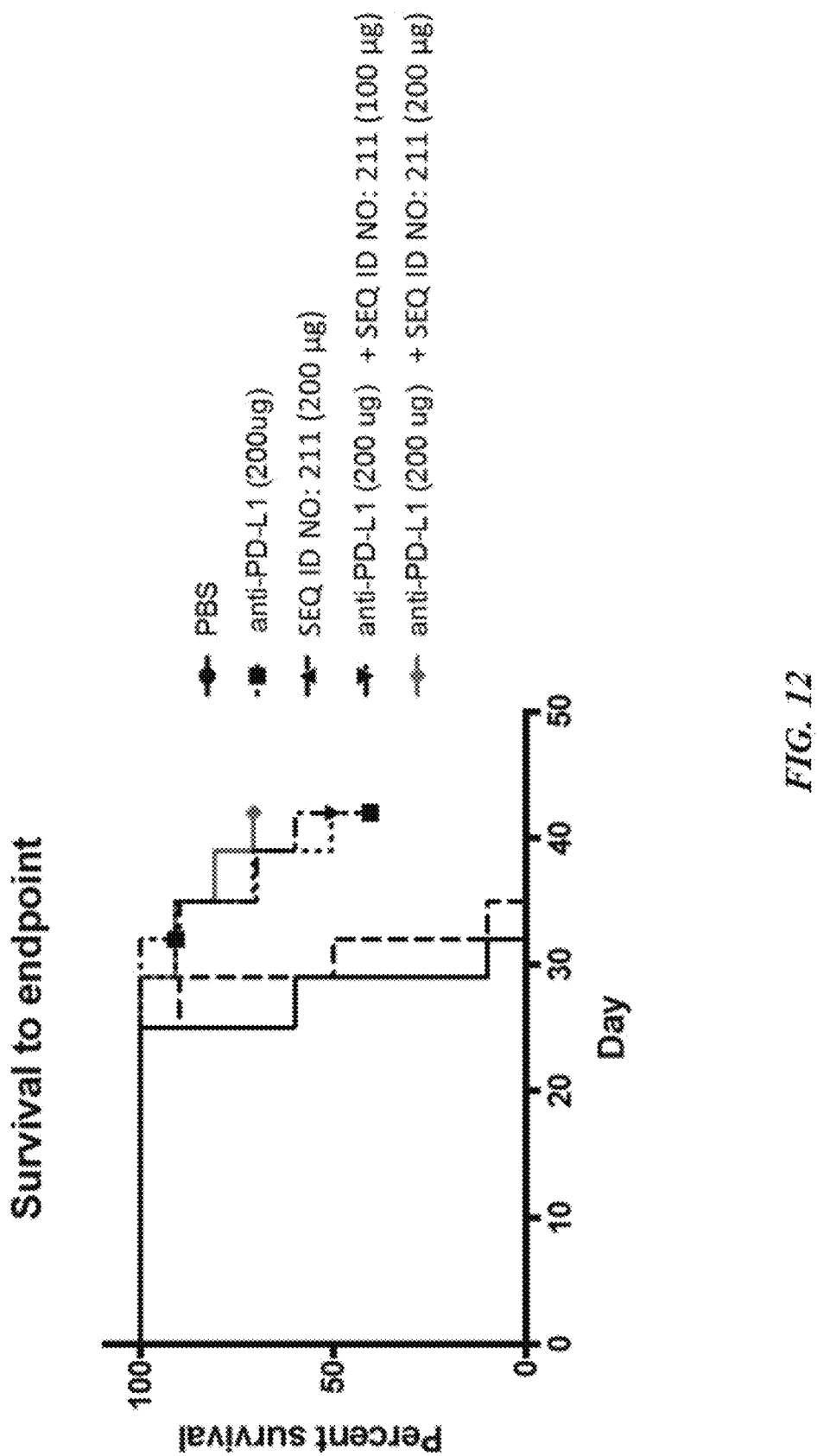
FIG. 12 exemplifies survival curves of mice syngeneic tumor models treated with SIRP-α polypeptide constructs and anti-mPD-L1.

Tumors grew to various degrees in all five groups. Among mice dosed with vehicle or SEQ ID NO: 211 (200 µg) (Groups 1 and 3, respectively), sacrifices began during the 4$^{th}$ week (from Day 25) and all animals in these groups were dead by the end of the 5$^{th}$ week (Day 35). Among mice dosed with anti-mPD-L1 (alone or in combination with SEQ ID NO: 211; Groups 2, 4, and 5), sacrifices began during the 5$^{th}$ week (from Day 29 or 32) but a subset (40-70%) of these animals survived to the scheduled study end (Day 42). FIG. 12 shows survival curves for each treatment group during the study period. Numerically, the anti-mPD-L1 plus 200 µg SEQ ID NO: 211 treatment group had the highest number of surviving animals, following by the anti-mPD-L1 plus 100 µg SEQ ID NO: 211 treatment group and anti-mPD-L1 alone group, with 7 out 10 (70%), 5 out 10 (50%) and 4 out of 10 (40%) mice remaining at Day 42, respectively (Table 25). Median survival was 29 and 30.5 days respectively for vehicle (Group 1) and SEQ ID NO: 211 alone (Group 3) treatments. Median survival increased to 42 days for anti-mPD-L1 alone (Group 2) and anti-PD-L1 plus 100 µg SEQ ID NO: 211 (Group 4) treatment. Median survival for anti-mPD-L1 plus 200 µg SEQ ID NO: 211 treatment (Group 5) was not determined as more than 50% of animals remained at the end of the study (Day 42).

TABLE 25

Animal Survival Data.

| Group | Treatment (3 IP doses - on Days 1, 4 and 7) | Number of Animals Alive on Indicated Day | | | | | | | | | | | |
|---|---|---|---|---|---|---|---|---|---|---|---|---|---|
| | | 1 | 4 | 7 | 11 | 14 | 18 | 22 | 25 | 29 | 32 | 35 | 39 | 42 |
| 1 | PBS | 10 | 10 | 10 | 10 | 10 | 10 | 10 | 6 | 1 | 0 | 0 | 0 | 0 |
| 2 | anti-mPD-L1 (200 μg) | 10 | 10 | 10 | 10 | 10 | 10 | 10 | 10 | 9 | 9 | 7 | 5 | 4 |
| 3 | SEQ ID NO: 211 (200 μg) | 10 | 10 | 10 | 10 | 10 | 10 | 10 | 9 | 5 | 1 | 0 | 0 | 0 |
| 4 | anti-mPD-L1 (200 μg) + SEQ ID NO: 211 (100 ug) | 10 | 10 | 10 | 10 | 10 | 10 | 10 | 10 | 10 | 9 | 7 | 6 | 5 |
| 5 | anti-mPD-L1 (200 ug) + SEQ ID NO: 211 (200 μg) | 10 | 10 | 10 | 10 | 10 | 10 | 10 | 10 | 9 | 9 | 8 | 7 | 7 |

Figure 13:
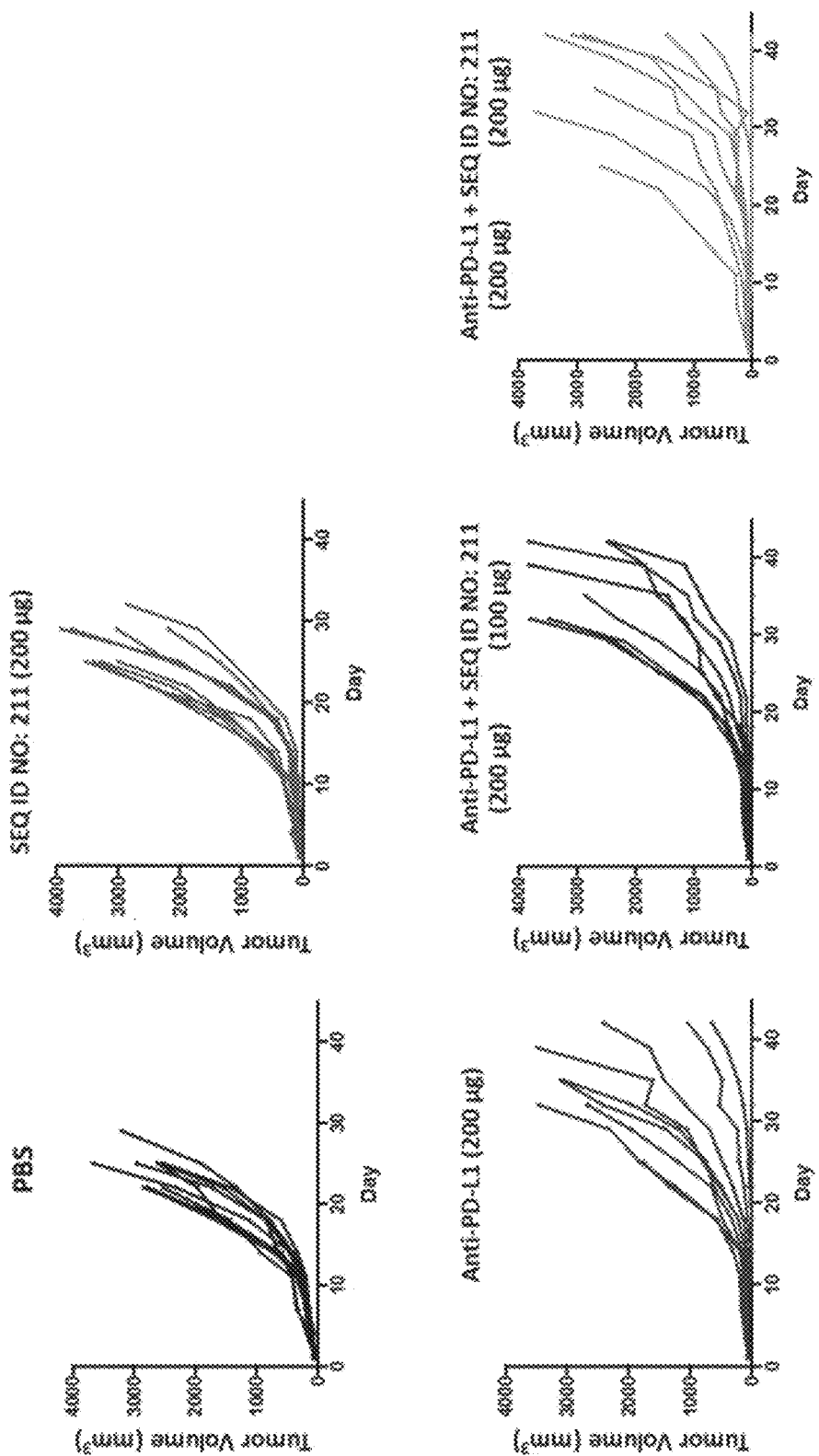
FIG. 13 exemplifies a tumor volume analysis of mice syngeneic tumor models treated with SIRP-α polypeptide constructs in combination with anti-mPD-L1.

Tumors exhibited rapid growth in the vehicle treated group, indicating ongoing tumor growth in the absence of effective treatment. Dosing with 200 μg SEQ ID NO: 211 (Group 3) yielded significant attenuation of tumor growth only at intermittent time points (Day 7 and 14, for both raw and normalized tumor volume) compared to dosing with vehicle. Dosing with 200 μg anti-mPD-L1, alone or in combination with SEQ ID NO: 211 (Groups 2, 4, and 5), provided significant attenuation of tumor growth from Day 4 or 7 (for raw or normalized tumor volume, respectively) compared to dosing with vehicle (FIG. 13 and Table 26). The addition of SEQ ID NO: 211 to the anti-mPD-L1 regimen (Group 2 vs. 4 or Group 2 vs. 5) produced additional tumor growth inhibition over anti-mPD-L1 treatment alone. Day-22 tumor volumes, including tumor growth inhibition (% TGI), are provided in Table 26. Day 22 is used for the comparison because this day is the last time point at which all animals were still alive. Tumor growth inhibition (% TGI) on Day 22 vs Day 1 were 83%, 81% and 77% for anti-mPD-L1 plus 200 μg SEQ ID NO: 211 group, anti-mPD-L1 plus 100 μg SEQ ID NO: 211 group and anti-mPD-L1 alone group, respectively (Table 26).

hematological cancer. Cancers may be recognized by the immune system, and under some circumstances, the immune system may be involved in eliminating tumors. Blockade of co-inhibitory molecules, such as CTLA-4, PD-1, and LAG-3, may be involved in amplifying T-cell responses against tumors. Polypeptides described herein are administered in combination with a checkpoint inhibitor, such as an antibody inhibitor of CTLA-4 (e.g., ipilimumab, tremelimumab), PD-1 (nivolumab, pidilizumab, MK3475 also known as pembrolizumab, BMS936559, and MPDL3280A), and LAG-3 (e.g., BMS986016).

Established A20 tumors in BALB/c mice (e.g., lymphoma models) are treated with an antibody inhibitor of CTLA-4 and a high affinity SIRP-α D1 variant fused to an IgG Fc variant provided herein (e.g., a SIRP-α construct). Starting on Day 1, mice are treated with vehicle (PBS), tremelimumab (200 μg)+SIRP-α construct (100 μg), or tremelimumab (200 μg)+SIRP-α construct (200 μg). Doses are administered by intraperitoneal (IP) injection at 0.05 mL/mouse on days 1, 4 and 7. Tumor response to combination therapy is determined daily by measuring tumor volume. If on day 4, tumor volume of mice treated with

TABLE 26

Tumor Volume Analysis

| Group | Agent (Three doses on Day 1, 4 and 7, IP) | Day-1 Tumor Volume (B, mm³) Mean ± SD | Day-22^ Tumor Volume (T, mm³) Mean ± SD | Day 22* vs. Day 1 | | Mean Normalized Day-22^ Volume % Day 1 |
|---|---|---|---|---|---|---|
| | | | | T-B (mm³) Δ tumor volume | % TGI % Group 1 Δ | |
| 1 | Vehicle | 52 ± 13 | 2126 ± 599 | 2074.2 | 0% | 4380% |
| 2 | anti-mPD-L1 (200 μg) | 52 ± 12 | 537 ± 464 | 484.6 | 77% | 1062% |
| 3 | SEQ ID NO: 211 (200 μg) | 51 ± 12 | 1697 ± 679 | 1645.4 | 21% | 3384% |
| 4 | anti-mPD-L1 (200 μg) + SEQ ID NO: 211 (100 μg) | 52 ± 13 | 456 ± 368 | 404.3 | 81% | 959% |
| 5 | anti-mPD-Ll (200 μg) + SEQ ID NO: 211 (200 μg)0 | 52 ± 11 | 399 ± 497 | 347.9 | 83% | 728% |

*Day 22 is the last day on which all animals of all groups remained alive.

Example 15

Optimizing Combination Therapy for Treating Cancer

Polypeptides including a high affinity SIRP-α D1 variant are co-administered with checkpoint inhibitors to treat mouse models of various cancers, e.g., solid tumor and combination therapy shows no significant improvement, tremelimumab is replaced with ipilimumab. Similarly, if on day 7, tumor volume of mice treated with combination therapy show no significant improvement, tremelimumab is replaced with ipilimumab. It is expected that while tremelimumab and ipilimumab target the same checkpoint protein, they have different therapeutic efficacies and synergistic effects with the SIRP-α construct due to their differing Fc regions. Tremelimumab is an IgG2 antibody that may be more effective at fixing complement while ipilimumab is an IgG1 antibody that may be useful in preventing the elimination of activated T-cells.

Example 16

Method of Treating a Cancer Expressing an Epithelial Marker

SIRP-α polypeptide constructs, such as a high affinity SIRP-α D1 variant (e.g., any variant provided in Tables 2, 5, and 6) fused to an IgG Fc variant, are administered to treat a cancer expressing an epithelial cell marker. Increased phagocytosis resulting from the blockade of CD47 signaling, for example by a SIRP-α D1 construct, may depend on the presence of macrophages. Therefore, administration of a SIRP-α D1 polypeptide construct in combination with an antibody targeting an epithelial marker that is expressed in or on a cancer cell is used to treat the cancer reducing the risk of side effects, e.g., phagocytosis of epithelial cells, due to a low abundance of macrophages at the skin periphery.

Mouse models of a cancer expressing an epithelial marker, for example EGFR or EpCAM, are administered a SIRP-α construct in combination with an antibody that targets the epithelial marker, e.g., an anti-EGFR antibody or an anti-EpCAM antibody. Antibodies targeting epithelial markers can recognize both cancerous cells and non-cancerous cells, for example non-cancerous cells at the skin periphery. However, it is expected that non-cancerous cells at the skin periphery will not be susceptible to phagocytosis due to a low abundance of macrophages near the skin.

Example 17

Phagocytosis by Single Arm SIRP-α-Fc Fusions

To obtain quantitative measurements of phagocytosis induced by SIRP-α-Fc fusions having a single SIRP-α molecule (e.g., a single arm molecule) (depicted in FIGS. 1, 4A, and 4B), a phagocytosis assay with different cell types MM1R and N87 cells was performed using methods as described in Example 8.

Six single arm constructs were tested for in vitro phagocytosis. These single-arm constructs are generated using knob & hole strategies. Homodimer SIRP-α Fc fusion of SEQ ID NO: 136 was used as a double arm comparison (control). A first single-arm SIRP-α Fc fusion (e.g., A) was formed from a heterodimer of SEQ ID NO: 139 (an Fc variant) and SEQ ID NO: 138 (a SIRP-α Fc fusion). A second single-arm SIRP-α Fc fusion (e.g., B) was formed from a heterodimer of SEQ ID NO: 141 (an Fc variant) and SEQ ID NO: 140 (a SIRP-α Fc fusion). A third single-arm SIRP-α Fc fusion (e.g., C) was formed from a heterodimer of SEQ ID NO: 139 (an Fc variant) and SEQ ID NO: 142 (a SIRP-α Fc fusion). A fourth single-arm SIRP-α Fc fusion (e.g., D) was formed from a heterodimer of SEQ ID NO: 141 (an Fc variant) and SEQ ID NO: 143 (a SIRP-α Fc fusion). A fifth single-arm SIRP-α Fc fusion (e.g., E) was formed from a heterodimer of SEQ ID NO: 147 (an Fc variant) and SEQ ID NO: 146 (a SIRP-α Fc fusion). A sixth single-arm SIRP-α Fc fusion (e.g., F) was formed from a heterodimer of SEQ ID NO: 149 (an Fc variant) and SEQ ID NO: 148 (a SIRP-α Fc fusion). The CD47 binding affinities ($K_D$) of the SIRP-α single-arm when tested as a monomer are as follows: ~10 pM (A, B), ~100 pM (C, D) and ~5 nM (E, F). The sequences are provided in Table 27 below.

TABLE 27

Amino Acid Sequences of SIRPα - Fc Fusions for the Construction of Heterodimers

| SEQ ID NO: | Amino Acid Sequence |
|---|---|
| 138 | EEELQIIQPDKSVLVAAGETATLRCTITSLFPVGPIQWFRGAGPGR VLIYNQRQGPFPRVTTVSDTTKRNNMDFSTRIGATTPADAGTYYCI KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 139 | DKTHTCPPCPAPEAAGAPSVFLFPPKPKDTLMISRTPEVTCVVVDV SHEDPEVKFNWYVDGVEVHNAKTKPREEQYASTYRVVSVLTVLHQD WLNGKEYKCKVSNKALPAPIEKTISKAKGQPREPQVYTLPPSREEM TKNQVSLSCAVKGFYPSDIAVEWESNGQPENNYKTTPPVLDSDGSF FLVSKLTVDKSRWQQGNVFSCSVMHEALHNHYTQKSLSLSPGK |
| 140 | EEELQIIQPDKSVLVAAGETATLRCTITSLFPVGPIQWFRGAGPGR VLIYNQRQGPFPRVTTVSDTTKRNNMDFSTRIGAITPADAGTYYCI KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLSCAVKGFYPSDI AVEWESNGQPENNYKTTPPVLDSDGSFFLVSKLTVDKSRWQQGNVF SCSVMHEALHNHYTQKSLSLSPGK |
| 141 | DKTHTCPPCPAPEAAGAPSVFLFPPKPKDTLMISRTPEVTCVVVDV SHEDPEVKFNWYVDGVEVHNAKTKPREEQYASTYRVVSVLTVLHQD WLNGKEYKCKVSNKALPAPIEKTISKAKGQPREPQVYTLPPSREEM TKNQVSLWCLVKGFYPSDIAVEWESNGQPENNYKTTPPVLDSDGSF FLYSKLTVDKSRWQQGNVFSCSVMHEALHNHYTQKSLSLSPGK |
| 142 | EEELQIIQPDKSVLVAAGETATLRCTITSLFPVGPIQWFRGAGPGR ELIYNQREGPFPRVTTVSDTTKRNNMDFSIRIGATTPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 143 | EEELQIIQPDKSVLVAAGETATLRCTITSLFPVGPIQWFRGAGPGR ELIYNQREGPFPRVTTVSDTTKRNNMDFSIRIGAITPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYASTYRVVSVLTVLHQDWLNGKEYKCKVSNKALPAP IEKTISKAKGQPREPQVYTLPPSREEMTKNQVSLSCAVKGFYPSDI AVEWESNGQPENNYKTTPPVLDSDGSFFLVSKLTVDKSRWQQGNVF SCSVMHEALHNHYTQKSLSLSPGK |
| 146 | EEELQVIQPDKSVLVAAGETATLRCTATSLFPVGPIQWFRGAGPGR ELIYNQRQGPFPRVTTVSDLTKRNNMDFSIRIGNITPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYNSTYRVVSVLTVLHQDWLNGKEYKCKVSNKALPAP IEKTISKAKGQPREPQVYTLPPSREEMTKNQVSLWCLVKGFYPSDI AVEWESNGQPENNYKTTPPVLDSDGSFFLYSKLTVDKSRWQQGNVF SCSVMHEALHNHYTQKSLSLSPGK |
| 147 | DKTHTCPPCPAPEAAGAPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLSCAVKGFYPSDIAVEWESNGQPENNYKTTPPVLDSDGSF FLVSKLTVDKSRWQQGNVFSCSVMHEALHNHYTQKSLSLSPGK |
| 148 | EEELQVIQPDKSVLVAAGETATLRCTATSLFPVGPIQWFRGAGPGR ELIYNQRQGPFPRVTTVSDLTKRNNMDFSIRIGNITPADAGTYYCV KFRKGSPDDVEFKSGAGTELSVRAKPSDKTHTCPPCPAPEAAGAPS VFLFPPKPKDTLMISRTPEVTCVVVDVSHEDPEVKFNWYVDGVEVH NAKTKPREEQYNSTYRVVSVLTVLHQDWLNGKEYKCKVSNKALPAP IEKTISKAKGQPREPQVYTLPPSREEMTKNQVSLSCAVKGFYPSDI AVEWESNGQPENNYKTTPPVLDSDGSFFLVSKLTVDKSRWQQGNVF SCSVMHEALHNHYTQKSLSLSPGK |

TABLE 27-continued

Amino Acid Sequences of SIRPα - Fc Fusions for the Construction of Heterodimers

| SEQ ID NO: | Amino Acid Sequence |
|---|---|
| 149 | DKTHTCPPCPAPEAAGAPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSREEM TKNQVSLWCLVKGFYPSDIAVEWESNGQPENNYKTTPPVLDSDGSF FLYSKLTVDKSRWQQGNVFSCSVMHEALHNHYTQKSLSLSPGK |

Figure 15:
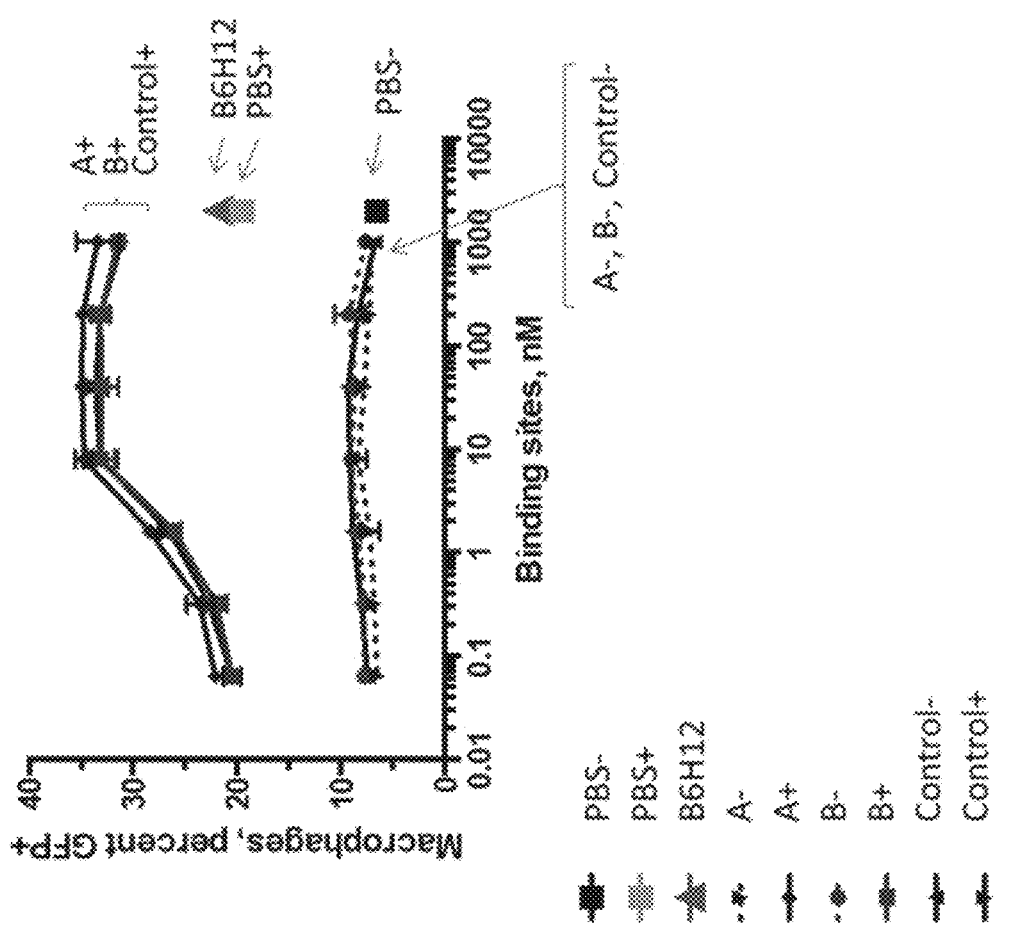
FIG. 15 exemplifies phagocytosis of MM1R cells by human monocyte-derived macrophages in the presence of varying concentrations of SIRP-α polypeptide constructs.
Figure 16:
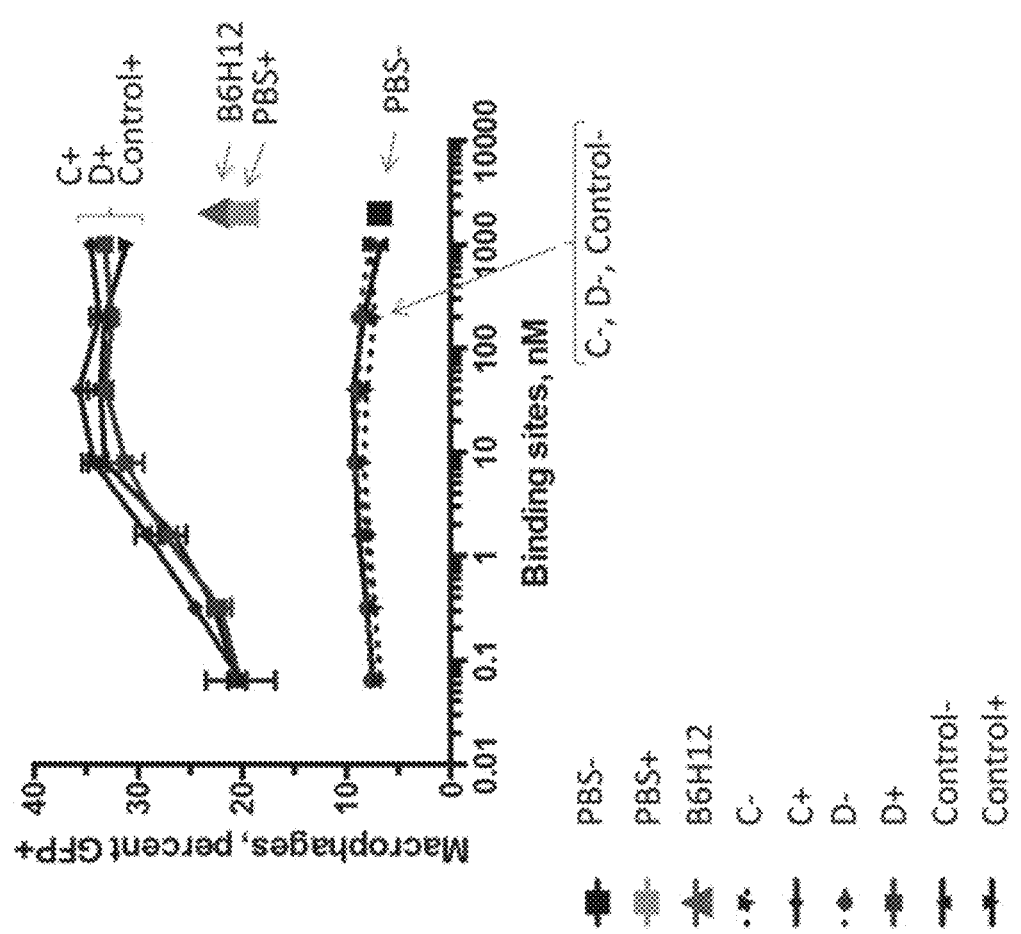
FIG. 16 exemplifies phagocytosis of MM1R cells by human monocyte-derived macrophages in the presence of varying concentrations of SIRP-α polypeptide constructs.
Figure 17:
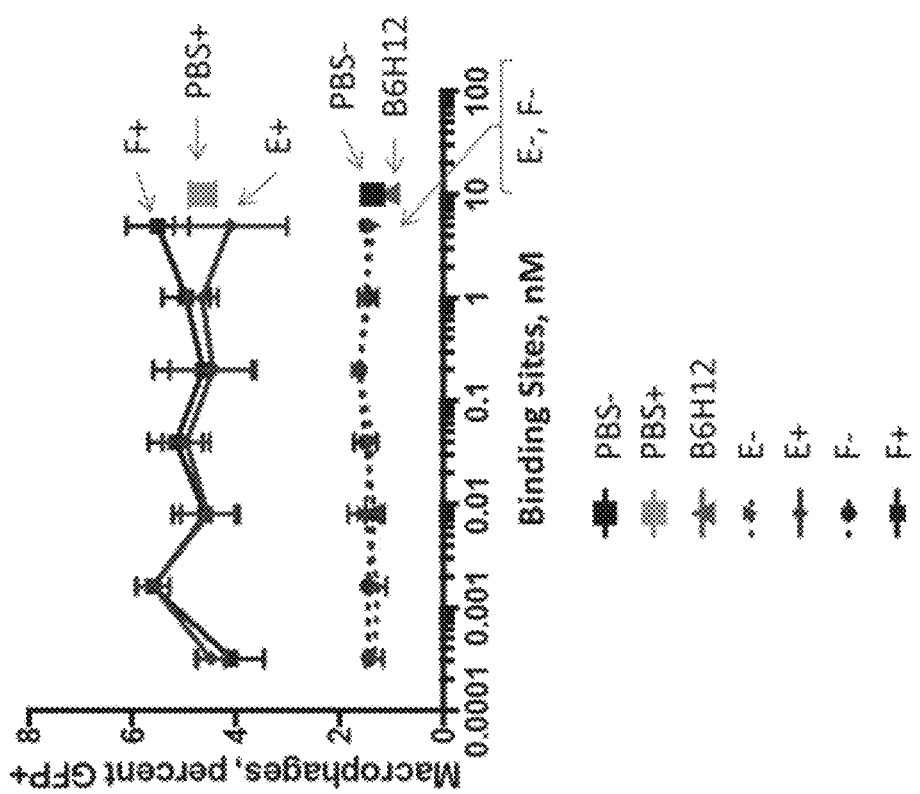
FIG. 17 exemplifies phagocytosis of N87 cells by human monocyte-derived macrophages in the presence of varying concentrations of SIRP-α polypeptide constructs.

FIGS. 15-17 shows phagocytosis of multiple myeloma line 1R (MM1R) and gastric carcinoma line N87 by non-polarized, human monocyte-derived macrophages. "+" and "−" denotes the addition or absence of Daratumumab (Dara) respectively in FIGS. 15-16. In FIG. 17, "+" and "−" denotes addition and absence of Herceptin/trastuzumab (Her) respectively.

FIG. 15 shows construct A in the presence of a control antibody (IgG1,k), e.g., "A−" has ablated phagocytosis as a single agent while it is able to increase Daratumumab (Dara) phagocytosis, e.g., "A+". Similarly, construct B in the presence of a control antibody (IgG1,k), e.g., "B−" has ablated phagocytosis as a single agent while it is able to increase Daratumumab (Dara) phagocytosis, e.g., "B+". The percent of macrophages that phagocytosed MM1R and are CFSE$^+$ is indicated on the y-axis. Concentration of CD47 binding sites from addition of construct A, B, or control construct is indicated on the x-axis. The levels of phagocytosis are comparable to the control construct (which is a double-arm SIRP-α). The level of phagocytosis resulting from incubation with an anti-CD47 antibody, e.g. B6H12 (100 nM), is comparable to incubation with Dara, e.g. PBS+. As shown, single arm SIRP-α-Fc fusions can increase Dara phagocytosis comparable to a double arm SIRP-α-Fc fusions.

FIG. 16 shows construct C in the presence of a control antibody (IgG1,k), e.g., "C−" has ablated phagocytosis in the phagocytosis assay as a single agent while it is able to increase Daratumumab (Dara) phagocytosis, e.g., "C+". Similarly, construct D in the presence of a control antibody (IgG1,k), e.g., "D−" has ablated phagocytosis in the phagocytosis assay as a single agent while it is able to increase Daratumumab (Dara) phagocytosis, e.g., "D+". The percent of macrophages that phagocytosed MM1R and are CFSE$^+$ is indicated on the y-axis. Concentration of CD47 binding sites from addition of construct C, D, or control construct is indicated on the x-axis. The levels of phagocytosis are comparable to the control construct (which is a double-arm SIRP-α). The level of phagocytosis resulting from incubation with an anti-CD47 antibody, e.g. B6H12 (100 nM), is comparable to incubation with Dara, e.g. PBS+. As shown, single arm SIRP-α-Fc fusions can increase Dara phagocytosis comparable to a double arm SIRP-α-Fc fusions. As shown, single arm SIRP-α-Fc fusions can increase Dara phagocytosis comparable to a double arm SIRP-α-Fc fusions.

FIG. 17 shows phagocytosis in the presence of low affinity single-arm SIRP-α constructs (E, F) performed similarly as above examples. As shown, these low affinity single-arm SIRP-α constructs (E, F) in combination with Herceptin showed comparable phagocytosis of N87 cells to Herceptin alone (PBS+). Therefore, 5 nM affinity for CD47 is not sufficient for single-arm SIRP-α-Fc fusion to enhance further in vitro phagocytosis in combination with Herceptin.

Example 17

Cross Reactivity of High Affinity SIRP-α D1 Variants

Polypeptides of high affinity SIRP-α D1 variants were generated as previously described. Binding to human, mouse, and rat CD47 was determined using SPR as measured by a Biacore T100 instrument (GE Healthcare) and Proteon XPR36 (Bio-rad, Hercules, Calif.) as described in Example 1. SEQ ID NO: 215 is an engineered SIRP-α D1 variant that does not bind to human, mouse, or rat CD47 and was utilized as a negative control.

TABLE 28

Representative Cross-Species CD47 Binding Affinity for High Affinity SIRP-α Variants

| | $K_D$ (M) | | |
|---|---|---|---|
| SEQ ID NO: | Human | Mouse | Rat |
| 85 | $2.03 \times 10^{-10}$ | $2.16 \times 10^{-9}$ | $1.96 \times 10^{-8}$ |
| 198 | $1.55 \times 10^{-10}$ | $1.41 \times 10^{-9}$ | $9.88 \times 10^{-9}$ |
| 199 | $1.26 \times 10^{-9}$ | $1.25 \times 10^{-9}$ | $1.07 \times 10^{-8}$ |
| 200 | $3.04 \times 10^{-10}$ | $1.17 \times 10^{-9}$ | $1.42 \times 10^{-8}$ |
| 204 | $6.53 \times 10^{-10}$ | $4.48 \times 10^{-10}$ | $3.42 \times 10^{-9}$ |
| 205 | $2.48 \times 10^{-10}$ | $5.69 \times 10^{-10}$ | $4.28 \times 10^{-9}$ |
| 206 | $9.67 \times 10^{-10}$ | $2.88 \times 10^{-10}$ | $1.49 \times 10^{-9}$ |
| 207 | $1.04 \times 10^{-9}$ | $8.80 \times 10^{-10}$ | $5.90 \times 10^{-9}$ |
| 208 | $2.19 \times 10^{-10}$ | $8.32 \times 10^{-10}$ | $5.17 \times 10^{-9}$ |
| 209 | $1.01 \times 10^{-9}$ | $3.71 \times 10^{-10}$ | $2.26 \times 10^{-9}$ |
| 210 | $1.65 \times 10^{-9}$ | $6.12 \times 10^{-10}$ | $4.59 \times 10^{-9}$ |
| 136 | $1.3904 \times 10^{-10}$ | $1.1407 \times 10^{-8}$ | $6.43 \times 10^{-9}$ |
| 214 | $2.00 \times 10^{-9}$ | $6.30 \times 10^{-8}$ | $8.00 \times 10^{-8}$ |
| 215 | Non-Binding | Non-Binding | Non-Binding |

SEQ ID NO: 215:
EEELQVIQPDKSVLVAAGETATLRCTATSLIPRGPIQWFRGAGPGRELIY
NRKEGHFPRVTTVSDLTKRNNMDFSIRIGNITPADAGTYYCVKFRKGSPD
DVEFKSGAGTELSVRAKPSDKTHTCPPCPAPEAAGAPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

Example 18

Anti-Tumor Activity of High Affinity SIRP-α Constructs in a Mouse Xenograft Tumor Model Immunodeficient NOD scid gamma (NSG) mice (NOD.Cg-Prkdc$^{scid}$ Il2rg$^{tm1 Wjl}$/SzJ; 50 females, plus spares) were purchased as 6- to 10-week-old animals. Human lymphoma cell line GFP-Luc-Raji cells were grown in RPMI 1640 containing 10% fetal bovine serum, penicillin, streptomycin, and L-glutamine. Cells then were spun down and re-suspended at a concentration of $1.0 \times 10^7$ cells/mL in serum-free medium without additives and combined 1:1 with Matrigel™ (Trevigen, Gaithersburg, Md.). On Day −11 (i.e., 11 days before the projected staging day), the mice were implanted by subcutaneous injection into the left flank with 200 µL (1.0×10⁶ cells) per mouse of the freshly prepared GFP-Luc-Raji:Matrigel mixture. When the tumors reached a mean volume of approximately 55 mm³, fifty animals with established tumors and moderate body weights were randomized into 5 treatment groups (Group 1-5, n=10 mice each). Starting on Day 1, Groups 1 to 5 were treated with (1) SEQ ID NO: 215 [10 mg/kg (mpk), 3×/week]; (2) SEQ ID NO: 104 (10 mpk, 3×/week); (3) rituximab (5 mpk, 2×/week)+SEQ ID NO: 100 (10 mpk, 3×/week); (4) rituximab (5 mpk, 2×/week)+SEQ ID NO: 104 (10 mpk, 3×/week); or (5) rituximab (5 mpk, 2×/week)+SEQ ID NO: 215 (10 mpk, 3×/week), respectively. Doses were administered by intraperitoneal (IP) injection at 0.05 mL/mouse. For all animals, doses were administered starting on the staging day and continuing for a total of 31 days (Days 1-31).

Clinical observations were recorded twice per day (morning and evening). Additional findings were recorded as observed. Body weights were measured three times per week using an electronic balance (Ohaus SCOUT® PRO). Tumor sizes were measured three times per week, and at study completion, using microcalipers (Mitutoyo, Aurora, Ill.) to measure the perpendicular minor (width, W, and height, H) and major (length, L) dimensions. Tumor volume (mm³) was calculated using the formula for the volume of an ellipsoid sphere (L×W×H/2). Blood samples were drawn from 20 animals on Day 1 (baseline; prior to group assignment) and from all animals on Day 8 (Week 1) and Day 31 (at termination). Blood specimens were submitted for complete blood counts (CBCs) on the respective day of draw.

Figure 19A:
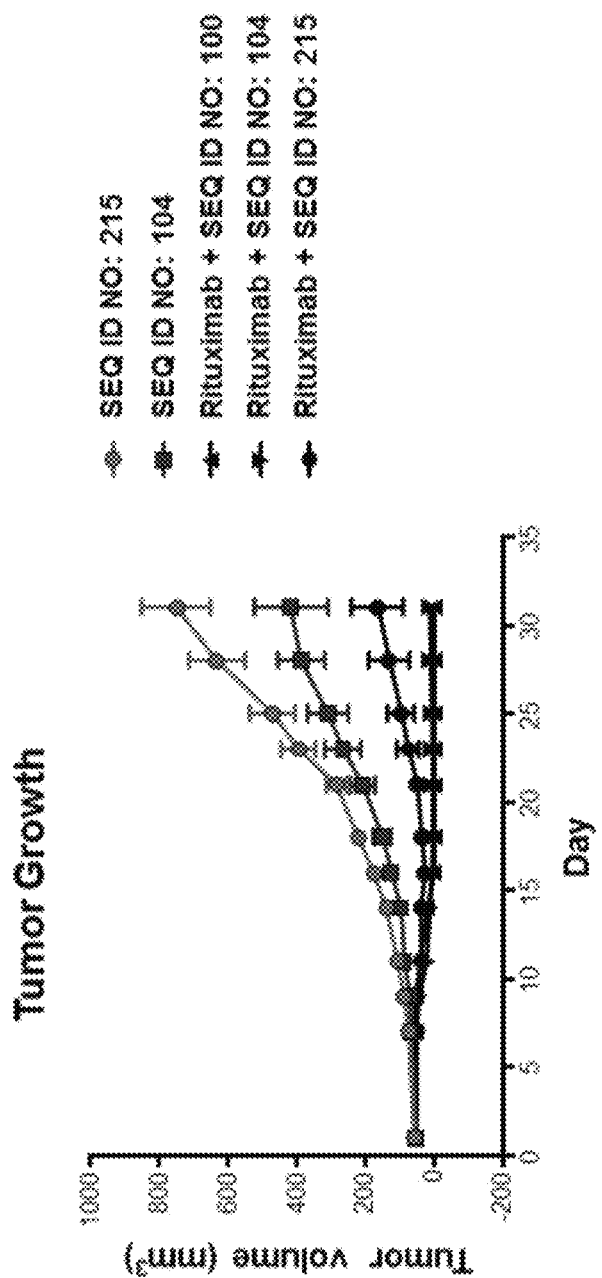
FIG. 19A exemplifies tumor growth of human GFP-Luc-Raji lymphoma cells in a NOD scid gamma (NSG) mouse model of cancer treated with various SIRP-α constructs with or without rituximab.

The SIRP-α construct of SEQ ID NO: 215 does not exhibit measurable binding to CD47 (see Table 28). Tumors in the SEQ ID NO: 215-dosed group (Group 1) grew linearly through Day 31 (FIG. 19A), similar to tumors observed in the PBS vehicle group of the same model (data not shown). This observation demonstrates ongoing tumor growth in the absence of effective treatment.

Figure 19B:
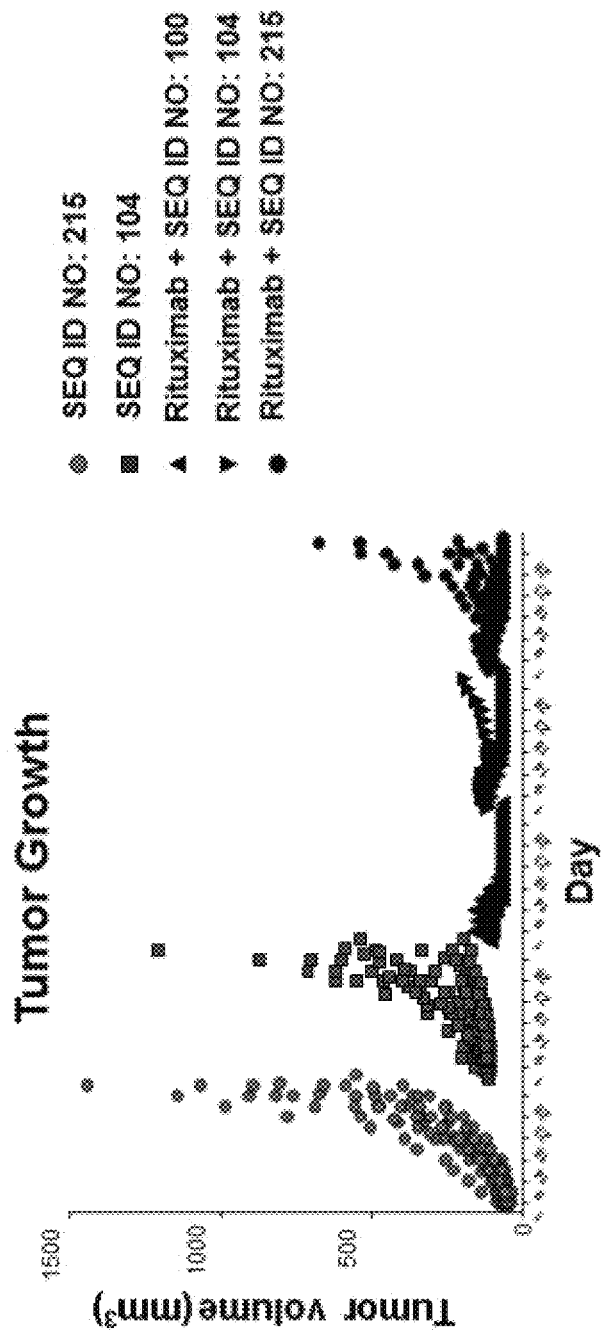
FIG. 19B exemplifies a scatter plot of tumor volume of the tumors described in FIG. 19A.

Comparisons between Groups 1 and 5 (SEQ ID NO: 215 with or without rituximab) and between Groups 2 and 4 (SEQ ID NO: 104 with or without rituximab) reveal that the combination treatments yielded significant attenuation of tumor volume, both as raw values (from Day 9) and normalized values (from Day 7). By Day 16, the majority of mice in Group 3 (SEQ ID NO: 100+rituximab) and Group 4 (SEQ ID NO: 104+rituximab) no longer harbored detectable tumors; these two combination treatments showed similar efficacy. In contrast, tumor growth appeared to recover in animals of Group 5 (SEQ ID NO: 215+rituximab) from Day 18 on. Tumor volumes of all five groups over the study period (mean+/−SEM and individual scatter plots) are presented in FIG. 19A and FIG. 19B respectively.

Figure 19C:
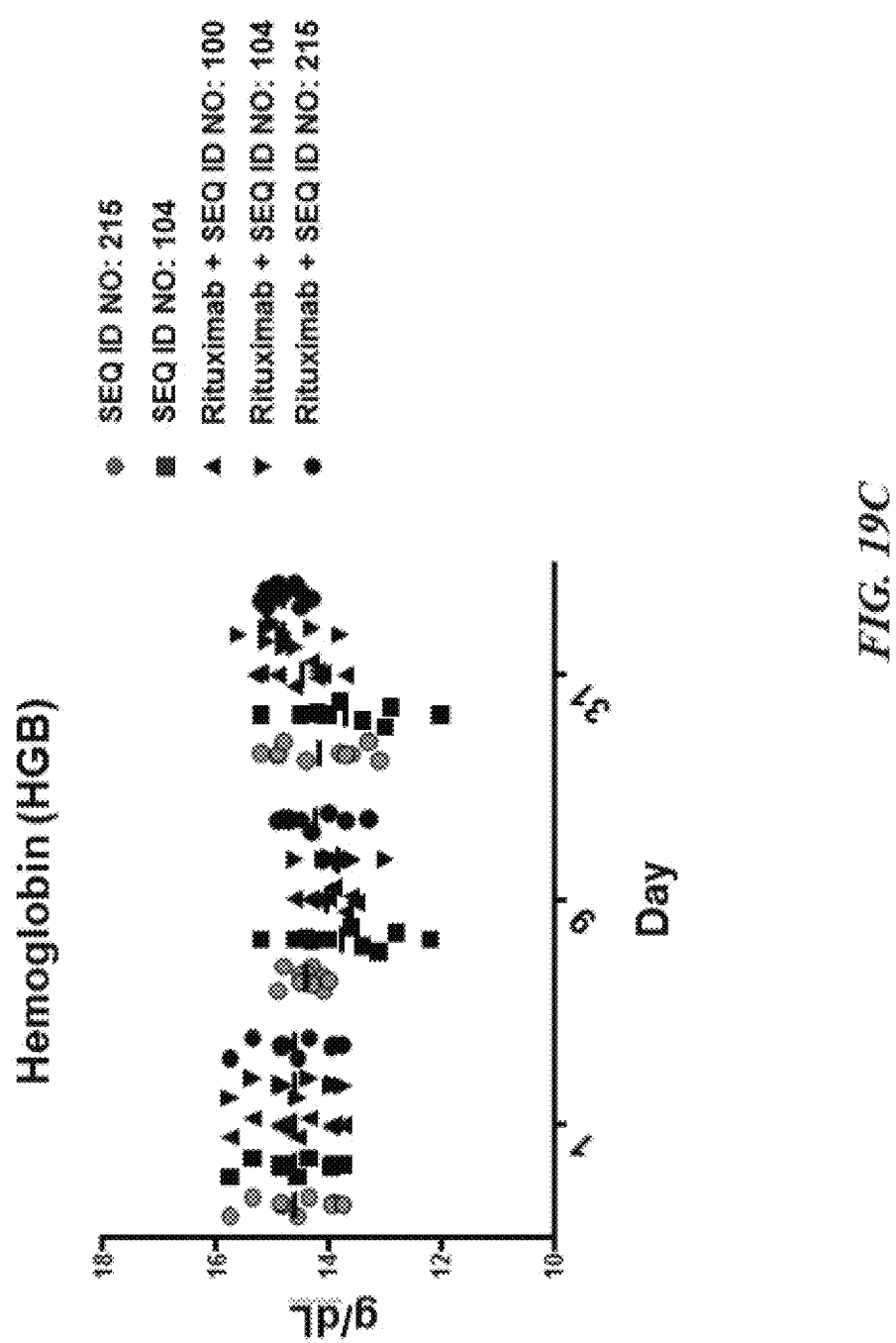
FIG. 19C exemplifies hemoglobin values of the treated mice described in FIG. 19A.

Complete blood count (CBC) values (red blood cells, hemoglobin, hematocrit, platelets, etc.) measured pre-dose (Day 1), 1 week after dosing (Day 9), and 4 weeks after dosing (Day 31). Parameters did not differ significantly at Week 1 or Week 4 among the five groups. Hemoglobin (HGB) values are shown in FIG. 19C. These results demonstrate that high affinity SIRP-α constructs can effectively attenuate tumor growth and synergize with rituximab in an in vivo mouse model of cancer. Furthermore, in contrast to anti-CD47 based antibody treatments, no acute episodes of anemia were observed in any of the test groups treated with the high affinity SIRP-α constructs.

Example 19

SIRP-α Fc Variant Constructs Exhibit Decreased Red Blood Cell Toxicity

Figure 20:
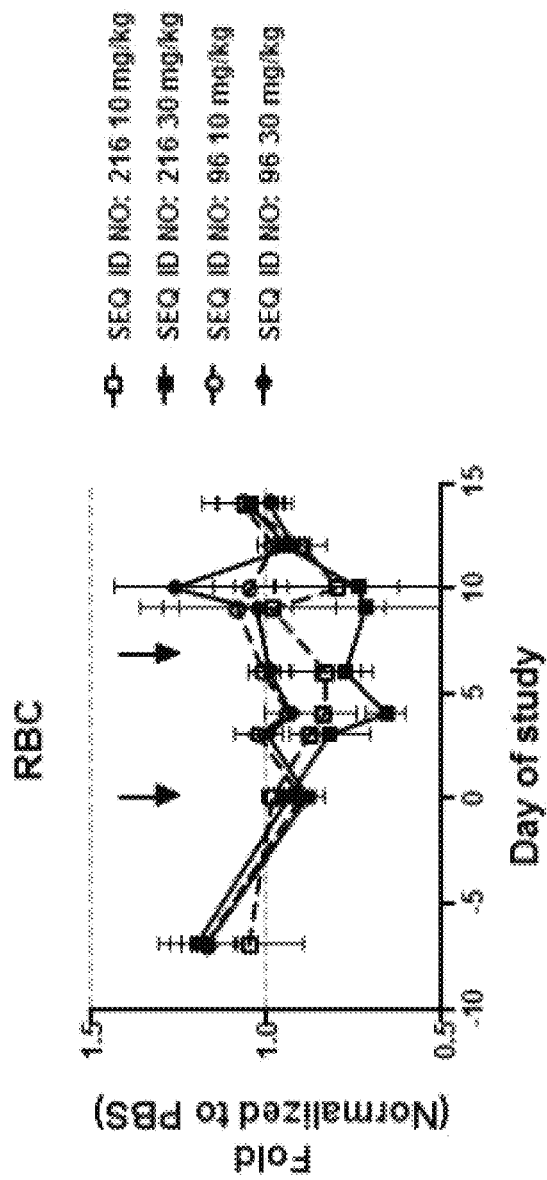
FIG. 20 exemplifies red blood cell counts taken from mice treated with either a SIRP-α wildtype IgG1 Fc construct or a SIRP-α IgG1 Fc variant construct.

Red blood cell loss is a concern when targeting CD47. To examine the effects of a SIRP-α Fc variant construct on red blood cell toxicity, mice were treated with a high affinity SIRP-α variant construct containing either a wildtype IgG1 Fc construct (SEQ ID NO: 216) or a IgG1 Fc variant construct (SEQ ID NO:96) with IgG1 mutations L234A, L235A, G237A, and N297A (IgG1_AAA_N297A). Mice were assigned to five groups of six and were treated on day 1 and 7 (see solid arrows in FIG. 20) with either: (1) PBS; (2) 10 mg/kg SEQ ID NO: 216 (wildtype IgG1 Fc); (3) 30 mg/kg SEQ ID NO: 216; (4) 10 mg/kg SEQ ID NO: 96 (IgG1_AAA_N297A); or (5) 30 mg/kg SEQ ID NO: 96. Baseline complete blood count (CBC) measurements were taken from all animals on day −7 and for three of six animals on day 1. The blood draws (see FIG. 20) rotated between three mice from each group to not exceed the amount of blood withdrawal allowed per week. As demonstrated in FIG. 20, treatment with a wildtype IgG1 containing SIRP-α D1 variant construct resulted in a dose-dependent decrease in red blood cell counts. Conversely, treatment with an IgG1_AAA_N297A containing SIRP-α D1 variant construct resulted in red blood cell counts similar to the PBS treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A polypeptide, comprising:
   (a) a signal-regulatory protein α (SIRP-α) D1 variant comprising SEQ ID NO: 80; and
   (b) a human IgG1 Fc region comprising L234A, L235A, G237A, and N297A mutations, wherein numbering is according to the EU index,
   wherein the C-terminus of the SIRP-αD1 variant is linked to the N-terminus of the human IgG1 Fc region.

2. A nucleic acid encoding the polypeptide of claim 1.

3. A vector comprising the nucleic acid of claim 2.

4. A host cell comprising the nucleic acid of claim 2.

5. A method of producing a polypeptide, comprising culturing the host cell of claim 4 under appropriate conditions to cause expression of the polypeptide and recovering the polypeptide.

6. A pharmaceutical composition comprising the polypeptide of claim 1.

7. A pharmaceutical composition comprising
   (a) a dimer comprising the polypeptide of claim 1, and
   (b) a pharmaceutically acceptable excipient.

8. The pharmaceutical composition of claim 7, where the dimer is a homodimer.

9. A method of treating an individual having cancer, the method comprising administering to the individual a pharmaceutical composition comprising the polypeptide of claim 1.

10. The method of claim 9, further comprising administering at least one additional agent to the individual, wherein the at least one additional agent is an antibody, a tumor associated antigen, or a non-antibody therapeutic.

11. A method of treating an individual having cancer, the method comprising administering to the individual a pharmaceutical composition comprising a dimer and a pharmaceutically acceptable excipient, wherein the dimer comprises the polypeptide of claim 1.

12. The method of claim 11, wherein the dimer is a homodimer.

13. The method of claim 11, further comprising administering at least one additional agent to the individual, wherein the at least one additional agent is an antibody, a tumor associated antigen, or a non-antibody therapeutic.

14. A dimer comprising a polypeptide that comprises the amino acid sequence set forth in SEQ ID NO: 137.

15. The dimer of claim 14, wherein each monomer in the dimer comprises a polypeptide that comprises the amino acid sequence set forth in SEQ ID NO: 137.

16. A nucleic acid encoding a polypeptide that comprises the amino acid sequence set forth in SEQ ID NO: 137.

17. A vector comprising the nucleic acid of claim 16.

18. A host cell comprising the nucleic acid of claim 16.

19. A method of producing a polypeptide, comprising culturing the host cell of claim 18 under appropriate conditions to cause expression of the polypeptide and recovering the polypeptide.

20. A pharmaceutical composition comprising a polypeptide that comprises the amino acid sequence set forth in SEQ ID NO: 137 and a pharmaceutically acceptable excipient.

21. A pharmaceutical composition comprising (a) the dimer of claim 14 and (b) a pharmaceutically acceptable excipient.

22. The pharmaceutical composition of claim 21, wherein the dimer is a homodimer.

23. A method of treating an individual having cancer, the method comprising administering to the individual the pharmaceutical composition of claim 20.

24. The method of claim 23, further comprising administering at least one additional agent to the individual, wherein the at least one additional agent is an antibody, a tumor associated antigen, or a non-antibody therapeutic.

25. A method of treating an individual having cancer, the method comprising administering to the individual the pharmaceutical composition of claim 21.

26. A method of treating an individual having cancer, the method comprising administering to the individual the pharmaceutical composition of claim 22.

27. The method of claim 25, further comprising administering at least one additional agent to the individual, wherein the at least one additional agent is an antibody, a tumor associated antigen, or a non-antibody therapeutic.

28. A polypeptide, comprising:
   (a) a signal-regulatory protein α (SIRP-α) D1 variant comprising SEQ ID NO: 85; and
   (b) a human IgG2 Fc region comprising A330S, P331S, and N297A mutations, wherein numbering is according to the EU index,
   wherein the C-terminus of the SIRP-αD1 variant is linked to the N-terminus of the human IgG1 Fc region.

29. A nucleic acid encoding a polypeptide that comprises the polypeptide of claim 28.

30. A vector comprising the nucleic acid of claim 29.

31. A host cell comprising the nucleic acid of claim 29.

32. A method of producing a polypeptide, comprising culturing the host cell of claim 31 under appropriate conditions to cause expression of the polypeptide and recovering the polypeptide.

33. A pharmaceutical composition comprising the polypeptide of claim 28.

34. A pharmaceutical composition comprising
   (a) a dimer comprising the polypeptide of claim 28, and
   (b) a pharmaceutically acceptable excipient.

35. The pharmaceutical composition of claim 34, wherein the dimer is a homodimer.

36. A method of treating an individual having cancer, the method comprising administering to the individual the pharmaceutical composition of claim 33.

37. The method of claim 36, further comprising administering at least one additional agent to the individual, wherein the at least one additional agent is an antibody, a tumor associated antigen, or a non-antibody therapeutic.

38. A method of treating an individual having cancer, the method comprising administering to the individual a pharmaceutical composition comprising a dimer and a pharmaceutically acceptable excipient, wherein the dimer comprises the polypeptide of claim 28.

39. The method of claim 38, wherein the dimer is a homodimer.

40. The method of claim 38, further comprising administering at least one additional agent to the individual, wherein the at least one additional agent is an antibody, a tumor associated antigen, or a non-antibody therapeutic.

41. A dimer comprising a polypeptide that comprises the amino acid sequence set forth in SEQ ID NO: 113.

42. The dimer of claim 41, wherein each monomer in the dimer comprises a polypeptide that comprises the amino acid sequence set forth in SEQ ID NO: 113.

43. A nucleic acid encoding a polypeptide comprising the amino acid sequence set forth in SEQ ID NO: 113.

44. A vector comprising the nucleic acid of claim 43.

45. A host cell comprising the nucleic acid of claim 43.

46. A method of producing a polypeptide, comprising culturing the host cell of claim 45 under appropriate conditions to cause expression of the polypeptide and recovering the polypeptide.

47. A pharmaceutical composition comprising a polypeptide comprising the amino acid sequence set forth in SEQ ID NO: 113 and a pharmaceutically acceptable excipient.

48. A pharmaceutical composition comprising (a) the dimer of claim 41 and (b) a pharmaceutically acceptable excipient.

49. The pharmaceutical composition of claim 48, wherein the dimer is a homodimer.

50. A method of treating an individual having cancer, the method comprising administering to the individual a pharmaceutical composition comprising a polypeptide that comprises the amino acid sequence of SEQ ID NO: 113 and a pharmaceutically acceptable excipient.

51. The method of claim 50, further comprising administering at least one additional agent to the individual, wherein the at least one additional agent is an antibody, a tumor associated antigen, or a non-antibody therapeutic.

52. A method of treating an individual having cancer, the method comprising administering to the individual a pharmaceutical composition comprising the dimer of claim 41 and a pharmaceutically acceptable excipient.

53. The method of claim 52, wherein the dimer is a homodimer.

54. The method of claim 52, further comprising administering at least one additional agent to the individual, wherein the at least one additional agent is an antibody, a tumor associated antigen, or a non-antibody therapeutic.

* * * * *

UNITED STATES PATENT AND TRADEMARK OFFICE
CERTIFICATE OF CORRECTION

PATENT NO. : 11,208,459 B2
APPLICATION NO. : 16/825850
DATED : December 28, 2021
INVENTOR(S) : Jaume Pons et al.

It is certified that error appears in the above-identified patent and that said Letters Patent is hereby corrected as shown below:

On the Title Page

Item (71), Line 2, please replace "CO" with -- CA --;

On Page 3, item (56), under "OTHER PUBLICATIONS", in Column 2, Line 8, please replace "Chem," with -- Chem. --;

On Page 3, item (56), under "OTHER PUBLICATIONS", in Column 2, Line 10, please replace "1.98(a)(2)(ii)" with -- 1.98(a)(2)(iii) --;

On Page 3, item (56), under "OTHER PUBLICATIONS", in Column 2, Line 22, please replace "Common" with -- Commun --;

On Page 3, item (56), under "OTHER PUBLICATIONS", in Column 2, Line 35, please replace "Proc Natl Acad Sci" with -- Proc. Natl. Acad. Sci. --;

On Page 4, item (56), under "OTHER PUBLICATIONS", in Column 1, Line 16, please replace "Biochim" with -- Biochem --;

On Page 4, item (56), under "OTHER PUBLICATIONS", in Column 2, Line 48, please replace "Proc Natl Acad Sci" with -- Proc. Natl. Acad. Sci. --;

On Page 5, item (56), under "OTHER PUBLICATIONS", in Column 2, Line 13, please replace "Proc Natl Acad Sci" with -- Proc. Natl. Acad. Sci. --;

In the Drawings

In Fig. 7, Sheet 7 of 22, Line 2, please replace "IgG1k" with -- IgG1,k --;

Signed and Sealed this
Fifth Day of September, 2023

Katherine Kelly Vidal
*Director of the United States Patent and Trademark Office*

CERTIFICATE OF CORRECTION (continued)
U.S. Pat. No. 11,208,459 B2

In the Specification

In Column 1, Line 28, after "KB)" insert -- . --;

In Column 2, Line 2, please replace "S,G," with -- S, G, --;

In Column 5, Line 41, please replace "$5\times10^{-6}$M." with -- $5\times10^{-6}$ M. --;

In Column 8, Line 59, please replace "MED16469," with -- MEDI6469, --;

In Column 8, Line 62, please replace "mogamalizumab," with -- mogamulizumab, --;

In Column 9, Line 21, please replace "n the" with -- the --;

In Column 9, Line 29, please replace "pantimumab." with -- panitumumab. --;

In Column 12, Line 57, please replace "sum total of" with -- sum of total --;

In Column 13, Line 7, please replace "increasing" with -- increased --;

In Columns 13-14, in Table 1, Line 2, please replace "SIRP-a" with -- SIRP-α --;

In Columns 15-16, in Table 1, Line 2, please replace "SIRP-a" with -- SIRP-α --;

In Column 17, Line 17, please replace "(NHP)" with -- (NHPs) --;

In Columns 17-18, in Table 2, Line 2, please replace "SIRP-a" with -- SIRP-α --;

In Columns 17-18, in Table 2, Line 18, please replace "Xs" with -- $X_5$ --;

In Columns 17-18, in Table 2, Line 27, please replace "Xs" with -- $X_5$ --;

In Columns 19-20, in Table 2, Line 2, please replace "SIRP-a" with -- SIRP-α --;

In Columns 19-20, in Table 2, Line 23, please replace "Xr" with -- $X_8$ --;

In Columns 19-20, in Table 2, Line 60, please replace "$X_{18}$" with -- $X_{10}$ --;

In Columns 19-20, in Table 2, Line 62, please replace "D," with -- D; --;

In Column 22, Line 22, delete "$1\times10^{-8}$M less than $5\times10^{-8}$ M," with -- $1\times10^{-8}$M, less than $5\times10^{-9}$ M, --;

In Column 22, Line 22, please replace "$1\times10^{-9}$M," with -- $1\times10^{-9}$ M, --;

In Column 22, Line 23, please replace "less $5\times10^{-10}$ M," with -- less than $5\times10^{-10}$ M, --;

CERTIFICATE OF CORRECTION (continued)
U.S. Pat. No. 11,208,459 B2

In Column 22, Line 23, please replace "$1\times10^{-10}$M" with -- $1\times10^{-10}$ M, --;

In Column 23, Line 50, please replace "less 5" with -- less than 5 --;

In Column 24, Line 36, please replace "less 5" with -- less than 5 --;

In Column 25, Line 42, please replace "less 5" with -- less than 5 --;

In Columns 29 & 30, Line 23, please replace "ABLE 5" with -- TABLE 5 --;

In Columns 29 & 30, in Table 5, Line 17, please replace "$X_9p$" with -- $X_9$ --;

In Columns 31 & 32, Line 1, please replace "ABLE 5" with -- TABLE 5 --;

In Columns 31 & 32, Line 9, please replace "$X_8G_9$" with -- $X_8GX_9$ --;

In Columns 31 & 32, in Table 5, Line 12, please replace "$L,_1,$" with -- L, I, --;

In Columns 31 & 32, in Table 5, Line 21, please replace "$L,_1,$" with -- L, I, --;

In Columns 31 & 32, in Table 5, Line 47, please replace "$PDTEX_{16},$ KSGAGTELSVRAKPS" with -- $PDTEX_{16}$KSGAGTELSVRAKPS --;

In Columns 31 & 32, in Table 5, Line 61, please replace "$X_{16} = D,$" with -- $X_{17} = D,$ --;

In Columns 33 & 34, Line 1, please replace "ABLE 5" with -- TABLE 5 --;

In Columns 33 & 34, in Table 5, Line 3, please replace "$X_4 = T,_1;$" with -- $X_4 = T, I;$ --;

In Columns 33 & 34, in Table 5, Line 59, please replace "S,G," with -- S, G, --;

In Columns 33 & 34, in Table 5, Line 68, please replace "S,G," with -- S, G, --;

In Columns 33 & 34, in Table 5, Line 69, please replace "P ;" with -- P; --;

In Column 35, Line 50, please replace "$X_{12}ITXDAD$" with -- $X_{12}ITX_{13}AD$ --;

In Column 36, Line 51, please replace "less 5" with -- less than 5 --;

In Column 38, Line 28, please replace "less 5" with -- less than 5 --;

In Column 39, Line 23, please replace "less 5" with -- less than 5 --;

In Column 40, Line 38, please replace "less 5" with -- less than 5 --;

In Column 41, Line 43, please replace "less 5" with -- less than 5 --;

In Column 42, Line 34, please replace "less 5" with -- less than 5 --;

In Column 43, Line 51, please replace "less 5" with -- less than 5 --;

In Column 45, Lines 12-13, please replace "less 5" with -- less than 5 --;

In Column 45, Line 13, please replace "M less" with -- M, less --;

In Column 45, Line 29, please replace "of" with -- or --;

In Column 46, Lines 41-42, please replace "less 5" with -- less than 5 --;

In Column 46, Line 42, please replace "M less" with -- M, less --;

In Column 46, Line 42, please replace "$1\times10^{-10}$ M." with -- $1\times10^{-11}$ M. --;

In Column 46, Line 59, please replace "S,G," with -- S, G, --;

In Column 54, Line 6, please replace "Md." with -- MD. --;

In Column 55, Line 26, please replace "(1991)." with -- "(1991)). --;

In Column 56, Lines 58-59, please replace "FIEAL" with -- HEAL --;

In Column 58, Line 34, please replace "Ni+2" with -- $Ni^{+2}$ --;

In Column 58, Line 42, please replace "Ni+2" with -- $Ni^{+2}$ --;

In Column 58, Line 44, please replace "Ni+2" with -- $Ni^{+2}$ --;

In Column 59, Line 33, please replace "Clq" with -- C1q --;

In Columns 61-62, SEQ ID NO: 99, Line 7, please replace "MFIEALFINH" with -- MHEALHNH --;

In Columns 61-62, in Table 8, SEQ ID NO: 101, Line 7, please replace "MFIEAL" with -- MHEAL --;

In Columns 63-64, in Table 8, SEQ ID NO: 105, Line 7, please replace "LFINH" with -- LHNH --;

In Columns 63-64, in Table 8, SEQ ID NO: 108, Line 4, please replace "VFTNA" with -- VHNA --;

In Columns 65-66, in Table 8, SEQ ID NO: 117, Line 7, please replace "LFTNH" with -- LHNH --;

In Columns 65-66, in Table 8, SEQ ID NO: 118, Line 7, please replace "LFINH" with -- LHNH --;

CERTIFICATE OF CORRECTION (continued)
U.S. Pat. No. 11,208,459 B2

In Columns 65-66, in Table 8, SEQ ID NO: 121, Line 4, please replace "VFINA" with -- VHNA --;

In Columns 67-68, in Table 8, SEQ ID NO: 127, Line 4, please replace "VFINA" with -- VHNA --;

In Columns 67-68, in Table 8, SEQ ID NO: 128, Line 7, please replace "MFIEAL" with -- MHEAL --;

In Columns 67-68, in Table 8, SEQ ID NO: 130, Line 5, please replace "LFIQD" with -- LHQD --;

In Columns 69-70, in Table 8, SEQ ID NO: 131, Line 5, please replace "LFIQD" with -- LHQD --;

In Columns 69-70, in Table 8, SEQ ID NO: 132, Line 4, please replace "VFTNA" with -- VHNA --;

In Columns 69-70, in Table 8, SEQ ID NO: 133, Line 6, please replace "sqeemtknqvsltclvkgfypsdiavewesngQpennykttppvldsdgs" with -- SQEEMTKNQVSLTCLVKGFYPSDIAVEWESNGQPENNYKTTPPVLDSDGS --;

In Columns 69-70, in Table 8, SEQ ID NO: 135, Line 7, please replace "LITNH" with -- LHNH --;

In Column 73, in Table 10, Line 1, please replace "SIRP-α - Fc" with -- SIRP-α-Fc --;

In Column 73, Line 58, please replace "VFLEP" with -- VFLFP --;

In Column 74, in Table 10-continued, Line 11, please replace "SIRP-α - Fc" with -- SIRP-α-Fc --;

In Column 74, in Table 10-continued, SEQ ID NO: 147, Line 1, please replace "VFLEP" with -- VFLFP --;

In Column 74, in Table 10-continued, SEQ ID NO: 149, Line 1, please replace "VFLEP" with -- VFLFP --;

In Column 77, Line 36, please replace "SEQ" with -- (SEQ --;

In Column 79, in Table 13, SEQ ID NO: 159, Line 1, please replace "TSLEP" with -- TSLFP --;

In Column 83, Line 11, please replace "SLTRK6," with -- SLITRK6, --;

In Column 83, Line 35, please replace "1991." with -- 1991). --;

In Column 84, Lines 51-52, please replace "having a having a" with -- having a --;

In Column 89, Line 62, please replace "λ1776" with -- λ 1776 --;

In Column 89, Line 62, please replace "31,537," with -- 31,537), --;

CERTIFICATE OF CORRECTION (continued)
U.S. Pat. No. 11,208,459 B2

In Column 90, Lines 21-22, please replace "Streptococcus lividans." with -- Streptococcus viridans. --;

In Column 91, Lines 28-38, please replace "POROUS Protein.... used." and insert the same on Line 27 after "(e.g.," as a continuation paragraph;

In Column 92, Lines 48-49, please replace "butyl orbenzyl alcohol;" with -- butyl or benzyl alcohol; --;

In Column 93, Line 61, please replace "poly-(methylmethacrylate)" with -- poly-(methylmethacylate) --;

In Column 94, Lines 4-5, please replace "polylactides," with -- polylactide, --;

In Column 94, Line 51, please replace "intraotically," with -- intrathecally, --;

In Column 94, Line 54, please replace "Aradigm," with -- Aradigm®, --;

In Column 96, Line 3, please replace "human." with -- humans. --;

In Column 98, Line 59, please replace "SIRP-a" with -- SIRP-α --;

In Column 99, Line 53, please replace "152-159." with -- 152-159; --;

In Column 100, Line 25, please replace "SLTRK6," with -- SLITRK6, --;

In Column 100, Line 62, please replace "SLTRK6," with -- SLITRK6, --;

In Column 101, Line 30, please replace "SLTRK6," with -- SLITRK6, --;

In Column 101, Line 43, please replace "SIRP-a" with -- SIRP-α --;

In Column 101, Line 47, please replace "MED16469," with -- MEDI6469, --;

In Column 101, Line 50, please replace "mogamalizumab," with -- mogamulizumab, --;

In Column 102, Line 30, please replace "MED16469," with -- MEDI6469, --;

In Column 102, Line 33, please replace "mogamalizumab," with -- mogamulizumab, --;

In Column 103, Line 54, please replace "pantimumab." with -- panitumumab. --;

In Column 105, Line 42, please replace "MED16469," with -- MEDI6469, --;

In Column 105, Line 45, please replace "mogamalizumab," with -- mogamulizumab, --;

In Column 106, Line 25, please replace "pantimumab." with -- panitumumab. --;

In Column 107, Line 15, please replace "(NHP)." with -- (NHPs). --;

In Column 107, Line 44, please replace "SIRP-a" with -- SIRP-α --;

In Column 107, Line 49, please replace "Nrp 1," with -- Nrp1, --;

In Column 108, Line 21, please replace "also be treated," with -- also being treated, --;

In Column 108, Line 25, please replace "dosage" with -- dosages --;

In Column 108, Line 42, please replace "varies" with -- vary --;

In Column 110, Line 45, please replace "Proteon" with -- ProteOn --;

In Column 110, Line 50, please replace "Proteon" with -- ProteOn --;

In Column 110, Line 53, please replace "KD value," with -- $K_D$ value, --;

In Column 113, in Table 19, under "KD(M)", Line 1, please replace "10-10" with -- $10^{-10}$ --;

In Column 113, in Table 19, under "KD(M)", Line 2, please replace "10-10" with -- $10^{-10}$ --;

In Column 113, in Table 19, under "KD(M)", Line 3, please replace "10-10" with -- $10^{-10}$ --;

In Column 113, in Table 19, under "KD(M)", Line 4, please replace "10-11" with -- $10^{-11}$ --;

In Column 113, in Table 19, under "KD(M)", Line 5, please replace "10-10" with -- $10^{-10}$ --;

In Column 113, in Table 19, under "KD(M)", Line 6, please replace "10-10" with -- $10^{-10}$ --;

In Column 113, in Table 19, under "KD(M)", Line 7, please replace "10-10" with -- $10^{-10}$ --;

In Column 113, in Table 19, under "KD(M)", Line 8, please replace "10-10" with -- $10^{-10}$ --;

In Column 113, in Table 19, under "KD(M)", Line 9, please replace "10-10" with -- $10^{-10}$ --;

In Column 113, in Table 19, under "KD(M)", Line 10, please replace "10-9" with -- $10^{-9}$ --;

In Column 113, in Table 19, under "KD(M)", Line 11, please replace "10-8" with -- $10^{-8}$ --;

In Column 113, in Table 19, under "KD(M)", Line 12, please replace "10-6" with -- $10^{-6}$ --;

In Column 113, in Table 19, under "KD(M)", Line 13, please replace "10-10" with -- $10^{-10}$ --;

CERTIFICATE OF CORRECTION (continued)
U.S. Pat. No. 11,208,459 B2

In Column 113, in Table 19, under "KD(M)", Line 14, please replace "10-10" with -- $10^{-10}$ --;

In Column 113, in Table 19, under "KD(M)", Line 15, please replace "10-10" with -- $10^{-10}$ --;

In Column 113, in Table 19, under "KD(M)", Line 16, please replace "10-10" with -- $10^{-10}$ --;

In Column 113, in Table 19, under "KD(M)", Line 17, please replace "10-10" with -- $10^{-10}$ --;

In Column 113, in Table 19, under "KD(M)", Line 18, please replace "10-9" with -- $10^{-9}$ --;

In Column 113, in Table 19, under "KD(M)", Line 19, please replace "10-9" with -- $10^{-9}$ --;

In Column 113, in Table 19, under "KD(M)", Line 20, please replace "10-9" with -- $10^{-9}$ --;

In Column 114, in Table 20, SEQ ID NO: 142, Line 4, please replace "VFLEP" with -- VFLFP --;

In Column 115, SEQ ID NO: 217, Line 4, please replace "VFLEP" with -- VFLFP --;

In Column 115, Line 16, please replace "Proteon" with -- ProteOn --;

In Column 115, Lines 18-19, please replace "30 uL/min" with -- 30 μL/min --;

In Column 116, Lines 38-39, please replace "aglycosylation or the deglycosylating" with -- a glycosylation or the deglycosylation --;

In Column 117, Line 6, please replace "isotherm. $K_D$.app." with -- isotherm, $K_{D,app.}$ --;

In Column 117, Line 10, please replace "($_{KD\ app}$=k$_{d,app}$/k$_{a,app}$)" with -- ($K_{D,app}$=k$_{d,app}$/k$_{a,app}$). --;

In Column 117, Line 17, please replace "aglycosylation or the deglycosylating" with -- a glycosylation or the deglycosylation --;

In Column 118, Line 23, please replace "does not to bind" with -- does not bind to --;

In Column 119, Line 23, please replace "underlayed" with -- underlaid --;

In Column 119, Line 56, please replace "preincubated" with -- preincubated for --;

In Column 119, Line 58, please replace "incubated" with -- incubated for --;

In Column 120, Line 10, please replace "CF SE." with -- CFSE. --;

In Column 121, Line 33, please replace "(1 ug/mL)" with -- (1 μg/mL) --;

In Column 121, Line 36, please replace "+IgG1k)." with -- +IgG1,k). --;

CERTIFICATE OF CORRECTION (continued)

In Column 121, Line 39, please replace "N297A" with -- N297A) --;

In Column 121, Line 63, please replace "+IgG1k)." with -- +IgG1,k). --;

In Column 123, Line 41, please replace "0.25 ug/mL" with -- 0.25 µg/mL --;

In Column 123, Line 53, please replace "incubated" with -- incubated for --;

In Column 124, Lines 25-26, please replace "200-300 uL/well 1× TB ST." with -- 200-300 µL/well using 1× TBST. --;

In Column 124, Line 29, please replace "incubated" with -- incubated for --;

In Column 124, Lines 42-43, please replace "2 ug/ml, 100 ul/well" with -- 2 µg/ml, 100 µl/well --;

In Column 125, Line 6, please replace "incubated" with -- incubated for --;

In Column 125, Line 34, please replace "underlayed" with -- underlaid --;

In Column 126, Line 12, please replace "by administered" with -- administered by --;

In Column 126, Line 15, please replace "SED" with -- SEQ --;

In Column 126, Line 56, please replace "following" with -- followed --;

In Columns 127 & 128, in Table 25, Line 9, please replace "(100 ug)" with -- (100 µg) --;

In Columns 127 & 128, in Table 25, Line 10, please replace "(200 ug)" with -- (200 µg) --;

In Column 130, in Table 27, Line 1, please replace "SIRPα - Fc" with -- SIRP-α Fc --;

In Column 130, in Table 27, SEQ ID NO: 138, Line 2, please replace "STRI" with -- SIRI --;

In Column 130, in Table 27, SEQ ID NO: 140, Line 2, please replace "STRI" with -- SIRI --;

In Column 131, in Table 27-continued, Line 1, please replace "SIRPα - Fc" with -- SIRP-α Fc --;

In Column 132, Line 13, please replace "Proteon" with -- ProteOn --;

In Column 133, Line 42, please replace "By Day 16," with -- By day 16, --;

In the Claims

In Column 461, Line 16, in Claim 1, please replace "SIRP-αD1" with -- SIRP-α D1 --;

CERTIFICATE OF CORRECTION (continued)
U.S. Pat. No. 11,208,459 B2

In Column 461, Line 28, in Claim 7, please replace "comprising" with -- comprising: --;

In Column 462, Line 37, in Claim 28, please replace "SIRP-αD1" with -- SIRP-α D1 --;

In Column 462, Line 49, in Claim 34, please replace "comprising" with -- comprising: --.